(12) United States Patent
Dominguez et al.

(10) Patent No.: US 8,946,197 B2
(45) Date of Patent: Feb. 3, 2015

(54) TRANSGLUTAMINASE TG2 INHIBITORS, PHARMACEUTICAL COMPOSITIONS, AND METHODS OF USE THEREOF

(75) Inventors: Celia Dominguez, Los Angeles, CA (US); John Wityak, Carlsbad, CA (US); Michael Prime, Oxfordshire (GB); Stephen Martin Courtney, Oxfordshire (GB); Christopher Yarnold, Oxfordshire (GB); Frederick Brookfield, Oxfordshire (GB); Richard Marston, Oxfordshire (GB); Douglas Macdonald, Los Angeles, CA (US)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 13/509,783

(22) PCT Filed: Nov. 12, 2010

(86) PCT No.: PCT/US2010/056614
§ 371 (c)(1), (2), (4) Date: Nov. 30, 2012

(87) PCT Pub. No.: WO2011/060321
PCT Pub. Date: May 19, 2011

(65) Prior Publication Data
US 2013/0116216 A1  May 9, 2013

Related U.S. Application Data

(60) Provisional application No. 61/261,506, filed on Nov. 16, 2009.

(51) Int. Cl.

| | | |
|---|---|---|
| A61K 31/635 | (2006.01) |
| C07C 311/46 | (2006.01) |
| C07D 211/34 | (2006.01) |
| C07D 211/54 | (2006.01) |
| C07D 211/58 | (2006.01) |
| C07D 211/96 | (2006.01) |
| C07D 213/38 | (2006.01) |
| C07D 213/40 | (2006.01) |
| C07D 213/56 | (2006.01) |
| C07D 215/38 | (2006.01) |
| C07D 217/14 | (2006.01) |
| C07D 217/22 | (2006.01) |
| C07D 239/42 | (2006.01) |
| C07D 263/58 | (2006.01) |
| C07D 277/42 | (2006.01) |
| C07D 295/205 | (2006.01) |
| C07D 295/26 | (2006.01) |
| C07D 307/52 | (2006.01) |
| C07D 401/04 | (2006.01) |
| C07D 487/04 | (2006.01) |
| C07D 495/04 | (2006.01) |

(52) U.S. Cl.
CPC ............ *C07C 311/46* (2013.01); *C07D 211/34* (2013.01); *C07D 211/54* (2013.01); *C07D 211/58* (2013.01); *C07D 211/96* (2013.01); *C07D 213/38* (2013.01); *C07D 213/40* (2013.01); *C07D 213/56* (2013.01); *C07D 215/38* (2013.01); *C07D 217/14* (2013.01); *C07D 217/22* (2013.01); *C07D 239/42* (2013.01); *C07D 263/58* (2013.01); *C07D 277/42* (2013.01); *C07D 295/205* (2013.01); *C07D 295/26* (2013.01); *C07D 307/52* (2013.01); *C07D 401/04* (2013.01); *C07D 487/04* (2013.01); *C07D 495/04* (2013.01); *C07C 2101/14* (2013.01)
USPC .......................................................... 514/157

(58) Field of Classification Search
None
See application file for complete search history.

(56) References Cited

U.S. PATENT DOCUMENTS

| | | | |
|---|---|---|---|
| 4,247,549 A | 1/1981 | Ohnmacht et al. |
| 4,970,297 A | 11/1990 | Castelhano et al. |
| 5,565,567 A | 10/1996 | Share |
| 5,670,505 A | 9/1997 | Matsuo et al. |
| 6,344,358 B1 | 2/2002 | Matsuoka et al. |
| 6,451,816 B1 | 9/2002 | Biedermann et al. |

(Continued)

FOREIGN PATENT DOCUMENTS

| | | |
|---|---|---|
| EP | 1814551 | 8/2007 |
| EP | 2316458 | 5/2011 |

(Continued)

OTHER PUBLICATIONS

Intl Search Report—Written Opinion. PCT/US2010/056614 (Jan. 12, 2011).

(Continued)

*Primary Examiner* — San-Ming Hui
*Assistant Examiner* — Jeanmarie Calvillo

(57) ABSTRACT

Certain compounds and pharmaceutically acceptable salts are provided herein. Also provided are pharmaceutical compositions comprising at least one compound or pharmaceutically acceptable salt therein and one or more pharmaceutically acceptable vehicle. Methods of treating patients suffering from certain disease states responsive to the inhibition of transglutaminase TG2 activity are described. These disease states include neurodegenerative disorders such as Huntington's disease. Also described are methods of treatment include administering at least one compound or pharmaceutically acceptable salt thereof as a single active agent or administering at least one compound or pharmaceutically acceptable salt thereof in combination with one or more other therapeutic agents.

50 Claims, No Drawings

(56) References Cited

U.S. PATENT DOCUMENTS

| | | |
|---|---|---|
| 6,699,891 B1 | 3/2004 | Kawanishi et al. |
| 6,710,043 B1 | 3/2004 | Yamada et al. |
| 7,417,058 B2 | 8/2008 | Halazy et al. |
| 7,910,741 B2 | 3/2011 | Nishizawa et al. |
| 8,012,995 B1 | 9/2011 | Arkinstall et al. |
| 8,471,063 B2 | 6/2013 | Oertel |
| 2004/0077632 A1 | 4/2004 | Halazy et al. |
| 2006/0014807 A1* | 1/2006 | Lin .................. 514/357 |
| 2006/0160864 A1 | 7/2006 | Shiraishi et al. |
| 2010/0009353 A1 | 1/2010 | Barnes et al. |
| 2011/0117073 A1 | 5/2011 | Singh et al. |
| 2011/0230476 A1 | 9/2011 | Niu et al. |
| 2011/0230487 A1 | 9/2011 | Ly et al. |
| 2012/0302539 A1 | 11/2012 | Prime et al. |

FOREIGN PATENT DOCUMENTS

| | | |
|---|---|---|
| WO | WO-95/25443 | 9/1995 |
| WO | WO-2006/034341 A2 | 3/2006 |
| WO | WO 2010 001366 | 1/2010 |
| WO | WO-2010/001366 A1 | 1/2010 |
| WO | WO 2011 035159 | 3/2011 |

OTHER PUBLICATIONS

Prime et al. "Irreversible 4-Aminopiperidine Transglutaminase 2 Inhibitors forHuntington's Disease" ACS Med. Chem. Lett. 2012, 3, 731-735.

Caccamo et al. "Potential of transglutaminase 2 as a therapeutic target" Exp. Opin. ther Targets 14(9) p. 989-1003 (2010).

Cheng et al. "Pd2(dba)3 promoted synthesis of 3-N substituted 4-aryl-1,2,3,6-tetrahydropyridine" Tetrahedron Lett. 51, p. 4886-4889 (2010).

Duval et al. "Structure-activity relationship study of novel tissue transglutaminase inhibitors" Bioorg. Med. Chem. Lett. 15, p. 1885-1889 (2005).

Enzyme Active site "Structural biochemistry/enzyme/active site" Wikipedia p. 1-9 (2014).

* cited by examiner

TRANSGLUTAMINASE TG2 INHIBITORS, PHARMACEUTICAL COMPOSITIONS, AND METHODS OF USE THEREOF

This application is a 35 USC 371 National Stage Entry of PCT/US2010/056614 filed Nov. 12, 2010, which claims priority to U.S. Provisional Application No. 61/261,506 filed Nov. 16, 2009, both of which is incorporated herein by reference.

Provided herein are certain transglutaminase TG2 inhibitors, pharmaceutical compositions thereof, and methods of their use.

Transglutaminases (TGases, EC 2.3.2.13) are calcium-dependent enzymes that catalyze the intermolecular cross-linking of certain proteins through the formation of γ-glutamyl-ε-lysine side chain bridges. In mammals, three types of TGases have been characterized to date and are found in tissue, plasma and epidermis. Tissue TGases are involved in diverse biological processes such as endocytosis, apoptosis and cell growth regulation. The plasma-soluble form of TGase, Factor XIIIa, stabilizes blood clots by catalyzing the cross-linking of fibrin during hemostasis. Epidermal TGase plays a role in the synthesis of the cornified envelope of epidermal keratinocytes.

Several members of the transglutaminase family have been linked to disease, including tissue transglutaminase (TG2), and the skin transglutaminases, TG1 and TG3. TG2 is a cytoplasmic enzyme present in many cells, including those in the blood vessel wall. Aberrant TG2 activity is believed to play a role in neurological disorders such as Alzheimer's, Parkinson's and Huntington's disease. Expression of TG1 and TG2 have been correlated with various types of malignancies, including glioblastomas, lung and breast cancers, suggesting an important role for TG2 in tumor proliferation and survival.

Provided is at least a compound of Formula I

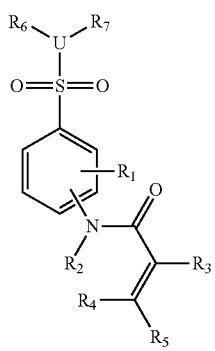

Formula I or a pharmaceutically acceptable salt thereof, wherein
U is N or CH;
$R_1$ is chosen from hydrogen, —$R^a$, —$OR^b$, —$SR^b$, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$,
where $R^a$ is chosen from optionally substituted $C_1$-$C_6$ alkyl, optionally substituted aryl, and optionally substituted heteroaryl;
$R^b$ is chosen from H, optionally substituted $C_1$-$C_6$ alkyl, optionally substituted aryl, and optionally substituted heteroaryl; and
$R^c$ is chosen from hydrogen and optionally substituted $C_1$-$C_4$ alkyl; or
$R^b$ and $R^c$, and the nitrogen to which they are attached, form an optionally substituted heterocycloalkyl group; and
where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl);
$R_2$ is chosen from hydrogen and optionally substituted alkyl;
$R_3$, $R_4$, and $R_5$ are independently chosen from hydrogen, halo, and optionally substituted alkyl or $R_3$ taken together with $R_4$ forms a bond and $R_5$ is chosen from hydrogen and optionally substituted alkyl;
$R_6$ is chosen from hydrogen, optionally substituted alkyl, and optionally substituted cycloalkyl; and
$R_7$ is chosen from hydrogen —V—$R_8$ wherein
V is lower alkylene, optionally substituted with one or more halo or lower alkyl groups; and
$R_8$ is chosen from phenyl, heterocycloalkyl, and heteroaryl, each of which phenyl, heterocycloalkyl, and heteroaryl groups is optionally substituted with a group chosen from halo, lower alkyl, heterocycloalkyl, heterocycloalkyloxy, and heteroaryl, alkyl substituted with phenyl, alkyl substituted with cycloalkyl, alkyl substituted with heterocycloalkyl, alkyl substituted with heteroaryl, each of which substituents, except for halo, being optionally further substituted with one or more alkyl groups and when said substituent is a heterocycloalkyl, then said heterocycloalkyl may also be further substituted with a benzyloxycarbonyl;
or $R_6$ and $R_7$, taken together with the atom to which they are bound, form an optionally substituted 4- to 7-membered cycloalkyl or heterocycloalkyl ring.

Also provided are pharmaceutical compositions comprising a compound described herein, or a pharmaceutically acceptable salt thereof, and a pharmaceutically acceptable excipient.

Also provided are methods of inhibiting transglutaminase TG2 activity, the methods comprising: contacting transglutaminase TG2 in vitro with an amount of a compound or a pharmaceutically acceptable salt thereof described herein, sufficient to inhibit an activity of the transglutaminase TG2.

Also provided are methods of treating a disease state in which inhibition of transglutaminase TG2 is desired, the methods comprising: administering to a subject in need thereof, a therapeutically effective amount of a compound described herein, or a pharmaceutically acceptable salt thereof, so as to inhibit the activity of the transglutaminase TG2, thereby treating the disease state.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" encompasses:
  5- and 6-membered carbocyclic aromatic rings, for example, benzene;
  bicyclic ring systems wherein at least one ring is carbocyclic and aromatic, for example, naphthalene, indane, and tetralin; and
  tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
  5- to 7-membered aromatic, monocyclic rings containing one or more, for example, from 1 to 4, or In some embodiments, from 1 to 3, heteroatoms chosen from N, O, and S, with the remaining ring atoms being carbon; and
  bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —NH($C_1$-$C_4$ alkyl), —$N(C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH$ ($C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —$S(O_2)$—H, —$S(O_2)$-(optionally substituted ($C_1$-$C_6$)alkyl), —$S(O_2)$-optionally substituted aryl), —$S(O_2)$-optionally substituted heteroaryl), —$S(O_2)$-(optionally substituted heterocycloalkyl), —$S(O_2)$-(optionally substituted alkoxy), —$S(O_2)$-optionally substituted aryloxy), —$S(O_2)$-optionally substituted heteroaryloxy), —$S(O_2)$-(optionally substituted heterocycyloxy); and —$S(O_2)$-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z— and E- forms (or cis- and trans- forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of transglutaminase TG2 activity.

The term "inhibition" indicates a significant decrease in the baseline activity of a biological activity or process. "Inhibition of transglutaminase TG2 activity" refers to a decrease in the activity of TG2 as a direct or indirect response to the presence of at least one compound or pharmaceutically acceptable salt thereof described herein, relative to the activity of TG2 in the absence of at least one compound or pharmaceutically acceptable salt thereof. The decrease in activity may be due to the direct interaction of the compound with TG2, or due to the interaction of the compounds or salts described herein with one or more other factors that in turn affect TG2 activity. For example, the presence of the compound or pharmaceutically acceptable salt thereof may decrease TG2 activity by directly binding to the TG2, by causing (directly or indirectly) another factor to decrease TG2 activity, or by (directly or indirectly) decreasing the amount of TG2 present in the cell or organism.

In some embodiments, the compounds and pharmaceutical acceptable salts thereof described herein inhibit TG2.

In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

"Treatment" or "treating" means any treatment of a disease state in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications.

In some embodiments, the subject is a mammal; and in some embodiments the subject is human.

Provided is a compound of Formula I

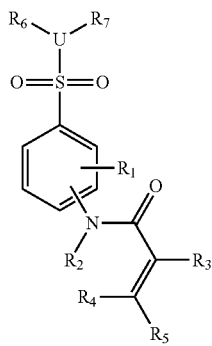

Formula I or a pharmaceutically acceptable salt thereof, wherein
U is N or CH;
$R_1$ is chosen from hydrogen, $-R^a$, $-OR^b$, $-SR^b$, $-NR^bR^c$, halo, cyano, nitro, $-COR^b$, $-CO_2R^b$, $-CONR^bR^c$, $-OCOR^b$, $-OCO_2R^a$, $-OCONR^bR^c$, $-NR^cCOR^b$, $-NR^cCO_2R^a$, $-NR^cCONR^bR^c$, $-CO_2R^b$, $-CONR^bR^c$, $-NR^cCOR^b$, $-SOR^a$, $-SO_2R^a$, $-SO_2NR^bR^c$, and $-NR^cSO_2R^a$,
where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and
$R^c$ is chosen from hydrogen and optionally substituted $C_1$-$C_4$ alkyl; or
$R^b$ and $R^c$, and the nitrogen to which they are attached, form an optionally substituted heterocycloalkyl group; and
where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, $-OC_1$-$C_4$ alkyl, $-OC_1$-$C_4$ alkylphenyl, $-C_1$-$C_4$ alkyl-OH, $-OC_1$-$C_4$ haloalkyl, halo, $-OH$, $-NH_2$, $-C_1$-$C_4$ alkyl-$NH_2$, $N(C_1$-$C_4$ alkyl)($C_1$-$C_4$ alkyl), $-NH(C_1$-$C_4$ alkyl), $-N(C_1$-$C_4$ alkyl)($C_1$-$C_4$ alkylphenyl), $-NH(C_1$-$C_4$ alkylphenyl), cyano, nitro, oxo (as a substituent for heteroaryl), $-CO_2H$, $-C(O)OC_1$-$C_4$ alkyl, $-CON(C_1$-$C_4$ alkyl)($C_1$-$C_4$ alkyl), $-CONH(C_1$-$C_4$ alkyl), $-CONH_2$, $-NHC(O)(C_1$-$C_4$ alkyl), $-NHC(O)$(phenyl), $-N(C_1$-$C_4$ alkyl)$C(O)(C_1$-$C_4$ alkyl), $-N(C_1$-$C_4$ alkyl)$C(O)$(phenyl), $-C(O)C_1$-$C_4$ alkyl, $-C(O)C_1$-$C_4$ phenyl, $-C(O)C_1$-$C_4$ haloalkyl, $-OC(O)C_1$-$C_4$ alkyl, $-SO_2(C_1$-$C_4$ alkyl), $-SO_2$(phenyl), $-SO_2(C_1$-$C_4$ haloalkyl), $-SO_2NH_2$, $-SO_2NH(C_1$-$C_4$ alkyl), $-SO_2NH$(phenyl), $-NHSO_2(C_1$-$C_4$ alkyl), $-NHSO_2$(phenyl), and $-NHSO_2(C_1$-$C_4$ haloalkyl);
$R_2$ is chosen from hydrogen and optionally substituted alkyl;
$R_3$, $R_4$, and $R_5$ are independently chosen from hydrogen, halo, and optionally substituted alkyl or $R_3$ taken together with $R_4$ forms a bond and $R_5$ is chosen from hydrogen and optionally substituted alkyl;
$R_6$ is chosen from hydrogen, optionally substituted alkyl, and optionally substituted cycloalkyl; and
$R_7$ is chosen from hydrogen $-V-R_8$ wherein
V is lower alkylene, optionally substituted with one or more halo or lower alkyl groups; and
$R_8$ is chosen from phenyl, heterocycloalkyl, and heteroaryl,
each of which phenyl, heterocycloalkyl, and heteroaryl groups is optionally substituted with a group chosen from halo, lower alkyl, heterocycloalkyl, heterocycloalkyloxy, and heteroaryl, alkyl substituted with phenyl, alkyl substituted with cycloalkyl, alkyl substituted with heterocycloalkyl, alkyl substituted with heteroaryl, each of which substituents, except for halo, being optionally further substituted with one or more alkyl groups and when said substituent is a heterocycloalkyl, then said heterocycloalkyl may also be further substituted with a benzyloxycarbonyl;
or $R_6$ and $R_7$, taken together with the atom to which they are bound, form an
optionally substituted 4- to 7-membered cycloalkyl or heterocycloalkyl ring.

Provided is a compound of Formula I

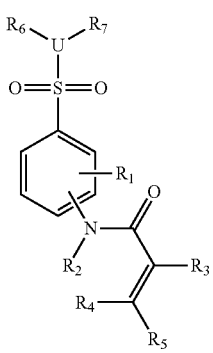

Formula I or a pharmaceutically acceptable salt thereof, wherein
U is N or CH;
$R_1$ is chosen from hydrogen, —$R^a$, —$OR^b$, —$SR^b$, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)(C_1$-$C_4$ alkyl), —$N(C_1$-$C_4$ alkyl)C(O)(phenyl)$, —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl);

$R_2$ is chosen from hydrogen and optionally substituted alkyl;

$R_3$, $R_4$, and $R_5$ are independently chosen from hydrogen and optionally substituted alkyl;

$R_6$ is chosen from hydrogen, optionally substituted alkyl, and optionally substituted cycloalkyl; and $R_7$ is chosen from hydrogen —V—$R_8$ wherein
V is lower alkylene, optionally substituted with one or more halo or lower alkyl groups; and
$R_8$ is chosen from phenyl, heterocycloalkyl, and heteroaryl,
each of which phenyl, heterocycloalkyl, and heteroaryl groups is optionally substituted with a group chosen from halo, lower alkyl, heterocycloalkyl, heterocycloalkyloxy, and heteroaryl, alkyl substituted with phenyl, alkyl substituted with cycloalkyl, alkyl substituted with heterocycloalkyl, alkyl substituted with heteroaryl, each of which substituents, except for halo, being optionally further substituted with one or more alkyl groups and when said substituent is a heterocycloalkyl, then said heterocycloalkyl may also be further substituted with a benzyloxycarbonyl;

or $R_6$ and $R_7$, taken together with the atom to which they are bound, form an optionally substituted 4- to 7-membered cycloalkyl or heterocycloalkyl ring.

In some embodiments, U is N.
In some embodiments, U is CH.
In some embodiments, $R_1$ is chosen from hydrogen, lower alkyl, —$CF_3$, amino, alkylamino, dialkylamino, lower alkoxy, lower haloalkoxy, and halo. In some embodiments, $R_1$ is hydrogen.

In some embodiments, $R_2$ is chosen from hydrogen and optionally substituted lower alkyl. In some embodiments, $R_2$ is chosen from hydrogen and lower alkyl. In some embodiments, $R_2$ is hydrogen.

In some embodiments, $R_3$ is chosen from hydrogen, halo, and optionally substituted lower alkyl. In some embodiments, $R_3$ is chosen from hydrogen, fluoro, chloro, and lower alkyl. In some embodiments, $R_3$ is hydrogen or fluoro.

In some embodiments, $R_3$ is chosen from hydrogen and optionally substituted lower alkyl. In some embodiments, $R_3$ is chosen from hydrogen and lower alkyl. In some embodiments, $R_3$ is hydrogen.

In some embodiments, $R_4$ is chosen from hydrogen, halo, and optionally substituted lower alkyl. In some embodiments, $R_4$ is chosen from hydrogen, halo, and lower alkyl. In some embodiments, $R_4$ is hydrogen, methyl, fluoro, or chloro. In some embodiments, $R_4$ is hydrogen, chloro, or methyl. In some embodiments, $R_4$ is chloro. In some embodiments, $R_4$ is methyl.

In some embodiments, $R_4$ is chosen from hydrogen and optionally substituted lower alkyl. In some embodiments, $R_4$ is chosen from hydrogen and lower alkyl. In some embodiments, $R_4$ is hydrogen.

In some embodiments, $R_3$ taken together with $R_4$ forms a bond, i.e., a triple bond links $R_5$ to the amide carbonyl, and $R_5$ is chosen from hydrogen and optionally substituted alkyl. In some embodiments, $R_3$ taken together with $R_4$ forms a bond and $R_5$ is chosen from hydrogen and lower alkyl.

In some embodiments, $R_5$ is chosen from hydrogen, halo, and optionally substituted lower alkyl. In some embodiments, $R_5$ is chosen from hydrogen, halo, and lower alkyl. In some embodiments, $R_5$ is hydrogen, methyl, fluoro, or chloro. In some embodiments, $R_5$ is methyl. In some embodiments, $R_5$ is chloro.

In some embodiments, $R_5$ is chosen from hydrogen and optionally substituted lower alkyl. In some embodiments, $R_5$ is chosen from hydrogen and lower alkyl. In some embodiments, $R_5$ is hydrogen.

In some embodiments, the amide residue —$N(R_2)C(O)C(R_3)$=$C(R_4)(R_5)$ is attached to the 3-position of the phenyl ring.

In some embodiments, amide residue —$N(R_2)C(O)C(R_3)$=$C(R_4)(R_5)$ is attached to the 4-position of the phenyl ring.

In some embodiments, $R_6$ is chosen from hydrogen, optionally substituted lower alkyl, and optionally substituted cycloalkyl. In some embodiments, $R_6$ is chosen from hydrogen, benzyl, lower alkyl, and cycloalkyl.mmIn some embodiments, $R_6$ is chosen from hydrogen and lower alkyl. In some embodiments, $R_6$ is hydrogen.

In some embodiments, $R_7$ is —V—$R_8$ wherein
V is lower alkylene, optionally substituted with one or more halo or lower alkyl groups; and
$R_8$ is chosen from phenyl, heterocycloalkyl, and heteroaryl,
each of which phenyl, heterocycloalkyl, and heteroaryl groups is optionally substituted with a group chosen from halo, lower alkyl, heterocycloalkyl, heterocycloalkyloxy, and heteroaryl, alkyl substituted with phenyl, alkyl substituted with cycloalkyl, alkyl substituted with heterocycloalkyl, alkyl substituted with heteroaryl, each of which substituents, except for halo, being optionally further substituted with one or more alkyl groups and when said substituent is a heterocycloalkyl, then said heterocycloalkyl may also be further substituted with a benzyloxycarbonyl.

In some embodiments, V is —$CH_2$—.

In some embodiments, $R_8$ is phenyl optionally substituted with a group chosen from halo, alkyl substituted with heterocycloalkyl, and heterocycloalkyl, each of which substituents, except for halo, being optionally further substituted with one or more alkyl groups. In some embodiments, $R_8$ is phenyl optionally substituted with a group chosen from halo and methylene substituted with a heterocycloalkyl group chosen from pyrrolidin-1-yl, 1,4-diazepan-1-yl, piperazin-1-yl, piperidin-1-yl, and morpholin-4-yl, each of which heterocycloalkyl groups being optionally substituted with one or more alkyl groups.

In some embodiments, $R_8$ is a heterocycloalkyl group chosen from piperidin-3-yl, piperidin-4-yl, morpholin-4-yl, and pyrrolidin-3-yl, each of which heterocycloalkyl groups being optionally substituted with a substituent chosen from lower alkyl, benzyl, heteroaryl optionally substituted with one or more alkyl groups or benzyloxycarbonyl.

In some embodiments, $R_8$ is a heteroaryl group chosen from pyrimidin-5-yl, pyridin-4-yl, pyridin-3-yl, and thiazol-4-yl, each of which heteroaryl groups being optionally substituted with a substituent chosen from heterocycloalkyl and heterocycloalkoxy. In some embodiments, $R_8$ is a heteroaryl group chosen from pyrimidin-5-yl, pyridin-4-yl, pyridin-3-yl, and thiazol-4-yl, each of which heteroaryl groups being optionally substituted with a substituent chosen from morpholin-4-yl, piperidin-1-yl, and tetrahydro-2H-pyran-4-yloxy.

Also provided is a compound of Formula II

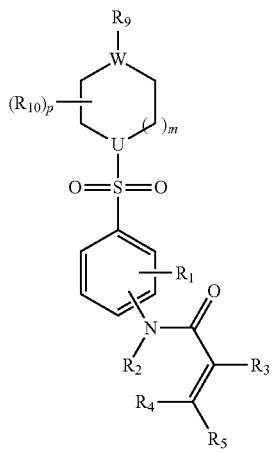

Formula II or a pharmaceutically acceptable salt thereof,
wherein $R_1$, $R_2$, $R_3$, $R_4$, $R_5$, and U are as described for compounds of Formula I and further wherein
m is 0, 1, or 2;
p is 0, 1, or 2;
W is —CH or N;
$R_9$ is chosen from
hydrogen,
lower alkyl optionally substituted with optionally substituted amino, cycloalkyl, heterocycloalkyl, heteroaryl, or alkoxy, each of which, excluding optionally substituted amino, is optionally substituted with one or more groups chosen from lower alkoxy and halo,
cycloalkyl optionally substituted with optionally substituted amino, heterocycloalkyl, heteroaryl, or alkoxy, each of which, excluding optionally substituted amino, is optionally substituted with one or more groups chosen from lower alkoxy and halo, —$NR_{12}R_{13}$ wherein $R_{12}$ and $R_{13}$ are independently chosen from hydrogen, lower alkyl, aralkyl, heteroaralkyl, —C(O)$R_{14}$, —C(O)O$R_{14}$, and —C(O)N$R_{14}R_{14}$ wherein for each occurrence $R_{14}$ is chosen from hydrogen, lower alkyl, cycloalkyl, aralkyl, aryl, heterocycloalkyl, heteroaralkyl, and heteroaryl,
phenyl optionally substituted with one or more groups chosen from halo, lower alkyl, $CF_3$, lower alkoxy, and phenyl,
aralkyl optionally substituted with one or more groups chosen from lower alkyl, lower alkoxy, alkylenedioxy, and phenyl,
heteroaryl optionally substituted with one or more groups chosen from halo, heteroaryl, lower alkyl, $CF_3$, and lower alkoxy, and
—X—Y—C(O)—Z—$(CH_2)_r$—$R_{11}$ wherein
X is absent or is —$CH_2$—;
Y is absent or Y is chosen from —$CH_2$— or —$NR_{12}$—;
Z is absent or Z is chosen from —O— and —$NR_{12}$—;
r is 0, 1, 2, or 3; and
$R_{11}$ is chosen from optionally substituted amino, lower alkyl, lower alkenyl, cycloalkyl, heterocycloalkyl, aryl, and heteroaryl, each of which, excluding optionally substituted amino, is optionally substituted with one or more groups chosen from halo, lower alkyl, lower alkoxy, $CF_3$, and phenoxy; and for each occurrence, $R_{10}$ is chosen from optionally substituted lower alkyl, optionally substituted alkoxy, optionally substituted aryloxy, optionally substituted heteroaryl, and optionally substituted aryl.

In some embodiments, W is N.
In some embodiments, W is CH.
In some embodiments, m is 0.
In some embodiments, m is 1.
In some embodiments, m is 2.
In some embodiments, $R_9$ is —X—Y—C(O)—Z—$(CH_2)_r$—$R_{11}$ wherein X is absent.
In some embodiments, $R_9$ is —X—Y—C(O)—Z—$(CH_2)_r$—$R_{11}$ wherein X is —$CH_2$—.
In some embodiments, $R_9$ is —X—Y—C(O)—Z—$(CH_2)_r$—$R_{11}$ wherein Y is absent.
In some embodiments, $R_9$ is —X—Y—C(O)—Z—$(CH_2)_r$—$R_{11}$ wherein Y is —$CH_2$—.
In some embodiments, $R_9$ is —X—Y—C(O)—Z—$(CH_2)_r$—$R_{11}$ wherein Y is —$NR_{12}$—.
In some embodiments, $R_9$ is —X—Y—C(O)—Z—$(CH_2)_r$—$R_{11}$ wherein Z is absent.
In some embodiments, $R_9$ is —X—Y—C(O)—Z—$(CH_2)_r$—$R_{11}$ wherein Z is —O—.
In some embodiments, $R_9$ is —X—Y—C(O)—Z—$(CH_2)_r$—$R_{11}$ wherein Z is —$NR_{12}$—.
In some embodiments, $R_9$ is —X—Y—C(O)—Z—$(CH_2)_r$—$R_{11}$ wherein r is 0.
In some embodiments, $R_9$ is —X—Y—C(O)—Z—$(CH_2)_r$—$R_{11}$ wherein r is 1.
In some embodiments, $R_9$ is —X—Y—C(O)—Z—$(CH_2)_r$—$R_{11}$ wherein r is 2.
In some embodiments, $R_9$ is —X—Y—C(O)—Z—$(CH_2)_r$—$R_{11}$ wherein r is 3.
In some embodiments, $R_9$ is hydrogen.
In some embodiments, $R_9$ is lower alkyl optionally substituted with cycloalkyl, morpholino, piperidinyl, —$NR_{15}R_{16}$ wherein $R_{15}$ and $R_{16}$ are independently chosen from hydrogen, lower alkyl, aralkyl, heteroaralkyl, —C(O)$R_{17}$, —C(O)O$R_{17}$, and —C(O)N$R_{17}R_{17}$ wherein for each occurrence $R_{17}$ is chosen from hydrogen, lower alkyl, cycloalkyl, aralkyl, aryl, heterocycloalkyl, heteroaralkyl, and heteroaryl.

In some embodiments, $R_9$ is phenyl optionally substituted with one or more groups chosen from halo, lower alkyl, $CF_3$, lower alkoxy, and phenyl.

In some embodiments, $R_9$ is cycloalkyl.

In some embodiments, $R_9$ is —$NR_{12}R_{13}$ wherein $R_{12}$ and $R_{13}$ are independently chosen from hydrogen, lower alkyl, aralkyl, heteroaralkyl, —C(O)$R_{14}$, —C(O)O$R_{14}$, and —C(O)$NR_{14}R_{14}$ wherein for each occurrence $R_{14}$ is chosen from hydrogen, lower alkyl, cycloalkyl, aralkyl, aryl, heterocycloalkyl, heteroaralkyl, and heteroaryl.

In some embodiments, $R_9$ is aralkyl optionally substituted with one or more groups chosen from lower alkyl and lower alkoxy.

In some embodiments, $R_9$ is 1,2,4-oxadiazolyl or pyridinyl, each of which is optionally substituted with one or more groups chosen from halo, heteroaryl, lower alkyl, $CF_3$, and lower alkoxy.

In some embodiments, p is 0.
In some embodiments, p is 1.
In some embodiments, p is 2.
In some embodiments, $R_{10}$ is chosen from lower alkyl, benzyl, and phenyl. In some embodiments, $R_{10}$ is lower alkyl.

Also provided is a compound chosen from tert-butyl 4-(4-acrylamidophenylsulfonyl)cyclohexylcarbamate;
4-(4-Acryloylamino-benzenesulfonyl)-piperazine-1-carboxylic acid benzyl ester;
4-(3-Acryloylamino-benzenesulfonyl)-piperazine-1-carboxylic acid benzyl ester;
4-(4-Acryloylamino-benzenesulfonyl)-[1,4]diazepane-1-carboxylic acid benzyl ester;
4-(4-Acryloylamino-benzenesulfonyl)-piperazine-1-carboxylic acid tert-butyl ester;
4-(4-Acryloylamino-benzenesulfonylamino)-piperidine-1-carboxylic acid benzyl ester;
[1-(4-Acryloylamino-benzenesulfonyl)-piperidin-4-yl]-carbamic acid benzyl ester;
4-(4-Acryloylamino-benzenesulfonyl)-piperazine-1-carboxylic acid 2-chloro-benzyl ester;
4-(4-Acryloylamino-benzenesulfonyl)-piperazine-1-carboxylic acid 3-trifluoromethyl-benzyl ester;
4-(4-Acryloylamino-benzenesulfonyl)-piperazine-1-carboxylic acid 2-chloro-benzyl ester;
N-[4-(4-Phenylacetyl-piperazine-1-sulfonyl)-phenyl]-acrylamide;
3-(4-Acryloylamino-benzenesulfonylamino)-(R)-pyrrolidine-1-carboxylic acid benzyl ester;
4-(4-Acryloylamino-2-trifluoromethyl-benzenesulfonyl)-piperazine-1-carboxylic acid benzyl ester;
{2-[(4-Acryloylamino-benzenesulfonyl)-methyl-amino]-ethyl}-methyl-carbamic acid benzyl ester;
4-[(4-Acryloylamino-benzenesulfonylamino)-methyl]-piperidine-1-carboxylic acid benzyl ester;
[1-(4-Acryloylamino-benzenesulfonyl)-piperidin-4-ylmethyl]-carbamic acid benzyl ester;
N-{4-[4-(4-Phenyl-butyryl)-piperazine-1-sulfonyl]-phenyl}-acrylamide;
4-(4-Acryloylamino-benzenesulfonyl)-piperazine-1-carboxylic acid 2-trifluoromethyl-benzyl ester;
4-(4-Acryloylamino-benzenesulfonyl)-piperazine-1-carboxylic acid 2,6-difluoro-benzyl ester;
4-(4-Acryloylamino-benzenesulfonyl)-piperazine-1-carboxylic acid 4-butyl-benzyl ester;
4-(4-Acryloylamino-benzenesulfonyl)-piperazine-1-carboxylic acid 4-methyl-benzyl ester;
4-(4-Acryloylamino-benzenesulfonyl)-piperazine-1-carboxylic acid 3-fluoro-benzyl ester;
4-(4-Acryloylamino-benzenesulfonyl)-piperazine-1-carboxylic acid naphthalen-2-ylmethyl ester;
4-(4-Acryloylamino-benzenesulfonyl)-piperazine-1-carboxylic acid 4-tert-butyl-benzyl ester;
4-(4-Acryloylamino-benzenesulfonyl)-piperazine-1-carboxylic acid 4-fluoro-benzyl ester;
4-(4-Acryloylamino-benzenesulfonyl)-piperazine-1-carboxylic acid naphthalen-1-ylmethyl ester;
4-(4-Acryloylamino-benzenesulfonyl)-piperazine-1-carboxylic acid 4-trifluoromethyl-benzyl ester;
3-(4-Acryloylamino-benzenesulfonylamino)-(S)-pyrrolidine-1-carboxylic acid benzyl ester;
4-(3-Acryloylamino-benzenesulfonyl)-piperazine-1-carboxylic acid tert-butyl ester;
N-{4-[4-(3-Phenyl-propionyl)-piperazine-1-sulfonyl]-phenyl}-acrylamide;
[4-(4-Acryloyl-piperazine-1-sulfonyl)-phenyl]-carbamic acid benzyl ester;
N-[4-(4-Phenyl-piperazine-1-sulfonyl)-phenyl]-acrylamide;
N-[4-(4-Acetyl-piperazine-1-sulfonyl)-phenyl]-acrylamide;
1-(4-Acryloylamino-benzenesulfonyl)-(S)-pyrrolidin-3-yl]-carbamic acid benzyl ester;
4-(4-Acryloylamino-benzenesulfonyl)-piperazine-1-carboxylic acid phenethyl ester;
4-(4-Acryloylamino-benzenesulfonyl)-piperazine-1-carboxylic acid 2,3-dimethoxy-benzyl ester;
4-(4-Acryloylamino-benzenesulfonyl)-piperazine-1-carboxylic acid 2-methyl-benzyl ester;
N-[4-(piperazine-1-sulfonyl)-phenyl]acrylamide;
4-(4-Acryloylamino-benzenesulfonyl)-piperazine-1-carboxylic acid ethyl ester;
4-(4-Acryloylamino-benzenesulfonyl)-piperazine-1-carboxylic acid isobutyl ester;
4-(4-Acryloylamino-benzenesulfonyl)-piperazine-1-carboxylic acid methyl ester;
4-(4-Acryloylamino-benzenesulfonyl)-piperazine-1-carboxylic acid isopropyl ester;
4-(4-Acryloylamino-benzenesulfonyl)-piperazine-1-carboxylic acid benzylamide;
[1-(4-Acryloylamino-benzenesulfonyl)-(R)-pyrrolidin-3-yl]-carbamic acid benzyl ester;
N-[4-(4-Biphenyl-4-ylmethyl-piperazine-1-sulfonyl)-phenyl]-acrylamide;
4-(4-Acryloylamino-benzenesulfonyl)-piperazine-1-carboxylic acid 3,5-difluoro-benzyl ester;
4-(4-Acryloylamino-benzenesulfonyl)-piperazine-1-carboxylic acid 3,5-dimethyl-benzyl ester;
4-(4-Acryloylamino-benzenesulfonyl)-piperazine-1-carboxylic acid 3-chloro-benzyl ester;
4-(4-Acryloylamino-benzenesulfonyl)-piperazine-1-carboxylic acid 2,3-difluoro-benzyl ester;
N-{4-[4-(2-Naphthalen-2-yl-acetyl)-piperazine-1-sulfonyl]-phenyl}-acrylamide;
N-[4-(4-Benzyl-piperazine-1-sulfonyl)-phenyl]-acrylamide;
N-[4-(4-Phenethyl-piperazine-1-sulfonyl)-phenyl]-acrylamide;
4-(4-Acryloylamino-benzenesulfonyl)-piperazine-1-carboxylic acid cyclopentyl ester;
N-{4-[4-(Piperidine-1-carbonyl)-piperazine-1-sulfonyl]-phenyl}-acrylamide;
N-[3-(4-Benzyl-piperazine-1-sulfonyl)-phenyl]-acrylamide;
N-[3-(4-Phenethyl-piperazine-1-sulfonyl)-phenyl]-acrylamide;
N-{3-[4-(3-Phenyl-propyl)-piperazine-1-sulfonyl]-phenyl}-acrylamide;
N-[3-(4-Phenyl-piperazine-1-sulfonyl)-phenyl]-acrylamide;
4-(4-Acryloylamino-benzenesulfonyl)-piperazine-1-carboxylic acid phenyl ester;
N-{4-[4-(Pyrrolidine-1-carbonyl)-piperazine-1-sulfonyl]-phenyl}-acrylamide;
N-[4-(4-Phenyl-piperidine-1-sulfonyl)-phenyl]-acrylamide;

N-{4-[4-(3-Phenyl-propyl)-piperazine-1-sulfonyl]-phenyl}-acrylamide;
N-{3-[4-(4-Phenyl-butyl)-piperazine-1-sulfonyl]-phenyl}-acrylamide;
4-(6-Acryloylamino-pyridine-3-sulfonyl)-piperazine-1-carboxylic acid benzyl ester;
N-{4-[4-(4-Phenyl-butyl)-piperazine-1-sulfonyl]-phenyl}-acrylamide;
4-(3-Acryloylamino-benzenesulfonyl)-piperazine-1-carboxylic acid isopropyl ester;
4-(4-Acryloylamino-benzenesulfonyl)-3,5-dimethyl-piperazine-1-carboxylic acid tert-butyl ester;
N-[3-(piperazine-1-sulfonyl)-phenyl]-acrylamide;
4-(4-Acryloylamino-benzenesulfonyl)-3,5-dimethyl-piperazine-1-carboxylic acid benzyl ester;
4-(4-Acryloylamino-benzenesulfonyl)-2,6-dimethyl-piperazine-1-carboxylic acid benzyl ester;
[1-(4-Acryloylamino-benzenesulfonyl)-piperidin-4-yl]-carbamic acid tert-butyl ester;
[1-(4-Acryloylamino-benzenesulfonyl)-piperidin-4-ylmethyl]-carbamic acid tert-butyl ester;
N-[4-(4-Amino-piperidine-1-sulfonyl)-phenyl]acrylamide;
N-[4-(4-Aminomethyl-piperidine-1-sulfonyl)-phenyl]-acrylamide;
4-(3-Acryloylamino-benzenesulfonyl)-piperazine-1-carboxylic acid ethyl ester;
4-(3-Acryloylamino-benzenesulfonyl)-piperazine-1-carboxylic acid methyl ester;
4-(3-Acryloylamino-benzenesulfonyl)-piperazine-1-carboxylic acid isobutyl ester;
N-(4-Diethylsulfamoyl-phenyl)-acrylamide;
N-{4-[4-(6-Trifluoromethyl-pyridin-3-yl)-piperazine-1-sulfonyl]-phenyl}-acrylamide;
N-[4-(Cyclohexyl-phenyl-sulfamoyl)-phenyl]-acrylamide;
N-{4-[4-(5-Chloro-2-methoxy-phenyl)-piperazine-1-sulfonyl]-phenyl}-acrylamide;
N-[4-(1,3-Dihydro-isoindole-2-sulfonyl)-phenyl]-acrylamide;
4-(3-Acryloylamino-benzenesulfonyl)-piperazine-1-carboxylic acid cyclopentyl ester;
N-[4-(4-Cyclopropanecarbonyl-piperazine-1-sulfonyl)-phenyl]-acrylamide;
N-[4-(4-Cyclopentanecarbonyl-piperazine-1-sulfonyl)-phenyl]-acrylamide;
N-{4-[4-(2-Phenyl-cyclopropanecarbonyl)-piperazine-1-sulfonyl]-phenyl}-acrylamide;
N-[1-(4-Acryloylamino-benzenesulfonyl)-piperidin-4-yl]-benzamide;
N-{3-[4-(Pyrrolidine-1-carbonyl)-piperazine-1-sulfonyl]-phenyl}-acrylamide;
N-{3-[4-(Piperidine-1-carbonyl)-piperazine-1-sulfonyl]-phenyl}-acrylamide;
N-[4-(4-Benzo[1,3]dioxol-5-ylmethyl-piperazine-1-sulfonyl)-phenyl]-acrylamide;
N-{4-[(1-Benzyl-piperidin-4-yl)-cyclopropyl-sulfamoyl]-phenyl}-acrylamide;
N-{4-[4-(4,4-Difluoro-piperidine-1-carbonyl)-piperazine-1-sulfonyl]-phenyl}-acrylamide;
N-[3-(4-Benzoyl-piperazine-1-sulfonyl)-phenyl]-acrylamide;
N-[3-(4-Phenylacetyl-piperazine-1-sulfonyl)-phenyl]-acrylamide;
N-{3-[4-(3-Phenyl-propionyl)-piperazine-1-sulfonyl]-phenyl}-acrylamide;
N-[1-(4-Acryloylamino-benzenesulfonyl)-piperidin-4-ylmethyl]benzamide;
N-[4-(4-Acetylamino-piperidine-1-sulfonyl)-phenyl]-acrylamide;
N-{4-[4-(Acetylamino-methyl)-piperidine-1-sulfonyl]-phenyl}-acrylamide;
N-[4-(4-Ethyl-piperazine-1-sulfonyl)-phenyl]-acrylamide;
N-[4-(4-Cyclopropylmethyl-piperazine-1-sulfonyl)-phenyl]-acrylamide;
N-[4-(4-Cyclopentylmethyl-piperazine-1-sulfonyl)-phenyl]-acrylamide;
5-(4-Acryloylamino-benzenesulfonyl)-hexahydro-pyrrolo[3,4-c]pyrrole-2-carboxylic acid tert-butyl ester;
N-[4-(7-Trifluoromethyl-3,4-dihydro-2H-quinoline-1-sulfonyl)-phenyl]-acrylamide;
N-{4-[4-(3-Pyridin-3-yl-propionyl)-piperazine-1-sulfonyl]-phenyl}-acrylamide;
N-[1-(4-Acryloylamino-benzenesulfonyl)-piperidin-4-yl]-benzamide;
N-[4-(1,1-Dimethyl-2-morpholin-4-yl-ethylsulfamoyl)-phenyl]-acrylamide;
4-(6-Acryloylamino-pyridine-3-sulfonyl)-piperazine-1-carboxylic acid tert-butyl ester;
5-(4-Acryloylamino-benzenesulfonyl)-hexahydro-pyrrolo[3,4-c]pyrrole-2-carboxylic acid benzyl ester;
N-{4-[4-(Adamantane-1-carbonyl)-piperazine-1-sulfonyl]-phenyl}-acrylamide;
N-{4-[4-(3-Piperidin-1-yl-propionyl)-piperazine-1-sulfonyl]-phenyl}-acrylamide;
4-(4-Acryloylamino-benzenesulfonyl)-2-phenyl-piperazine-1-carboxylic acid tert-butyl ester;
N-(4-{4-[(Dibenzylamino)-methyl]-piperidine-1-sulfonyl}-phenyl)-acrylamide;
4-(4-Acryloylamino-benzenesulfonyl)-piperazine-1-carboxylic acid 3-phenoxy-benzyl ester;
N-{4-[4-(2-Piperidin-1-yl-acetyl)-piperazine-1-sulfonyl]-phenyl}-acrylamide;
N-{4-[4-(3-Pyridin-4-yl-propionyl)-piperazine-1-sulfonyl]-phenyl}-acrylamide;
N-[4-(4-Phenethylamino-piperidine-1-sulfonyl)-phenyl]-acrylamide;
N-{4-[4-(Benzylamino-methyl)-piperidine-1-sulfonyl]-phenyl}-acrylamide;
N-[4-(1-Ethyl-piperidin-3-ylsulfamoyl)-phenyl]-acrylamide;
N-[4-(3-Pyrrolidin-1-ylmethyl-benzylsulfamoyl)-phenyl]-acrylamide;
4-(4-Acryloylamino-benzenesulfonyl)-2-phenyl-piperazine-1-carboxylic acid tea-butyl ester;
N-[4-(4-Acryloyl-2,5-dimethyl-piperazine-1-sulfonyl)-phenyl]-acrylamide;
N-{4-[(2,3-Dihydro-benzo[1,4]dioxin-2-ylmethyl)-isopropyl-sulfamoyl]-phenyl}-acrylamide;
N-{4-[Cyclopropyl-(4-piperidin-1-yl-benzyl)-sulfamoyl]-phenyl}-acrylamide;
N-{4-[Methyl-(3-morpholin-4-yl-benzyl)-sulfamoyl]-phenyl}-acrylamide;
N-{4-[Methyl-(2-morpholin-4-yl-pyridin-4-ylmethyl)-sulfamoyl]-phenyl}-acrylamide;
N-(4-{Methyl-[4-(4-methyl-piperazin-1-ylmethyl)-benzyl]-sulfamoyl}-phenyl)-acrylamide;
N-{4-[Methyl-(3,4,5,6-tetrahydro-2H[1,2']bipyridinyl-4'-ylmethyl)-sulfamoyl]-phenyl}-acrylamide;
N-{4-[Methyl-(2-morpholin-4-yl-thiazol-4-ylmethyl)-sulfamoyl]-phenyl}-acrylamide;
N-(4-{Methyl-[6-(tetrahydro-pyran-4-yloxy)-pyridin-3-yl]-methyl-sulfamoyl}-phenyl)-acrylamide'
N-{4-[Methyl-(1-thiophen-2-ylmethyl-piperidin-4-ylmethyl)-sulfamoyl]-phenyl}-acrylamide;

N-(4-{Methyl-[1-(6-methyl-pyrazin-2-yl)-piperidin-3-ylmethyl]-sulfamoyl}-phenyl)-acrylamide;
N-{4-[Methyl-(2-morpholin-4-yl-pyrimidin-5-ylmethyl)-sulfamoyl]-phenyl}-acrylamide;
N-{4-[4-(3-Pyridin-2-yl-propionyl)-piperazine-1-sulfonyl]-phenyl}-acrylamide;
N-(4-{4-[2-(2-Phenoxy-phenyl)-acetyl]-piperazine-1-sulfonyl}-phenyl)-acrylamide;
N-(4-{4-[2-(3-Phenoxy-phenyl)-acetyl]-piperazine-1-sulfonyl}-phenyl)-acrylamide;
N-(4-{4-[2-(4-Phenoxy-phenyl)-acetyl]-piperazine-1-sulfonyl}-phenyl)-acrylamide;
4-(4-Acryloylamino-benzenesulfonyl)-2,5-dimethyl-piperazine-1-carboxylic acid tert-butyl ester;
N-[4-(2,5-Dimethyl-piperazine-1-sulfonyl)-phenyl]-acrylamide;
4-[3-Acryloylamino-4-(isobutyl-methyl-amino)-benzenesulfonyl]-piperazine-1-carboxylic acid benzyl ester;
4-[4-(Acryloyl-methyl-amino)-benzenesulfonyl]-piperazine-1-carboxylic acid tert-butyl ester;
N-[4-(4-Amino-piperidine-1-sulfonyl)-phenyl]-acrylamide;
N-{4-[4-(Morpholine-4-carbonyl)-piperazine-1-sulfonyl]-phenyl}-acrylamide;
N-{4-[4-(Adamantane-1-carbonyl)-2,6-dimethyl-piperazine-1-sulfonyl]-phenyl}-acrylamide;
N-{5-[4-(Adamantane-1-carbonyl)-piperazine-1-sulfonyl]-pyridin-2-yl}-acrylamide;
Adamantane-1-carboxylic acid [1-(4-acryloylamino-benzenesulfonyl)-piperidin-4-yl]-amide;
[1-(4-Acryloylamino-benzenesulfonyl)-piperidin-4-yl]-methyl-carbamic acid tert-butyl ester;
N-(4-{Methyl-[4-(4-methyl-[1,4]diazepan-1-yl)-benzyl]-sulfamoyl}-phenyl)-acrylamide;
N-[4-(4-Benzyl-2-isopropyl-piperazine-1-sulfonyl)-phenyl]-acrylamide;
N-{4-[Benzyl-(4-chloro-benzyl)-sulfamoyl]-phenyl}-acrylamide;
N-{4-[4-(4,6-Dimethoxy-pyrimidin-2-ylmethyl)-piperazine-1-sulfonyl]-phenyl}-acrylamide;
N-{4-[4-(2-Oxo-2-piperidin-1-yl-ethyl)-piperazine-1-sulfonyl]-phenyl}-acrylamide;
N-{4-[4-(3-Pyrazin-2-yl-[1,2,4]oxadiazol-5-yl)-piperidine-1-sulfony-phenyl]-acrylamide;
N-{4-[4-(3-Morpholin-4-yl-propyl)-piperazine-1-sulfonyl]-phenyl}-acrylamide;
N-[4-(5-Dimethylsulfamoyl-2,3-dihydro-indole-1-sulfonyl)-phenyl]-acrylamide;
Adamantane-1-carboxylic acid [1-(4-acryloylamino-benzenesulfonyl)-piperidin-4-yl]-methyl-amide;
N-{4-[4-(Acetyl-methyl-amino)-piperidine-1-sulfonyl]-phenyl}-acrylamide;
N-[4-(4-Methylamino-piperidine-1-sulfonyl)-phenyl]acrylamide;
4-(4-Acryloylamino-benzenesulfonyl)-2-isopropyl-piperazine-1-carboxylic acid tert-butyl ester;
4-(4-Acryloylamino-benzenesulfonyl)-2-benzyl-piperazine-1-carboxylic acid tert-butyl ester;
N-[4-(3-Benzyl-piperazine-1-sulfonyl)-phenyl]-acrylamide;
N-{4-[Methyl-(3-pyrrolidin-1-ylmethyl-benzyl)-sulfamoyl]-phenyl}-acrylamide;
4-(3-Acryloylamino-4-propoxy-benzenesulfonyl)-piperazine-1-carboxylic acid benzyl ester;
N-{4-[4-(2-Morpholin-4-yl-acetyl)-piperazine-1-sulfonyl]-phenyl}-acrylamide;
N-{4-[4-(3-Morpholin-4-yl-propionyl)-piperazine-1-sulfonyl]-phenyl}-acrylamide;
N-{4-[4-(Octahydro-quinoline-1-carbonyl)-piperazine-1-sulfonyl]-phenyl}-acrylamide;
N-{4-[4-(Octahydro-isoquinoline-2-carbonyl)-piperazine-1-sulfonyl]-phenyl}-acrylamide;
4-(4-Acryloylamino-benzenesulfonyl)-piperazine-1-carboxylic acid adamantan-2-ylamide;
N-[5-(4-Cyclopropanecarbonyl-piperazine-1-sulfonyl)-pyridin-2-yl]-acrylamide;
N-{4-[4-(2-Trifluoromethyl-phenyl)-piperazine-1-sulfonyl]-phenyl}-acrylamide;
N-{4-[4-(3-Methyl-pyridin-2-yl)-piperazine-1-sulfonyl]-phenyl}-acrylamide;
N-{4-[4-(6-Trifluoromethyl-pyridin-2-yl)-piperazine-1-sulfonyl]-phenyl}-acrylamide;
N-{4-[4-(6-Methyl-pyridin-2-yl)-piperazine-1-sulfonyl]-phenyl}-acrylamide;
N-[4-(Hexahydro-pyrrolo[1,2-a]pyrazine-2-sulfonyl)-phenyl]-acrylamide;
N-{4-[4-(2-Methoxy-ethyl)-piperazine-1-sulfonyl]-phenyl}-acrylamide;
N-[4-(4-Cyclopentyl-piperazine-1-sulfonyl)-phenyl]-acrylamide;
N-[4-(4-Cyclohexyl-piperazine-1-sulfonyl)-phenyl]-acrylamide;
N-{4-[4-(Tetrahydro-furan-2-ylmethyl)-piperazine-1-sulfonyl]-phenyl}-acrylamide;
N-[4-(4-Cyclooctyl-piperazine-1-sulfonyl)-phenyl]-acrylamide;
N-[4-(3-Phenoxy-piperidine-1-sulfonyl)-phenyl]-acrylamide;
N-[4-(4-Furan-2-yl-2,3-dihydro-benzo[b][1,4]diazepine-1-sulfonyl)-phenyl]-acrylamide;
4-(4-Acryloylamino-benzenesulfonyl)-2-methyl-piperazine-1-carboxylic acid benzyl ester;
N-[4-(3-Isopropyl-piperazine-1-sulfonyl)-phenyl]-acrylamide;
4-(4-Acryloylamino-3-fluoro-benzenesulfonyl)-piperazine-1-carboxylic acid benzyl ester;
N-{4-[4-(4-Dimethylamino-piperidine-1-carbonyl)-piperazine-1-sulfonyl]-phenyl}-acrylamide;
N-{4-[4-(2,6-Dimethyl-morpholine-4-carbonyl)-piperazine-1-sulfonyl]-phenyl}-acrylamide;
N-{4-[4-(Tetrahydro-pyran-4-carbonyl)-piperazine-1-sulfonyl]-phenyl}-acrylamide;
4-[4-Acryloylamino-3-(isobutyl-methyl-amino)-benzenesulfonyl]-piperazine-1-carboxylic acid benzyl ester;
N-{4-[4-(2,2,6,6-Tetramethyl-piperidine-4-carbonyl)-piperazine-1-sulfonyl]-phenyl}-acrylamide;
4-(4-Acryloylamino-benzenesulfonyl)-2-furan-2-yl-piperazine-1-carboxylic acid tert-butyl ester;
N-[4-(4-Pyridin-2-yl-piperazine-1-sulfonyl)-phenyl]-acrylamide;
N-{4-[4-(2,4-Difluoro-phenyl)piperazine-1-sulfonyl]-phenyl}-acrylamide;
N-[4-(3-Furan-2-yl-piperazine-1-sulfonyl)phenyl]-acrylamide;
N-{4-[4-(Adamantane-1-carbonyl)-piperazine-1-sulfonyl]-2-fluoro-phenyl}-acrylamide;
N-{4-[4-(4-Chloro-2-fluoro-phenyl)-piperazine-1-sulfonyl]-phenyl}-acrylamide;
N-{4-[4-(1-Methyl-piperidin-4-yl)-piperazine-1-sulfonyl]-phenyl}-acrylamide;
N-{4-[4-(2-Dimethylamino-ethyl)-piperazine-1-sulfonyl]-phenyl}-acrylamide;
N-{4-[4-(2-Piperidin-1-yl)ethyl)-piperazine-1-sulfonyl]-phenyl}-acrylamide;

N-{4-[4-(3-Trifluoromethyl-phenyl)-piperazine-1-sulfonyl]-phenyl}-acrylamide,

4-[4-(2-Fluoro-acryloylamino)-benzenesulfonyl]-piperazine-1-carboxylic acid tert-butyl ester;

(Z)-tert-butyl 4-(4-but-2-enamidophenylsulfonyl)piperazine-1-carboxylate;

(E)-tert-butyl 4-(4-but-2-enamidophenylsulfonyl)piperazine-1-carboxylate;

(Z)-tert-butyl 4-(4-(3-chloroacrylamido)phenylsulfonyl)piperazine-1-carboxylate; and (E)-tert-butyl 4-(4-(3-chloroacrylamido)phenylsulfonyl)piperazine-1-carboxylate, and 4-[4-(1)-Oxo-but-2-ynylamino)-benzenesulfonyl]-piperazine-1-carboxylic acid tert-butyl ester, or a pharmaceutically acceptable salt thereof.

Methods for obtaining the compounds and pharmaceutically acceptable salts thereof described herein will be apparent to those of ordinary skill in the art, suitable procedures being described, for example, in the reaction schemes and examples below, and in the references cited herein.

The compounds of Formula I, or a pharmaceutically acceptable salt thereof, may be prepared by any process known to be applicable for the preparation of chemically-related compounds by one skilled in the art. Such processes, when used to prepare the compounds of Formula I, or a pharmaceutically-acceptable salt thereof, are provided as a further feature of the invention and are illustrated by the following schemes in which, unless otherwise stated, $R^1$, etc, T, X, Y and n are as described herein. Starting materials may be obtained by standard procedures of organic chemistry. The preparation of such starting materials is described within the accompanying non-limiting examples. Alternatively starting materials are obtainable by analogous procedures to those illustrated which are within the ordinary skill of an organic chemist.

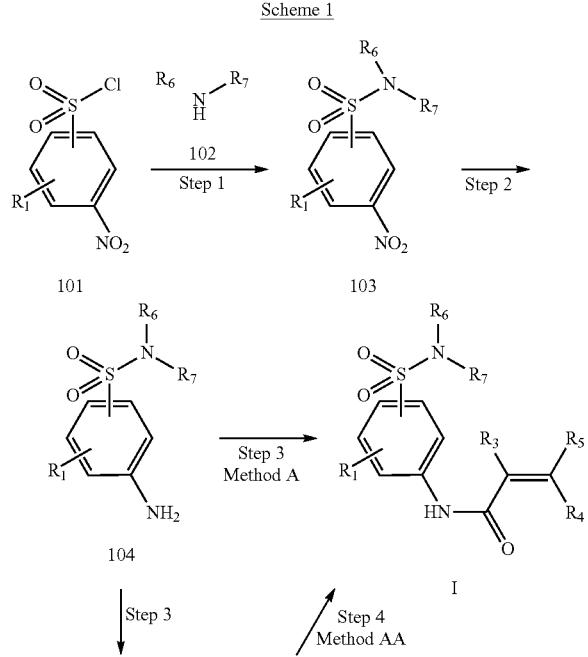

Scheme 1

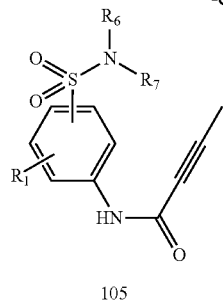

105

In step 1, scheme 1 the secondary amines of formula 102 are converted into their corresponding sulfonamides of formula 103, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 1 the obtained compounds of formula 103 (see scheme 1) are converted into their corresponding anilines of formula 104, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 3, scheme 1 the aniline derivatives of formula 104 are converted into their corresponding acrylamide of formula I or acetylide of formula 105, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride. Alternatively, coupling reagents such as EDC, CDI, or DCC may be used in conjunction with reagents such as acrylic acid or but-2-ynoic acid.

In step 4, scheme 1 the compounds of formula 105 are converted into their corresponding acrylamides of formula I, using methods well known to someone skilled in the art, e.g. reduction of an acetylene. The reaction is typically carried out in solvents like ethanol, methanol, ethyl acetate and acetic acid and mixtures thereof, at temperatures between 20° C. and 100° C. Typically used reducing reagents are palladium on carbon, Lindlar's catalyst or palladium hydroxide on carbon under a hydrogen atmosphere.

Scheme 2
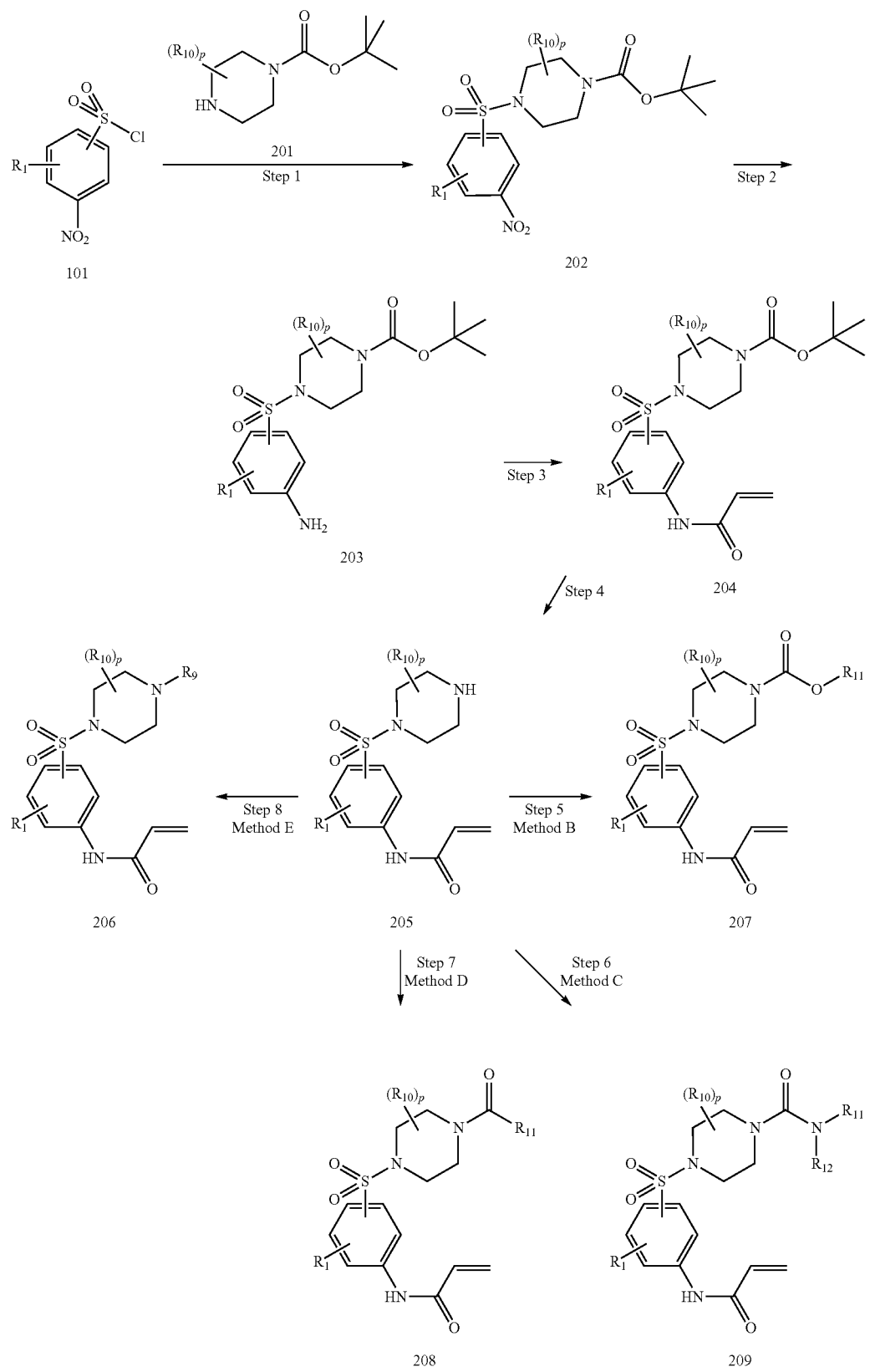

A method for the synthesis of the compounds of formula 205 starts from the corresponding functionalized piperazine of formula 201. In step 1, scheme 2 the functionalized piperazines of formula 201 are converted into their corresponding amides or sulfonamides of formula 202, using methods well known to someone skilled in the art, e.g. sulfonylation, acylation or aminocarboxylation of piperazines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine in conjuction with reagents such as acryloyl chloride.

In step 2, scheme 2 the obtained compounds of formula 202 (see scheme 2) are converted into their corresponding anilines of formula 203, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 3, scheme 2 the aniline derivatives of formula 203 are converted into their corresponding acrylamide of formula 204 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

In step 4, scheme 2 the acrylamide derivatives of formula 204 are converted into their corresponding secondary amines of formula 205 (where $R_{10}$=lower alkyl), using methods well known to someone skilled in the art, e.g. deprotection of acid labile protecting groups such as a Pert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

Compounds of formula 205 can be converted to carbamates of formula 207, ureas of formula 209, amides of formula 208 or tertiary amines of formula 206 using methods described herein.

In step 5, scheme 2 (method B) the secondary amines of formula 205 are converted into their corresponding carbamates of formula 207, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride. Typically used coupling reagents are phosgene, diphosgene or triphosgene in conjunction with reagents such as aryl or alkyl alcohols.

In step 6, scheme 2 (method C) the secondary amines of formula 205 are converted into their corresponding ureas of formula 209, using methods well known to someone skilled in the art, e.g. aminocarboxylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride. Typically used coupling reagents are phosgene, diphosgene or triphosgene in conjunction with reagents such as piperidine.

In step 7, scheme 2 (method D) the secondary amines of formula 205 are converted into their corresponding amides of formula 208, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-d iisopropylethylamine, N,N-dimethylaminopyridine and sodium hydride in conjunction with reagents such as acetyl chloride. Alternatively, secondary amines of formula 205 can be converted into amides of formula 208 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 8, scheme 2 (method E) the secondary amines of formula 205 are converted into their corresponding tertiary amines of formula 206, using methods well known to someone skilled in the art, e.g. alkylation of secondary amines. The reaction is typically carried out in solvents like N,N-dimethylformamide, N-methylpyrrolidinone, acetonitrile, dichloromethane and dichloroethane at temperatures between 0° C. and 100° C. Typically used bases are potassium carbonate, sodium hydride, lithium hexamethyldisilazide, sodium hexamethyldisilazide and potassium hexamethyldisilazide with alkylating agents such as alkyl halides, alkyl mesylates and alkyl triflates.

Scheme 3
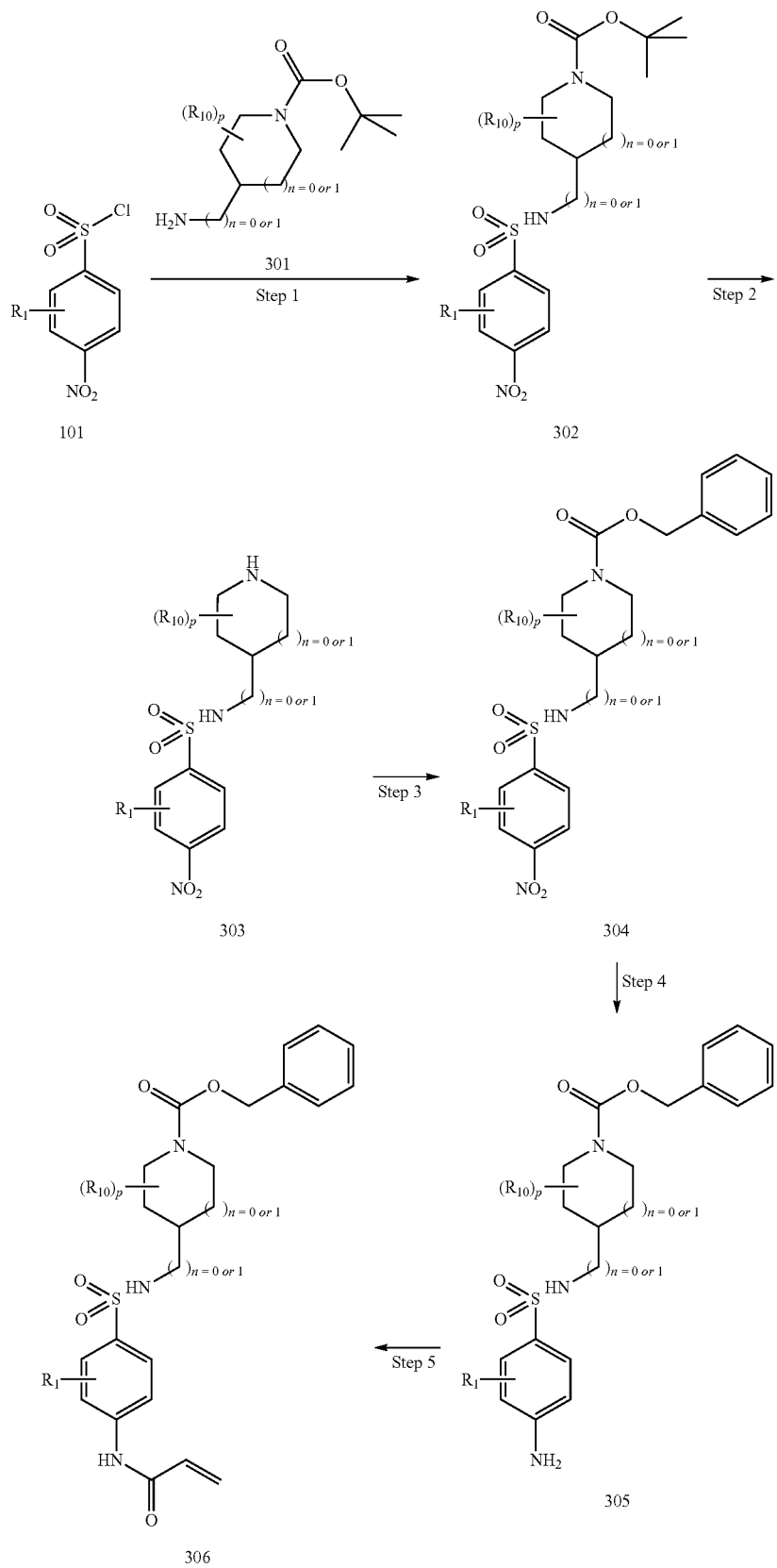

A method for the synthesis of the compounds of formula 306 starts from the corresponding functionalized primary amines of formula 301. In step 1, scheme 3 the functionalized primary amines of formula 301 are converted into their corresponding sulfonamides of formula 302, using methods well known to someone skilled in the art, e.g. sulfonylation of primary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 3 the sulfonamide derivatives of formula 302 are converted into their corresponding secondary amines of formula 303, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 3, scheme 3 the secondary amines of formula 303 are converted into their corresponding carbamates of formula 304, using methods well known to someone skilled in the art, e.g. carbobenzyloxylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as benzylchloroformate.

In step 4, scheme 3 the obtained compounds of formula 304 are converted into their corresponding anilines of formula 305, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 5, scheme 3 the aniline derivatives of formula 305 are converted into their corresponding acrylamides of formula 306 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

Scheme 4

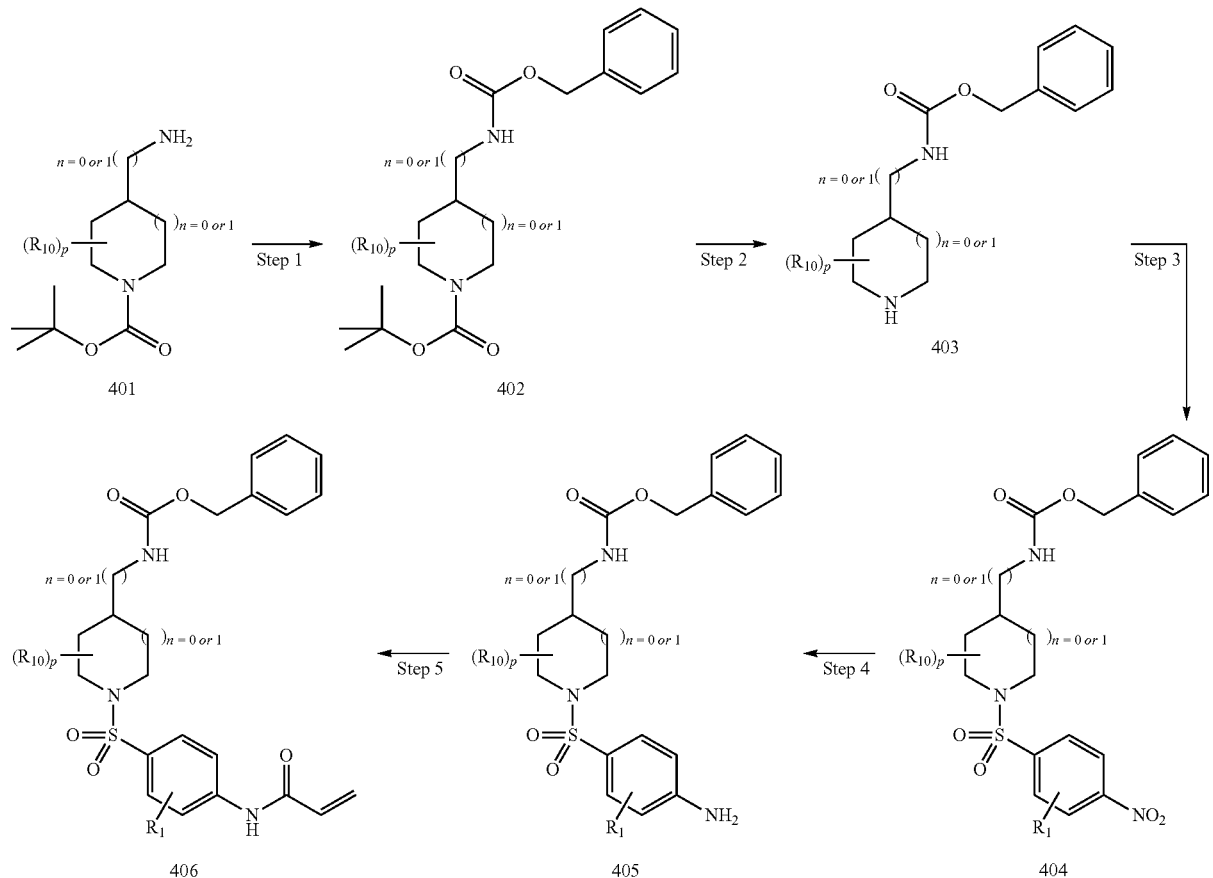

A method for the synthesis of the compounds of formula 406 starts from the corresponding functionalized primary amines of formula 401. In step 1, scheme 4 the primary amines of formula 401 are converted into their corresponding carbamates of formula 402, using methods well known to someone skilled in the art, e.g. carbobenzyloxylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as benzylchloroformate.

In step 2, scheme 4 the functionalized amine derivatives of formula 402 are converted into their corresponding secondary amines of formula 403, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 3, scheme 4 the functionalized secondary amines of formula 403 are converted into their corresponding sulfonamides of formula 404, using methods well known to someone skilled in the art, e.g. sulfonylation of primary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 4, scheme 4 the obtained sulfonamides of formula 404 are converted into their corresponding anilines of formula 405, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 5, scheme 4 the aniline derivatives of formula 405 are converted into their corresponding acrylamides of formula 406 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 5

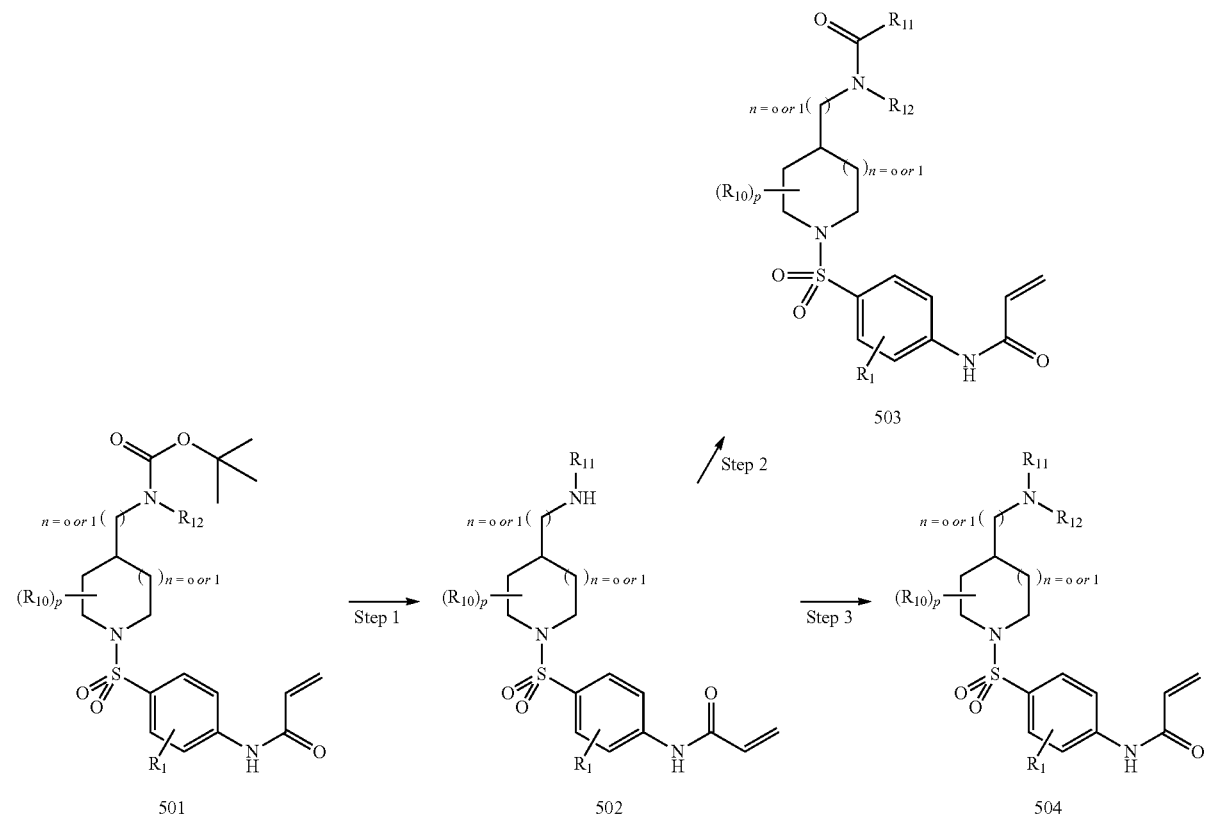

A method for the synthesis of the compounds of formula 502 starts from the corresponding functionalized amine (where $R_{12}$=H or alkyl) of formula 501. In step 1, scheme 5 the functionalized amine derivatives of formula 502 (prepared using methodology described previously in scheme 1) are converted into their corresponding amines of formula 502, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 2, scheme 5 the amine derivatives of formula 502 are converted into their corresponding amides of formula 503 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acetyl chloride.

In step 3, scheme 5 the amine derivatives of formula 503 are converted into their corresponding amides of formula 504 using methods well known to someone skilled in the art, e.g. reductive amination of aldehydes. The reaction is typically carried out in solvents such as dichloromethane, or dichloroethane at temperatures between 0° C. and 50° C. Typically used reducing agents are sodium triacetoxyborohydride, sodium cyanoborohydride or lithium aluminium hydride.

of formula 601. In step 1, scheme 6 the functionalized anilines of formula 601 are converted into their corresponding sulfonyl chlorides of formula 602, using methods well known to someone skilled in the art, e.g. diazotization followed by nucleophilic displacement. The reaction is typically carried out with solvents such as acetic acid, sulfuric acid, hydrochloric acid, water and mixtures thereof, at temperatures between −78° C. and 100° C.

In step 2, scheme 6 the functionalized sulfonyl chlorides of formula 602 are converted into their corresponding sulfonamides of formula 604 with secondary amines of formula 603 where $R_{11}$=benzyloxy or tert-butoxy using methods well known to someone skilled in the art, e.g. sulfonylation of sexondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 3, scheme 6 the obtained sulfonamides of formula 604 are converted into their corresponding anilines of formula 605, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

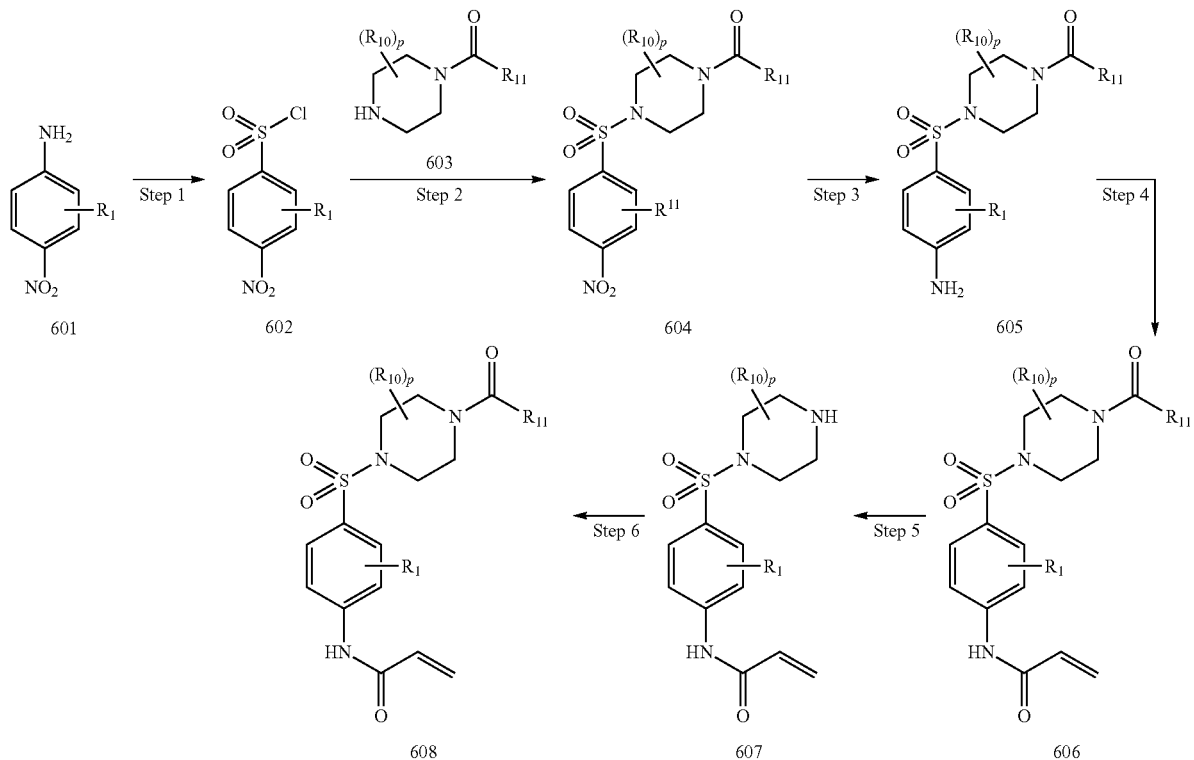

Scheme 6

A method for the synthesis of the compounds of formula 608 where $R_1$=alkyl, alkoxy, or halogen, $R_9$=alkyl, cycloalkyl or aryl starts from the corresponding functionalized anilines In step 4, scheme 6 the aniline derivatives of formula 605 are converted into their corresponding acrylamides of formula 606 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

In step 5, scheme 6 the functionalized acrylamides of formula 606 are converted into their corresponding secondary amines of formula 607, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 6, scheme 6 the secondary amines of formula 607 are converted into their corresponding amides of formula 608, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as adamantine-1-carbonyl chloride.

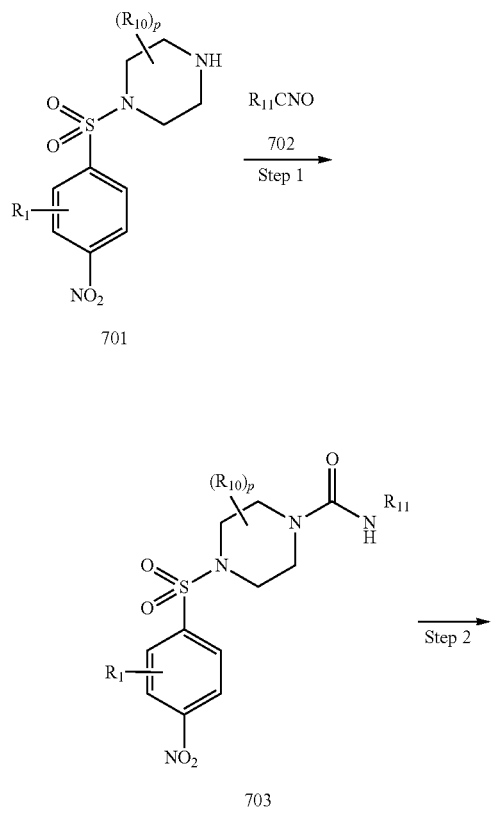

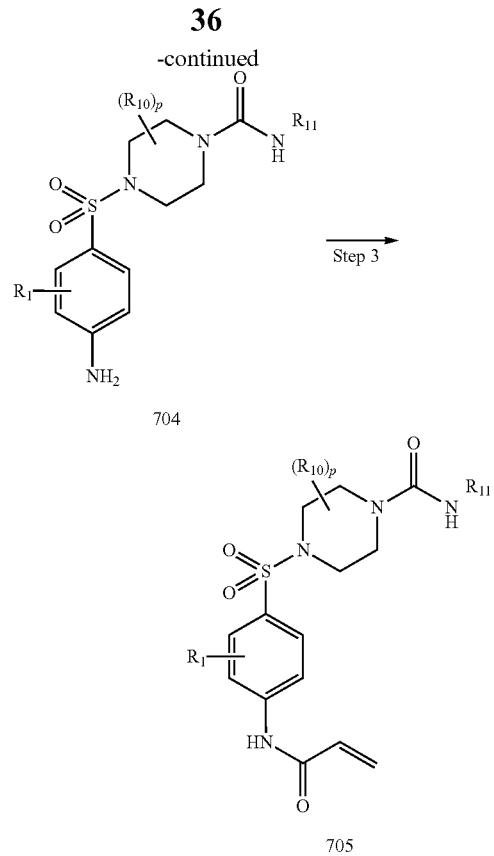

A method for the synthesis of the compounds of formula 705 where $R_{11}$=alkyl, cycloalkyl, alkoxy, or aryl, starts from the corresponding functionalized secondary amine of formula 701. In step 1, scheme 7 the functionalized amine of formula 701 is converted into the corresponding urea of formula 703, using methods well known to someone skilled in the art, e.g. nucleophilic attack of an amine with an isocyanate of formula 702. The reaction is typically carried out with solvents such as tetrahydrofuran, N,N-dimethylformamide, N-methylpyrrolidinone, acetonitrile, dichloromethane and dichloroethane at temperatures between 0° C. and 100° C. Typically used bases are pyridine, imidazole, triethylamine, N,N-diisopropylethylamine, N,N-dimethylaminopyridine and sodium hydride in conjunction with reagents such as benzylisocyanate.

In step 2, scheme 7 the obtained sulfonamides of formula 703 are converted into their corresponding anilines of formula 704, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 3, scheme 7 the aniline derivatives of formula 704 are converted into their corresponding acrylamides of formula 705 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

Scheme 8

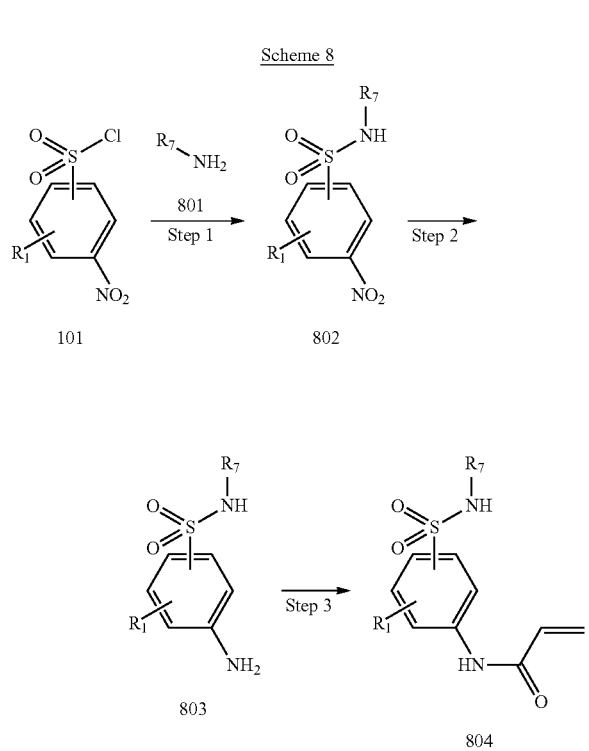

In step 1, scheme 8 the functionalized primary amines of formula 801 are converted into their corresponding sulfonamides of formula 802, using methods well known to someone skilled in the art, e.g. sulfonylation of primary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are pyridine, triethylamine, N,N-diisopropyl ethylamine, pyridine, potassium carbonate and N,N-dimethylaminopyridine.

In step 2, scheme 8 the obtained sulfonamides of formula 802 are converted into their corresponding anilines of formula 803, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 3, scheme 8 the aniline derivatives of formula 803 are converted into their corresponding acrylamides of formula 804 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

Scheme 9

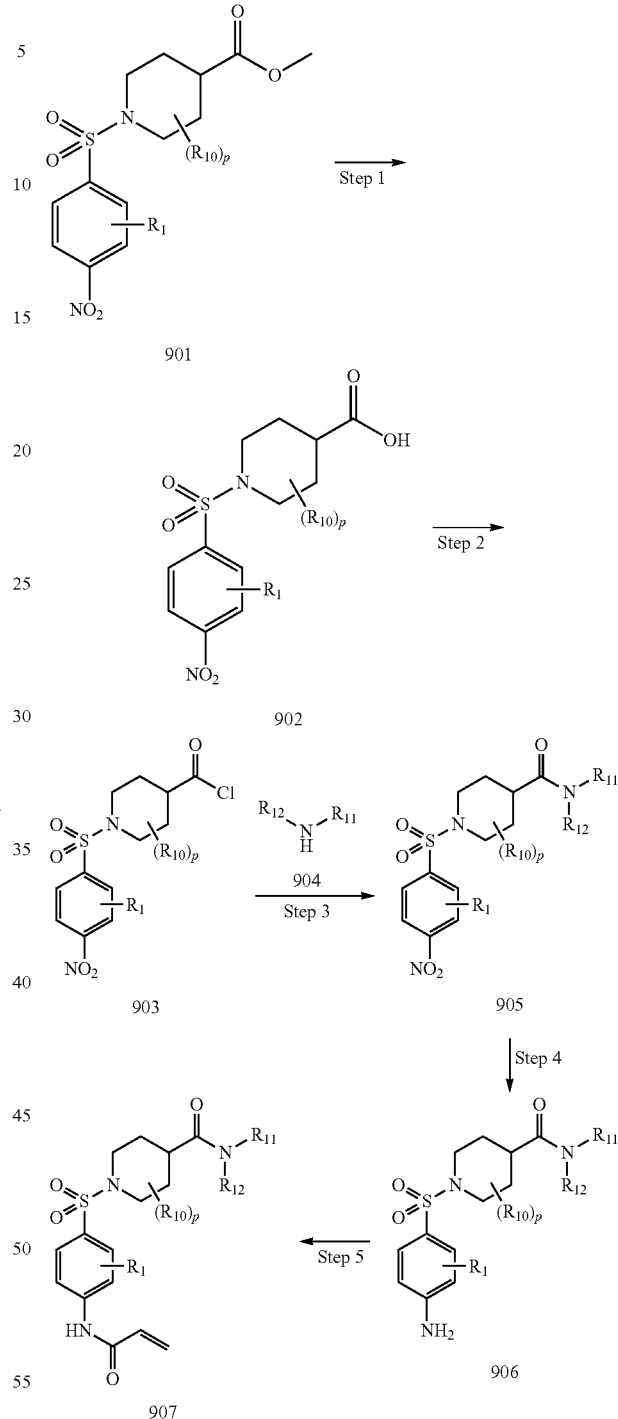

A method for the synthesis of the compounds of formula 907 where $R_{11}$ and $R_{12}$=hydrogen, alkyl, cycloalkyl, alkoxy, or aryl, starts from the sulfonamide of formula 901. In step 1, scheme 9 the functionalized sulfonamide of formula 901 is converted into the corresponding carboxylic acid of formula 902, using methods well known to someone skilled in the art, e.g. hydrolysis of an ester. The reaction is typically carried out with solvents such as tetrahydrofuran, acetonitrile, ethanol and water or mixtures thereof at temperatures between 0° C.

and 100° C. Typically used bases are sodium hydroxide, lithium hydroxide and potassium hydroxide.

In step 2, scheme 9 the carboxylic acid of formula 902 is converted into the corresponding acid chloride of formula 903, using methods well known to someone skilled in the art, e.g. chlorination of an acid. The reaction is typically carried out with solvents such as toluene, acetonitrile, dichloromethane or mixtures thereof at temperatures between 0° C. and 100° C. Typically used chlorine sources are oxalyl chloride or thionyl chloride.

In step 3, scheme 9 the functionalized amine of formula 904 is converted into the corresponding amide of formula 905, using methods well known to someone skilled in the art, e.g. nucleophilic attack of an amine with an acid chloride. The reaction is typically carried out with solvents such as tetrahydrofuran, N,N-dimethylformamide, N-methylpyrrolidinone, acetonitrile, dichloromethane and dichloroethane at temperatures between 0° C. and 100° C. Typically used bases are pyridine, imidazole, triethylamine, N,N-diisopropylethylamine, N,N-dimethylaminopyridine and sodium hydride in conjunction with reagents such as dimethylamine.

In step 4, scheme 9 the obtained sulfonamides of formula 905 are converted into their corresponding anilines of formula 906, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 5, scheme 9 the aniline derivatives of formula 906 are converted into their corresponding acrylamides of formula 907 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 10

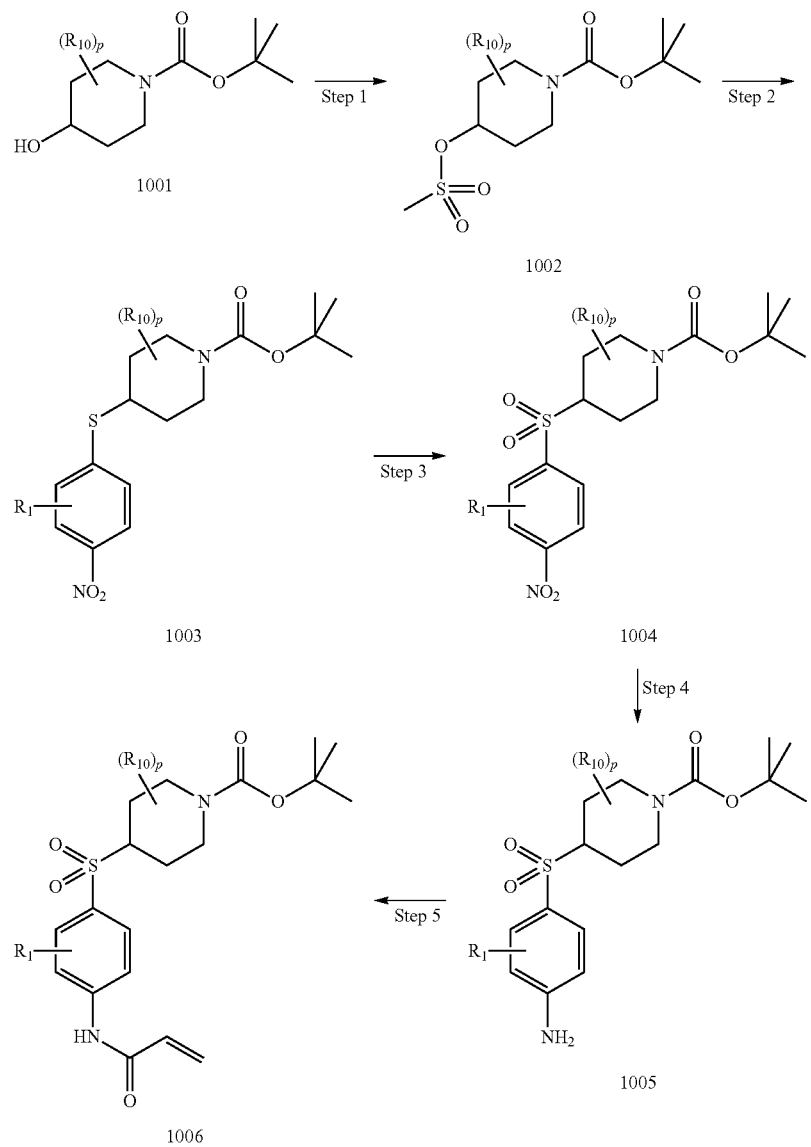

A method for the synthesis of the compounds of formula 1006 starts from the alcohol of formula 1001. In step 1, scheme 10 the functionalized alcohol of formula 1001 is converted into the corresponding mesylate of formula 1002, using methods well known to someone skilled in the art, e.g. activation of an alcohol. The reaction is typically carried out with solvents such as tetrahydrofuran, acetonitrile, dichloromethane, dichloroethane and N,N-dimethylformamide or mixtures thereof at temperatures between 0° C. and 20° C. Typically used bases are pyridine, imidazole, triethylamine, N,N-diisopropylethylamine, N,N-dimethylaminopyridine and sodium hydride in conjunction with reagents such as dmethane sulfonyl chloride.

In step 2, scheme 10 the activated alcohol of formula 1002 is converted into the corresponding sulfide of formula 1003 using methods well known to someone skilled in the art, e.g. nucleophilic displacement of a sulfone with a thiol. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine in conjunction with reagents such as thionitrophenol.

In step 3, scheme 10 the sulfide of formula 1003 is converted into the corresponding sulfoxide of formula 1004 using methods well known to someone skilled in the art, e.g. oxidation of a sulfide. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 20° C. Typically used oxidants are hydrogen-peroxide, meta-chloroperoxybenzoic acid or oxone.

In step 4, scheme 10 the obtained sulfonamides of formula 1004 are converted into their corresponding anilines of formula 1005, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 5, scheme 10 the aniline derivatives of formula 1005 are converted into their corresponding acrylamides of formula 1006 using methods well known to someone skilled in the art, e.g. acylation of amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjuction with reagents such as acryloyl chloride.

Provided is a method of inhibiting the activity of transglutaminase TG2, comprising contacting said transglutaminase TG2 with an effective amount of at least one compound or pharmaceutically acceptable salt thereof described herein.

Also provided is a method of treating a disease state mediated by transglutaminase TG2 activity in a subject in need of such a treatment, comprising administering to the subject a therapeutically effective amount of at least one compound or pharmaceutically acceptable salt thereof described herein. Also provided is a method of treating a neurodegenerative pathology mediated by transglutaminase TG2 activity in a subject in need of such a treatment, comprising administering to the subject a therapeutically effective amount of at least one compound or pharmaceutically acceptable salt thereof described herein. Also provided is a method for treating disease states mediated by (or at least in part by) the presence of transglutaminase TG2. Such disease states include, for example, neurodegenerative diseases, gluten sensitivity diseases such as Celiac disease, protein misfolding disorders, hepatic and renal injury, kidney disease, renal failure, neuropathy, cancer metastasis, leukemia, melanoma, autoimmune diseases, inflammatory diseases, degenerative joint disease such as osteoarthritis, psoriasis, cardiovascular disorders, ischemic, atherosclerosis, fibrosis, diabetes, lamellar ichthyosis, supranuclear palsey, Hb Koln and sickle cell disorders, acne, cataracts, myopia, immune system diseases, diabetic nephropathy, muscular dystrophies, wound remodelling and repair, and multiple sclerosis. In some embodiments, the disease state is chosen from acne, cataracts, immune system diseases, psoriasis, neuropathy, neurodegenerative disease, such as Alzheimer's disease, Huntington's disease, and Parkinson's disease, Celiac disease, cancer metastasis, inflammation, fibrosis, diabetes, autoimmune diseases, lamellar ichthyosis, psoriasis, supranuclear palsy, and renal failure. In some embodiments, the disease state is a gluten sensitivity disease. In some embodiments, the disease state is Celiac disease. In some embodiments, the neurodegenerative disease is chosen from Alzheimer's disease, amyotrophic lateral sclerosis, Huntington's disease, Parkinson's' disease, Prion disease and spinocerebellar ataxias. In some embodiments, the neurodegenerative disease is Huntington's disease.

Also provided are methods of treatment in which at least one compound or pharmaceutically acceptable salt thereof described herein is the only active agent given to the subject and also includes methods of treatment in which at least one compound or pharmaceutically acceptable salt thereof described herein is given to the subject in combination with one or more additional active agents.

In general, the compounds and pharmaceutically acceptable salts thereof described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and fonn of administration, and other factors well know to the skilled artisan. The drug can be administered at least once a day, such as once or twice a day.

In some embodiments, the compounds and pharmaceutically acceptable salts thereof described herein are administered as a pharmaceutical composition. Accordingly, provided are pharmaceutical compositions comprising at least one compound or pharmaceutically acceptable salt thereof described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or pharmaceutically acceptable salt thereof is sufficient to provide a practical quantity of material for administration per unit dose of the compound or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or pharmaceutically acceptable salt thereof described herein.

Effective concentrations of at least one compound or pharmaceutically acceptable salt thereof described herein are mixed with a suitable pharmaceutically acceptable vehicle. In instances in which the compound or pharmaceutically acceptable salt thereof exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound or pharmaceutically acceptable salt thereof described herein, the resulting mixture may be a solution, suspension, emulsion or the like. The form of the resulting mixture depends upon a number of factors, including the intended mode of administration and the solubility of the compound or pharmaceutically acceptable salt thereof in the chosen vehicle.

The effective concentration sufficient for ameliorating the symptoms of the disease treated may be empirically determined.

The compounds and pharmaceutically acceptable salts thereof described herein may be administered orally, topically, parenterally, intravenously, by, intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound or pharmaceutically acceptable salt thereof described herein. In some embodiments, oral pharmaceutical compositions contain at least 5% (weight %) of at least one compound or pharmaceutically acceptable salt thereof described herein. Some embodiments contain from 25% to 50% or from 5% to 75% of at least one compound or pharmaceutically acceptable salt thereof described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compounds and pharmaceutically acceptable salts thereof described herein can be incorporated into oral liquid preparations such as aqueous or oily suspensions, solutions, emulsions, syrups, or elixirs, for example. Moreover, pharmaceutical compositions containing these compounds and pharmaceutically acceptable salts thereof can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n- propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound or pharmaceutically acceptable salt thereof is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compounds and pharmaceutically acceptable salts thereof described herein may be administered parenterally in a sterile medium. Parenteral administration includes subcutaneous injections, intravenous, intramuscular, intrathecal injection or infusion techniques. The compounds and pharmaceutically acceptable salts thereof described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compounds and pharmaceutically acceptable salts thereof described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compounds and pharmaceutically acceptable salts thereof described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compounds and pharmaceutically acceptable salts thereof described herein may also be formulated for transdermal administration as a transdermal patch.

Topical pharmaceutical compositions comprising at least one compound or pharmaceutically acceptable salt thereof described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether; diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds and pharmaceutically acceptable salts thereof described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound or pharmaceutically acceptable salt thereof include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compounds and pharmaceutically acceptable salts thereof described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound or pharmaceutically acceptable salt thereof described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound or pharmaceutically acceptable salt thereof described herein, and instructions for using the composition to treat a subject (typically a human patient). In some embodiments, the instructions are for using the pharmaceutical composition to treat a subject suffering a disease state mediated by transglutaminase TG2 activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compounds or pharmaceutically acceptable salts thereof can be administered alone, as mixtures, or in combination with other active agents.

Also provided are methods for treating Celiac disease comprising administering to a subject, at least one compound or pharmaceutically acceptable salt thereof described herein. In some embodiments, the at least one compound or pharmaceutically acceptable salt thereof is administered, either simultaneously or sequentially, in combination with one or more additional agents used in the treatment of Celiac disease. In some embodiments, the at least one compound or pharmaceutically acceptable salt thereof and the one or more additional agents are present in a combined composition. In some embodiments, the at least one compound or pharmaceutically acceptable salt thereof and the one or more additional agents are administered separately.

Also provided are pharmaceutical compositions comprising at least one compound or pharmaceutically acceptable salt thereof described herein and one or more additional pharmaceutical agents used in the treatment of Celiac disease. Similarly, also provided are packaged pharmaceutical compositions containing a first pharmaceutical composition comprising at least one compound or pharmaceutically acceptable salt thereof described herein, and another composition comprising one or more additional pharmaceutical agents used in the treatment of Celiac disease.

The methods for treating Celiac disease, as provided herein, may be useful for both prophylactic and therapeutic purposes. Evidence of therapeutic effect may be any diminution in the severity of disease, particularly diminution of the severity of such symptoms as fatigue, chronic diarrhea, malabsorption of nutrients, weight loss, abdominal distension, and anemia. Other indicators of Celiac disease include the presence of antibodies specific for glutens, antibodies specific for tissue transglutaminase, the presence of pro-inflammatory T cells and cytokines, and degradation of the villus structure of the small intestine. Application of the methods and compositions provided herein can result in the improvement of any or all of these indicators of Celiac disease.

Subjects suitable for prophylaxis in accordance with the Celiac disease treatment methods provided herein may be identified by genetic testing for predisposition, e.g., by human leukocyte antigen (HLA) typing; by family history, and by other methods known in the art.

Patients who may benefit from the Celiac disease treatment methods provided herein include both adults and children. As is known in the art for other medications, and in accordance with the treatment method herein, dosages of the compounds and pharmaceutically acceptable salts thereof provided herein can be adjusted for pediatric use.

The methods described herein include methods for treating Huntington's disease, including treating memory and/or cognitive impairment associated with Huntington's disease, comprising administering to a subject, simultaneously or sequentially, at least one compound or pharmaceutically acceptable salt thereof described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chlorpromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound or pharmaceutically acceptable salt thereof described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one compound or pharmaceutically acceptable salt thereof described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one compound or pharmaceutically acceptable salt thereof described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one compound or pharmaceutically acceptable salt thereof described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds and pharmaceutically acceptable salts thereof described herein are typically administered at dosage levels and in a manner customary for transglutaminase TG2 inhibitors. For example, the compounds and pharmaceutically acceptable salts thereof can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound or pharmaceutically acceptable salt thereof described herein, for example, 0.1-50 mg of at least one compound or pharmaceutically acceptable salt thereof described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound or pharmaceutically acceptable salt thereof described herein.

A labeled form of a compound or pharmaceutically acceptable salt thereof described herein can be used as a diagnostic for identifying and/or obtaining compounds that have the function of modulating an activity of transglutaminase TG2 as described herein. The compounds and pharmaceutically acceptable salts thereof described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds and pharmaceutically acceptable salts thereof, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide EDC=HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=tert-butyl alcohol
LiHMDS=lithium hexamethyl-disilazide
LC/MS=liquid chomatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate
μL=microliter
μM=micromolar Experimental Commercially available reagents and solvents (HPLC grade) were used without further purification.

$^1$H NMR spectra were recorded on a Bruker DRX 500 MHz spectrometer or Bruker DPX 250 MHz spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical HPLC-MS was performed on Shimadzu LCMS-2010EV systems using reverse phase Atlantis dC18 columns (3 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2788 dual wavelength UV detector. Mass spectra were obtained over the range m/z 150 to 850 at a sampling rate of 2 scans per second using Waters LCT or analytical HPLC-MS on Shimadzu LCMS-2010EV systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array. Data were integrated and reported using Shimadzu psiport software.

The fluorescent screening assay for human TG2 was performed as described herein: Assay conditions were 20 nM TG2, 8 μM N,N-dimethylated Casein (NMC) and 16 μM K×D (used for all transglutaminase assays) in 25 mM Hepes, pH 7.4, 250 mM NaCl, 2 mM MgCl$_2$, 0.5 mM CaCl$_2$, 0.2 mM DTT, 0.05% Pluronic F-127 at 37° C. A time point was taken with a microplate reader (Safire or Ultra, Tecan; ex: 350 nm, em: 535 nm) every 3 minutes for up to 2 hours and the initial linear reaction progress was used to determine the reaction velocity as a measure for enzyme activity. Assay conditions were identical for human TG6 and similar for human TG1 and mouse TG2 apart from enzyme concentration (mTG2 at 5 nM; TG1 at 10 nM) and CaCl$_2$ concentration (0.2 mM for mTG2; 0.05 mM for TG1). Factor XIIIa was activated using 0.1 μg/μl thrombin (Sigma) in 35 mM Tris pH 8.0 for 20 min at 30° C. and the transamidation reaction was performed with 20 nM Factor XIIIa in 50 mM Tris pH 8.0, 1.25 mM CaCl2, 0.05% Pluronic, 0.2 mM DTT. TG3 was activated with 0.02 μg/μl thrombin under the same conditions as Factor XIIIa and assay conditions were 10 nM TG3 in 50 mM Hepes, pH 8, 20 mM CaCl$_2$, 0.2 mM DTT, 0.05% Pluronic F-127.

Method A

Example A-1

4-(4-Acryloylamino-benzenesulfonyl)-piperazine-1-carboxylic acid benzyl ester 4-(4-Nitro-benzenesulfonyl)-piperazine-1-carboxylic acid benzyl ester

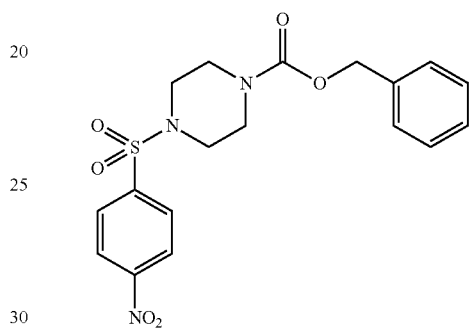

Diisopropylethylamine (0.82 ml, 4.95 mmol) was added in one portion to a stirred solution of piperazine-1-carboxylic acid benzyl ester (1.0 g, 4.5 mmol) in DCM (10 ml) at room temperature. To this mixture was added 4-nitrophenyl sulfonyl chloride (1.1 g, 4.95 mmol) in one portion and the mixture was stirred at room temperature under a nitrogen atmosphere for 1 hour. After this time the solvent was removed under vacuum and the resulting residue was purified by flash column chromatography (elution: 70% heptane, 30% ethyl acetate) to give the title compound (1.82 g, 100% yield) as a white solid. Tr=1.43 min m/z (ES$^+$) (M+Na$^+$) 428

4-(4-Amino-benzenesulfonyl)-piperazine-1-carboxylic acid benzyl ester

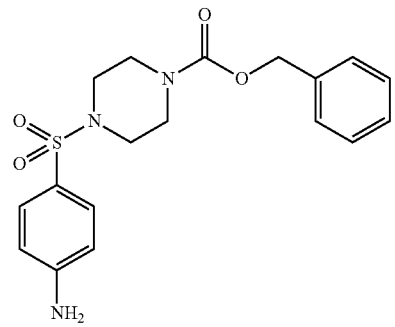 [SMILES: O=C(OCc1ccccc1)N1CCN(S(=O)(=O)c2ccc([N+](=O)[O-])cc2)CC1]

4-(4-Nitro-benzenesulfonyl)-piperazine-1-carboxylic acid benzyl ester (1.82 g, 4.5 mmol) was suspended in a 5:1 mixture of ethanol and water (30 ml). To this solution was added iron powder (0.65 g, 11.7 mmol) followed by saturated ammonium chloride solution (1 ml) and the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (1.5 g, 89% yield) as a white solid. Tr=1.29 min, m/z (ES$^+$) (M+H)$^+$ 376

4-(4-Acryloylamino-benzenesulfonyl)-piperazine-1-carboxylic acid benzyl ester

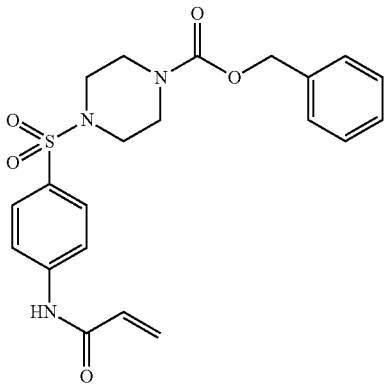 [SMILES: C=CC(=O)Nc1ccc(S(=O)(=O)N2CCN(C(=O)OCc3ccccc3)CC2)cc1]

4-(4-Amino-benzenesulfonyl)-piperazine-1-carboxylic acid benzyl ester (0.25 g, 0.67 mmol) was dissolved in THF (10 ml). To this was added diisopropylethylamine (0.33 ml, 1.9 mmol) in one portion followed by the drop wise addition of acryloyl chloride (0.06 ml, 0.74 mmol) and the mixture was stirred at room temperature under a nitrogen atmosphere for 3 hours. The THF was removed under vacuum and the resulting crude material was purified by column chromatography (elution: 20% heptane, 80% ethyl acetate) to give the title compound (57 mg, 20% yield) as a white powder.

Example A-1

4-(4-Acryloylamino-benzenesulfonyl)-piperazine-1-carboxylic acid benzyl ester $\delta_H$ (500 MHz, DMSO) 10.59 (1H, s), 7.92 (2H, d), 7.67 (2H, d), 7.57 (1H, d), 7.38-7.18 (5H, m), 6.53-6.23 (2H, m), 5.85 (1H, dd), 5.01 (2H, s), 3.58-3.42 (m, 4H), 2.92-2.78 (m, 4H). Tr=4.13 min, m/z (ES$^+$) (M+H)$^+$ 430.

Example A-2

4-(4-Acryloylamino-benzenesulfonyl)-[1,4]diazepane-1-carboxylic acid benzyl ester $\delta_H$ (500 MHz, DMSO) 10.54 (1H, s), 7.87 (2H, d), 7.78-7.70 (2H, m), 7.39-7.26 (5H, m), 6.50-6.39 (2H, m), 5.83 (1H, d), 5.05 (2H, s), 3.56-3.48 (2H, m), 3.43-3.37 (3H, m), 3.22-3.16 (3H, m), 1.75-1.65 (2H, m). Tr=4.10 min, m/z (ES$^+$) (M+H)$^+$ 444.

Example A-3

N-[4-(4-Phenyl-piperazine-1-sulfonyl)-phenyl]-acrylamide $\delta_H$ (500 MHz, DMSO) 10.55 (1H, s), 7.95 (2H, d), 7.73 (2H, d), 7.25 (2H, t), 6.95 (2H, d), 6.78 (1H, t), 6.46-6.32 (2H, m), 5.84 (1H, d), 3.26-3.13 (4H, m), 3.04-2.93 (4H, m). Tr=4.25 min, m/z (ES$^+$) (M+H)$^+$ 372.

Example A-4

N-[4-(4-Phenyl-piperidine-1-sulfonyl)-phenyl]-acrylamide $\delta_H$ (500 MHz, DMSO) 10.59 (1H, s), 7.93 (2H, d), 7.74 (2H, d), 7.31-7.12 (5H, m), 6.51-6.28 (2H, m), 5.82 (1H, s), 3.75 (2H, d), 2.28 (2H, t), 1.81 (2H, d), 1.72-1.60 (2H, m). Tr=4.51 min, m/z (ES$^+$) (M+H)$^+$ 371.

Example A-5

4-(4-Acryloylamino-benzenesulfonyl)-3,5-dimethyl-piperazine-1-carboxylic acid tert-butyl ester $\delta_H$ (500 MHz, DMSO) 10.51 (1H, s), 7.90-7.72 (5H, m), 6.51-6.19 (2H, m), 5.80 (1H, dd), 4.06-3.88 (2H, m), 373-3.58 (2H, m), 2.71-2.67 (2H, m), 1.36 (9H, s), 1.18 (6H, d). Tr=4.34 min, m/z (ES$^+$) (M+Na)$^+$ 446.

Example A-6

[1-(4-Acryloylamino-benzenesulfonyl)-piperidin-4-yl]-carbamic acid tert-butyl ester $\delta_H$ (500 MHz, DMSO) 10.54 (1H, s), 7.92 (2H, d), 7.67 (2H, d), 6.83 (1H, d), 6.49-6.27 (2H, m), 5.84 (1H, d), 3.54-3.38 (2H, m), 3.27-3.16 (1H, m), 2.46-2.38 (2H, m), 1.80-1.68 (2H, m), 1.34 (9H, s). Tr=4.26 min, m/z (ES$^+$) (M+Na)$^+$ 432.

Example A-7

[1-(4-Acryloylamino-benzenesulfonyl)-piperidin-4-ylmethyl]-carbamic acid tert-butyl ester $\delta_H$ (500 MHz, DMSO) 10.55 (1H, s), 7.89 (2H, d), 7.67 (2H, d), 6.88-6.76 (1H, m), 6.52-6.27 (2H, m), 5.83 (1H, d), 3.57 (2H, d), 2.75 (2H, t), 2.56 (1H, obscured), 2.18 (2H, t), 1.64 (2H, d), 1.36 (9H, s), 1.16-1.07 (2H, m). Tr=4.09 min, m/z (ES$^+$) (M+Na)$^+$ 446.

Example A-8

N-(4-Diethylsulfamoyl-phenyl)-acrylamide $\delta_H$ (500 MHz, MeOD) 7.85 (2H, d), 7.79 (2H, d), 6.54-6.37 (2H, m), 5.82 (1H, dd), 3.35 (1H, d), 3.23 (4H, q), 1.13 (6H, t). Tr=3.64 min, m/z (ES$^+$) (M+H)$^+$ 283.

Example A-9

N-{4-[4-(6-Trifluoromethyl-pyridin-3-yl)-piperazine-1-sulfonyl]-phenyl}-acrylamide $\delta_H$ (500 MHz, MeOD) 8.32 (1H, s), 7.89 (2H, d), 7.74 (2H, d), 7.68 (1H, d), 6.84 (1H, d), 6.50-6.36 (2H, m), 5.89 (1H, d), 3.81-3.65 (4H, m), 3.15-3.01 (4H, m). Tr=4.24 min, m/z (ES$^+$) (M+H)$^+$ 441.

Example A-10

N-[4-(Cyclohexyl-phenyl-sulfamoyl)-phenyl]-acrylamide $\delta_H$ (500 MHz, MeOD) 7.82 (2H, d), 7.69 (2H, d), 7.40-7.32 (5H, m), 7.03 (2H, d), 6.51-6.37 (2H, m), 5.82 (1H, dd), 4.16-4.03 (1H, m), 1.89-1.68 (4H, m), 1.58-1.50 (1H, m), 1.42-1.29 (2H, m), 0.92-0.79 (1H, m). Tr=4.54 min, m/z (ES⁺) (M+H)⁺ 385.

Example A-11

N-{4-[4-(5-Chloro-2-methoxy-phenyl)-piperazine-1-sulfonyl]-phenyl}-acrylamide $\delta_H$ (250 MHz, MeOD) 7.92-7.71 (4H, m), 7.01-6.82 (3H, m), 6.49-6.40 (2H, m), 5.88-5.78 (1H, m), 3.76 (3H, s), 3.17-3.01 (8H, m). Tr=4.33 min, m/z (ES⁺) (M+H)⁺ 436.

Example A-12

N-[4-(1,3-Dihydro-isoindole-2-sulfonyl)-phenyl]-acrylamide $\delta_H$ (250 MHz, MeOD) 7.85 (4H, s), 7.22 (4H, s), 6.43-6.38 (2H, m), 5.88-5.73 (1H, m), 4.60 (4H, s). Tr=3.82 min, m/z (ES⁺) (M+H)⁺ 329.

Example A-13

N-[4-(4-Benzo[1,3]dioxol-5-ylmethyl-piperazine-1-sulfonyl)-phenyl]-acrylamide $\delta_H$ (250 MHz, MeOD) 7.88 (2H, d), 7.74 (2H, d), 6.84-6.70 (3H, m), 6.50-6.36 (2H, m), 5.95-5.76 (3H, m), 3.45 (2H, s), 3.12-2.94 (4H, m), 2.62-2.49 (4H, m). Tr=2.73 min, m/z (ES⁺) (M+H)⁺ 430.

Example A-14

N-{4-[(1-Benzyl-piperidin-4-yl)-cyclopropyl-sulfamoyl]-phenyl}-acrylamide $\delta_H$ (250 MHz, MeOD) 7.92-7.78 (4H, m), 7.44-7.21 (5H, m), 6.48-6.337 (2H, m), 5.88-5.76 (1H, m), 3.91-3.66 (1H, m), 3.50-3.47 (2H, m), 2.94-2.83 (2H, m), 2.08-1.89 (5H, m), 1.56-1.42 (2H, m), 0.97-0.86 (2H, m), 0.83-0.72 (2H, m). Tr=2.90 min, m/z (ES⁺) (M+H)⁺ 440.

Example A-15

5-(4-Acryloylamino-benzenesulfonyl)-hexahydro-pyrrolo[3,4-c]pyrrole-2-carboxylic acid tert-butyl ester $\delta_H$ (250 MHz, DMSO) 10.54 (1H, s), 7.92 (2H, d), 7.73 (2H, d), 6.52-6.25 (2H, m), 5.75 (1H, dd), 3.34 (2H, obscured), 3.05-2.51 (8H, m), 1.28 (9H, s). Tr=3.83 min, m/z (ES⁺) (M+H)⁺ 422.

Example A-16

N-[4-(4-Benzyl-piperazine-1-sulfonyl)-phenyl]-acrylamide $\delta_H$ (500 MHz, DMSO) 10.58 (1H, s), 7.92 (2H, d), 7.66 (2H, d), 7.31-7.17 (5H, m), 6.50-6.29 (2H, m), 5.83 (1H, d), 3.46 (2H, s), 2.95-2.77 (4H, m), 2.46-2.39 (4H, m). Tr=2.91 min, m/z (ES⁺) (M+H)⁺ 386.

Example A-17

N-[4-(4-Phenethyl-piperazine-1-sulfonyl)-phenyl]-acrylamide $\delta_H$ (500 MHz, DMSO) 10.59 (1H, s), 7.93 (2H, d), 7.69 (2H, d), 7.38-7.02 (5H, m), 6.51-6.29 (2H, m), 5.83 (1H, d), 3.34 (2H, obscured), 2.96-2.77 (4H, m), 2.48 (2H, obscured), 2.72-2.60 (4H, m). Tr=3.01 min, m/z (ES⁺) (M+H)⁺ 400.

Example A-18

N-{4-[4-(3-Phenyl-propyl)-piperazine-1-sulfonyl]-phenyl}-acrylamide $\delta_H$ (500 MHz, DMSO) 10.60 (1H, s), 7.93 (2H, d), 7.68 (2H, d), 7.26-7.08 (5H, m), 6.50-6.27 (2H, m), 5.83 (1H, d), 2.92-2.77 (4H, m), 2.52 (2H, obscured), 2.47-2.33 (4H, m), 2.29-2.21 (2H, m), 1.69-1.58 (2H, m). Tr=2.94 min, m/z (ES⁺) (M+H)⁺ 414.85.

Example A-19

N-{4-[4-(4-Phenyl-butyl)-piperazine-1-sulfonyl]-phenyl}-acrylamide $\delta_H$ (250 MHz, DMSO) 10.55 (1H, s), 7.91 (2H, d), 7.65 (2H, d), 6.52-6.20 (2H, m), 5.83 (1H, d), 2.93-2.72 (4H, m), 2.42-2.31 (4H, m), 2.29-2.15 (2H, m), 1.58-1.19 (6H, m). Tr=3.07 min, m/z (ES⁺) (M+H)⁺ 428.45.

Example A-20

4-(3-Acryloylamino-benzenesulfonyl)-piperazine-1-carboxylic acid benzyl ester $\delta_H$ (500 MHz, DMSO) 10.59 (1H, s), 8.18 (1H, s), 7.95 (1H, d), 7.62 (1H, t), 7.41 (1H, d), 7.33-7.21 (5H, m), 6.48-6.26 (2H, m), 5.81 (1H, d), 4.95 (2H, s), 3.54-3.42 (4H, m), 3.00-2.83 (4H, m). Tr=4.11 min, m/z (ES⁺) (M+H)⁺ 430.

Example A-21

4-(4-Acryloylamino-benzenesulfonyl)-[1,4]diazepane-1-carboxylic acid benzyl ester $\delta_H$ (500 MHz, DMSO) 10.56 (1H, s), 7.34 (1H, d), 7.26-7.20 (1H, m), 7.38-7.26 (5H, m), 6.49-6.28 (2H, m), 5.35 (1H, d), 5.05 (2H, s), 3.56-3.48 (2H, m), 3.44-3.39 (3H, m), 3.21-3.16 (3H, m), 1.76-1.64 (2H, m). Tr=4.10 min, m/z (ES⁺) (M+H)⁺ 444.

Example A-22

4-(3-Acryloylamino-benzenesulfonyl)-piperazine-1-carboxylic acid tert-butyl ester $\delta_H$ (500 MHz, DMSO) 10.56 (1H, s), 8.15 (1H, s), 7.95 (1H, d), 7.61 (1H, t), 7.36 (1H, d), 6.49-6.21 (2H, m), 5.83 (1H, d), 3.39 (4H, obscured), 2.92-2.84 (4H, m), 1.31 (9H, s). Tr=3.77 min, m/z (ES⁺) (M+H)⁺ 418.

Example A-23

N-[3-(4-Benzyl-piperazine-1-sulfonyl)-phenyl]-acrylamide $\delta_H$ (500 MHz, DMSO) 10.51 (1H, s), 8.15 (1H, s), 7.95 (1H, d), 7.61 (1H, t), 7.43 (1H, d), 7.22-7.16 (5H, m), 6.48-

6.26 (2H, m), 5.81 (1H, d), 3.48 (2H, s), 2.94-2.85 (4H, m), 2.43-2.37 (4H, m). Tr=2.88 min, m/z (ES⁺) (M+H)⁺ 386.

Example A-24

N-[3-(4-Phenethyl-piperazine-1-sulfonyl)-phenyl]-acrylamide $\delta_H$ (500 MHz, DMSO) 10.59 (1H, s), 8.23 (1H, s), 7.99 (1H, d), 7.67 (1H, t), 7.49 (1H, d), 7.34-7.17 (5H, m), 6.54-6.32 (2H, m), 5.89 (1H, d), 3.34 (4H, obscured), 3.01-2.87 (6H, m), 2.76-2.63 (2H, m). Tr=3.03 min, m/z (ES⁺) (M+H)⁺ 400.

Example A-25

N-{3-[4-(3-Phenyl-propyl)-piperazine-1-sulfonyl]-phenyl}-acrylamide $\delta_H$ (500 MHz, DMSO) 10.51 (1H, s), 8.14 (1H, s), 7.92 (1H, d), 7.62 (1H, t), 7.41 (1H, d), 7.26-7.11 (5H, m), 6.45-6.28 (2H, m), 5.81 (1H, d), 2.94-2.82 (4H, m), 2.46-2.37 (4H, m), 2.29-2.21 (2H, m), 1.71-1.54 (2H, m). Tr=3.14 min, m/z (ES⁺) (M+H)⁺ 414.

Example A-26

N-[3-(4-Phenyl-piperazine-1-sulfonyl)-phenyl]-acrylamide $\delta_H$ (500 MHz, DMSO) 10.57 (1H, s), 8.21 (1H, s), 7.94 (1H, d), 7.62 (1H, t), 7.44 (1H, d), 7.18 (2H, t), 6.90 (2H, d), 6.79 (1H, t), 6.48-6.26 (2H, m), 5.84 (1H, d), 3.28-3.18 (4H, m), 3.06-2.98 (4H, m). Tr=4.30 min, m/z (ES⁺) (M+H)⁺ 372.

Example A-27

N-{3-[4-(4-Phenyl-butyl)-piperazine-1-sulfonyl]-phenyl}-acrylamide $\delta_H$ (500 MHz, DMSO) 10.51 (1H, s), 8.17 (1H, s), 7.92 (1H, d), 7.59 (1H, t), 7.42 (1H, d), 7.28-7.10 (5H, m), 6.49-6.38 (2H, m), 5.82 (1H, d), 2.91-2.82 (4H, m), 2.43-2.36 (4H, m), 2.25 (1H, t), 1.52-1.43 (2H, m), 1.41-1.28 (2H, m). Tr=3.22 min, m/z (ES⁺) (M+H)⁺ 428.

Example A-28

N-[4-(7-Trifluoromethyl-3,4-dihydro-2H-quinoline-1-sulfonyl)-phenyl]-acrylamide $\delta_H$ (500 MHz, CDCl₃) 8.09 (1H, s), 7.96 (1H, s), 7.64 (2H, d), 7.51 (2H, d), 7.27 (1H, t), 7.14 (1H, d), 6.50-6.22 (2H, m), 5.81 (1H, d), 3.82 (2H, t), 2.51 (2H, t), 1.71-1.62 (2H, m). Tr=4.65 min, m/z (ES⁺) (M+H)⁺ 411.

Example A-29

5-(4-Acryloylamino-benzenesulfonyl)-hexahydro-pyrrolo[3,4-c]pyrrole-2-carboxylic acid benzyl ester $\delta_H$ (250 MHz, DMSO) 10.56 (1H, s), 7.91 (2H, d), 7.72 (2H, d), 7.38-7.20 (5H, m), 6.51-6.22 (2H, m), 5.82 (1H, dd), 4.98 (2H, d), 3.34 (6H, obscured), 3.04-2.83 (4H, m), 2.81-2.70 (2H, m). Tr=3.91 min, m/z (ES⁺) (M+H)⁺ 456.

Example A-30

{2-[(4-Acryloylamino-benzenesulfonyl)-methyl-amino]-ethyl}-methyl-carbamic acid benzyl ester $\delta_H$ (500 MHz, CDCl₃) 7.72-7.56 (5H, m), 7.31-7.18 (5H, m), 6.44-6.15 (2H, m), 5.77 (1H, d), 5.06 (2H, s), 3.45-3.36 (2H, m), 3.16-3.03 (2H, m), 2.94-2.91 (3H, m), 2.74 (3H, s), 2.55 (2H, s). Tr=4.17 min, m/z (ES⁺) (M+H)⁺ 432.

Example A-31

4-(4-Acryloylamino-benzenesulfonyl)-2-phenyl-piperazine-1-carboxylic acid tert-butyl ester $\delta_H$ (500 MHz, CDCl₃) 7.83 (2H, d), 7.72 (2H, d), 7.58 (1H, s), 7.46-7.27 (5H, m), 6.54-6.26 (2H, m), 5.91 (1H, d), 5.41 (1H, s), 4.35 (1H, d), 3.98 (1H, d), 3.61 (1H, d), 3.05-2.91 (1H, m), 2.68-2.61 (1H, m), 2.43-2.38 (1H, m), 1.44 (9H, s). Tr=4.65 min, m/z (ES⁺) (M+Na)⁺ 494.

Example A-32

4-(4-Acryloylamino-benzenesulfonyl)-2-phenyl-piperazine-1-carboxylic acid tert-butyl ester $\delta_H$ (250 MHz, CDCl₃) 7.82-7.66 (4H, m), 7.42 (1H, s), 7.37-7.28 (5H, m), 6.55-6.16 (2H, m), 5.85 (1H, dd), 3.95 (1H, dd), 3.78-3.69 (2H, m), 3.20-3.06 (2H, m), 2.52-2.39 (1H, m), 2.20 (1H, t). Tr=4.65 min, m/z (ES⁺) (M+H)⁺ 494.

Example A-33

N-{4-[(2,3-Dihydro-benzo[1,4]dioxin-2-ylmethyl)-isopropyl-sulfamoyl]-phenyl}-acrylamide $\delta_H$ (500 MHz, MeOD) 7.90-7.81 (4H, m), 6.88-6.69 (4H, m), 6.48-6.36 (2H, m), 5.83 (1H, dd), 4.54-4.46 (1H, m), 4.38 (1H, dd), 4.09-4.02 (2H, m), 3.48-3.32 (2H, m), 2.04 (1H, s), 1.07 (3H, d), 0.99 (3H, d). Tr=4.32 min, m/z (ES⁺) (M+H)⁺ 417.

Example A-34

N-{4-[Cyclopropyl-(4-piperidin-1-yl-benzyl)-sulfamoyl]-phenyl}-acrylamide $\delta_H$ (250 MHz, MeOD) 7.82 (4H, q), 7.61-7.43 (5H, m), 6.46-6.38 (2H, m), 5.86 (1H, dd), 4.49 (2H, s), 3.68-3.58 (4H, m), 2.19-1.76 (8H, m), 0.67-0.61 (4H, m). Tr=3.11 min, m/z (ES⁺) (M+H)⁺ 440.55.

Example A-35

N-{4-[Methyl-(3-morpholin-4-yl-benzyl)-sulfamoyl]-phenyl}-acrylamide $\delta_H$ (500 MHz, MeOD) 7.94 (2H, d), 7.81 (2H, d), 7.21 (1H, t), 6.93-6.77 (4H, m), 6.49-6.38 (2H, m), 5.84 (1H, dd), 4.14 (2H, s), 3.84-3.78 (4H, m), 3.11-3.06 (4H, m), 2.59 (3H, s). Tr=4.03 min, m/z (ES⁺) (M+H)⁺ 415.95.

Example A-36

N-{4-[Methyl-(2-morpholin-4-yl-pyridin-4-ylmethyl)-sulfamoyl]-phenyl}-acrylamide $\delta_H$ (500 MHz, MeOD) 8.06 (1H, d), 7.92 (2H, d), 7.83 (2H, d), 6.71-6.67 (2H, m), 6.48-6.38 (2H, m), 5.86 (1H, dd), 4.16

(2H, s), 3.81-3.76 (4H, m), 3.44-3.39 (4H, m), 3.36 (3H, s), 2.65 (3H, s). Tr=2.73 min, m/z (ES$^+$) (M+H)$^+$417.05.

Example A-37

N-(4-{Methyl-[4-(4-methyl-piperazin-1-ylmethyl)-benzyl]-sulfamoyl}-phenyl)-acrylamide $\delta_H$ (500 MHz, MeOD) 7.94 (2H, d), 7.83 (2H, d), 7.46-7.22 (6H, m), 6.48-6.37 (2H, m), 5.89 (1H, dd), 4.21 (2H, s), 4.08 (2H, s), 3.46-3.38 (4H, m), 3.22-3.15 (4H, m), 2.94 (3H, s), 2.60 (3H, s), 2.05 (6H, s). Tr=2.65 min, m/z (ES$^+$) (M+H)$^+$ 443.10.

Example A-38

N-{4-[Methyl-(3,4,5,6-tetrahydro-2H-[1,2]bipyridinyl-4'-ylmethyl)-sulfamoyl]-phenyl}-acrylamide $\delta_H$ (500 MHz, MeOD) 7.99 (1H, d), 7.92 (2H, d), 7.81 (2H, d), 6.67 (1H, s), 6.58 (1H, d), 6.49-6.38 (2H, m), 5.84 (1H, dd), 4.14 (2H, s), 3.50-3.44 (4H, m), 2.66 (3H, s), 1.69-1.54 (6H, m). Tr=2.89 min, m/z (ES$^+$) (M+H)$^+$ 415.10.

Example A-39

N-{4-[Methyl-(2-morpholin-4-yl-thiazol-4-ylmethyl)-sulfamoyl]-phenyl}-acrylamide $\delta_H$ (250 MHz, MeOD) 7.84 (2H, d), 7.70 (2H, d), 6.58 (1H, s), 6.47-6.40 (2H, m), 5.84 (1H, dd), 4.16 (2H, s), 3.74-3.65 (4H, m), 3.36-3.28 (5H, m), 2.84 (3H, s), 2.04 (3H, s). Tr=3.73 min, m/z (ES$^+$) (M+H)$^+$ 423.

Example A-40: N-(4-{Methyl-[6-(tetrahydro-pyran-4-yloxy)-pyridin-3-ylmethyl]-sulfamoyl}-phenyl)-acrylamide $\delta_H$ (250 MHz, MeOD) 8.05-8.01 (1H, m), 7.94-7.79 (4H, m), 7.67-7.61 (1H, m), 6.75 (1H, d), 6.46-6.41 (2H, m), 5.84 (1H, m), 5.21-5.09 (1H, m), 4.09 (2H, s), 3.99-3.88 (2H, m), 3.66-3.57 (2H, m), 3.36-3.27 (3H, m), 2.58 (3H, s), 2.08 (1H, obscured), 1.81-1.63 (2H, m). Tr=3.97 min, m/z (ES$^+$) (M+H)$^+$ 432.05.

Example A-41

N-{4-[Methyl-(1-thiophen-2-ylmethyl-piperidin-4-ylmethyl)-sulfamoyl]-phenyl}-acrylamide $\delta_H$ (500 MHz, MeOD) 7.91 (2H, d), 7.75 (2H, d), 7.68 (1H, d), 7.36 (1H, s), 7.14 (1H, t), 6.47-6.37 (2H, m), 5.82 (1H, dd), 4.56 (2H, s), 3.57 (2H, d), 3.04-2.97 (2H, m), 2.87 (2H, d), 2.74 (3H, s), 2.10-2.08 (1H, s), 2.04 (3H, s), 1.98-1.87 (1H, m), 1.51-1.42 (2H, m). Tr=2.90 min, m/z (ES$^+$) (M+H)$^+$ 434.

Example A-42

N-(4-{Methyl-[1-(6-methyl-pyrazin-2-yl)-piperidin-3-ylmethyl]-sulfamoyl}-phenyl)-acrylamide $\delta_H$ (250 MHz, MeOD) 7.96-7.71 (4H, m), 7.58 (1H, s), 6.46-6.39 (2H, m), 5.81 (1H, dd), 4.31-4.08 (2H, m), 3.11-2.96 (2H, m), 2.88-2.74 (2H, m), 2.73 (3H, s), 2.33 (3H, s), 1.96-1.72 (3H, m), 1.61-1.32 (2H, m). Tr=4.04 min, m/z (ES$^+$) (M+H)$^+$ 430.49.

Example A-43

N-{4-[Methyl-(2-morpholin-4-yl-pyrimidin-5-ylmethyl)-sulfamoyl]-phenyl}-acrylamide $\delta_H$ (250 MHz, MeOD) 8.27 (1H, s), 7.91-7.76 (4H, m), 6.46-6.38 (2H, m), 5.81 (1H, dd), 4.02 (2H, s), 3.81-3.66 (8H, m), 2.57 (2H, s). Tr=3.66 min, m/z (ES$^+$) (M+H)$^+$ 418.05.

Example A-44

[1-(4-Acryloylamino-benzenesulfonyl)-piperidin-4-yl]-methyl-carbamic acid tert-butyl ester $\delta_H$ (500 MHz, DMSO) 10.59 (1H, s), 7.92 (2H, d), 7.70 (2H, d), 6.50-6.29 (2H, m), 5.82 (1H, dd), 3.79-3.52 (3H, m), 2.61 (3H, s), 2.29-2.20 (2H, m), 1.72-1.51 (4H, m), 1.42 (9H, s). Tr=4.25 min, m/z (ES$^+$) (M+Na)$^+$ 446.

Example A-45

N-(4-{Methyl-[4-(4-methyl-[1,4]diazepan-1-yl)-benzyl]-sulfamoyl}-phenyl)-acrylamide $\delta_H$ (500 MHz, CDCl$_3$) 7.92 (1H, s), 7.85 (1H, d), 7.76 (1H, d), 7.16 (2H, d), 6.61 (2H, d), 6.51-6.36 (2H, m), 5.87 (1H, dd), 4.15-4.06 (4H, m), 3.72-3.68 (1H, m), 3.61-3.38 (6H, m), 3.12-3.01 (2H, m), 2.81 (3H, s), 2.61 (3H, s), 2.32 (1H, m), 1.65-1.44 (11H, m). Tr=2.99 min, m/z (ES$^+$) (M+H)$^+$ 443.

Example A-46

N-[4-(4-Benzyl-2-isopropyl-piperazine-1-sulfonyl)-phenyl]-acrylamide $\delta_H$ (500 MHz, CDCl$_3$) 7.85-7.66 (5H, m), 7.32-7.19 (5H, m), 6.54-6.27 (2H, m), 5.86 (1H, dd), 3.72 (1H, d), 3.46-3.38 (2H, m), 3.29-3.14 (2H, m), 2.71 (1H, d), 2.54 (1H, d), 2.44-2.33 (1H, m), 1.80-1.71 (2H, m), 0.94 (3H, d), 0.78 (3H, d). Tr=3.10 min, m/z (ES$^+$) (M+H)$^+$ 428.

Example A-47

N-{4-[Benzyl-(4-chloro-benzyl)-sulfamoyl]-phenyl}-acrylamide $\delta_H$ (500 MHz, CDCl$_3$) 7.89 (1H, s), 7.82-7.75 (4H, m), 7.23-7.16 (5H, m), 7.07-6.95 (4H, m), 6.52-6.27 (2H, m), 5.84 (1H, dd), 4.31 (2H, s), 4.28 (2H, s). Tr=4.94 min, m/z (ES$^+$) (M+Na)$^+$ 463.

Example A-48

N-{4-[4-(4,6-Dimethoxy-pyrimidin-2-ylmethyl)-piperazine-1-sulfonyl]-phenyl}-acrylamide $\delta_H$ (250 MHz, CDCl$_3$) 8.07 (1H, s), 7.79-7.62 (4H, m), 6.54-6.22 (2H, m), 5.92 (1H, s), 5.81 (1H, dd), 3.92 (6H, s), 3.66 (3H, s), 3.14-3.02 (4H, m), 2.82-2.71 (4H, m). Tr=2.72 min, m/z (ES$^+$) (M+H)$^+$ 448.

Example A-49

N-{4-[4-(2-Oxo-2-piperidin-1-yl-ethyl)-piperazine-1-sulfonyl]-phenyl}-acrylamide $\delta_H$ (250 MHz, CDCl$_3$) 8.62 (1H, s), 7.83-7.59 (4H, m), 6.52-6.28 (2H, m), 5.77 (1H, dd), 3.59-3.48 (3H, m), 3.47-

3.34 (2H, m), 3.21 (2H, s), 3.11-2.95 (4H, m), 2.66-2.54 (4H, m), 1.66-1.42 (7H, m). Tr=2.58 min, m/z (ES$^+$) (M+H)$^+$421.

Example A-50

N-{4-[4-(3-Pyrazin-2-yl-[1,2,4]oxadiazol-5-yl)-piperidine-1-sulfonyl]-phenyl}-acrylamide $\delta_H$ (250 MHz, CDCl$_3$) 9.33 (1H, s), 8.78-8.74 (2H, m), 7.82-7.67 (5H, m), 6.51-6.20 (2H, m), 5.82 (1H, dd), 3.81-3.69 (2H, m), 3.15-3.01 (1H, m), 2.67-2.53 (2H, m), 2.31-2.02 (4H, m). Tr=3.64 min, m/z (ES$^+$) (M+Na)$^+$ 463.

Example A-51

N-{4-[4-(3-Morpholin-4-yl-propyl)-piperazine-1-sulfonyl]-phenyl}-acrylamide $\delta_H$ (500 MHz, CDCl$_3$) 7.82-7.69 (5H, m), 6.51-6.26 (2H, m), 5.89 (1H, dd), 3.78-3.66 (4H, m), 3.07-2.96 (4H, m), 2.56-2.48 (4H, m), 2.46-2.28 (8H, m), 1.66-1.57 (2H, m). Tr=1.90 min, m/z (ES$^+$) (M+H)$^+$ 423.

Example A-52

N-[4-(5-Dimethylsulfamoyl-2,3-dihydro-indole-1-sulfonyl)-phenyl]-acrylamide $\delta_H$ (500 MHz, CDCl$_3$) 7.82-7.10 (7H, m), 7.48 (1H, s), 6.51-6.23 (2H, m), 5.84 (1H, dd), 4.01 (2H, t), 3.05 (2H, t), 2.76 (2H, s), 2.68 (5H, s). Tr=3.98 min, m/z (ES$^+$) (M+Na)$^+$ 457.

Example A-53

4-(4-Acryloylamino-benzenesulfonyl)-2-isopropyl-piperazine-1-carboxylic acid tert-butyl ester $\delta_H$ (500 MHz, CDCl$_3$) 7.79-7.68 (4H, m), 7.60 (1H, s), 6.48-6.26 (2H, m), 5.88 (1H, dd), 4.11-3.87 (1H, m), 3.87-3.58 (3H, m), 3.09-3.01 (1H, m), 2.58-2.19 (3H, m), 1.40 (9H, s), 1.04 (3H, d), 0.87 (3H, d). Tr=4.40 min, m/z (ES$^+$) (M+Na)$^+$ 460.

Example A-54

4-(4-Acryloylamino-benzenesulfonyl)-2-benzyl-piperazine-1-carboxylic acid tert-butyl ester $\delta_H$ (500 MHz, CDCl$_3$) 7.83-7.69 (5H, m), 7.35-7.19 (5H, m), 6.52-6.26 (2H, m), 5.89 (1H, dd), 4.38-4.26 (1H, m), 4.15-3.95 (1H, m), 4.78-3.69 (1H, m), 3.57 (1H, d), 3.36-3.22 (1H, m), 3.14-3.06 (1H, m), 2.92-2.80 (1H, m), 2.27-2.17 (2H, m), 1.36 (9H, s). Tr=4.81 min, m/z (ES$^+$) (M+Na)$^+$ 508.

Example A-55

N-[4-(3-Benzyl-piperazine-1-sulfonyl)-phenyl]-acrylamide $\delta_H$ (500 MHz, CDCl$_3$) 8.04 (1H, s), 7.86-7.70 (4H, m), 7.37-7.15 (5H, m), 6.54-6.32 (2H, m), 5.87 (1H, dd), 5.36 (2H, s), 3.71-3.56 (2H, m), 3.07-2.96 (2H, m), 2.84-2.75 (2H, m), 2.53-2.39 (2H, m), 2.16 (1H, t), 1.92 (1H, br s). Tr=2.80 min, m/z (ES$^+$) (M+H)$^+$ 386.

Example A-56

N-{4-[Methyl-(3-pyrrolidin-1-ylmethyl-benzyl)-sulfamoyl]-phenyl}-acrylamide $\delta_H$ (500 MHz, MeOD) 7.94-7.81 (4H, m), 7.52-7.43 (4H, m), 6.53-6.38 (2H, m), 5.83 (1H, dd), 4.38 (2H, s), 4.23 (2H, s), 2.61 (3H, s), 2.14-1.97 (4H, m), 1.39-1.22 (6H, m). Tr=2.83 min, m/z (ES$^+$) (M+H)$^+$ 414.

Example A-57

N-{4-[4-(2-Trifluoromethyl-phenyl)-piperazine-1-sulfonyl]-phenyl}-acrylamide $\delta_H$ (500 MHz, CDCl$_3$) 7.86-7.79 (4H, m), 7.63-7.45 (3H, m), 7.35 (1H, d), 7.27-7.24 (3H, m), 6.54-6.26 (2H, m), 5.87 (1H, dd), 3.24-3.15 (4H, m), 3.05-2.97 (4H, m). Tr=4.36 min, m/z (ES$^+$) (M+H)$^+$ 440.

Example A-58

N-{4-[4-(3-Methyl-pyridin-2-yl)-piperazine-1-sulfonyl]-phenyl}-acrylamide $\delta_H$ (500 MHz, CDCl$_3$) 8.13 (1H, dd), 7.84-7.75 (4H, m), 7.58 (1H, s), 7.38 (1H, dd), 6.90-6.86 (1H, m), 6.54-6.31 (2H, m), 5.86 (1H, dd), 3.28-3.16 (8H, m), 2.18 (3H, s). Tr=3.02 min, m/z (ES$^+$) (M+H)$^+$ 387.

Example A-59

N-{4-[4-(6-Trifluoromethyl-pyridin-2-yl)-piperazine-1-sulfonyl]-phenyl}-acrylamide $\delta_H$ (500 MHz, CDCl$_3$) 7.82-7.71 (4H, m), 7.63-7.58 (1H, m), 7.42 (1H, s), 6.95 (1H, d), 6.74 (1K' d), 6.54-6.18 (2H, m), 5.85 (1H, dd), 3.77-3.68 (4H, m), 3.16-3.07 (4H, m). Tr=4.32 min, m/z (ES$^+$) (M+H)$^+$ 441.

Example A-60

N-{4-[4-(6-Methyl-pyridin-2-yl)-piperazine-1-sulfonyl]-phenyl}-acrylamide $\delta_H$ (250 MHz, CDCl$_3$) 7.82-7.69 (4H, m), 7.59 (1H, s), 7.36 (1H, t), 6.55-6.21 (4H, m), 5.86 (1H, dd), 3.68-3.59 (4H, m), 3.14-3.06 (4H, m), 2.38 (3H, s). Tr=2.64 min, m/z (ES$^+$) (M+H)$^+$ 387.

Example A-61

N-[4-(Hexahydro-pyrrolo[1,2-]pyrazine-2-sulfonyl)-phenyl]-acrylamide $\delta_H$ (500 MHz, CDCl$_3$) 7.81-7.76 (4H, m), 7.59 (1H, s), 6.54-6.26 (2H, m), 5.86 (1H, dd), 3.90-3.84 (1H, m), 3.75-3.66 (1H, m), 3.06-2.98 (2H, m), 2.54-2.48 (1H, m), 2.36-2.28 (3H, m), 1.91-1.68 (3H, m), 1.36-1.27 (1H, m). Tr=2.38 min, m/z (ES$^+$) (M+H)$^+$ 336.

Example A-62

N-{4-[4-(2-Methoxy-ethyl)-piperazine-1-sulfonyl]-phenyl}-acrylamide $\delta_H$ (500 MHz, CDCl$_3$) 7.79-7.67 (4H, m), 7.63 (1H, s), 6.54-6.26 (2H, m), 5.88 (1H, dd), 3.46 (2H, t), 3.32 (3H, s), 3.09-3.04 (4H, m), 2.63-2.54 (6H, m). Tr=2.32 min, m/z (ES$^+$) (M+H)$^+$ 354.

Example A-63

N-[4-(4-Cyclopentyl-piperazine-1-sulfonyl)-phenyl]-acrylamide $\delta_H$ (500 MHz, CDCl$_3$) 7.78-7.64 (5H, m), 6.52-6.26 (2H, m), 5.86 (1H, dd), 3.12-3.00 (4H, m), 2.62-2.47 (5H, m), 1.88-1.78 (2H, m), 1.68-1.47 (5H, m), 1.34-1.21 (2H, m). Tr=2.58 min, m/z (ES$^+$) (M+H)$^+$ 364.

Example A-64

N-[4-(4-Cyclohexyl-piperazine-1-sulfonyl)-phenyl]-acrylamide $\delta_H$ (500 MHz, CDCl$_3$) 7.79-7.67 (4H, m), 7.59 (1H, s), 6.52-6.24 (2H, m), 5.84 (1H, dd), 3.08-2.96 (4H, m), 2.68-2.59 (4H, m), 2.29-2.16 (1H, m), 1.81-1.73 (4H, m), 1.66-1.54 (2H, m), 1.57-1.02 (6H, m). Tr=2.74 min, m/z (ES$^+$) (M+H)$^+$ 378.

Example A-65

N-{4-[4-(Tetrahydro-furan-2-ylmethyl)-piperazine-1-sulfonyl]-phenyl}-acrylamide $\delta_H$ (500 MHz, CDCl$_3$) 7.79-7.65 (5H, m), 6.53-6.26 (2H, m), 5.84 (1H, dd), 4.00-3.93 (1H, m), 3.87-3.81 (1H, m), 3.74-3.66 (1H, m), 3.08-2.98 (4H, m), 2.66-2.54 (4H, m), 2.49-2.38 (2H, m), 1.98-1.78 (3H, m), 1.48-1.41 (1H, m). Tr=2.51 min, m/z (ES$^+$) (M+H)$^+$ 380.

Example A-66

N-[4-(4-Cyclooctyl-piperazine-1-sulfonyl)-phenyl]-acrylamide $\delta_H$ (500 MHz, CDCl$_3$) 7.78-7.68 (4H, m), 7.53 (1H, s), 6.52-6.26 (2H, m), 5.86 (1H, dd), 3.07-2.94 (4H, m), 2.64-2.50 (5H, m), 1.73-1.36 (16H, m). Tr=2.99 min, m/z (ES$^+$) (M+H)$^+$ 406.

Example A-67

N-[4-(3-Phenoxy-piperidine-1-sulfonyl)-phenyl]-acrylamide $\delta_H$ (500 MHz, CDCl$_3$) 7.83-7.71 (4H, m), 7.63 (1H, s), 7.31-7.26 (3H, m), 7.01-6.86 (3H, m), 6.52-6.26 (2H, m), 5.86 (1H, dd), 4.41-4.36 (1H, m), 3.89-3.78 (1H, m), 3.57-3.49 (1H, m), 2.61-2.52 (2H, m), 2.11-2.02 (3H, m), 1.92-1.86 (1H, m), 1.77-1.66 (1H, m), 1.51-1.42 (1H, m). Tr=4.22 min, m/z (ES$^+$) (M+H)$^+$ 387.

Example A-68

N-[4-(4-Furan-2-yl-2,3-dihydro-benzo[ ][1,4]diazepine-1-sulfonyl)-phenyl]-acrylamide $\delta_H$ (500 MHz, CDCl$_3$) 7.60-7.56 (1H, m), 7.52-7.38 (6H, m), 7.24-7.11 (2H, m), 6.78 (1H, d), 6.48-6.16 (3H, m), 5.84 (1H, dd), 4.46-4.38 (2H, m), 2.75-2.68 (2H, m). Tr=3.64 min, m/z (ES$^+$) (M+H)$^+$ 422.

Example A-69

4-(4-Acryloylamino-benzenesulfonyl)-2-methyl-piperazine-1-carboxylic acid benzyl ester $\delta_H$ (500 MHz, CDCl$_3$) 7.80-7.66 (5H, m), 7.37-7.27 (5H, m), 6.52-6.22 (2H, m), 5.86 (1H, dd), 5.08 (2H, q), 4.48-4.36 (1H, m), 4.00 (1H, d), 3.68 (1H, d), 3.52 (1H, d), 3.21 (1H, t), 2.44-2.37 (1H, m), 2.28-2.21 (1H, m), 1.32 (3H, d). Tr=4.28 min, m/z (ES$^+$) (M+Na)$^+$ 466.

Example A-70

N-[4-(3-Isopropyl-piperazine-1-sulfonyl)-phenyl]-acrylamide $\delta_H$ (250 MHz, MeOD) 7.91 (2H, d), 7.74 (2H, d), 6.52-6.42 (2H, m), 5.82 (1H, dd), 3.71-3.52 (2H, m), 3.06-2.96 (1H, m), 2.86-2.73 (1H, m), 2.48-2.25 (2H, m), 2.06-1.97 (2H, m), 1.62-1.51 (1H, m), 0.93-0.81 (6H, m). Tr=2.65 min, m/z (ES$^+$) (M+H)$^+$ 338.

Example A-71

4-(4-Acryloylamino-benzenesulfonyl)-2-furan-2-yl-piperazine-1-carboxylic acid tert-butyl ester $\delta_H$ (250 MHz, CDCl$_3$) 7.84-7.65 (5H, m), 7.36 (1H, d), 6.54-6.22 (4H, m), 5.91 (1H, dd), 5.36 (1H, br s), 4.18-4.14 (1H, m), 3.99-3.62 (1H, m), 3.07-2.93 (1H, m), 2.64-2.57 (1H, m), 2.39-2.26 (1H, m), 1.44 (9H, s). Tr=4.26 min, m/z (ES$^+$) (M+Na)$^+$ 484.

Example A-72

N-[4-(4-Pyridin-2-yl-piperazine-1-sulfonyl)-phenyl]-acrylamide $\delta_H$ (500 MHz, CDCl$_3$) 8.16-8.12 (1H, m), 7.80-7.72 (4H, m), 7.54-7.47 (2H, m), 6.67-6.61 (2H, m), 6.51-6.22 (2H, m), 5.89 (1H, dd), 3.69-3.62 (4H, m), 3.14-3.08 (4H, m). Tr=2.55 min, m/z (ES$^+$) (M+H)$^+$ 373.

Example A-73

N-{4-[4-(2,4-Difluoro-phenyl)-piperazine-1-sulfonyl]-phenyl}-acrylamide $\delta_H$ (500 MHz, CDCl$_3$) 7.84-7.73 (4H, m), 7.49 (1H, s), 6.93-6.74 (3H, m), 6.54-6.22 (2H, m), 5.86 (1H, dd), 3.24-3.09 (8H, m). Tr=4.24 min, m/z (ES$^+$) (M+H)$^+$ 408.

Example A-74

N-[4-(3-Furan-2-yl-piperazine-1-sulfonyl)-phenyl]-acrylamide $\delta_H$ (500 MHz, CDCl$_3$) 7.91 (1H, s), 7.79 (2H, d), 7.71 (2H, d), 7.34 (1H, s), 6.51-6.22 (4H, m), 5.82 (1H, d), 4.04-4.00 (1H, m), 3.78-3.72 (1H, m), 3.59-3.54 (1H, m), 3.11-2.96 (2H, m), 2.57-2.49 (2H, m), 1.90 (1H, br s). Tr=2.47 min, m/z (ES$^+$) (M+H)$^+$ 362.

Example A-75

N-{4-[4-(4-Chloro-2-fluoro-phenyl)-piperazine-1-sulfonyl]-phenyl}-acrylamide $\delta_H$ (500 MHz, DMSO) 10.61 (1H, s), 7.92 (2H, d), 7.73 (2H, d), 7.34 (1H, dd), 7.15 (1H, d), 7.05 (1H, t), 6.49-6.28 (2H, m), 5.81 (1H, dd), 3.09-2.98 (8H, m). Tr=4.47 min, m/z (ES$^+$) (M+H)$^+$ 424.

Example A-76

N-{4-[4-(1-Methyl-piperidin-4-yl)-piperazine-1-sulfonyl]-phenyl}-acrylamide $\delta_H$ (250 MHz, CDCl$_3$) 7.81-7.66 (4H, m), 7.59 (1H, s), 6.55-6.23 (2H, m), 5.86 (1H, dd), 3.07-2.96 (4H, m), 2.95-2.83 (2H, m), 2.67-2.58 (4H, m), 2.29-2.16 (4H, m), 1.99-1.84 (2H, m), 1.77-1.64 (2H, m), 1.57-1.48 (2H, m). Tr=1.88 min, m/z (ES$^+$) (M+H)$^+$ 393.

Example A-77

N-{4-[4-(2-Dimethylamino-ethyl)-piperazine-1-sulfonyl]-phenyl}-acrylamide $\delta_H$ (250 MHz, CDCl$_3$) 7.82-4.69 (4H, m), 7.61 (1H, s), 6.56-6.22 (2H, m), 5.85 (1H, dd), 3.08-3.00 (4H, m), 2.61-2.55 (4H, m), 2.48-2.37 (4H, m), 2.22 (6H, s). Tr=2.28 min, m/z (ES$^+$) (M+H)$^+$ 367.

Example A-78

N-{4-[4-(2-Piperidin-1-yl-ethyl)-piperazine-1-sulfonyl]-phenyl}-acrylamide $\delta_H$ (250 MHz, CDCl$_3$) 7.84-7.66 (4H, m), 7.62 (1H, s), 6.56-6.21 (2H, m), 5.85 (1H, dd), 3.08-2.95 (4H, m), 2.61-2.27 (12H, m), 1.62-1.35 (6H, m). Tr=2.41 min, m/z (ES$^+$) (M+H)$^+$ 407.

Example A-793

N-{4-[4-(3-Trifluoromethyl-phenyl)-piperazine-1-sulfonyl]-phenyl}-acrylamide $\delta_H$ (500 MHz, CDCl$_3$) 7.82-7.77 (4H, m), 7.47 (1H, s), 7.34 (1H, t), 7.14 (1H, d), 7.08 (1H, s), 7.04 (1H, dd), 6.54-6.24 (2H, m), 5.87 (1H, dd), 3.36-3.28 (4H, m), 3.22-3.16 (4H, m). Tr=4.43 min, m/z (ES$^+$) (M+H)$^+$ 440.

Example A-80

N-{4-[4-(4-Trifluoromethyl-phenyl)-piperazine-1-sulfonyl]-phenyl}-acrylamide $\delta_H$ (500 MHz, CDCl$_3$) 7.84-7.73 (4H, m), 7.51-7.43 (3H, m), 6.87 (2H, d), 6.53-6.22 (2H, m), 5.87 (1H, dd), 3.37-3.32 (4H, m), 3.19-3.14 (4H, m). Tr=4.51 min, m/z (ES$^+$) (M+H)$^+$ 440.

Example A-81

N-{4-[4-(3-Trifluoromethyl-pyridin-2-yl)-piperazine-1-sulfonyl]-phenyl}-acrylamide $\delta_H$ (500 MHz, CDCl$_3$) 8.44 (1H, dd), 7.86 (1H, dd), 7.84-7.73 (4H, m), 7.47 (1H, s), 7.06-7.01 (1H, m), 6.54-6.24 (2H, m), 5.84 (1H, dd), 3.40-3.33 (4H, m), 3.21-3.14 (4H, m). Tr=4.19 min, m/z (ES$^+$) (M+H)$^+$ 441.

Example A-82

N-{4-[2-(4-Trifluoromethyl-phenyl)-pyrrolidine-1-sulfonyl]-phenyl}-acrylamide $\delta_H$ (250 MHz, MeOD) 7.92-7.76 (4H, m), 7.62-7.50 (4H, m), 6.52-6.41 (2H, m), 5.84 (1H, dd), 4.86-4.77 (1H, m), 3.68-3.58 (1H, m), 3.52-3.41 (1H, m), 2.15-2.03 (1H, m), 1.92-1.54 (3H, m). Tr=4.41 min, m/z (ES$^+$) (M+H)$^+$ 425.

Example A-83

N-{4-[3-(Piperidine-1-carbonyl)-piperidine-1-sulfonyl]-phenyl}-acrylamide $\delta_H$ (250 MHz, MeOD) 7.96-7.64 (4H, m), 6.51-6.38 (2H, m), 5.82 (1H, dd), 3.84-3.72 (2H, m), 3.56-3.445 (4H, m), 2.96-2.82 (1H, m), 2.46-2.18 (2H, m), 1.88-1.22 (10H, m). Tr=3.70 min, m/z (ES$^+$) (M+H)$^+$ 406.

Example A-84

N-[4-(Thiomorpholine-4-sulfonyl)-phenyl]-acrylamide $\delta_H$ (500 MHz, CDCl$_3$) 7.82-7.69 (4H, m), 7.46 (1H, s), 6.54-6.23 (2H, m), 5.86 (1H, dd), 3.40-3.31 (4H, m), 2.74-2.71 (4H, m). Tr=3.54 min, m/z (ES$^+$) (M+H)$^+$ 313.

Example A-85

N-[4-(4-Thiazol-2-yl-piperazine-1-sulfonyl)-phenyl]-acrylamide $\delta_H$ (500 MHz, CDCl$_3$) 7.81-7.68 (5H, m), 7.14 (1H, d), 6.60 (1H, d), 6.52-6.25 (2H, m), 5.84 (1H, dd), 3.62-3.57 (4H, m), 3.14-3.09 (4H, m). Tr=3.27 min, m/z (ES$^+$) (M+H)$^+$ 379.

Example A-86

N-[4-(4-Adamantan-1-yl-piperazine-1-sulfonyl)-phenyl]-acrylamide $\delta_H$ (500 MHz, CDCl$_3$) 7.82-7.77 (5H, m), 6.53-6.26 (2H, m), 5.84 (1H, d), 3.16-2.96 (4H, m), 2.95-2.72 (4H, m), 2.15 (3H, s), 1.68-1.54 (14H, m). Tr=2.80 min, m/z (ES$^+$) (M+H)$^+$ 430.

Example A-87

4-(4-Acryloylamino-benzenesulfonyl)-piperazine-1-carboxylic acid dimethylamide $\delta_H$ (500 MHz, DMSO) 10.59 (1H, s), 7.92 (2H, d), 7.71 (2H, d), 6.51-6.29 (2H, m), 5.82 (1H, d), 3.18-3.16 (4H, m), 2.89-2.83 (4H, m), 2.68 (6H, s). Tr=3.15 min, m/z (ES$^+$) (M+H)$^+$ 367.

Example A-88

4-(4-Acryloylamino-benzenesulfonyl)-2-methoxycarbonylmethyl-piperazine-1-carboxylic acid benzyl ester $\delta_H$ (500 MHz, CDCl$_3$) 7.84 (2H, d), 7.70 (2H, d), 7.50 (1H, s), 7.36-7.28 (5H, m), 6.52-6.22 (2H, m), 5.87 (1H, dd), 5.14-5.04 (2H, m), 4.76 (1H, br s), 4.08 (1H, br s), 3.74-3.60 (5H, m), 3.16 (1H, br s), 2.89 (1H, dd), 2.64 (1H, dd), 2.42 (1H, dd), 2.28-2.24 (1H, m). Tr=4.07 min, m/z (ES$^+$) (M+Na)$^+$ 524.

Example A-89

1-(4-Acryloylamino-benzenesulfonyl)-piperidine-4-carboxylic acid methyl ester $\delta_H$ (500 MHz, DMSO) 10.58 (1H, s), 7.91 (2H, d), 7.70 (2H, d), 6.49-6.29 (2H, m), 5.82 (1H, dd), 3.58 (3H, s), 3.52-3.48 (2H, m), 2.41-2.33 (3H, m), 1.92-1.86 (2H, m), 1.61-1.50 (2H, m). Tr=3.50 min, m/z (ES$^+$) (M+H)$^+$ 353.

Example A-90

N-{4-[4-(2-Morpholin-4-yl-2-oxo-ethyl)-piperazine-1-sulfonyl]-phenyl}-acrylamide $\delta_H$ (250 MHz CDCl$_3$) 7.83-7.70 (5H, m), 6.56-6.23 (2H, m), 5.86 (1H, dd), 3.72-3.48 (8H, m), 3.18 (2H, s), 3.09-2.98 (4H, m), 2.69-2.53 (4H, m). Tr=2.36 min, m/z (ES$^+$) (M+H)$^+$ 423.

Example A-91

N-{4-[4-(4-Methoxy-phenyl)-piperazine-1-sulfonyl]-phenyl}-acrylamide $\delta_H$ (500 MHz, DMSO) 15.8 (1H, s), 7.92 (2H, d), 7.73 (2H, d), 6.88 (2H, d), 6.78 (2H, d), 6.47-6.28 (2H, m), 5.83 (1H, dd), 3.66 (3H, s), 3.11-2.88 (8H, m). Tr=4.25 min, m/z (ES$^+$) (M+H)$^+$ 402.

Example A-92

N-[4-(4-Benzooxazol-2-yl-piperazine-1-sulfonyl)-phenyl]-acrylamide $\delta_H$ (500 MHz, CDCl$_3$) 7.82-7.22 (4H, m), 7.51 (1H, s), 7.36-7.01 (4H, m), 6.54-6.22 (2H, m), 6.85 (1H, d), 4.84-4.76 (4H, m), 3.18-3.09 (4H, m). Tr=3.83 min, m/z (ES$^+$) (M+H)$^+$ 413.

Example A-93

5-(4-Acryloylamino-benzenesulfonyl)-2,5-diazabicyclo[2.2.1]heptane-2-carboxylic acid tert-butyl ester $\delta_H$ (500 MHz, CDCl$_3$) 7.86-7.77 (4H, m), 7.58 (1H, s), 6.51-6.25 (2H, m), 5.86 (1H, d), 4.47 (2H, s), 3.51-3.13 (4H, m), 1.74-1.66 (1H, m), 1.46-1.24 (1H, m). Tr=3.81 min, m/z (ES$^+$) (M+Na)$^+$ 430.

Example A-94

N-[4-(4-Naphthalen-1-yl-piperazine-1-sulfonyl)-phenyl]-acrylamide $\delta_H$ (500 MHz, CDCl$_3$) 8.01 (1H, d), 7.88-7.81 (5H, m), 7.59-7.53 (2H, m), 7.48-7.39 (3H, m), 7.07 (1H, d), 6.56-6.26 (2H, m), 5.87 (1H, d), 3.48-3.06 (8H, m). Tr=4.56 min, m/z (ES$^+$) (M+H)$^+$ 422.

Example A-95

N-{4-[4-(4-Trifluoromethyl-pyrimidin-2-yl)-piperazine-1-sulfonyl]-phenyl}-acrylamide $\delta_H$ (250 MHz, CDCl$_3$) 8.47 (1H, d), 7.82-7.71 (4H, m), 7.52 (1H, s), 6.77 (1H, d), 6.54-6.18 (2H, m), 5.85 (1H, dd), 4.06-3.91 (4H, m), 3.12-3.04 (4H, m). Tr=4.26 min, m/z (ES$^+$) (M+H)$^+$ 442.

Example A-96

N-[4-(4-Pyrimidin-2-yl-piperazine-1-sulfonyl)-phenyl]-acrylamide $\delta_H$ (250 MHz, DMSO) 10.54 (1H, s), 8.31 (2H, d), 7.91 (2H, m), 7.69 (2H, m), 6.62 (1H, t), 6.50-6.23 (2H, m), 5.81 (1H, dd), 3.88-3.76 (4H, m), 2.99-2.91 (4H, m). Tr=3.60 min, m/z (ES$^+$) (M+H)$^+$ 374.

Example A-97

N-[4-(4-Furo[3,2-c]pyridin-4-yl-piperazine-1-sulfonyl)-phenyl]-acrylamide $\delta_H$ (250 MHz, DMSO) 10.55 (1H, s), 7.96-7.88 (4H, m), 7.74 (2H, d), 7.11 (2H, dd), 6.51-6.25 (2H, m), 5.80 (1H, dd), 3.74-3.63 (4H, m), 3.08-3.00 (4H, m). Tr=1.26 min, m/z (ES$^+$) (M+H)$^+$ 413.

Example A-98

N-{4-[4-(6-Methoxy-pyridin-2-yl)-piperazine-1-sulfonyl]-phenyl}-acrylamide $\delta_H$ (250 MHz, DMSO) 10.61 (1H, s), 7.92 (2H, d), 7.71 (2H, d), 7.41 (1H, t), 6.51-6.00 (4H, m), 5.82 (1H, dd), 3.73 (3H, s), 3.56-3.50 (4H, m), 2.98-2.90 (4H, m). Tr=4.09 min, m/z (ES$^+$) (M+H)$^+$ 403.

Example A-99

N-{4-[4-(4-Methoxy-pyrimidin-2-yl)-piperazine-1-sulfonyl]-phenyl}-acrylamide

δH (500 MHz, DMSO) 10.58 (1H, s), 8.04 (1H, d), 7.88 (2H, d), 7.71 (2H, d), 6.48-6.30 (2H, m), 6.06 (1H, d), 5.82 (1H, dd), 3.83-3.78 (7H, m), 2.94-2.88 (4H, m). Tr=3.28 min, m/z (ES⁺) (M+H)⁺ 404.

Example A-100

N-[4-(2,3,5,6-Tetrahydro-[1,2']bipyrazinyl-4-sulfonyl)-phenyl]-acrylamide $\delta_H$ (500 MHz, DMSO) 10.59 (1H, s), 8.28 (1H, s), 8.04 (1H, s), 7.92-7.71 (5H, m), 6.48-6.29 (2H, m), 5.82 (1H, dd), 3.69-3.61 (4H, m), 2.99-2.91 (4H, m). Tr=3.40 min, m/z (ES⁺) (M+H)⁺ 374.

Example A-101

N-{4-[4-(4-Methyl-pyridin-2-yl)-piperazine-1-sulfonyl]-phenyl}-acrylamide $\delta_H$ (500 MHz, DMSO) 10.58 (1H, s), 7.94-7.68 (5H, m), 6.62 (1H, s), 6.48-6.27 (3H, m), 5.82 (1H, dd), 3.58-3.52 (4H, m), 2.98-2.89 (4H, m), 2.18 (3H, s). Tr=2.71 min, m/z (ES⁺) (M+H)⁺ 387.

Example A-102

N-{4-[4-(4,6-Dimethyl-pyrimidin-2-yl)-piperazine-1-sulfonyl]-phenyl}-acrylamide $\delta_H$ (500 MHz, DMSO) 10.59 (1H, s), 7.89 (2H, d), 7.68 (2H, d), 6.49-6.28 (3H, m), 5.82 (1H, dd), 3.84-3.76 (4H, m), 2.93-2.88 (4H, m), 2.17 (6H, s). Tr=3.78 min, m/z (ES⁺) (M+H)⁺ 402.

Example A-103

[1-(4-Acryloylamino-benzenesulfonyl)-azetidin-3-ylmethyl]-methyl-carbamic acid tert-butyl ester $\delta_H$ (500 MHz, DMSO) 10.63 (1H, s), 7.96 (2H, d), 7.76 (2H, d), 6.51-6.29 (2H, m), 5.84 (1H, dd), 3.74-3.63 (2H, m), 3.31 (2H, obscured), 3.18-3.09 (2H, m), 2.61-2.54 (5H, m), 1.36 (9H, s). Tr=4.70 min, m/z (ES⁺) (M+Na)⁺ 432.

Example A-104

N-{4-[4-(2-Morpholin-4-yl-ethyl)-piperazine-1-sulfonyl]-phenyl}-acrylamide $\delta_H$ (500 MHz, CDCl3) 7.80 (2H, d), 7.68 (2H, d), 7.64 (1H, s), 6.52-6.26 (2H, m), 5.86 (1H, d), 3.71 (4H, s), 3.03 (4H, s), 2.61-2.36 (12H, m). Tr=2.33 min, m/z (ES⁺) (M+H)⁺ 409.

Example A-105

N-{4-[4-(1-Methyl-piperidin-4-ylmethyl)-piperazine-1-sulfonyl]-phenyl}-acrylamide $\delta_H$ (500 MHz, DMSO) 10.60 (1H, s), 7.92 (2H, d), 7.68 (2H, d), 6.49-6.28 (2H, m), 5.83 (1H, dd), 2.89-2.76 (4H, m), 2.68-2.61 (2H, m), 2.39-2.30 (4H, m), 2.07 (5H, s), 1.73-1.68 (2H, m), 1.53-1.50 (2H, m), 1.36-1.29 (1H, m), 1.02-0.93 (1H, m). Tr=1.84 min, m/z (ES⁺) (M+H)⁺ 407.

Example A-106

N-{4-[4-(2-Methyl-quinolin-5-yl)-piperazine-1-sulfonyl]-phenyl}-acrylamide $\delta_H$ (500 MHz, DMSO) 10.71 (1H, s), 8.05 (1H, d), 8.02-7.91 (4H, m), 7.76 (2H, d), 7.62 (1H, t), 7.27 (1H, s), 6.48-6.27 (2H, m), 5.81 (1H, d), 3.78 (4H, s), 3.19 (4H, s), 2.68 (3H, s). Tr=2.86 min, m/z (ES⁺) (M+H)⁺ 437.

Example A-107

N-[4-(4-Quinolin-2-yl-piperazine-1-sulfonyl)-phenyl]-acrylamide $\delta_H$ (500 MHz, DMSO) 10.58 (1H, s), 8.04-7.83 (3H, m), 7.77-7.64 (3H, m), 7.53-7.48 (2H, m), 7.24-7.16 (2H, m), 6.43-6.23 (2H, m), 5.73 (1H, d), 3.82 (4H, s), 2.99 (4H, s). Tr=2.83 min, m/z (ES⁺) (M+H)⁺ 423.

Example A-108

N-{4-[4-(5-Chloro-pyridin-2-yl)-piperazine-1-sulfonyl]-phenyl}-acrylamide $\delta_H$ (500 MHz, DMSO) 10.57 (1H, s), 8.04 (1H, dd), 7.90 (2H, d), 7.72 (2H, d), 7.56 (1H, d), 6.83 (1H, d), 6.44-6.28 (2H, m), 5.81 (1H, d), 3.61-3.54 (4H, m), 3.02-2.96 (4H, m). Tr=4.08 min, m/z (ES⁺) (M+H)⁺ 407.

Example A-109

N-{4-[4-(5-Methyl-pyridin-2-yl)-piperazine-1-sulfonyl]-phenyl}-acrylamide $\delta_H$ (500 MHz, DMSO) 10.59 (1H, s), 7.93-7.89 (3H, m), 7.61 (2H, d), 7.34 (1H, dd), 6.72 (1H, d), 6.48-6.26 (2H, m), 5.82 (1H, dd), 3.54-3.48 (4H, m), 2.98-2.81 (4H, m), 2.10 (3H, s). Tr=2.65 min, m/z (ES⁺) (M+H)⁺ 387.

Example A-110

N-[4-(4-Biphenyl-3-yl-piperazine-1-sulfonyl)-phenyl]-acrylamide $\delta_H$ (500 MHz, DMSO) 10.59 (1H, s), 7.93 (2H, d), 7.76 (2H, d), 7.59 (2H, d), 7.48-7.22 (4H, m), 7.14-7.06 (2H, m), 6.91 (1H, d), 6.48-6.28 (2H, m), 5.81 (1H, d), 3.30-3.24 (4H, m), 3.06-2.95 (4H, m). Tr=4.64 Min, m/z (ES⁺) (M+H)⁺ 448.

Example A-111: N-[4-(4-Benzothiazol-2-yl-piperazine-1-sulfonyl)-phenyl]-acrylamide $\delta_H$ (500 MHz, DMSO) 10.59 (1H, s), 7.92 (2H, d), 7.75-7.71 (3H, m), 7.41 (1H, d), 7.26 (1H, t), 7.04 (1H, t), 6.46-6.27 (2H, m), 5.82 (1H, dd), 3.66-3.62 (4H, m), 3.06-3.01 (4H, m). Tr=4.03 min, m/z (ES⁺) (M+H)⁺ 429.

Example A-112: N-[4-(2-Phenyl-morpholine-4-sulfonyl)-phenyl]-acrylamide $\delta_H$ (250 MHz, DMSO) 10.62 (1H, br s), 7.88 (2H, d), 7.71 (2H, d), 7.36-7.27 (5H, m), 6.52-6.24 (2H, m), 5.84 (1H, dd), 4.57 (1H, dd), 4.13 (1H, br s), 4.04 (1H, dd), 3.78-3.43 (3H, m), 2.41-2.38 (1H, m), 2.13-2.09 (1H, m). Tr=3.99 min, m/z (ES$^+$) (M+Na)$^+$ 395.

Example A-113

N-{4-[4-(3-Chloro-phenoxy)-piperidine-1-sulfonyl]-phenyl}-acrylamide $\delta_H$ (250 MHz, DMSO) 10.62 (1H, br s), 7.93 (2H, d), 7.71 (2H, d), 7.22 (1H, t), 7.04-6.83 (3H, m), 6.53-6.27 (2H, m), 5.82 (1H, dd), 4.51-4.47 (1H, m), 3.31-3.18 (2H, m), 2.81-2.76 (2H, m), 2.04-1.96 (2H, m), 1.71-1.65 (2H, m). Tr=4.44 min, m/z (ES$^+$) (M+Na)$^+$ 443.

Example A-114

N-[4-(4-Isoquinolin-1-yl-piperazine-1-sulfonyl)-phenyl]-acrylamide $\delta_H$ (500 MHz, d$_6$-Acetone) 9.82 (1H, s), 8.10-8.03 (4H, m), 7.83-7.79 (3H, m), 7.65 (1H, t), 7.52 (1H, t), 7.36 (1H, d), 6.53-6.40 (2H, m), 5.78 (1H, dd), 3.50-3.42 (4H, m), 3.26-3.33 (4H, m). Tr=1.65 min, m/z (ES$^+$) (M+H)$^+$ 423.

Example A-115

N-[4-(4-Naphthalen-2-yl-piperazine-1-sulfonyl)-phenyl]-acrylamide $\delta_H$ (500 MHz, DMSO) 10.59 (1H, s), 7.92 (2H, d), 7.80-7.68 (5H, m), 7.37 (1H, t), 7.29-7.22 (2H, m), 7.13 (1H, d), 6.48-6.27 (2H, m), 5.82 (1H, dd), 3.30 (4H, obscured), 3.06-3.01 (4H, m). Tr=4.48 min, m/z (ES$^+$) (M+H)$^+$ 422.

Example A-116: N-{4-[4-(4-Dimethylamino-pyrimidin-2-yl)-piperazine-1-sulfonyl]-phenyl}-acrylamide $\delta_H$ (500 MHz, DMSO) 10.58 (1H, s), 7.89 (2H, d), 7.68 (1H, d), 7.72 (2H, d), 6.48-6.28 (2H, m), 5.92 (1H, d), 5.83 (1H, dd), 3.78-3.73 (4H, m), 2.96 (6H, s), 2.88-2.84 (4H, m). Tr=2.95 min, m/z (ES$^+$) (M+H)$^+$ 417.

Example A-117

N-{4-[4-(4-Morpholin-4-yl-pyrimidin-2-yl)-piperazine-1-sulfonyl]-phenyl}-acrylamide $\delta_H$ (500 MHz, DMSO) 10.60 (1H, s), 7.91 (2H, d), 7.84 (1H, d), 7.71 (2H, d), 6.48-6.26 (2H, m), 5.81 (1H, dd), 3.74 (4H, br s), 3.58 (8H, br s), 2.91 (4H, br s). Tr=3.17 min, m/z (ES$^+$) (M+H)$^+$ 459.

Example A-118

N-[4-(4-Thieno[2,3-d]pyrimidin-4-yl-piperazine-1-sulfonyl)-phenyl]-acrylamide $\delta_H$ (500 MHz, DMSO) 10.58 (1H, s), 8.37 (1H, s), 7.90 (2H, d), 7.74 (2H, d), 7.64 (1H, d), 7.58 (1H, d), 6.46-6.28 (2H, m), 5.82 (1H, dd), 3.96-3.92 (4H, m), 3.06-3.01 (4H, m). Tr=3.64 min, m/z (ES$^+$) (M+H)$^+$ 430.

Example A-119

N-{4-[4-(2-Oxo-benzooxazol-3-yl)-piperidine-1-sulfonyl]-phenyl}-acrylamide $\delta_H$ (500 MHz, d$_6$-Acetone) 9.80 (1H, s), 8.04 (2H, d), 7.77 (2H, d), 7.24-7.09 (4H, m), 6.54-6.38 (2H, m), 5.81 (1H, dd), 4.24-4.16 (1H, m), 3.99-3.91 (2H, m), 2.61-2.38 (4H, m), 1.98-1.95 (2H, m). Tr=3.95 min, m/z (ES$^+$) (M+H)$^+$ 428.

Example A-120

N-{4-[4-(4-Methoxy-pyridin-2-yl)-piperazine-1-sulfonyl]-phenyl}-acrylamide $\delta_H$ (500 MHz, DMSO) 10.59 (1H, s), 7.93-7.88 (3H, m), 7.72-7.69 (2H, d), 6.49-6.26 (4H, m), 5.81 (1H, dd), 3.73 (3H, s), 3.59-3.52 (4H, m), 2.96-2.88 (4H, m). Tr=2.82 min, m/z (ES$^+$) (M+H)$^+$ 403.

Example A-121

N-{4-[4-(2-Dimethylamino-pyrimidin-4-yl)-piperazine-1-sulfonyl]-phenyl}-acrylamide $\delta_H$ (500 MHz, DMSO) 10.59 (1H, s), 7.91 (2H, d), 7.82 (1H, d), 7.70 (2H, d), 6.48-6.28 (2H, m), 5.98 (1H, d), 5.82 (1H, dd), 3.64-3.59 (4H, m), 2.98 (6H, s), 2.92-2.87 (4H, m). Tr=3.72 min, m/z (ES$^+$) (M+H)$^+$ 417.

Example A-122

N-{4-[4-(2-Morpholin-4-yl-pyrimidin-4-yl)-piperazine-1-sulfonyl]-phenyl}-acrylamide $\delta_H$ (500 MHz, DMSO) 10.58 (1H, s), 7.93-7.88 (3H, m), 7.72 (2H, d), 6.49-6.28 (2H, m), 6.06 (1H, d), 5.82 (1H, dd), 3.66 (4H, br s), 3.59-3.52 (8H, m), 2.92-2.87 (4H, m). Tr=3.12 min, m/z (ES$^+$) (M+H)$^+$ 459.

Example A-123

N-{4-[4-(2-Methyl-1,2,3,4-tetrahydro-isoquinolin-1-yl)-piperidine-1-sulfonyl]-phenyl}-acrylamide $\delta_H$ (500 MHz, MeOD) 7.88 (2H, d), 7.71 (2H, d), 7.40-7.28 (3H, m), 7.13 (1H, d), 6.43-6.38 (2H, m), 5.82 (1H, dd), 4.22 (1H, dd), 3.87 (1H, d), 3.80-3.76 (2H, m), 3.18-3.09 (2H, m), 2.89 (3H, s), 2.36-2.31 (1H, m), 2.22-2.17 (1H, m), 1.97 (1H, d), 1.83-1.78 (1H, m), 1.66-1.49 (2H, m), 1.34-1.29 (1H, m). Tr=4.11 min, m/z (ES$^+$) (M+H)$^+$ 440.

Example A-124

N-[4-(2,3-Dihydro-indole-1-sulfonyl)-phenyl]-acrylamide $\delta_H$ (500 MHz, DMSO) 10.52 (1H, s), 7.79-7.71 (4H, m), 7.42 (1H, d), 7.19-7.11 (2H, m), 6.97-6.93 (1H, m), 6.41-6.26 (2H, m), 5.79 (1H, dd), 3.88 (2H, t), 2.84 (2H, t). Tr=4.50 min, m/z (ES$^+$) (M+Na)$^+$ 351.

Example A-125

N-[4-(4-Isoquinolin-3-yl-piperazine-1-sulfonyl)-phenyl]-acrylamide $\delta_H$ (500 MHz, DMSO) 10.59 (1H, s), 8.93 (1H, s), 7.92 (2H, d), 7.90 (1H, d), 7.72 (2H, d), 7.63 (1H, d), 7.54 (1H, t), 7.28 (1H, t), 6.99 (1H, s), 6.42-6.23 (2H, m), 5.71 (1H, dd), 3.64-3.61 (4H, m), 3.05-2.91 (4H, m). Tr=4.92 min, m/z (ES$^+$) (M+H)$^+$ 423.

Example A-126

N-[4-(4-Isoquinolin-3-yl-piperazine-1-sulfonyl)-phenyl]-acrylamide $\delta_H$ (500 MHz, DMSO) 10.56 (1H, s), 8.46 (1H, s), 8.21 (1H, d), 7.88 (2H, d), 7.71 (2H, d), 7.41 (1H, d), 6.44-6.27 (2H, m), 5.81 (1H, dd), 4.03-3.97 (4H, m), 3.07-3.01 (4H, m). Tr=2.57 min, m/z (ES$^+$) (M+H)$^+$ 430.

Example A-127

N-{4-[4-(3-Chloro-5-trifluoromethyl-pyridin-2-yl)-piperazine-1-sulfonyl]-phenyl}-acrylamide $\delta_H$ (500 MHz, DMSO) 10.62 (1H, s), 8.52 (1H, s), 8.20 (1H, s), 7.93 (2H, d), 7.73 (2H, d), 6.49-6.30 (2H, m), 5.83 (1H, dd), 3.56-3.51 (4H, m), 3.04-3.00 (4H, m). Tr=4.67 min, m/z (ES$^+$) (M+H)$^+$ 475.

Example A-128

N-[4-(3,4-Dihydro-1H-isoquinoline-2-sulfonyl)-phenyl]-acrylamide $\delta_H$ (500 MHz, DMSO) 10.58 (1H, s), 7.89 (2H, d), 7.77 (2H, d), 7.16-7.08 (4H, m), 6.48-6.28 (2H, m), 5.82 (1H, dd), 4.18 (2H, s), 3.26 (2H, t), 2.84 (2H, t). Tr=4.15 min, m/z (ES$^+$) (M+Na)$^+$ 365.

Example A-129

4-(4-Acryloylamino-benzenesulfonyl)-2-(adamantan-2-ylcarbamoyl)-piperazine-1-carboxylic acid tert-butyl ester $\delta_H$ (500 MHz, CDCl$_3$) 7.81 (2H, d), 7.75 (2H, d), 6.51 (1H, d), 6.40 (1H, br s), 6.28 (1H, dd), 5.86 (1H, d), 4.72 (1H, br s), 4.37 (1H, d), 4.08 (2H, d), 3.66 (1H, br s), 3.09 (1H, br s), 2.52-2.36 (2H, m), 1.98-1.56 (22H, m), 1.44 (9H, s). Tr=4.88 min, m/z (ES$^+$) (M+H)$^+$ 573.

Example A-130

4-(4-Acryloylamino-benzenesulfonyl)-2-(adamantan-2-ylcarbamoylmethyl)-piperazine-1-carboxylic acid benzyl ester Tr=4.59 min, m/z (ES$^+$) (M+H)$^+$ 621.

Example A-130

4-(4-Acryloylamino-benzenesulfonyl)-2-pyridin-3-yl-piperazine-1-carboxylic acid tert-butyl ester $\delta_H$ (500 MHz, DMSO) 10.62 (1H, s), 8.52-8.49 (2H, m), 7.92 (2H, d), 7.72-7.68 (3H, m), 7.47-7.43 (1H, m), 6.50-6.29 (2H, m), 5.83 (1H, dd), 5.72 (2H, s), 5.31 (1H, s), 4.14 (1H, d), 3.93 (1H, d), 3.56 (2H, d), 2.88 (1H, t), 2.51 (2H, obscured), 2.32-2.29 (1H, m), 1.40 (9H, s). Tr=3.30 min, m/z (ES$^+$) (M+H)$^+$ 473.

Example A-131

4-(4-Acryloylamino-benzenesulfonyl)-2-(5-methyl-furan-2-yl)-piperazine-1-carboxylic acid tert-butyl ester $\delta_H$ (500 MHz, CDCl$_3$) 7.80 (2H, d), 7.72 (2H, d), 6.53-6.24 (3H, m), 5.96-5.87 (2H, m), 5.27 (1H, br s), 4.13 (1H, d), 3.94 (1H, d), 3.66 (1H, d), 3.03 (1H, t), 2.57 (1H, dd), 2.36-2.32 (1H, m), 2.26 (3H, s), 1.43 (9H, s). Tr=4.40 min, m/z (ES$^+$) (M+Na)$^+$ 498.

Example A-132

N-{4-[4-(2-Chloro-pyrimidin-4-yl)-piperazine-1-sulfonyl]-phenyl}-acrylamide $\delta_H$ (250 MHz, DMSO) 10.56 (1H, s), 8.06 (1H, d), 7.90 (2H, d), 7.71 (2H, d), 6.70 (1H, d), 6.51-6.26 (2H, m), 5.82 (1H, dd), 3.72-3.67 (4H, m), 2.99-2.22 (4H, m). Tr=4.14 min, m/z (ES$^+$) (M+H)$^+$ 408.

Example A-133

N-{4-[5-(Piperidine-1-sulfonyl)-2,3-dihydro-indole-1-sulfonyl]-phenyl}-acrylamide $\delta_H$ (500 MHz, DMSO) 10.64 (1H, s), 7.96-7.91 (4H, m), 7.69 (1H, d), 7.62 (1H, d), 7.53 (1H, d), 6.49-6.33 (2H, m), 5.88 (1H, dd), 4.02 (2H, t), 3.11 (2H, t), 2.88-2.83 (4H, m), 1.57-1.53 (4H, m), 1.42-1.39 (2H, m). Tr=4.32 min, m/z (ES$^+$) (M+H)$^+$ 476.

Example A-134

4-(4-(E)-But-2-enoylamino-benzenesulfonyl)-piperazine-1-carboxylic acid tert-butyl ester $\delta_H$ (500 MHz, CDCl$_3$) 7.61-7.81 (m, 4 H) 7.42 (s, 1 H) 6.92-7.16 (m, 1 H) 5.98 (dd, J=15.13, 1.56 Hz, 1 H) 3.51 (t, J=4.77 Hz, 4 H) 2.96 (br. s., 4 H) 1.96 (dd, J=6.88, 1.38 Hz, 3 H) 1.42 (s, 9 H). Tr=4.04 min, m/z (ES$^+$) (M+Na)$^+$ 432.

Example A-135

4-[4(Z)-3-Chloro-acryloylamino)-benzenesulfonyl]-piperazine-1-carboxylic acid tert-butyl ester 3-Chloroacrylic acid (0.12 g, 1.1 mmol) followed by pyridine (0.3 ml), were added sequentially portion wise to a stirred solution of 4-(4-amino-benzenesulfonyl)-piperazine-1-carboxylic acid tert-butyl ester (0.1 g, 0.29 mmol) in THF/DMA (3:2, 5 ml) at room temperature. To this mixture was added EDC (0.29 g, 1.5 mmol) in one portion and the mixture was stirred at room temperature under a nitrogen atmosphere for 1 hour. After this time the mixture was diluted with ethyl acetate (50 ml) and washed with water (100 ml), saturated NaHCO$_3$ (100 ml) and HCl (100 ml, 2M). The organic layer was separated, dried (MgSO$_4$), filtered and concentrated under vacuum and the resulting residue was purified by flash column chromatography (elution, 40% ethyl acetate, 60% heptane) to give the title compound (0.009 g, 5% yield) as a white solid.)

$\delta_H$ (250 MHz, DMSO) 10.66 (s, 1 H) 7.88 (d, J=8.68 Hz, 2 H) 7.69 (d, J=8.68 Hz, 2 H) 7.00 (d, J=8.07 Hz, 1 H) 6.57 (d, J=7.77 Hz, 1 H) 3.40-3.57 (m, 4 H) 2.77-2.89 (m, 5 H) 1.33 (s, 10 H). Tr=4.32 min, m/z (ES$^+$) (M+Na)$^+$ 452.

Example A-136

4-[4-((E)-3-Chloro-acryloylamino)-benzenesulfonyl]-piperazine-1-carboxylic acid tert-butyl ester $\delta_H$ (250 MHz, DMSO) 10.65 (br. s., 1 H) 7.83-7.92 (m, 2 H) 7.69 (d, J=8.83 Hz, 2 H) 7.47 (s, 1 H) 6.63 (d, J=13.10 Hz, 1 H) 2.72-2.96 (m, 6 H) 1.32 (s, 11 H). Tr=4.36 min, m/z (ES$^+$) (M+Na)$^+$ 452, 453.

Example A-137

4-[4-(2-Fluoro-acryloylamino)-benzenesulfonyl]-piperazine-1-carboxylic acid tert-butyl ester $\delta_H$ (500 MHz, DMSO) 10.71 (s, 1 H) 8.01 (d, J=8.80 Hz, 2 H) 7.72 (d, J=8.80 Hz, 2 H) 5.68-5.86 (m, 1 H) 5.51 (dd, J=15.59, 3.85 Hz, 1 H) 2.83 (t, J=4.68 Hz, 4 H) 1.33 (s, 9 H). Tr=4.19 min, m/z (ES$^+$) (M+Na)$^+$ 436.

Method AA

Example AA-1

4-(4-(Z)-But-2-enoylamino-benzenesulfonyl)-piperazine-1-carboxylic acid tert-butyl ester 4-[4-(1-Oxo-but-2-ynylamino)-benzenesulfonyl]-piperazine-1-carboxylic acid tert-butyl ester

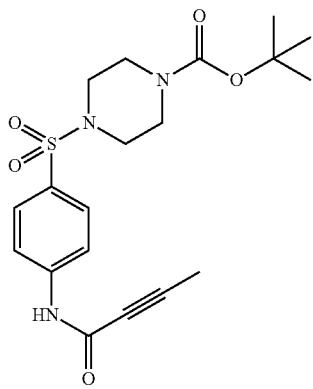 [SMILES: CC#CC(=O)Nc1ccc(S(=O)(=O)N2CCN(C(=O)OC(C)(C)C)CC2)cc1]

But-2-ynoic acid (0.19 g, 2.36 mmol) followed by pyridine (0.6 ml), were added sequentially portion wise to a stirred solution of 4-(4-amino-benzenesulfonyl)-piperazine-1-carboxylic acid tert-butyl ester (0.2 g, 0.59 mmol) in THF/DMA (3:2, 5 ml) at room temperature. To this mixture was added EDC (0.6 g, 3.1 mmol) in one portion and the mixture was stirred at room temperature under a nitrogen atmosphere for 1 hour. After this time the mixture was diluted with ethyl acetate (50 ml) and washed with water (100 ml), saturated NaHCO$_3$ (100 ml) and HCl (100 ml, 2M). The organic layer was separated, dried (MgSO$_4$), filtered and concentrated under vacuum and the resulting residue was purified by flash column chromatography (elution, 20% ethyl acetate, 80% DCM) to give the title compound (0.05 g, 19% yield) as a white solid. Tr=4.12 min, m/z (ES$^+$) (M+Na)$^+$ 430.

4-(4-(Z)-But-2-enoylamino-benzenesulfonyl)-piperazine-1-carboxylic acid tert-butyl ester

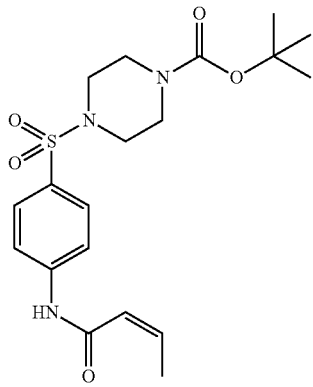 [SMILES: C/C=C\C(=O)Nc1ccc(S(=O)(=O)N2CCN(C(=O)OC(C)(C)C)CC2)cc1]

Lindlar's catalyst (0.005 g, 0.001 mmol) was added in one portion to a stirred solution of 4-[4-(1-oxo-but-2-ynylamino)-benzenesulfonyl]-piperazine-1-carboxylic acid tert-butyl ester (0.05 g, 0.11 mmol) in methanol (5 ml) at room temperature, the resulting mixture was then stirred at room temperature under a hydrogen atmosphere for 2 hours. After this time, the reaction mixture was filtered through celite and concentrated under vacuum to give the title compound (0.02 g, 40% yield) as a white solid.

Example AA-1

4-(4-(Z)-But-2-enoylamino-benzenesulfonyl)-piperazine-1-carboxylic acid tert-butyl ester $\delta_H$ (500 MHz, DMSO) 10.44 (s, 1 H) 7.89 (d, J=8.62 Hz, 2 H) 7.67 (d, J=8.62 Hz, 2 H) 6.31 (dq, J=11.42, 7.26 Hz, 1 H) 6.04 (dd, J=11.37, 1.65 Hz, 1 H) 3.39 (br. s., 3 H) 2.82 (t, J=4.68 Hz, 4 H) 2.13 (dd, J=7.15, 1.47 Hz, 3 H) 1.34 (s, 10 H). Tr=4.26 min, m/z (ES$^+$) (M+Na)$^+$ 432.

Method B

Example B-4

4-(4-Acryloylamino-benzenesulfonyl)-piperazine-1-carboxylic acid 2-chloro-benzyl ester 4-(4-Nitro-benzenesulfonyl)-piperazine-1-carboxylic acid tert-butyl ester

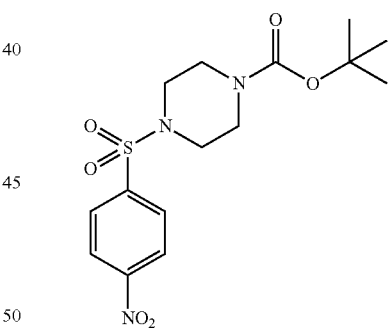

Diisopropylethylamine (7.8 ml, 45 mmol) was added in one portion to a stirred solution of piperazine-1-carboxylic acid tert-butyl ester (7.6 g, 41 mmol) in DCM (100 ml) at room temperature. To this mixture was added 4-nitrophenyl sulfonyl chloride (10.0 g, 45 mmol) in one portion and the mixture was stirred at room temperature under a nitrogen atmosphere for 1 hour. After this time the mixture was diluted with DCM (50 ml) and washed with water (100 ml), saturated NaHCO$_3$ (100 ml) and HCl (100 ml, 2M). The organic layer was separated, dried (MgSO$_4$), filtered and concentrated under vacuum to give the title compound (14.9 g, 89% yield) as a white solid. $\delta_H$ (500 MHz, DMSO) 8.45 (2H, d), 7.97

(2H, d), 3.34 (4H, obscured), 2.96-2.92 (4H, m), 1.33 (9H, s). Tr=1.91 min m/z (ES⁺) ([(M−100)+H]⁺) 272.

4-(4-Amino-benzenesulfonyl)-piperazine-1-carboxylic acid tert-butyl ester

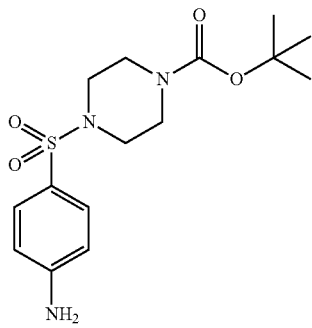 [SMILES: CC(C)(C)OC(=O)N1CCN(S(=O)(=O)c2ccc([N+](=O)[O-])cc2)CC1]

4-(4-Nitro-benzenesulfonyl)-piperazine-1-carboxylic acid tert-butyl ester (10.0 g, 27 mmol) was suspended in a 5:1 mixture of ethanol and water (80 ml). To this solution was added iron powder (3.9 g, 70.2 mmol) and saturated ammonium chloride solution (8 ml), the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO₄, filtered and concentrated to afford the title compound (1.5 g, 89% yield) as a white solid. $\delta_H$ (500 MHz, CDCl₃) 7.53 (2H, d), 6.73 (2H, d), 4.36 (2H, br s), 3.56-3.49 (4H, m), 2.98-2.91 (4H, m), 1.42 (9H, s). Tr=1.81 min, m/z (ES⁺) ([(M−100)+H]⁺) 242.

4(4-Acryloylamino-benzenesulfonyl)-piperazine-1-carboxylic acid tert-butyl ester

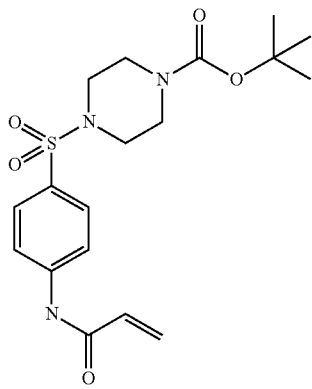 [SMILES: C=CC(=O)Nc1ccc(S(=O)(=O)N2CCN(C(=O)OC(C)(C)C)CC2)cc1]

4-(4-Amino-benzenesulfonyl)-piperazine-1-carboxylic acid tert-butyl ester (7.1 g, 21 mmol) was dissolved in DCM (70 ml). To this was added diisopropylethylamine (7.3 ml, 42 mmol) in one portion followed by the drop wise addition of acryloyl chloride (1.54 ml, 19 mmol) and the mixture was stirred at room temperature under a nitrogen atmosphere for 18 hours. The THF was removed under vacuum and the resulting crude material was purified by column chromatography (elution: 60% heptane, 40% ethyl acetate) to give the title compound (5.3 g, 20% yield) as a pale yellow powder.

Example B-1

4-(4-Acryloylamino-benzenesulfonyl)-piperazine-1-carboxylic acid tert-butyl ester $\delta_H$ (500 MHz, DMSO) 10.59 (1H, s), 7.91 (2H, d), 7.67 (2H, d), 6.49-6.38 (2H, m), 5.82 (1H, d), 3.36 (4H, obscured), 2.88-2.76 (4H, m), 1.34 (9H, s). Tr=4.05 min, m/z (ES⁺) (M+Na)⁺ 418.

Example B-2

4-(4-Acryloylamino-benzenesulfonyl)-3,5-dimethyl-piperazine-1-carboxylic acid benzyl ester $\delta_H$ (500 MHz, DMSO) 10.51 (1H, s), 7.87 (2H, d), 7.74 (2H, d), 7.38-7.26 (5H, m), 6.48-6.26 (2H, m), 5.82 (1H, dd), 5.12-5.02 (2H, m), 4.07-3.98 (2H, m), 3.74-3.68 (2H, m), 2.85-2.71 (2H, m), 1.15 (6H, d). Tr=4.15 min, m/z (ES⁺) (M+H)⁺ 458.

N-[4-(piperazine-1-sulfonyl)-phenyl]-acrylamide

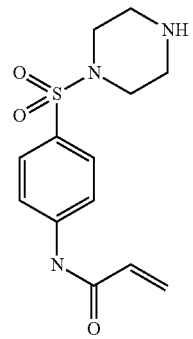 [SMILES: C=CC(=O)Nc1ccc(S(=O)(=O)N2CCNCC2)cc1]

Trifluoroacetic acid (3 ml) was added in one portion to a solution of 4-(4-Acryloylamino-benzenesulfonyl)-piperazine-1-carboxylic acid tert-butyl ester (1.23 g, 3.11 mmol) in DCM (6 ml). The resulting mixture was stirred at room temperature for 2 hours under a nitrogen atmosphere. After which time, the mixture was concentrated under vacuum to give the title compound (0.9 g, 98% yield) as an orange foam which was used without further purification.

Example B-2

N-[4-(piperazine-1-sulfonyl)-phenyl]-acrylamide $\delta_H$ (500 MHz, DMSO) 10.62 (1H, s), 8.62 (1H, br s), 7.93 (2H, d), 7.76 (2H, d), 6.55-6.24 (2H, m), 5.86 (1H, d), 3.26-3.18 (4H, m), 3.09-3.04 (4H, m). Tr=2.35 min, m/z (ES⁺) (M+H)⁺ 296.1

Example B-3

N-[3-(piperazine-1-sulfonyl)-phenyl]-acrylamide $\delta_H$ (500 MHz, DMSO) 8.59 (1H, br s), 8.24 (1H, s), 7.93 (1H, d), 7.67 (1H, t), 7.44 (1H, d), 6.48-6.27 (2H, m), 5.86 (1H, dd), 3.25-3.18 (4H, m), 3.13-3.06 (4H, m). Tr=2.29 min, m/z (ES+) (M+H)+ 296.

Example B-4

N-[4-(4-Amino-piperidine-1-sulfonyl)-phenyl]-acrylamide $\delta_H$ (500 MHz, DMSO) 10.61 (1H, s), 9.10 (2H, br s), 7.91 (2H, d), 7.84 (2H, d), 6.49-6.28 (2H, m), 5.84 (1H, dd), 4.24-4.19 (2H, m), 3.14 (2H, d), 2.71-2.68 (2H, m), 1.34 (6H, d). Tr=1.14 min, m/z (ES$^+$) (M+H)$^+$ 324.

Example B-5

4-(4-Acryloylamino-benzenesulfonyl)-piperazine-2-carboxylic acid adamantan-2-ylamide $\delta_H$ (500 MHz, DMSO) 10.60 (1H, s), 7.91 (2H, d), 7.72-7.63 (3H, m), 6.43-6.32 (2H, m), 5.82 (2H, d), 3.81 (1H, d), 3.19 (1H, d), 2.86 (1H, d), 2.69-2.62 (2H, m), 2.22 (2H, t), 1.89-1.72 (12H, m), 1.47 (3H, t). Tr=3.21 min, m/z (ES$^+$) (M+H)$^+$ 473.

Example B-6

N-[4-(3-Pyridin-3-yl-piperazine-1-sulfonyl)-phenyl]-acrylamide $\delta_H$ (500 MHz, DMSO) 10.59 (1H, s), 8.56 (1H, s), 8.48-8.46 (1H, m), 7.99 (2H, d), 7.73 (1H, d), 7.68 (2H, d), 7.32-7.29 (1H, m), 6.51-6.26 (2H, m), 5.92 (1H, dd), 3.83 (1H, dd), 3.50 (2H, obscured), 3.01 (1H, d), 2.88 (1H, br s), 2.82-2.79 (1H, m), 2.26-2.22 (1H, m). Tr=2.34 min, m/z (ES$^+$) (M+H)$^+$ 373.

Example B-7

N-{4-[3-(5-Methyl-furan-2-yl)-piperazine-1-sulfonyl]-phenyl}-acrylamide $\delta_H$ (500 MHz, CDCl$_3$) 7.84-7.72 (4H, m), 6.53-6.28 (2H, m), 6.15 (1H, s), 6.00-5.86 (2H, m), 4.04-4.01 (1H, m), 3.77 (1H, d), 3.62 (1H, d), 3.14-3.02 (1H, m), 2.61-2.55 (1H, m), 2.28-2.25 (3H, m). Tr=2.63 min, m/z (ES$^+$) (M+H)$^+$ 376.

4-(4-Acryloylamino-benzenesulfonyl)-piperazine-1-carboxylic acid 2-chloro-benzyl ester

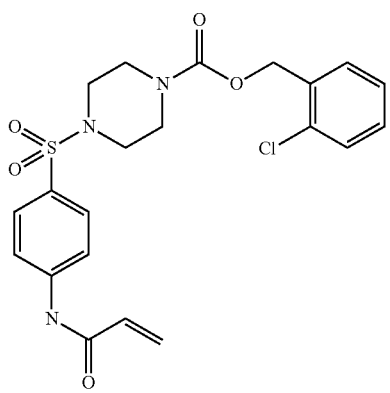 [SMILES: C=CC(=O)Nc1ccc(S(=O)(=O)N2CCN(C(=O)OCc3ccccc3Cl)CC2)cc1]

Phosgene (0.5 ml, 20% solution in toluene) was added in one portion to a stirred solution of 2-chlorobenzyl alcohol (0.1 g, 0.7 mmol) in THF (2 ml) and the resulting mixture was stirred at room temperature under a nitrogen atmosphere for 3 hours. After this time the reaction mixture was concentrated under vacuum and the resulting residue was diluted with DMF (2 ml) and added drop wise to a stirred solution of N-[4-(piperazine-1-sulfonyl)-phenyl]-acrylamide (0.16 g, 0.54 mmol) and diisopropylethylamine (0.19 ml, 1.1 mmol) in DMF (4 ml). The resulting mixture was stirred at room temperature under a nitrogen atmosphere for 18 hours. After this time the reaction mixture was concentrated under vacuum and the residue was purified by Prep HPLC to give the title compound (0.029 g, 12% yield) as a white powder.

Example B-8

4-(4-Acryloylamino-benzenesulfonyl)-piperazine-1-carboxylic acid 2-chloro-benzyl ester $\delta_H$ (500 MHz, DMSO) 10.61 (1H, s), 7.93 (2H, d), 7.68 (2H, d), 7.49-7.28 (4H, m), 6.51-6.29 (2H, m), 5.84 (1H, d), 5.07 (2H, s), 3.52-3.44 (4H, m), 2.93-2.80 (4H, m). Tr=4.34 min, m/z (ES$^+$) (M+H)$^+$ 464.

Example B-9

4-(4-Acryloylamino-benzenesulfonyl)-piperazine-1-carboxylic acid 3-trifluoromethyl-benzyl ester $\delta_H$ (500 MHz, DMSO) 10.61 (1H, s), 7.93 (2H, d), 7.76-7.52 (6H, m), 6.51-6.26 (2H, m), 5.83 (1H, d), 5.11 (2H, s), 3.54-3.36 (4H, m), 2.93-2.81 (4H, m). Tr=4.42 min, m/z (ES$^+$) (M+H)$^+$ 498.

Example B-10

4-(4-Acryloylamino-benzenesulfonyl)-piperazine-1-carboxylic acid 2-trifluoromethyl-benzyl ester $\delta_H$ (500 MHz, DMSO) 10.62 (1H, s), 7.92 (2H, d), 7.76-7.51 (6H, m), 6.49-6.30 (2H, m), 5.83 (1H, d), 5.18 (2H, s), 3.53-3.44 (4H, m), 2.92-2.83 (4H, m). Tr=4.43 min, m/z (ES$^+$) (M+H)$^+$ 498.

Example B-11

4-(4-Acryloylamino-benzenesulfonyl)-piperazine-1-carboxylic acid 2,6-difluoro-benzyl ester $\delta_H$ (250 MHz, DMSO) 10.61 (1H, br s), 7.92 (2H, d), 7.68 (2H, d), 7.52-7.38 (1H, m), 7.21-7.01 (2H, m), 6.59-6.18 (2H, m), 5.78 (1H, dd), 5.06 (2H, s), 3.41 (4H, obscured), 2.92-2.73 (4H, m). Tr=4.17 min, m/z (ES$^+$) (M+H)$^+$ 466.

Example B-12

4-(4-Acryloylamino-benzenesulfonyl)-piperazine-1-carboxylic acid 4-butyl-benzyl ester $\delta_H$ (250 MHz, DMSO) 10.60 (1H, s), 7.93 (2H, d), 7.67 (2H, d), 7.18 (2H, q), 6.57-6.22 (2H, m), 5.81 (1H, dd), 4.99 (2H, s), 3.41-3.50 (4H, m), 2.82-2.69 (4H, m), 1.59-1.41 (2H, m), 1.32-1.20 (2H, m), 0.84 (3H, t). Tr=5.03 min, m/z (ES$^+$) (M+H)$^+$ 508.

Example B-13

4-(4-Acryloylamino-benzenesulfonyl)-piperazine-1-carboxylic acid 4-methyl-benzyl ester $\delta_H$ (250 MHz, DMSO) 10.61 (1H, s), 7.92 (2H, d), 7.68 (2H, d), 7.15 (4H, q), 6.51-6.23 (2H, m), 5.82 (1H, dd), 4.95

(2H, s), 3.48-3.41 (4H, m), 2.89-2.76 (4H, m), 2.24 (3H, s). Tr=4.42 min, m/z (ES⁺) (M+H)⁺ 466.

Example B-14

4-(4-Acryloylamino-benzenesulfonyl)-piperazine-1-carboxylic acid 3-fluoro-benzyl ester $\delta_H$ (250 MHz, DMSO) 10.59 (1H, s), 7.92 (2H, d), 7.69 (2H, d), 7.42-7.31 (1H, m), 7.26-7.00 (3H, m), 6.59 (2H, m), 5.82 (1H, dd), 5.01 (2H, s), 3.51-3.42 (4H, m), 2.93-2.80 (4H, m). Tr=4.27 min, m/z (ES⁺) (M+H)⁺ 448.

Example B-15

4-(4-Acryloylamino-benzenesulfonyl)-piperazine-1-carboxylic acid naphthalen-2-ylmethyl ester $\delta_H$ (500 MHz, DMSO) 10.60 (1H, br s), 7.94-7.80 (6H, m), 7.71 (2H, d), 7.56-7.48 (2H, m), 7.43 (1H, m), 6.52-6.27 (2H, m), 5.85 (1H, d), 5.18 (2H, s), 3.59-3.42 (4H, m), 2.97-2.80 (4H, m). Tr=4.60 min, m/z (ES⁺) (M+Na)⁺ 502.

Example B-16

4-(4-Acryloylamino-benzenesulfonyl)-piperazine-1-carboxylic acid 4-tert-butyl-benzyl ester $\delta_H$ (500 MHz, DMSO) 10.61 (1H, br s), 7.93 (2H, d), 7.67 (2H, d), 7.33 (2H, d), 7.21 (2H, d), 6.48-6.27 (2H, m), 5.82 (1H, d), 4.95 (2H, s), 3.50-3.42 (4H, m), 2.91-2.82 (4H, m), 1.23 (9H, s). Tr=4.89 min, m/z (ES⁺) (M+Na)⁺ 508.

Example B-17

4-(4-Acryloylamino-benzenesulfonyl)-piperazine-1-carboxylic acid 4-fluoro-benzyl ester $\delta_H$ (500 MHz, DMSO) 10.61 (1H, br s), 7.93 (2H, d), 7.69 (2H, d), 7.38-7.31 (2H, m), 7.16 (2H, t), 6.50-6.27 (2H, m), 5.83 (1H, d), 4.98 (2H, s), 3.51-3.42 (4H, m), 2.89-2.81 (4H, m). Tr=4.26 min, m/z (ES⁺) (M+H)⁺ 448.

Example B-18

4-(4-Acryloylamino-benzenesulfonyl)-piperazine-1-carboxylic acid naphthalen-1-ylmethyl ester $\delta_H$ (500 MHz, DMSO) 10.62 (1H, s), 7.96-7.80 (5H, m), 7.66 (2H, d), 7.53-7.40 (4H, m), 6.50-6.29 (2H, m), 6.85 (1H, dd), 5.47 (2H, s), 3.51-3.39 (4H, m), 2.84-2.72 (4H, m). Tr=4.53 min, m/z (ES⁺) (M+Na)⁺ 502.

Example B-19

4-(4-Acryloylamino-benzenesulfonyl)-piperazine-1-carboxylic acid 4-trifluoromethyl-benzyl ester $\delta_H$ (500 MHz, CDCl₃) 7.89 (2H, d), 7.73 (2H, d), 7.60 (2H, d), 7.43 (2H, d), 6.54-6.21 (2H, m), 5.88 (2H, d), 5.13 (2H, s), 3.66-3.57 (4H, m), 3.04-2.95 (4H, m). Tr=4.59 min, m/z (ES⁺) (M+H)⁺ 498.

Example B-20

4-(4-Acryloylamino-benzenesulfonyl)-piperazine-1-carboxylic acid phenethyl ester $\delta_H$ (500 MHz, DMSO) 10.62 (1H, s), 7.93 (2H, d), 7.68 (2H, d), 7.21-7.12 (5H, m), 6.52-6.27 (2H, m), 5.86 (1H, d), 4.15 (2H, t), 3.42-3.36 (4H, m), 2.87-2.73 (6H, m). Tr=4.23 min. m/z (ES⁺) (M+H)⁺ 444.

Example B-21

4-(4-Acryloylamino-benzenesulfonyl)-piperazine-1-carboxylic acid 2,3-dimethoxy-benzyl ester $\delta_H$ (500 MHz, DMSO) 10.58 (1H, s), 7.93 (2H, d), 7.67 (2H, d), 7.06-6.98 (2H, m), 6.90-6.78 (1H, m), 6.50-6.27 (2H, m), 5.85 (1H, dd), 5.00 (2H, s), 3.79 (3H, s), 3.66 (3H, s), 3.50-3.41 (4H, m), 2.98-2.80 (4H, m). Tr=4.13 min, m/z (ES⁺) (M+H)⁺ 490.

Example B-22

4-(4-Acryloylamino-benzenesulfonyl)-piperazine-1-carboxylic acid 2-methyl-benzyl ester $\delta_H$ (500 MHz, DMSO) 10.59 (1H, s), 7.92 (2H, d), 7.68 (2H, d), 7.25-7.10 (4H, m), 6.51-6.24 (2H, m), 5.85 (1H, dd), 5.02 (2H, s), 3.49-3.40 (4H, m), 2.89-2.77 (4H, m), 2.23 (3H, s). Tr=4.30 min, m/z (ES⁺) (M+H)⁺ 444.

Example B-23

4-(4-Acryloylamino-benzenesulfonyl)-piperazine-1-carboxylic acid 3,5-difluoro-benzyl ester $\delta_H$ (500 MHz, DMSO) 10.59 (1H, s), 7.91 (2H, d), 7.73 (2H, d), 7.19-7.01 (3H, m), 6.51-6.24 (2H, m), 5.81 (1H, d), 5.03 (2H, s), 3.57-3.40 (4H, m), 2.93-2.87 (4H, m). Tr=4.26 min, m/z (ES⁺) (M+H)⁺ 466.

Example B-24

4-(4-Acryloylamino-benzenesulfonyl)-piperazine-1-carboxylic acid 3,5-dimethyl-benzyl ester $\delta_H$ (500 MHz, DMSO) 10.57 (1H, s), 7.92 (2H, d), 7.68 (2H, d), 6.94-6.86 (3H, m), 6.50-6.28 (2H, m), 5.83 (1H, d), 4.94 (2H, s), 3.51-3.40 (4H, m), 2.90-2.81 (4H, m), 2.21 (6H, s). Tr=4.52 min, m/z (ES⁺) (M+H)⁺ 458.

Example B-25

4-(4-Acryloylamino-benzenesulfonyl)-piperazine-1-carboxylic acid 3-chloro-benzyl ester $\delta_H$ (500 MHz, DMSO) 10.61 (1H, s), 7.92 (2H, d), 7.68 (2H, d), 7.39-7.22 (4H, m), 6.50-6.27 (2H, m), 5.83 (1H, d), 5.02 (2H, s), 3.53-3.43 (4H, m), 2.93-2.80 (4H, m). Tr=4.37 min, m/z (ES⁺) (M+H)⁺ 464.

Example B-26

4-(4-Acryloylamino-benzenesulfonyl)-piperazine-1-carboxylic acid 2,3-difluoro-benzyl ester $\delta_H$ (500 MHz, DMSO) 10.59 (1H, s), 7.92 (2H, d), 7.68 (2H, d), 7.42-7.36 (1H, m), 7.22-7.07 (2H, m), 6.51-6.26 (2H, m), 5.82 (1H, d), 5.10 (2H, s), 3.51-3.42 (4H, m), 2.93-2.78 (4H, m). Tr=4.23 min, m/z (ES$^+$) (M+H)$^+$ 466.

Example B-27

4-(4-Acryloylamino-benzenesulfonyl)-piperazine-1-carboxylic acid 3-phenoxy-benzyl ester $\delta_H$ (250 MHz, MeOH) 7.91 (2H, d), 7.74 (2H, d), 7.38-7.26 (3H, m), 7.14-6.88 (6H, m), 6.47-6.39 (2H, m), 5.89-5.77 (1H, m), 5.03 (2H, s), 3.57-3.48 (4H, m), 2.98-2.89 (4H, m). Tr=4.72 min, m/z (ES$^+$) (M+H)$^+$ 522.

Example B-28

N-{4-[4-(Tetrahydro-pyran-4-carbonyl)-piperazine-1-sulfonyl]-phenyl}-acrylamide $\delta_H$ (500 MHz, DMSO) 10.59 (1H, s), 7.92 (2H, d), 7.68 (2H, d), 6.48-6.27 (2H, m), 5.82 (1H, dd), 3.81-3.76 (2H, m), 3.59-3.48 (4H, m), 3.31-3.26 (2H, m), 2.89-2.74 (5H, m), 1.51-1.39 (4H, m). Tr=3.07 min, m/z (ES$^+$) (M+H)$^+$ 408.

Example B-29

4-(4-Acryloylamino-benzenesulfonyl)-2,6-dimethyl-piperazine-1-carboxylic acid benzyl ester $\delta_H$ (500 MHz, DMSO) 10.58 (1H, s), 7.90 (2H, d), 7.69 (2H, d), 7.38-7.28 (5H, m), 6.50-6.29 (2H, m), 5.84 (1H, dd), 5.07 (2H, s), 4.22-4.14 (2H, m), 3.46-3.40 (2H, m), 2.40-2.33 (2H, m), 1.24 (6H, d). Tr=4.20 min, m/z (ES$^+$) (M+H)$^+$ 458.

Example B-30

4-[4-(Acryloyl-methyl-amino)-benzenesulfonyl]-piperazine-1-carboxylic acid tert-butyl ester Sodium hydride (0.050 g, 26 mmol) was added in one portion to a stirred solution of 4-(4-acryloylamino-benzene-sulfonyl)-piperazine-1-carboxylic acid tert-butyl ester (0.1 g, 0.25 mmol) in THF (1 ml). The reaction was stirred at room temperature for 5 minutes before methyl iodide (0.05 g, 0.25 mmol) was added in one portion and stirring continued for 1 hour. After this time, the reaction mixture was concentrated under vacuum and the resulting residue purified by prep HPLC to give the title compound (6.6 mg, 7% yield) as a white solid.

$\delta_H$ (500 MHz, MeOD) 7.81 (2H, d), 7.42 (2H, d), 6.26-6.05 (2H, m), 5.59 (1H, dd), 3.45-3.36 (4H, m), 3.29 (3H, s), 2.92-2.81 (4H, m), 1.32 (9H, s). Tr=3.95 min, m/z (ES$^+$) (M+Na)$^+$ 432.

Method C

Example C-1

N-{4-[4-(Piperidine-1-carbonyl)-piperazine-1-sulfonyl]-phenyl}-acrylamide

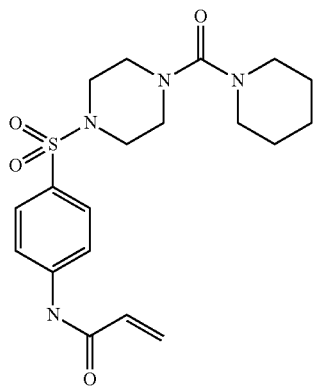 [SMILES: C=CC(=O)Nc1ccc(S(=O)(=O)N2CCN(C(=O)N3CCCCC3)CC2)cc1]

Phosgene (0.5 ml, 20% solution in toluene) was added in one portion to a stirred solution of piperidine (0.1 g, 0.7 mmol) in THF (2 ml) and the resulting mixture was stirred at room temperature under a nitrogen atmosphere for 3 hours. After this time the reaction mixture was concentrated under vacuum and the resulting residue was diluted with DMF (2 ml) and added drop wise to a stirred solution of N-[4-(Piperazine-1-sulfonyl)-phenyl]-acrylamide (0.16 g, 0.54 mmol) and diisopropylethylamine (0.19 ml, 1.1 mmol) in DMF (4 ml). The resulting mixture was stirred at room temperature under a nitrogen atmosphere for 18 hours. After this time the reaction mixture was concentrated under vacuum and the residue was purified by Prep HPLC to give the title compound (0.032 g, 14% yield) as a white powder.

Example C-1

N-{4-[4-(Piperidine-1-carbonyl)-piperazine-1-sulfonyl]-phenyl}-acrylamide $\delta_H$ (500 MHz, DMSO) 10.59 (1H, s), 7.92 (2H, d), 7.69 (2H, d), 6.49-6.28 (2H, m), 5.82 (1H, d), 3.19-3.13 (4H, m), 3.08-3.00 (4H, m), 2.89-2.71 (4H, m), 1.51-1.43 (2H, m), 1.42-1.36 (4H, m). Tr=3.89 min, m/z (ES$^+$) (M+H)$^+$ 407.05.

Example C-2

N-{4-[4-(Pyrrolidine-1-carbonyl)-piperazine-1-sulfonyl]-phenyl}-acrylamide $\delta_H$ (500 MHz, DMSO) 10.59 (1H, s), 7.92 (2H, d), 7.69 (2H, d), 6.51-6.28 (2H, m), 5.82 (1H, d), 3.26-3.13 (8H, m), 2.92-2.80 (4H, m), 1.71-1.62 (4H, m). Tr=3.82 min, m/z (ES$^+$) (M+H)$^+$ 393.

Example C-3

N-{3-[4-(Pyrrolidine-1-carbonyl)-piperazine-1-sulfonyl]-phenyl}-acrylamide $\delta_H$ (500 MHz, DMSO) 10.52 (1H, s), 8.19 (1H, s), 7.92 (1H, d), 7.61 (1H, t), 7.42 (1H, d), 6.48-6.26 (2H, m), 5.82 (1H, d), 3.28-3.13 (10H, m), 2.93-2.81 (4H, m), 1.77-1.62 (6H, m). Tr=3.56 min, m/z (ES$^+$) (M+H)$^+$ 393.05.

Example C-4

N-{4-[4-(4,4-Difluoro-piperidine-1-carbonyl)-piperazine-1-sulfonyl]-phenyl}-acrylamide $\delta$H (500 MHz, DMSO) 10.65 (1H, s), 7.96 (2H, d), 7.77 (2H, d), 6.59-6.36 (2H, m), 5.89 (1H, dd), 3.29-3.20 (8H, m), 2.94-2.90 (4H, m), 1.99-1.90 (4H, m). Tr=3.64 min, m/z (ES+) (M+H)+443.

Example C-5

N-{4-[4-(Morpholine-4-carbonyl)-piperazine-1-sulfonyl]-phenyl}-acrylamide $\delta_H$ (500 MHz, DMSO) 10.59 (1H, s), 7.92 (2H, d), 6.48-6.29 (2H, m), 5.82 (1H, dd), 3.51-3.47 (4H, m), 3.23-3.16 (4H, m), 3.09-3.04 (4H, m), 2.89-2.83 (4H, m). Tr=3.22 min, m/z (ES$^+$) (M+H)$^+$ 409.

Example C-6

N-{4-[4-(Octahydro-quinoline-1-carbonyl)-piperazine-1-sulfonyl]-phenyl}-acrylamide $\delta_H$ (500 MHz, DMSO) 10.59 (1H, s), 7.92 (2H, d), 7.68 (2H, d), 6.49-6.26 (2H, m), 5.82 (1H, dd), 3.61-3.57 (1H, m), 3.24-3.22 (1H, m), 3.17-3.08 (4H, m), 2.89-2.77 (5H, m), 1.79-1.62 (4H, m), 1.57-1.43 (3H, m), 1.32-1.10 (6H, m). Tr=4.40 min, m/z (ES$^+$) (M+H)$^+$ 461.

Example C-7

N-{4-[4-(Octahydro-isoquinoline-2-carbonyl)-piperazine-1-sulfonyl]-phenyl}-acrylamide $\delta_H$ (500 MHz, DMSO) 10.59 (1H, s), 7.92 (2H, d), 7.68 (2H, d), 6.49-6.29 (2H, m), 5.82 (1H, dd), 3.22-3.11 (5H, m), 2.91-2.73 (6H, m), 1.72-1.18 (12H, m). Tr=4.42 min, m/z (ES$^+$) (M+H)$^+$ 461.

Example C-8

4-(4-Acryloylamino-benzenesulfonyl)-piperazine-1-carboxylic acid adamantan-2-ylamide $\delta_H$ (500 MHz, DMSO) 10.59 (1H, s), 7.92 (2H, d), 7.68 (2H, d), 6.48-6.29 (2H, m), 5.96 (1H, d), 5.83 (1H, dd), 3.59 (1H, s), 3.40-3.37 (4H, m), 2.83-2.74 (4H, m), 1.92-1.87 (2H, m), 1.86-1.63 (10H, m), 1.43-1.36 (2H, m). Tr=4.31 min, m/z (ES$^+$) (M+H)$^+$ 473.

Example C-9

N-{4-[4-(4-Dimethylamino-piperidine-1-carbonyl)-piperazine-1-sulfonyl]-phenyl}-acrylamide $\delta_H$ (500 MHz, DMSO) 10.56 (1H, s), 7.91 (2H, d), 7.68 (2H, d), 6.43-6.28 (2H, m), 5.81 (1H, dd), 3.49 (2H, d), 3.19-3.11 (4H, m), 2.89-2.81 (4H, m), 2.62 (3H, t), 2.18-2.09 (7H, m), 1.63-1.58 (2H, m), 1.22-1.15 (2H, m). Tr=2.43 min, m/z (ES$^+$) (M+H)$^+$ 450.

Example C-10

N-{4-[4-(2,6-Dimethyl-morpholine-4-carbonyl)-piperazine-1-sulfonyl]-phenyl}-acrylamide $\delta_H$ (500 MHz, DMSO) 10.57 (1H, s), 7.91 (2H, d), 7.69 (2H, d), 6.49-6.28 (2H, m), 5.82 (1H, dd), 3.46-3.37 (5H, m), 3.23-3.14 (4H, m), 2.91-2.84 (4H, m), 2.42-2.36 (2H, m), 1.01 (6H, s). Tr=3.41 min, m/z (ES$^+$) (M+H)$^+$ 437.

Example C-11

5-[4-(4-Acryloylamino-benzenesulfonyl)-piperazine-1-carbonyl]-2,5-diaza-bicyclo[2.2.1]heptane-2-carboxylic acid tert-butyl ester $\delta_H$ (250 MHz, DMSO) 10.59 (1H, s), 7.88 (2H, d), 7.65 (2H, d), 6.50-6.25 (2H, m), 5.82 (1H, dd), 4.29-4.18 (2H, m), 3.41-3.18 (6H, m), 3.03-2.72 (6H, m), 1.72-1.55 (2H, m), 1.36 (9H, s). Tr=3.70 min, m/z (ES$^+$) (M+H)$^+$ 520.

Method D

Example D-1

N-[4-(4-Benzoyl-piperazine-1-sulfonyl)-phenyl]-acrylamide

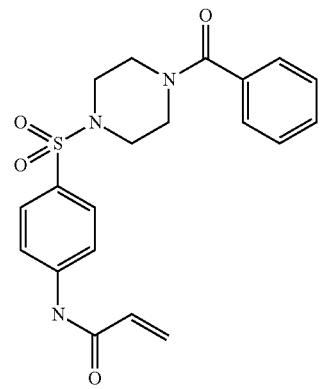 [SMILES: C=CC(=O)Nc1ccc(S(=O)(=O)N2CCN(C(=O)c3ccccc3)CC2)cc1]

Diisopropylethylamine (0.24 ml, 1.36 mmol) was added in one portion to a stirred solution of N-[4-(piperazine-1-sulfonyl)-phenyl]-acrylamide (0.1 g, 0.34 mmol) in THF (5 ml). The mixture was stirred at room temperature for 5 minutes before benzoyl chloride (0.05 ml, 0.44 mmol) was added drop wise and the resulting mixture was stirred at room temperature under a nitrogen atmosphere for 18 hours. The crude reaction mixture was concentrated under vacuum and the residue was purified by Prep HPLC to give the title compound (0.018 g, 13% yield) as a white powder.

Example D-1

4-(4-Acryloylamino-benzenesulfonyl)-piperazine-1-carboxylic acid 2-chloro-benzyl ester $\delta_H$ (500 MHz, DMSO) 10.59 (1H, s), 7.91 (2H, d), 7.68 (2H, d), 7.42-7.26 (5H, m), 6.51-6.29 (2H, m), 5.82 (1H, d), 3.78-3.52 (4H, m), 3.08-2.81 (4H, m). Tr=3.63 min, m/z (ES$^+$) (M+H)$^+$ 400.05.

Example D-2

N-[4-(4-Phenylacetyl-piperazine-1-sulfonyl)-phenyl]-acrylamide $\delta_H$ (500 MHz, DMSO) 10.60 (1H, s), 7.92 (2H, d), 7.63 (2H, d), 7.25-7.09 (5H, m), 6.51-6.32 (2H, m), 5.83 (1H, d), 3.63 (2H, s), 3.59-3.49 (4H, m), 2.86-2.69 (4H, m). Tr=3.66 min, m/z (ES$^+$) (M+H)$^+$ 414.10.

Example D-3

N-{4-[4-(4-Phenyl-butyryl)-piperazine-1-sulfonyl]-phenyl}-acrylamide $\delta_H$ (500 MHz, DMSO) 10.58 (1H, s), 7.92 (2H, d), 7.69 (2H, d), 7.24-7.08 (5H, m), 6.50-6.27 (2H, m), 5.83 (1H, d), 3.53-3.42 (4H, m), 2.87-2.79 (4H, m), 2.24 (2H, t), 1.72-1.63 (2H, m). Tr=4.13 min, m/z (ES$^+$) (M+H)$^+$ 442.10.

Example D-4

N-{3-[4-(Piperidine-1-carbonyl)-piperazine-1-sulfonyl]-phenyl}-acrylamide $\delta_H$ (500 MHz, DMSO) 10.53 (1H, s), 8.15 (1H, s), 7.94 (1H, d), 7.62 (1H, t), 7.43 (1H, d), 6.48-6.27 (2H, m), 5.84 (1H, dd), 3.22-3.16 (4H, m), 3.08-3.01 (4H, m), 2.93-2.86 (4H, m), 1.52-1.37 (6H, m). Tr=3.71 min, m/z (ES$^+$) (M+H)$^+$ 407.45.

Example D-5

N-{4-[4-(3-Phenyl-propionyl)-piperazine-1-sulfonyl]-phenyl}-acrylamide $\delta_H$ (500 MHz, DMSO) 10.62 (1H, s), 7.93 (2H, d), 7.67 (2H, d), 7.21-7.05 (5H, m), 6.51-6.28 (2H, m), 5.84 (1H, d), 3.56-3.41 (4H, m), 2.80-2.63 (6H, m), 2.53 (2H, obscured). Tr=3.91 min, m/z (ES$^+$) (M+H)$^+$ 428.00.

Example D-6

N-[4-(4-Acetyl-piperazine-1-sulfonyl)-phenyl]-acrylamide $\delta_H$ (500 MHz, DMSO) 10.60 (1H, s), 7.92 (2H, d), 7.71 (2H, d), 6.51-6.28 (2H, m), 5.83 (1H, d), 3.56-3.43 (4H, m), 2.93-2.76 (4H, m), 1.91 (3H, s). Tr=3.08 min, m/z (ES$^+$) (M+H)$^+$ 338.40.

Example D-7

4-(4-Acryloylamino-benzenesulfonyl)-piperazine-1-carboxylic acid ethyl ester $\delta_H$ (500 MHz, DMSO) 10.59 (1H, s), 7.92 (2H, d), 7.68 (2H, d), 6.50-6.31 (2H, m), 5.82 (1H, d), 3.96 (2H, q), 3.49-3.38 (4H, m), 2.90-2.76 (4H, m), 1.11 (3H, t). Tr=3.66 min, m/z (ES$^+$) (M+H)$^+$ 368.

Example D-8

4-(4-Acryloylamino-benzenesulfonyl)-piperazine-1-carboxylic acid isobutyl ester $\delta_H$ (500 MHz, DMSO) 10.59 (1H, s), 7.91 (2H, d), 7.69 (2H, d), 6.51-6.28 (2H, m), 5.82 (1H, d), 3.72 (2H, d), 3.50-3.39 (4H, m), 2.89-2.83 (4H, m), 1.89-1.70 (1H, m), 0.82 (6H, d). Tr=4.11 min, m/z (ES$^+$) (M+H)$^+$ 396.

Example D-9

4-(4-Acryloylamino-benzenesulfonyl)-piperazine-1-carboxylic acid methyl ester $\delta_H$ (500 MHz, DMSO) 10.59 (1H, s), 7.92 (2H, d), 7.68 (2H, d), 6.51-6.24 (2H, m), 5.82 (1H, d), 3.54 (3H, s), 3.48-3.29 (4H, m), 2.88-2.82 (4H, m). Tr=3.44 min, m/z (ES$^+$) (M+H)$^+$ 354.

Example D-10

4-(4-Acryloylamino-benzenesulfonyl)-piperazine-1-carboxylic acid isopropyl ester $\delta_H$ (500 MHz, DMSO) 10.59 (1H, s), 7.93 (2H, d), 7.70 (2H, d), 6.51-6.25 (2H, m), 5.82 (1H, d), 4.73-4.64 (1H, m), 3.46-3.39 (4H, m), 2.86-2.79 (4H, m), 1.10 (6H, d). Tr=3.87 min, m/z (ES$^+$) (M+H)$^+$ 382.

Example D-11

4-(4-Acryloylamino-benzenesulfonyl)-piperazine-1-carboxylic acid cyclopentyl ester $\delta_H$ (500 MHz, DMSO) 10.59 (1H, s), 7.92 (2H, d), 7.69 (2H, d), 6.51-6.28 (2H, m), 5.82 (1H, dd), 4.93-4.87 (1H, m), 3.43-3.38 (4H, m), 2.89-2.78 (4H, m), 1.78-1.69 (2H, m), 1.61-1.42 (6H, m). Tr=4.25 min, m/z (ES$^+$) (M+H)$^+$ 407.95.

Example D-12

4-(4-Acryloylamino-benzenesulfonyl)-piperazine-1-carboxylic acid phenyl ester $\delta_H$ (500 MHz, DMSO) 10.62 (1H, s), 7.93 (2H, d), 7.75 (2H, d), 7.24 (2H, t), 7.18 (1H, t), 7.09-7.00 (2H, m), 6.51-6.29 (2H, m), 5.84 (1H, d), 3.72-3.63 (2H, m), 3.55-3.48 (2H, m), 3.05-2.91 (4H, m). Tr=4.08 min, m/z (ES$^+$) (M+H)$^+$ 416.

Example D-13

4-(3-Acryloylamino-benzenesulfonyl)-piperazine-1-carboxylic acid isopropyl ester $\delta_H$ (250 MHz, DMSO) 10.51 (1H, s), 8.18-8.13 (1H, m), 7.95-7.88 (1H, m), 7.61 (1H, t), 7.46-7.38 (1H, m), 6.49-6.23

(2H, m), 5.82 (1H, dd), 4.80-4.63 (1H, m), 3.51-3.38 (4H, m), 2.95-2.86 (4H, m), 1.14 (6H, d). Tr=4.09 min, m/z (ES$^+$) (M+H)$^+$ 382.00.

Example D-14

4-(3-Acryloylamino-benzenesulfonyl)-piperazine-1-carboxylic acid ethyl ester $\delta_H$ (500 MHz, DMSO) 10.52 (1H, s), 8.16 (1H, s), 7.93 (1H, dd), 7.59 (1H, t), 7.42 (1H, d), 6.49-6.27 (2H, m), 5.82 (1H. Dd), 3.98 (2H, q), 3.49-3.41 (4H, m), 2.93-2.85 (4H, m), 1.14 (3H, t). Tr=3.92 min, m/z (ES$^+$) (M+H)$^+$ 368.

Example D-15

4-(3-Acryloylamino-benzenesulfonyl)-piperazine-1-carboxylic acid methyl ester $\delta_H$ (500 MHz, DMSO) 10.51 (1H, s), 8.18 (1H, s), 7.92 (1H, d), 7.59 (1H, t), 7.39 (1H, d), 6.48-6.27 (2H, m), 5.82 (1H, dd), 3.54 (3H, s), 3.45-3.41 (4H, m), 2.93-2.83 (4H, m). Tr=3.47 min, m/z (ES$^+$) (M+H)$^+$ 353.90.

Example D-16

4-(3-Acryloylamino-benzenesulfonyl)-piperazine-1-carboxylic acid isobutyl ester $\delta_H$ (500 MHz, DMSO) 10.51 (1H, s), 8.16 (1H, s), 7.92 (1H, d), 7.61 (1H, t), 7.41 (1H, d), 6.47-6.28 (2H, m), 5.81 (1H, dd), 3.72 (2H, d), 3.51-3.40 (4H, m), 2.94-2.86 (4H, m), 1.86-1.73 (1H, m), 0.82 (6H, d). Tr=4.46 min, m/z (ES$^+$) (M+H)$^+$ 396.40.

Example D-17

4-(3-Acryloylamino-benzenesulfonyl)-piperazine-1-carboxylic acid cyclopentyl ester $\delta_H$ (500 MHz, DMSO) 10.51 (1H, s), 8.16 (1H, s), 7.92 (1H, d), 7.61 (1H, t), 7.41 (1H, d), 6.48-6.27 (2H, m), 5.83 (1H, dd), 4.93-4.88 (1H, m), 3.48-3.39 (4H, m), 2.93-2.81 (4H, m), 1.78-1.66 (2H, m), 1.62-1.43 (6H, m). Tr=4.21 min, m/z (ES$^+$) (M+Na)$^+$ 429.95.

Example D-18

N-[4-(4-Cyclopropanecarbonyl-piperazine-1-sulfonyl)-phenyl]-acrylamide $\delta_H$ (500 MHz, DMSO) 10.59 (1H, s), 7.90 (2H, d), 7.68 (2H, d), 6.49-6.23 (2H, m), 5.82 (1H, dd), 3.72-3.61 (2H, m), 3.60-3.48 (2H, m), 2.92-2.74 (4H, m), 1.91-1.81 (1H, m), 0.67-0.61 (4H, m). Tr=3.25 min, m/z (ES$^+$) (M+H)$^+$ 364.

Example D-19

N-[4-(4-Cyclopentanecarbonyl-piperazine-1-sulfonyl)-phenyl]-acrylamide $\delta_H$ (500 MHz, DMSO) 10.60 (1H, s), 7.91 (2H, d), 7.70 (2H, d), 6.51-6.23 (2H, m), 5.82 (1H, dd), 3.60-3.49 (4H, m), 2.92-2.80 (5H, m), 1.70-1.62 (2H, m), 1.58-1.42 (6H, m). Tr=3.67 min, m/z (ES$^+$) (M+H)$^+$ 392.

Example D-20

N-{4-[4-(2-Phenyl-cyclopropanecarbonyl)-piperazine-1-sulfonyl]-phenyl}-acrylamide $\delta_H$ (500 MHz, DMSO) 10.59 (1H, s), 7.91 (2H, d), 7.70 (2H, d), 7.27-7.21 (2H, m), 7.20-7.08 (3H, m), 6.50-6.29 (2H, m), 5.82 (1H, d), 3.77-3.47 (4H, m), 2.93-2.77 (4H, m), 2.28-2.15 (2H, m), 1.34-1.27 (1H, m), 1.19-1.08 (1H, m). Tr=3.90 min, m/z (ES$^+$) (M+H)$^+$ 440.

Example D-21

N-[3-(4-Benzoyl-piperazine-1-sulfonyl)-phenyl]-acrylamide $\delta_H$ (500 MHz, DMSO) 10.54 (1H, s), 8.14 (1H, s), 7.96 (1H, d), 7.63 (1H, t), 7.47-7.28 (5H, m), 6.48-6.27 (2H, m), 5.70 (1H, d), 3.78-3.36 (4H, m), 3.08-2.86 (4H, m). Tr=3.69 min, m/z (ES$^+$) (M+H)$^+$ 399.95.

Example D-22

N-[3-(4-Phenylacetyl-piperazine-1-sulfonyl)-phenyl]-acrylamide $\delta_H$ (500 MHz, DMSO) 10.52 (1H, s), 8.13 (1H, s), 7.94 (1H, d), 7.61 (1H, t), 7.36 (1H, d), 7.22-7.16 (5H, m), 6.49-6.28 (2H, m), 5.83 (1H, d), 3.65 (2H, s), 3.59-3.51 (4H, m), 2.89-2.69 (4H, m). Tr=3.78 min, m/z (ES$^+$) (M+H)$^+$ 414.

Example D-23

N-{3-[4-(3-Phenyl-propionyl)-piperazine-1-sulfonyl]-phenyl}-acrylamide $\delta_H$ (500 MHz, DMSO) 10.52 (1H, s), 8.14 (1H, s), 7.95 (1H, d), 7.62 (1H, t), 7.38 (1H, d), 7.18-7.01 (5H, m), 6.47-6.23 (2H, m), 5.81 (1H, d), 3.57-3.43 (4H, m), 2.86-2.68 (6H, m), 2.58-2.51 (2H, m). Tr=3.87 min, m/z (ES$^+$) (M+H)$^+$ 427.95.

Example D-24

N-{4-[4-(2-Naphthalen-2-yl-acetyl)-piperazine-1-sulfonyl]-phenyl}-acrylamide $\delta_H$ (500 MHz, DMSO) 10.57 (1H, s), 7.93-7.83 (3H, m), 7.76-7.72 (2H, m), 7.68-7.59 (3H, m), 7.48-7.41 (2H, m), 7.32-7.26 (1H, m), 6.54-6.30 (2H, m), 5.84 (1H, dd), 3.84 (2H, s), 3.63-3.53 (4H, m), 2.90-2.76 (4H, m). Tr=4.08 min, m/z (ES$^+$) (M+H)$^+$ 464.05.

Example D-25

N-{4-[4-(Adamantane-1-carbonyl)-2,6-dimethyl-piperazine-1-sulfonyl]-phenyl}-acrylamide $\delta_H$ (500 MHz, DMSO) 10.54 (1H, s), 7.88 (2H, d), 7.78 (2H, d), 6.48-6.26 (2H, m), 5.82 (1H, dd), 4.10-3.98 (4H, m), 2.73-2.70 (2H, m), 1.96-1.72 (9H, m), 1.68-1.59 (6H, m), 1.21 (6H, s). Tr=4.70 min, m/z (ES$^+$) (M+H)$^+$ 486.

Example D-26

N-{4-[4-(3-Pyridin-3-yl-propionyl)-piperazine-1-sulfonyl]-phenyl}-acrylamide

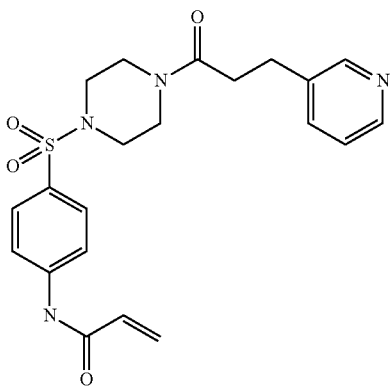 [SMILES: C=CC(=O)Nc1ccc(S(=O)(=O)N2CCN(C(=O)CCc3cccnc3)CC2)cc1]

Triethylamine (0.28 ml, 2.04 mmol) was added in one portion to a stirred solution of N-[4-(piperazine-1-sulfonyl)-phenyl]-acrylamide (0.2 g, 0.68 mmol) and 3-pyridine propionic acid (0.1 g, 0.68 mmol) in THF (5 ml). The mixture was stirred at room temperature for 5 minutes before EDC (0.26 g, 1.36 mmol) was added in one portion and the resulting mixture and stirred at room temperature under a nitrogen atmosphere for 18 hours. The crude reaction mixture was concentrated under vacuum and the resulting residue dissolved in DCM (20 ml), washed with water (20 ml), dried (MgSO$_4$), filtered and concentrated under vacuum. The crude product was purified by Prep HPLC to give the title compound (0.046 g, 15% yield) as a white powder.

Example D-27

N-{4-[4-(3-Pyridin-3-yl-propionyl)-piperazine-1-sulfonyl]-phenyl}-acrylamide $\delta_H$ (500 MHz, DMSO) 10.61 (1H, br s), 8.41 (1H, s), 8.32 (1H, d), 7.92 (2H, d), 7.19 (2H, d), 7.08 (1H, d), 7.23-7.18 (1H, m), 6.49-6.28 (2H, m), 5.86 (1H, d), 3.57-3.49 (4H, m), 2.83-2.70 (6H, m), 2.62-2.53 (2H, m). Tr=2.40 min, m/z (ES$^+$) (M+H)$^+$ 430.

Example D-28

N-{4-[4-(Adamantane-1-carbonyl)-piperazine-1-sulfonyl]-phenyl}-acrylamide $\delta_H$ (500 MHz, DMSO) 10.59 (1H, s), 7.88 (2H, d), 7.68 (2H, d), 6.49-6.26 (2H, m), 5.81 (1H, d), 3.68-3.59 (4H, m), 2.85-2.76 (4H, m), 1.91-1.53 (15H, m). Tr=4.46 min, m/z (ES$^+$) (M+H)$^+$ 458.

Example D-29

N-{4-[4-(3-Piperidin-1-yl-propionyl)-piperazine-1-sulfonyl]-phenyl}-acrylamide $\delta_H$ (500 MHz, DMSO) 10.59 (1H, s), 7.92 (2H, d), 7.69 (2H, d), 6.50-6.28 (2H, m), 5.81 (1H, dd), 3.54-3.51 (4H, m), 2.89-2.77 (4H, m), 2.40-2.36 (4H, m), 2.21-2.08 (4H, m), 1.32-1.21 (6H, m). Tr=2.53 min, m/z (ES$^+$) (M+H)$^+$ 435.

Example D-30

N-{4-[4-(2-Piperidin-1-yl-acetyl)-piperazine-1-sulfonyl]-phenyl}-acrylamide $\delta_H$ (250 MHz, DMSO) 10.59 (1H, s), 7.91 (2H, d), 7.68 (2H, d), 6.51-6.23 (2H, m), 5.83 (1H, dd), 3.61-3.49 (4H, m), 3.15-2.95 (2H, m), 2.91-2.77 (4H, m), 2.23-2.13 (4H, m), 1.31-1.20 (6H, m). Tr=2.52 min, m/z (ES$^+$) (M+H)$^+$ 421.

Example D-31

N-{4-[4-(3-Pyridin-4-yl-propionyl)-piperazine-1-sulfonyl]-phenyl}-acrylamide $\delta_H$ (500 MHz, DMSO) 10.59 (1H, s), 8.39 (2H, d), 7.92 (2H, d), 7.69 (2H, d), 7.16 (2H, d), 6.49-6.28 (2H, m), 5.82 (1H, d), 3.54-3.01 (4H, m), 2.87-2.81 (4H, m), 2.76-2.71 (2H, m), 2.64-2.60 (4H, m). Tr=2.53 min, m/z (ES$^+$) (M+H)$^+$ 429.

Example D-32

N-{4-[4-(3-Pyridin-2-yl-propionyl)-piperazine-1-sulfonyl]-phenyl}-acrylamide $\delta_H$ (500 MHz, DMSO) 10.61 (1H, s), 8.29 (1H, d), 7.93 (2H, d), 7.71 (2H, d), 7.58 (1H, t), 7.20 (1H, d), 7.05 (1H, t), 6.49-6.28 (2H, m), 5.84 (1H, dd), 3.59-3.51 (4H, m), 2.88 (2H, t), 2.87-2.76 (4H, m), 2.71-2.66 (2H, t). Tr=2.57 min, m/z (ES$^+$) (M+H)$^+$ 429.

Example D-33

N-(4-{4-[2-(2-Phenoxy-phenyl)-acetyl]-piperazine-1-sulfonyl}-phenyl)-acrylamide $\delta_H$ (500 MHz, DMSO) 10.60 (1H, s), 7.93 (2H, d), 7.64 (2H, d), 7.24-7.19 (4H, m), 7.05 (1H, t), 6.96 (1H, t), 6.78 (3H, d), 6.52-6.39 (2H, m), 5.86 (1H, dd), 3.61 (2H, s), 3.54-3.43 (4H, m), 2.76-2.70 (4H, m). Tr=4.28 min, m/z (ES$^+$) (M+H)$^+$ 506.

Example D-34

N-(4-{4-[2-(3-Phenoxy-phenyl)-acetyl]-piperazine-1-sulfonyl}-phenyl)-acrylamide $\delta_H$ (500 MHz, DMSO) 10.59 (1H, s), 7.92 (2H, d), 7.64 (2H, d), 7.34 (2H, t), 7.23 (1H, t), 7.12 (1H, t), 6.92-6.74 (5H, m), 6.49-6.28 (2H, m), 5.83 (1H, dd), 3.63 (2H, s), 3.57-3.48 (4H, m), 2.82-2.70 (4H, m). Tr=4.30 min, m/z (ES$^+$) (M+H)$^+$ 506.

Example D-35

N-(4-{4-[2-(4-Phenoxy-phenyl)-acetyl]-piperazine-1-sulfonyl}-phenyl)-acrylamide $\delta_H$ (500 MHz, DMSO) 10.58 (1H, s), 7.92 (2H, d), 7.67 (2H, d), 7.36 (2H, t), 7.16-7.04 (3H, m), 6.92 (2H, d), 6.88 (2H, d), 6.49-6.28 (2H, m), 5.83 (1H, d), 3.62 (2H, s), 3.60-3.52 (4H, m), 2.84-2.79 (4H, m). Tr=4.32 min, m/z (ES$^+$) (M+H)$^+$ 506.

Example D-36

N-{4-[4-(2-Morpholin-4-yl-acetyl)-piperazine-1-sulfonyl]-phenyl}-acrylamide $\delta_H$ (500 MHz, DMSO) 10.58 (1H, s), 7.92 (2H, d), 7.69 (2H, d), 6.49-6.28 (2H, m), 5.82 (1H, dd), 3.61-3.49 (4H, m), 3.41 (4H, s), 3.07 (2H, s), 2.92-2.80 (4H, m), 2.24 (4H, s). Tr=2.39 min, m/z (ES$^+$) (M+H)$^+$ 423.

Example D-37

N-{4-[4-(3-Morpholin-4-yl-propionyl)-piperazine-1-sulfonyl]-phenyl}-acrylamide $\delta_H$ (500 MHz, DMSO) 10.59 (1H, s), 7.92 (2H, d), 7.68 (2H, d), 6.48-6.29 (2H, m), 5.84 (1H, dd), 3.54-3.42 (8H, m), 2.89-2.78 (4H, m), 2.41 (4H, s), 2.26 (4H, s). Tr=2.42 min, m/z (ES$^+$) (M+H)$^+$ 437.

Example D-38

N-{4-[4-(2,2,6,6-Tetramethyl-piperidine-4-carbonyl)-piperazine-1-sulfonyl]-phenyl}-acrylamide $\delta_H$ (500 MHz, MeOD) 7.91 (2H, d), 7.76 (2H, d), 6.49-6.38 (2H, m), 5.82 (1H, dd), 3.71-3.66 (4H, m), 3.09-3.00 (4H, m), 1.82-1.73 (2H, m), 1.66-1.58 (2H, m), 1.48 (6H, s), 1.39 (6H, s). Tr=2.59 min, m/z (ES$^+$) (M+H)$^+$ 463.

Example D-39

N-{4-[4-(Oxazole-5-carbonyl)-piperazine-1-sulfonyl]-phenyl}-acrylamide $\delta_H$ (500 MHz, DMSO) 10.58 (1H, s), 8.52 (1H, s), 7.92 (1H, d), 7.72-7.62 (3H, m), 6.49-6.28 (2H, m), 5.84 (1H, dd), 3.76-3.68 (4H, m), 2.97-2.91 (4H, m). Tr=3.45 min, m/z (ES$^+$) (M+H)$^+$ 391.

Method E

Example E-1

N-[4-(4-Ethyl-piperazine-1-sulfonyl)-phenyl]-acrylamide

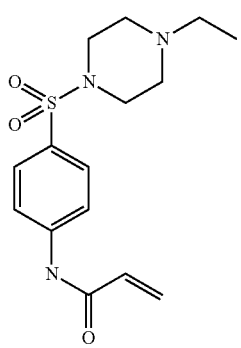 [SMILES: C=CC(=O)Nc1ccc(S(=O)(=O)N2CCN(CC)CC2)cc1]

Potassium carbonate (0.2 g, 1.36 mmol) was added in one portion to a stirred solution of N-[4-(piperazine-1-sulfonyl)-phenyl]-acrylamide (0.1 g, 0.34 mmol) in DMF (5 ml). The mixture was stirred at room temperature for 5 minutes before iodoethane (0.03 ml, 0.44 mmol) was added dropwise and the resulting mixture heated to 60° C. and stirred under a nitrogen atmosphere for 18 hours. The crude reaction mixture was concentrated under vacuum and the residue was purified by Prep HPLC to give the title compound (0.015 g, 11% yield) as a white powder.

Example E-1

N-[4-(4-Ethyl-piperazine-1-sulfonyl)-phenyl]-acrylamide $\delta_H$ (500 MHz, CDCl$_3$) 7.78 (2H, d), 7.72 (2H, d), 7.54 (1H, br s), 6.53-6.24 (2H, m), 5.82 (1H, d), 3.25-2.96 (4H, m), 2.64-2.36 (6H, m), 1.14-0.99 (3H, m). Tr=2.33 min, m/z (ES$^+$) (M+H)$^+$ 324.

Example E-2

N-[4-(4-Cyclopropylmethyl-piperazine-1-sulfonyl)-phenyl]-acrylamide $\delta_H$ (500 MHz, CDCl$_3$) 7.82 (2H, d), 7.74 (2H, d), 7.66 (1H, br s), 6.52-6.24 (2H, m), 5.85 (1H, d), 3.21-2.98 (4H, m), 2.74-2.53 (4H, m), 2.34-2.21 (2H, m), 0.81 (1H, br s), 0.56-0.48 (2H, m), 0.14-0.11 (2H, m). Tr=2.39 min, m/z (ES$^+$) (M+H)$^+$ 350.

Example E-3

N-[4-(4-Cyclopentylmethyl-piperazine-1-sulfonyl)-phenyl]-acrylamide

δH (500 MHz, CDCl$_3$) 7.79 (2H, d), 7.73 (2H, d), 7.59 (1H, br s), 6.51-6.26 (2H, m), 5.84 (1H, d), 3.12-2.95 (4H, m), 2.61-2.43 (4H, m), 2.29-2.16 (2H, m), 2.01 (1H, br s), 1.71-1.43 (7H, m), 1.16-1.05 (2H, m). Tr=2.64 min, m/z (ES$^+$) (M+H)$^+$ 378.

Example E-4

N-[4-(4-Biphenyl-4-ylmethyl-piperazine-1-sulfonyl)-phenyl]-acrylamide

δH (500 MHz, DMSO) 10.59 (1H, s), 7.92 (2H, d), 7.68 (2H, d), 7.61 (2H, d), 7.54 (2H, d), 7.41 (2H, t), 7.36-7.30 (3H, m), 6.51-6.28 (2H, m), 5.82 (1H, d), 3.49 (3H, s), 2.93-2.81 (4H, m), 2.48-2.40 (4H, m). Tr=3.40 min, m/z (ES$^+$) (M+H)$^+$ 462.

Method F

Example F-1

4-(4-Acryloylamino-benzenesulfonylamino)-piperidine-1-carboxylic acid benzyl ester 4-(4-Nitro-benzenesulfonylamino)-piperidine-1-carboxylic acid tert-butyl ester

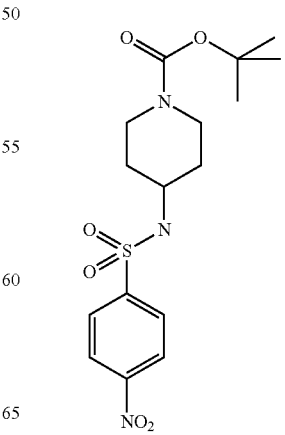

4-Nitrophenyl sulfonyl chloride (1.1 g, 5.4 mmol) was added in one portion to a stirred solution of 4-amino-piperidine-1-carboxylic acid tert-butyl ester (1.0 g, 4.9 mmol) and diisopropylethylamine in THF (10 ml). The resulting mixture was stirred at room temperature under a nitrogen atmosphere for 1 hour, after which time the solvent was removed under vacuum to give the title compound (1.92 g, 100% yield) as an orange solid which was used without further purification. Tr=2.00 min m/z (ES$^+$) (M+Na$^+$) 408.

4-Nitro-N-piperidin-4-yl-benzenesulfonamide

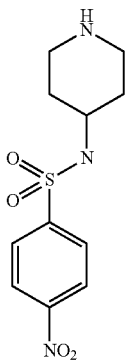

HCl (20 ml, 4M solution in dioxane) was added in one portion to a stirred solution of 4-(4-Nitro-benzenesulfonylamino)-piperidine-1-carboxylic acid tert-butyl ester (1.92 g, 4.9 mmol) in dioxane (5 ml) and the suspension was stirred at room temperature under a nitrogen atmosphere for 3 hours. After this time the reaction was concentrated under vacuum and the resulting solid was collected by filtration, washed with TBME (3×100 ml) and dried under vacuum to give the title compound (1.4 g, 100% yield) as a white solid. Tr=0.91 min m/z (ES$^+$) (M+H$^+$) 286.

4-(4-Nitro-benzenesulfonylamino)-piperidine-1-carboxylic acid benzyl ester

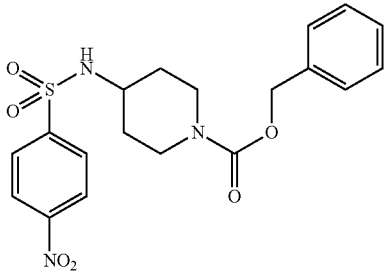 [SMILES: O=C(OCc1ccccc1)N1CCC(NS(=O)(=O)c2ccc([N+](=O)[O-])cc2)CC1]

Benzyl chloroformate (0.7 ml, 4.9 mmol) was added drop wise to a cool (0° C.) solution of 4-nitro-N-piperidin-4-yl-benzenesulfonamide (1.4 g, 4.9 mmol) and diisopropylethylamine (1.6 ml, 9.8 mmol) in THF (10 ml). The resulting mixture was warmed to room temperature and stirred under a nitrogen atmosphere for 18 hours. After this time, the mixture was diluted with ethyl acetate (50 ml), washed with water (50 ml), the organic layer was separated and dried (MgSO$_4$), filtered and concentrated under vacuum. The resulting residue was purified by flash column chromatography (elution: 50% heptane, 50% ethyl acetate) to give the title compound (0.98 g, 48% yield) as a white solid. Tr=2.04 min m/z (ES$^+$) (M+H$^+$) 420.

4-(4-Amino-benzenesulfonylamino)-piperidine-1-carboxylic acid benzyl ester

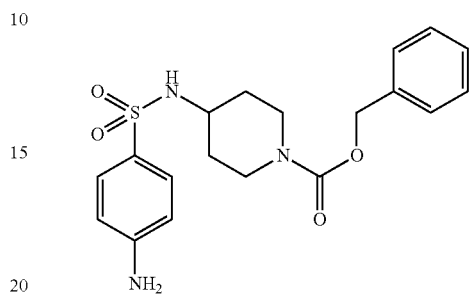

4-(4-Nitro-benzenesulfonylamino)-piperidine-1-carboxylic acid benzyl ester (0.98 g, 2.4 mmol) was suspended in a 5:1 mixture of ethanol and water (30 ml). To this solution was added iron powder (0.34 g, 6.1 mmol) followed by saturated ammonium chloride solution (1 ml) and the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (1 g, 100% yield) as a brown solid. Tr=1.80 min, m/z (ES$^+$) (M+H)$^+$ 390.

4-(4-Acryloylamino-benzenesulfonylamino)-piperidine-1-carboxylic acid benzyl ester

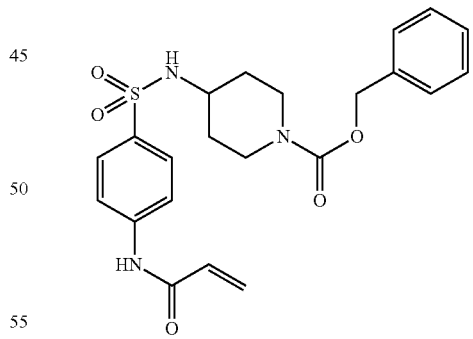

4-(4-Amino-benzenesulfonylamino)-piperidine-1-carboxylic acid benzyl ester (1 g, 2.4 mmol) was dissolved in THF (10 ml). To this was added diisopropylethylamine (1.27 ml, 7.2 mmol) in one portion followed by the drop wise addition of acryloyl chloride (0.2 ml, 2.6 mmol) and the mixture was stirred at room temperature under a nitrogen atmosphere for 3 hours. The THF was removed under vacuum and the resulting crude material was purified by column chromatography (elution: 40% heptane, 60% ethyl acetate) to give the title compound (89 mg, 8% yield) as a white powder.

Example F-1

4-(4-Acryloylamino-benzenesulfonylamino)-piperidine-1-carboxylic acid benzyl ester $\delta_H$ (500 MHz, DMSO) 10.58 (1H, s), 7.92 (2H, d), 7.81 (2H, d), 7.75 (1H, d), 7.46-7.31 (5H, m), 6.57-6.30 (2H, m), 5.88 (1H, d), 5.08 (2H, s), 3.90-3.78 (2H, m), 3.28-3.16 (1H, m), 3.07-2.84 (2H, m), 1.79-1.56 (2H, m), 1.38-1.20 (2H, m). Tr=3.97 min, m/z (ES$^+$) (M+H)$^+$ 444.

Example F-2

3-(4-Acryloylamino-benzenesulfonylamino)-(R)-pyrrolidine-1-carboxylic acid benzyl ester $\delta_H$ (500 MHz, DMSO) 10.52 (1H, s), 7.91 (1H, s), 7.88 (2H, d), 7.75 (2H, d), 7.39-7.24 (5H, m), 6.47-6.28 (2H, m), 5.82 (1H, d), 5.0.1 (2H, d), 3.68-3.61 (1H, m), 3.34 (2H, obscured), 3.26-3.19 (1H, m), 3.11-2.99 (1H, m), 1.92-1.81 (1H, m), 1.72-1.63 (1H, m). Tr=3.84 min, m/z (ES$^+$) (M+H)$^+$ 430.

Example F-3

4-[(4-Acryloylamino-benzenesulfonylamino)-methyl]-piperidine-1-carboxylic acid benzyl ester $\delta_H$ (500 MHz, DMSO) 10.50 (1H, s), 7.83 (2H, d), 7.75 (2H, d), 7.56 (1H, t), 7.39-7.28 (5H, m), 6.48-6.26 (2H, m), 5.81 (1H, d), 5.04 (2H, s), 3.96 (2H, d), 2.81-2.59 (4H, m), 1.64-1.48 (3H, m), 0.99-0.88 (2H, m). Tr=4.09 min, m/z (ES$^+$) (M+H)$^+$ 458.

Example F-4

3-(4-Acryloylamino-benzenesulfonylamino)-(S)-pyrrolidine-1-carboxylic acid benzyl ester $\delta_H$ (500 MHz, DMSO) 10.54 (1H, s), 7.92 (1H, d), 7.85 (2H, d), 7.76 (2H, d), 7.39-7.26 (5H, m), 6.50-6.27 (2H, m), 5.83 (1H, d), 5.02 (2H, d), 3.71-3.62 (1H, m), 3.34 (2H, obscured), 3.28-3.21 (1H, m), 3.11-3.04 (1H, m), 1.91-1.84 (1H, m), 1.72-1.61 (1H, m). Tr=3.85 min, m/z (ES$^+$) (M+H)$^+$ 430.

Method G

Example G-1

[1-(4-Acryloylamino-benzenesulfonyl)-piperidin-4-yl]carbamic acid benzyl ester

4-Benzyloxycarbonylamino-piperidine-1-carboxylic acid tert-butyl ester

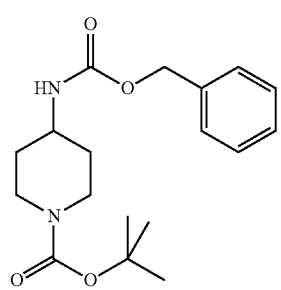 [SMILES: CC(C)(C)OC(=O)N1CCC(NC(=O)OCc2ccccc2)CC1]

Diisopropylethylamine (0.9 ml, 5.5 mmol) was added in one portion to a stirred solution of 4-amino-piperidine-1-carboxylic acid tert-butyl ester (1.0 g, 5.0 mmol) in THF (10 ml) at room temperature. To this mixture was added benzyl chloroformate (0.78 ml, 5.5 mmol) drop wise and the mixture was stirred at room temperature under a nitrogen atmosphere for 18 hours. After this time the mixture was diluted with ethyl acetate (50 ml) and washed with water (100 ml), saturated NaHCO$_3$ (100 ml) and HCl (100 ml, 2M). The organic layer was separated, dried (MgSO$_4$), filtered and concentrated under vacuum. The resulting residue was purified by flash column chromatography (elution: 50% heptane, 50% ethyl acetate) to give the title compound (1.2 g, 73% yield) as a colourless oil. Tr=2.08 min m/z (ES$^+$) (M+Na$^+$) 357.

Piperidin-4-yl-carbamic acid benzyl ester

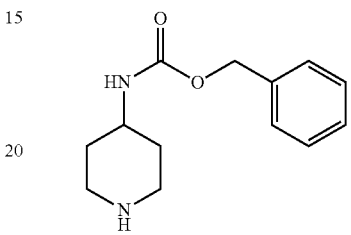

HCl (10 ml, 4M solution in dioxane) was added in one portion to a stirred solution of 4-benzyloxycarbonylamino-piperidine-1-carboxylic acid tert-butyl ester (1.2 g, 3.6 mmol) in dioxane (5 ml) and the suspension was stirred at room temperature under a nitrogen atmosphere for 3 hours. After this time the reaction was concentrated under vacuum and the resulting solid was collected by filtration, washed with TBME (3×100 ml) and dried under vacuum to give the title compound (0.74 g, 88% yield) as a white solid. Tr=1.03 min m/z (ES$^+$) (M+H$^+$) 236.

[1-(4-Nitro-benzenesulfonyl)-piperidin-4-yl]-carbamic acid benzyl ester

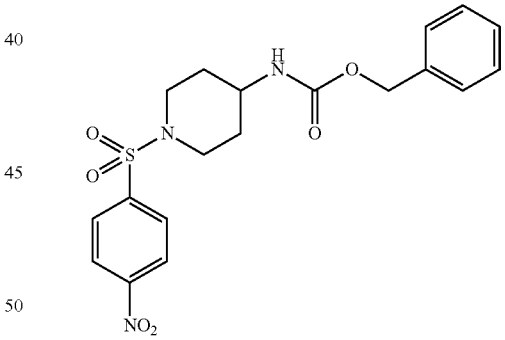

Diisopropylethylamine (1.04 ml, 7.0 mmol) was added in one portion to a stirred solution of piperidin-4-yl-carbamic acid benzyl ester (0.74 g, 3.1 mmol) in THF (10 ml) at room temperature. To this mixture was added 4-nitrophenyl sulfonyl chloride (0.77 g, 3.5 mmol) in one portion and the mixture was stirred at room temperature under a nitrogen atmosphere for 1 hour. After this time the solvent was removed under vacuum and the resulting residue was partitioned between ethyl acetate (50 ml) and HCl (50 ml, 1M solution), the organic layer was separated and washed with brine (50 ml) before being dried (MgSO$_4$), filtered and concentrated under vacuum. The resulting white solid was suspended in heptane and collected by filtration, washed with water (50 ml), heptane (50 ml) and TBME (50 ml) before being dried under vacuum to afford the title compound (1.3 g, 100% yield) as a white solid. Tr=2.09 min m/z (ES$^+$) (M+H$^+$) 420.

[1-(4-Amino-benzenesulfonyl)-piperidin-4-yl]-carbamic acid benzyl ester

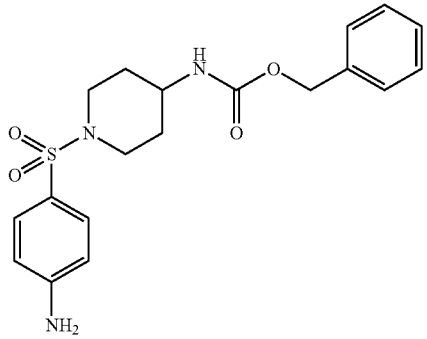 [SMILES: Nc1ccc(S(=O)(=O)N2CCC(NC(=O)OCc3ccccc3)CC2)cc1]

[1-(4-Nitro-benzenesulfonyl)-piperidin-4-yl]-carbamic acid benzyl ester (1.3 g, 3.5 mmol) was suspended in a 5:1 mixture of ethanol and water (30 ml). To this solution was added iron powder (0.48 g, 9.1 mmol) followed by saturated ammonium chloride solution (1 ml) and the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (1.25 g, 99% yield) as a brown solid. Tr=1.81 min, m/z (ES$^+$) (M+H)$^+$ 390.

[1-(4-Acryloylamino-benzenesulfonyl)-piperidin-4-yl]-carbamic acid benzyl ester

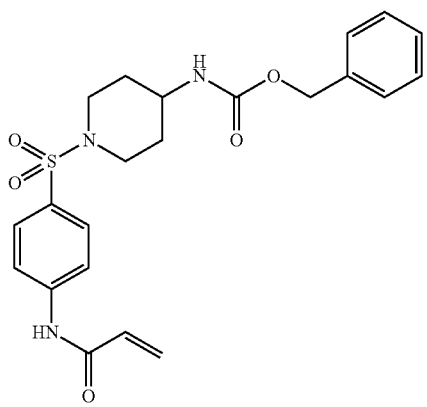 [SMILES: C=CC(=O)Nc1ccc(S(=O)(=O)N2CCC(NC(=O)OCc3ccccc3)CC2)cc1]

[1-(4-Amino-benzenesulfonyl)-piperidin-4-yl]-carbamic acid benzyl ester (1.29 g, 3.3 mmol) was dissolved in DCM (20 ml). To this was added diisopropylethylamine (1.64 ml, 9.9 mmol) in one portion followed by the drop wise addition of acryloyl chloride (0.3 ml, 3.6 mmol) and the mixture was stirred at room temperature under a nitrogen atmosphere for 18 hours. The THF was removed under vacuum and the resulting crude material was purified by Prep HPLC to give the title compound (10.4 mg, 1% yield) as a white powder.

Example G-1

[1-(4-Acryloylamino-benzenesulfonyl)-piperidin-4-yl]carbamic acid benzyl ester $\delta_H$ (250 MHz, DMSO) 10.54 (1H, s), 7.87 (2H, d), 7.64 (2H, d), 7.41-7.29 (5H, m), 6.51-6.25 (2H, m), 5.81 (1H, dd), 4.96 (2H, s), 3.42 (3H, obscured), 2.42 (2H, obscured), 1.81-1.70 (2H, m), 1.52-1.31 (2H, m). Tr=4.03 min, m/z (ES$^+$) (M+H)$^+$ 444.

Example G-2

[1-(4-Acryloylamino-benzenesulfonyl)-piperidin-4-ylmethyl]carbamic acid benzyl ester $\delta_H$ (500 MHz, DMSO) 10.57 (1H, s), 7.89 (2H, d), 7.67 (2H, d), 7.39-7.21 (5H, m), 6.50-6.28 (2H, m), 5.74 (1H, d), 4.98 (2H, s), 3.57 (2H, d), 2.83 (2H, t), 2.16 (2H, t), 1.68 (2H, d), 1.39-1.28 (1H, m), 1.16-1.03 (1H, m). Tr=4.10 min, m/z (ES$^+$) (M+H)$^+$ 458.

Example G-3

[1-(4-Acryloylamino-benzenesulfonyl)-(S)-pyrrolidin-3-yl]-carbamic acid benzyl ester $\delta_H$ (250 MHz, DMSO) 10.54 (1H, s), 7.89 (2H, d), 7.72 (2H, d), 7.43-7.21 (6H, m), 6.52-6.24 (2H, m), 5.81 (1H, dd), 4.92 (2H, q), 3.92-3.78 (1H, m), 3.30-2.98 (4H, m), 1.98-1.82 (1H, m), 1.70-1.51 (1H, m). Tr=3.93 min, m/z (ES$^+$) (M+H)$^+$ 430.

Example G-4

[1-(4-Acryloylamino-benzenesulfonyl)-(R)-pyrrolidin-3-yl]-carbamic acid benzyl ester $\delta_H$ (500 MHz, DMSO) 10.52 (1H, s), 7.92 (2H, d), 7.71 (2H, d), 7.41-7.28 (6H, m), 6.51-6.29 (2H, m), 5.83 (1H, s), 4.92 (2H, q), 3.89-3.80 (1H, m), 3.35 (2H, obscured), 3.21-3.00 (2H, m), 1.94-1.87 (1H, m), 1.69-1.62 (1H, m). Tr=3.94 min, m/z (ES$^+$) (M+H)$^+$ 430.

Method GG

Example GG-1

N-[4-(4-Amino-piperidine-1-sulfonyl)-phenyl]-acrylamide

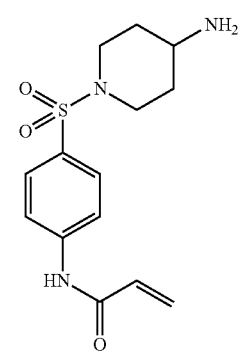 [SMILES: C=CC(=O)Nc1ccc(S(=O)(=O)N2CCC(N)CC2)cc1]

To a solution of [1-(4-Acryloylamino-benzenesulfonyl)-piperidin-4-yl]-carbamic acid tert-butyl ester (0.57 g, 1.4 mmol) in DCM (10 ml) was added trifluoroacetic acid (10 ml) in one portion. The resulting mixture was then stirred at room temperature under a nitrogen atmosphere for 3 hours. After this time the reaction was concentrated under vacuum to afford the title compound (0.40 g, 93% yield) as an orange solid.

$\delta_H$ (500 MHz, DMSO) 10.56 (1H, s), 7.95-7.74 (5H, m), 7.63 (2H, d), 6.43-6.21 (2H, m), 5.77 (1H, d), 3.54 (1H, obscured), 3.04-2.92 (1H, m), 2.26 (2H, t), 1.86 (2H, d), 1.52-1.38 (2H, m). Tr=2.13 min, m/z (ES$^+$) (M+H)$^+$ 310.

Example GG-2

N-[4-(4-Aminomethyl-piperidine-1-sulfonyl)-phenyl]-acrylamide $\delta_H$ (500 MHz, DMSO) 10.63 (1H, s), 7.92 (2H, d), 7.79 (3H, s), 7.68 (2H, d), 6.51-6.27 (2H, m), 5.82 (1H, d), 3.62 (2H, d), 2.75-2.64 (2H, m), 2.15 (2H, t), 1.75 (2H, d), 1.57-1.42 (1H, m), 1.30-1.13 (2H, m). Tr=2.24 min, m/z (ES$^+$) (M+H)$^+$ 324.

Example GG-3

N-[1-(4-Acryloylamino-benzenesulfonyl)-piperidin-4-yl]-benzamide

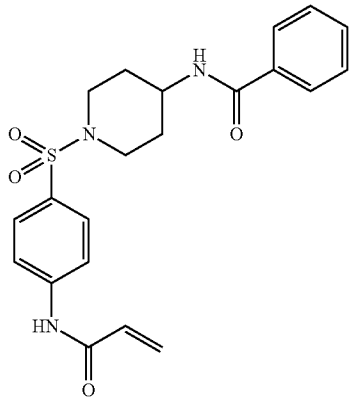 [SMILES: C=CC(=O)Nc1ccc(S(=O)(=O)N2CCC(NC(=O)c3ccccc3)CC2)cc1]

Diisopropylethylamine (0.14 ml, 0.8 mmol) was added in one portion to a stirred solution of N-[4-(4-amino-piperidine-1-sulfonyl)-phenyl]-acrylamide (0.1 g, 0.32 mmol) in THF (3 ml) at room temperature. To this mixture was added benzoyl chloride (0.048 ml, 0.42 mmol) in one portion and the mixture was stirred at room temperature under a nitrogen atmosphere for 1 hour. After this time, the mixture was concentrated under vacuum and the resulting residue purified by flash column chromatography (elution: 70% heptane, 30% ethyl acetate to 40% heptane, 60% ethyl acetate) to give the title compound (7 mg, 5% yield) as a white solid.

Example GG-3

N-[1-(4-Acryloylamino-benzenesulfonyl)-piperidin-4-yl]-benzamide $\delta_H$ (500 MHz, DMSO) 10.62 (1H, s), 8.33 (1H, d), 7.96 (2H, d), 7.84 (2H, d), 7.78 (2H, d), 7.59-7.43 (5H, m), 6.59-6.31 (2H, m), 5.91 (1H, d), 3.87-3.72 (1H, m), 3.23-3.11 (2H, m), 2.51-2.40 (2H, m), 1.97-1.86 (2H, m), 1.71-1.60 (2H, m). Tr=3.72 min, m/z (ES$^+$) (M+H)$^+$ 414.

Example GG-4

N-[1-(4-Acryloylamino-benzenesulfonyl)-piperidin-4-ylmethyl]-benzamide $\delta_H$ (500 MHz, DMSO) 10.58 (1H, s), 8.42 (1H, t), 7.89 (2H, d), 7.78 (2H, d), 7.69 (2H, d), 7.52-7.38 (3H, m), 6.49-6.28 (2H, m), 5.81 (1H, d), 3.61-3.54 (2H, m), 3.14-3.08 (2H, m), 2.24-2.18 (2H, m), 1.74-1.68 (2H, m), 1.56-1.48 (1H, m), 1.22-1.16 (2H, m). Tr=3.62 min, m/z (ES$^+$) (M+H)$^+$ 428.

Example GG-5

N-[4-(4-Acetylamino-piperidine-1-sulfonyl)-phenyl]-acrylamide $\delta_H$ (500 MHz, DMSO) 10.56 (1H, s), 7.91 (2H, d), 7.80 (1H, d), 7.72 (2H, d), 6.50-6.28 (2H, m), 5.82 (1H, d), 3.43-3.41 (2H, m), 2.42 (2H, obscured), 1.79-1.72 (5H, m), 1.41-1.32 (2H, m), 1.26-1.20 (2H, m). Tr=2.92 min, m/z (ES$^+$) (M+H)$^+$ 352.35.

Example GG-6

N-{4-[4-(Acetylamino-methyl)-piperidine-1-sulfonyl]-phenyl}-acrylamide $\delta_H$ (500 MHz, DMSO) 10.58 (1H, s), 7.92 (2H, d), 5.82-5.74 (1H, m), 7.68 (2H, d), 6.50-6.28 (2H, m), 5.82 (1H, d), 3.61-3.52 (2H, m), 2.89-2.80 (2H, m), 2.21-2.13 (2H, m), 1.76 (3H, s), 1.71-1.59 (2H, m), 1.38-1.34 (1H, m), 1.12-1.08 (2H, m). Tr=2.97 min, m/z (ES$^+$) (M+H)$^+$ 366.40.

Example GG-7

Adamantane-1-carboxylic acid [1-(4-acryloylamino-benzenesulfonyl)-piperidin-4-yl]-amide $\delta_H$ (500 MHz, MeOD) 7.88 (2H, d), 7.75 (2H, d), 6.48-6.36 (2H, m), 5.82 (1H, dd), 3.72 (2H, d), 3.65-3.54 (1H, m), 2.41-2.34 (2H, m), 1.99 (3H, s), 1.82-1.68 (14H, m), 1.63-1.56 (2H, m).

Example GG-8

Adamantane-1-carboxylic acid [1-(4-acryloylamino-benzenesulfonyl)-piperidin-4-yl]-methyl-amide $\delta_H$ (500 MHz, DMSO) 10.58 (1H, s), 7.92 (2H, d), 7.73 (2H, d), 6.51-6.28 (2H, d), 5.82 (1H, dd), 4.09-4.00 (1H, m), 3.71 (2H, d), 2.78 (3H, s), 2.34-2.28 (2H, m), 1.97-1.89 (3H, m), 1.88-1.82 (6H, m), 1.80-1.72 (3H, m), 1.64-1.58 (6H, m), 1.57-1.50 (2H, m). Tr=4.61 min, m/z (ES$^+$) (M+H)$^+$ 486.

Example GG-9

N-{4-[4-(Acetyl-methyl-amino)-piperidine-1-sulfonyl]-phenyl}-acrylamide $\delta_H$ (500 MHz, DMSO) 10.59 (1H, s), 7.92 (2H, d), 7.71 (2H, t), 6.50-6.29 (2H, m), 5.82 (1H, m), 4.18-4.09 (1H, m), 3.72-3.61 (2H, m), 3.61-3.53 (1H, m), 2.75 (2H, s), 2.61 (2H, s), 2.38-2.22 (2H, m), 1.94 (3H, s), 1.81-1.61 (3H, m), 1.52-1.46 (1H, m). Tr=3.08 min, m/z (ES$^+$) (M+H)$^+$ 366.

Example GG-10

N-[4-(4-Methylamino-piperidine-1-sulfonyl)-phenyl]-acrylamide $\delta_H$ (500 MHz, DMSO) 10.61 (1H, s), 8.53 (2H, br s), 7.91 (2H, d), 7.71 (2H, d), 6.49-6.28 (2H, m), 5.82 (1H, dd), 3.71-3.62 (2H, m), 3.01-2.93 (1H, m), 2.31-2.24 (2H, m), 2.04-1.98 (2H, m), 1.52-1.46 (2H, m). Tr=2.20 min, m/z (ES$^+$) (M+H)$^+$ 324.

Example GG-11

N-[4-(4-Phenethylamino-piperidine-1-sulfonyl)-phenyl]-acrylamide

To a solution of N-[4-(4-amino-piperidine-1-sulfonyl)-phenyl]-acrylamide (0.2 g, 3.1 mmol) and phenylacetaldehyde (0.06 ml, 0.52 mmol) in DCE (15 ml) was added triethylamine (0.066 ml, 0.47 mmol) in one portion. The resulting mixture was then stirred at room temperature under a nitrogen atmosphere for 30 minutes, after which time sodium triacetoxy borohydride (0.1 g, 0.47 mmol) was added portion wise. The reaction mixture was stirred at room temperature under a nitrogen atmosphere for a further 2 hours before being concentrated under vacuum. The resulting residue was purified by Prep HPLC to afford the title compound (8 mg, 7% yield) as an off-white powder.

$\delta_H$ (500 MHz, DMSO) 10.61 (1H, s), 7.92 (2H, d), 7.71 (2H, d), 7.35-7.24 (5H, m), 6.49-6.28 (2H, m), 5.83 (1H, d), 3.73-3.62 (2H, m), 3.16-3.07 (3H, m), 2.89-2.82 (2H, m), 2.31-2.26 (2H, m), 2.12-2.03 (2H, m), 1.61-1.50 (2H, m). Tr=2.86 min, m/z (ES$^+$) (M+H)$^+$ 414.45.

Example GG-12

N-{4-[4-(Benzylamino-methyl)-piperidine-1-sulfonyl]-phenyl}-acrylamide $\delta_H$ (500 MHz, DMSO) 10.59 (1H, s), 8.62 (1H, br s), 7.92 (2H, d), 7.71 (2H, d), 7.48-7.37 (5H, m), 6.49-6.31 (2H, m), 5.82 (1H, dd), 4.09 (2H, s), 3.63-3.57 (2H, m), 2.83-2.77 (2H, m), 2.20 (2H, t), 1.84-1.76 (2H, m), 1.71-1.65 (1H, m), 1.29-1.17 (2H, m). Tr=2.86 min, m/z (ES$^+$) (M+H)$^+$ 414.45.

Method H

Example H-1

4-(4-Acryloylamino-2-trifluoromethyl-benzenesulfonyl)-piperazine-1-carboxylic acid benzyl ester 4-Nitro-2-trifluoromethyl-benzenesulfonyl chloride

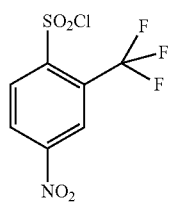

Sodium nitrite (1.8 g, 26 mmol) was added portion wise to a stirred solution of 4-nitro-2-trifluoromethyl-phenylamine (5.0 g, 24 mmol) in acetic acid (37 ml) and HCl (concentrated, 7.5 ml) while maintaining the temperature below 15° C. This solution was then added drop wise to a stirred solution of saturated sulfur dioxide, copper (II) chloride (0.6 g, 4.5 mmol) and water (7.5 ml) in acetic acid (24 ml) at 5° C. The reaction mixture was allowed to warm to room temperature and poured over ice water and stirred for a further 15 minutes. The resulting precipitate was collected by filtration, washed with water and dried overnight in a vacuum oven to give the title compound (3.5 g, 71% yield) as a yellow solid which was used without further purification.

4-(4-Nitro-2-trifluoromethyl-benzenesulfonyl)-piperazine-1-carboxylic acid benzyl ester

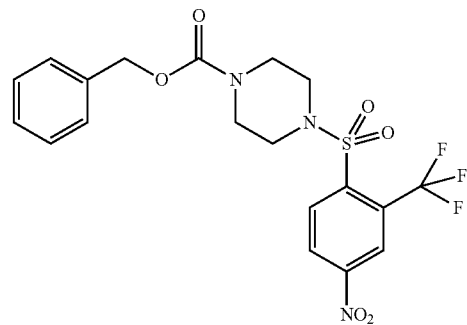 [SMILES: O=C(OCc1ccccc1)N1CCN(S(=O)(=O)c2ccc([N+](=O)[O-])cc2C(F)(F)F)CC1]

Diisopropylethylamine (1.2 ml, 7.0 mmol) was added in one portion to a stirred solution of piperazine-1-carboxylic acid benzyl ester (0.76 g, 3.5 mmol) in DCM (15 ml) at room temperature. To this mixture was added 4-nitro-2-trifluoromethyl-benzenesulfonyl chloride (1.0 g, 3.5 mmol) in one portion and the mixture was stirred at room temperature under a nitrogen atmosphere for 1 hour. After this time, the mixture was diluted with DCM (20 ml), washed with HCl (1M, 20 ml) and NaOH (1M, 20 ml). The organic layer was separated, dried (MgSO$_4$), filtered and concentrated under vacuum to give the title compound (1.43 g, 87% yield) as a purple solid. $\delta_H$ (500 MHz, DMSO) 8.65-8.60 (2H, m), 8.31 (1H, d), 7.38-7.29 (5H, m), 5.07 (2H, s), 3.56-3.46 (4H, m), 3.30-3.25 (4H, m). Tr=2.25 min m/z (ES$^+$) (M+Na$^+$) 496.

4-(4-Amino-2-trifluoromethyl-benzenesulfonyl)-piperazine-1-carboxylic acid benzyl ester

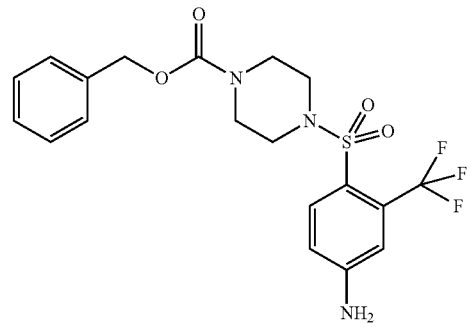 [SMILES: Nc1ccc(S(=O)(=O)N2CCN(C(=O)OCc3ccccc3)CC2)c(C(F)(F)F)c1]

4-(4-Nitro-2-trifluoromethyl-benzenesulfonyl)-piperazine-1-carboxylic acid benzyl ester (0.5 g, 1.0 mmol) was suspended in a 5:1 mixture of ethanol and water (20 ml). To this solution was added iron powder (0.16 g, 2.6 mmol) followed by saturated ammonium chloride solution (1 ml) and the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with $MgSO_4$, filtered and concentrated to afford the title compound (0.44 g, 94% yield) as a yellow solid. Tr=2.03 min, m/z (ES$^+$) (M+H)$^+$ 444.

4-(4-Acryloylamino-2-trifluoromethyl-benzenesulfonyl)-piperazine-1-carboxylic acid benzyl ester

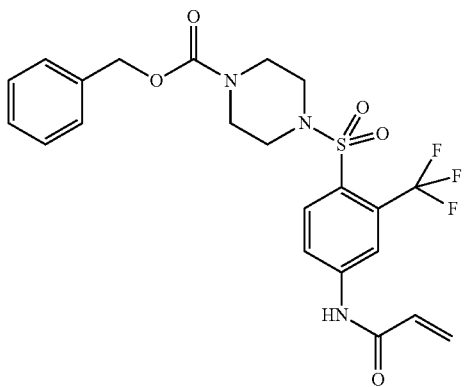 [SMILES: C=CC(=O)Nc1ccc(S(=O)(=O)N2CCN(C(=O)OCc3ccccc3)CC2)c(C(F)(F)F)c1]

4-(4-Amino-2-trifluoromethyl-benzensulfonyl)-piperazine-1-carboxylic acid benzyl ester (0.44 g, 0.11 mmol) was dissolved in THF (15 ml). To this solution was added diisopropylethylamine (0.52 ml, 0.33 mmol) in one portion followed by the drop wise addition of acryloyl chloride (0.09 ml, 0.11 mmol) and the mixture was stirred at room temperature under a nitrogen atmosphere for 3 hours. The THF was removed under vacuum and the resulting crude material, was purified by preparative HPLC to give the title compound (70 mg, 14% yield) as a white solid.

Example H-1

4-(4-Acryloylamino-2-trifluoromethyl-benzenesulfonyl)-piperazine-1-carboxylic acid benzyl ester $\delta_H$ (500 MHz, CDCl$_3$) 8.12-7.99 (4H, m), 7.37-7.29 (5H, m), 6.55-6.25 (2H, m), 5.88 (1H, d), 5.13 (2H, s), 3.60-3.55 (4H, m), 3.24-3.18 (4H, m). Tr=4.57 min, m/z (ES$^+$) (M+Na)$^+$ 520.

Example H-2

4-(4-Acryloylamino-2-chloro-benzenesulfonyl)-piperazine-1-carboxylic acid tert-butyl ester $\delta_H$ (250 MHz, DMSO) 10.67 (1H, s), 8.04 (1H, d), 7.90 (1H, d), 7.67 (1H, dd), 6.49-6.26 (2H, m), 5.83 (1H, dd), 3.39-3.32 (4H, m), 3.13-3.04 (4H, m), 1.34 (9H, s). Tr=4.38 min, m/z (ES$^+$) (M+Na)$^+$ 452/454.

Example H-3

4-(4-Acryloylamino-2-methoxy-benzenesulfonyl)-piperazine-1-carboxylic acid tert-butyl ester $\delta_H$ (500 MHz, DMSO) 10.54 (1H, s), 7.68 (2H, d), 7.32 (2H, d), 6.47-6.28 (2H, m), 5.83 (1H, dd), 3.82 (3H, s), 3.06-2.98 (4H, m), 1.36 (9H, m). Tr=3.93 min, m/z (ES$^+$) (M+Na)$^+$ 448.

Example H-4

4-(4-Acryloylamino-3-fluoro-benzenesulfonyl)-piperazine-1-carboxylic acid benzyl ester $\delta_H$ (250 MHz, DMSO) 9.61 (1H, s), 8.00-7.92 (1H, m), 7.64-7.53 (2H, m), 7.39-7.21 (5H, m), 6.57-6.18 (2H, m), 5.81 (1H, dd), 5.02 (2H, s), 3.49-3.38 (4H, m), 3.02-2.91 (4H, m). Tr=4.35 min, m/z (ES$^+$) (M+H)$^+$ 448.

Example H-5

4-(4-Acryloylamino-2-methyl-benzenesulfonyl)-piperazine-1-carboxylic acid tert-butyl ester $\delta_H$ (500 MHz, DMSO) 10.49 (1H, s), 7.76-7.68 (3H, m), 6.48-6.28 (2H, m), 5.82 (1H, d), 3.41-3.35 (4H, m), 3.00-2.94 (4H, m), 2.54 (3H, s), 1.37 (9H, s). Tr=4.04 min, m/z (ES$^+$) (M+Na)$^+$ 432.

Example H-6

N-[3-Methoxy-4-(piperazine-1-sulfonyl)-phenyl]-acrylamide

To a solution of 4-(4-Acryloylamino-2-methoxy-benzenesulfonyl)-piperazine-1-carboxylic acid tert-butyl ester (2.0 g, 4.7 mmol) in DCM (20 ml) was added trifluoroacetic acid (5 ml) in one portion. The resulting mixture was then stirred at room temperature under a nitrogen atmosphere for 3 hours. After this time the reaction was concentrated under vacuum to afford the title compound (1.3 g, 93% yield) as an orange gum.

$\delta_H$ (500 MHz, DMSO) 10.62 (1H, s), 8.77 (1H, br s), 7.78-7.66 (2H, m), 7.32 (1H, dd), 6.49-6.28 (2H, m), 5.83 (1H, dd), 3.86 (3H, s), 3.29-3.23 (4H, m), 3.19-3.12 (4H, m). Tr=2.14 min, m/z (ES$^+$) (M+H)$^+$ 326.

Example H-7

N-[3-Methyl-4-(piperazine-1-sulfonyl)-phenyl]-acrylamide $\delta_H$ (500 MHz, DMSO) 10.52 (1H, s), 8.66 (1H, br s), 7.82-7.71 (3H, m), 6.49-6.28 (2H, m), 5.83 (1H, d), 3.22-3.09 (8H, m), 2.54 (3H, s). Tr=2.5 min, m/z (ES$^+$) (M+H)$^+$ 310.

Example H-8

N-{4-[4-(Adamantane-1-carbonyl)-piperazine-1-sulfonyl]-3-methoxy-phenyl}-acrylamide Diisopropylethylamine (0.12 ml, 0.68 mmol) was added in one portion to a stirred solution of N-[3-Methoxy-4-(piperazine-1-sulfonyl)-phenyl]-acrylamide (0.1 g, 0.31 mmol) in THF (5 ml). The mixture was stirred at room temperature for 5 minutes before adamantine-1-carbonyl chloride (0.07 g, 0.33 mmol) was added drop wise and the resulting mixture was stirred at room temperature under a nitrogen atmosphere for 18 hours. The crude reaction mixture was concentrated under vacuum and the residue was purified by flash column chromatography (elution: 40% heptane, 60% ethyl acetate) to give the title compound (0.017 g, 6% yield) as a white powder.

$\delta_H$ (500 MHz, DMSO) 10.53 (1H, s), 7.71-7.63 (2H, m), 7.33 (1H, d), 6.49-6.28 (2H, m), 5.82 (1H, dd), 3.82 (3H, s), 3.63-3.58 (4H, m), 3.04-2.98 (4H, m), 1.97-1.92 (3H, s), 1.82 (6H, s), 1.69-1.58 (6H, m). Tr=4.24 min, m/z (ES$^+$) (M+H)$^+$ 488.

Example H-9

N-{4-[4-(Adamantane-1-carbonyl)-piperazine-1-sulfonyl]-3-methyl-phenyl}-acrylamide $\delta_H$ (500 MHz, DMSO) 10.49 (1H, s), 7.78-7.69 (3H, m), 6.48-6.27 (2H, m), 5.82 (1H, dd), 3.66-3.59 (4H, m), 2.99-2.92 (4H, m), 2.53 (3H, s), 1.96-1.91 (3H, m), 1.84-1.79 (6H, m), 1.68-1.59 (6H, m), 1.27-1.20 (3H, m). Tr=4.41 min, m/z (ES$^+$) (M+H)$^+$ 472.

Method I

Example I-1

4-(4-Acryloylamino-benzenesulfonyl)-piperazine-1-carboxylic acid benzylamide 4-(4-Nitro-benzenesulfonyl)-piperazine-1-carboxylic acid benzylamide

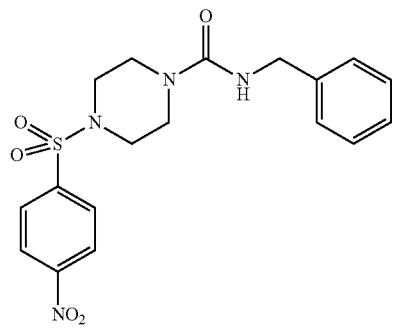

To a solution of 1-(4-Nitro-benzenesulfonyl)-piperazine (1.0 g, 2.6 mmol) in pyridine (10 ml) was added benzyl isocyanate (0.35 ml, 2.85 mmol) in one portion. The resulting mixture was then heated at 50° C. for 2 hours before being cooled to room temperature and concentrated under vacuum. The resulting residue was dissolved in ethyl acetate (50 ml) and washed with 1M HCl (100 ml), the organic layer was separated, dried (MgSO$_4$), filtered and concentrated under vacuum to give the title compound (0.5 g, 47% yield) as a yellow solid which was used without further purification. Tr=1.86 min, m/z (ES$^+$) (M+H)$^+$ 405.

4-(4-Amino-benzenesulfonyl)-piperazine-1-carboxylic acid benzylamide

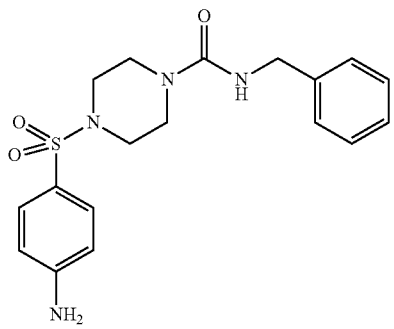 [SMILES: O=C(NCc1ccccc1)N1CCN(S(=O)(=O)c2ccc([N+](=O)[O-])cc2)CC1]

4-(4-Nitro-benzenesulfonyl)-piperazine-1-carboxylic acid benzylamide (0.5 g, 1.2 mmol) was suspended in a 5:1 mixture of ethanol and water (30 ml). To this solution was added iron powder (0.18 g, 3.1 mmol) followed by saturated ammonium chloride solution (1 ml) and the mixture was heated to 80° C. for three hours. After this time, the reaction mixture was cooled to room temperature and filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (0.47 g, 100% yield) as a colourless oil. Tr=1.60 min, m/z (ES$^+$) (M+H)$^+$ 375.

4-(4-Acryloylamino-benzenesulfonyl)-piperazine-1-carboxylic acid benzylamide

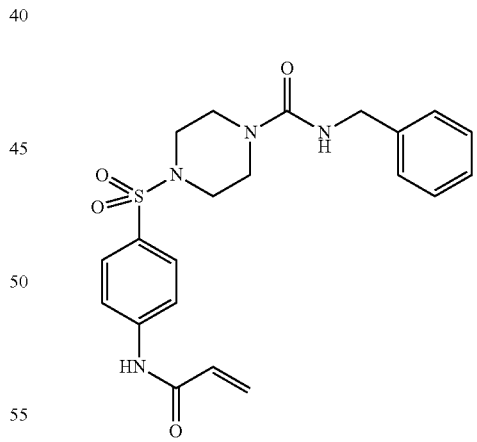

4-(4-Amino-benzenesulfonyl)-piperazine-1-carboxylic acid benzylamide (0.47 g, 1.25 mmol) was dissolved in DMF (10 ml). To this was added diisopropylethylamine (0.33 ml, 1.9 mmol) in one portion followed by the drop wise addition of acryloyl chloride (0.12 ml, 1.5 mmol) and the mixture was stirred at room temperature under a nitrogen atmosphere for 3 hours. The THF was removed under vacuum and the resulting crude material was purified by column chromatography (elution: 50% heptane, 50% ethyl acetate to 100% ethyl acetate) to give the title compound (54 mg, 10% yield) as a white solid.

Example I-1

4-(4-Acryloylamino-benzenesulfonyl)-piperazine-1-carboxylic acid benzylamide $\delta_H$ (250 MHz, DMSO) 10.59 (1H, s), 7.92 (2H, d), 7.68 (2H, d), 7.24-7.06 (6H, m), 6.51-6.24 (2H, m), 5.83 (1H, dd), 4.13 (2H, d), 3.38 (4H, obscured), 2.82-2.73 (4H, m). Tr=3.68 min, m/z (ES$^+$) (M+H)$^+$ 428.95.

Method J

Example J-1

N-[4-(2-Morpholin-4-yl-ethylsulfamoyl)-phenyl]-acrylamide N-(2-Morpholin-4-yl-ethyl)-4-nitro-benzenesulfonamide

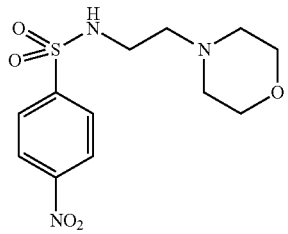 [SMILES: O=[N+]([O-])c1ccc(S(=O)(=O)NCCN2CCOCC2)cc1]

4-(2-Aminoethyl) morpholine (0.06 ml, 0.45 mmol) was added in one portion to a stirred solution of 4-nitrophenyl sulfonyl chloride (0.1 g, 0.45 mmol) in pyridine (3 ml) at room temperature and the mixture was stirred at room temperature under a nitrogen atmosphere for 18 hours. After this time, the mixture was concentrated under vacuum to give the title compound (0.14 g, 100% yield) which was used without further purification. Tr=0.71 min, m/z (ES$^+$) (M+H)$^+$ 316.30.

4-Amino-N-(2-morpholin-4-yl-ethyl)-benzenesulfonamide

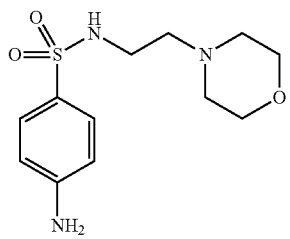

N-(2-Morpholin-4-yl-ethyl)-4-nitro-benzenesulfonamide (0.14 g, 0.45 mmol) was suspended in a 5:1 mixture of ethanol and water (3 ml). To this solution was added iron powder (0.13 g, 2.25 mmol) followed by saturated ammonium chloride solution (0.1 ml) and the mixture was stirred at room temperature for 18 hours. After this time, the reaction mixture was filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (0.1 g, 78% yield) as a brown solid. Tr=0.35 min, m/z (ES$^+$) (M+H)$^+$ 285.

N-[4-(2-Morpholin-4-yl-ethylsulfamoyl)-phenyl]-acrylamide

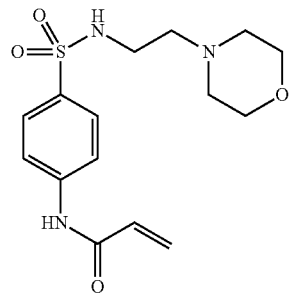 [SMILES: C=CC(=O)Nc1ccc(S(=O)(=O)NCCN2CCOCC2)cc1]

Diisopropylethylamine (0.09 ml, 0.5 mmol) was added in one portion to a stirred solution of 4-amino-N-(2-morpholin-4-yl-ethyl)-benzenesulfonamide (0.1 g, 0.35 mmol) in THF (3 ml) at room temperature. To this mixture was added acryloyl chloride (0.03 ml, 0.38 mmol) in one portion and the mixture was stirred at room temperature under a nitrogen atmosphere for 1 hour. After this time, the mixture was concentrated under vacuum and the resulting residue purified by Prep HPLC to give the title compound (6 mg, 5% yield) as a white solid.

Example J-1

N-[1-(4-Acryloylamino-benzenesulfonyl)-piperidin-4-yl]-benzamide $\delta_H$ (500 MHz, CDCl$_3$) 7.85 (2H, d), 7.74 (2H, d), 7.61 (1H, s), 6.51-6.24 (2H, m), 5.88 (1H, d), 5.21 (1H, br s), 3.61-3.58 (4H, m), 3.06-3.01 (2H, m), 2.48-2.31 (2H, m), 2.32-2.28 (4H, m). Tr=2.04 min, m/z (ES$^+$) (M+H)$^+$ 340.

Example J-2

N-[4-(1,1-Dimethyl-2-morpholin-4-yl-ethylsulfamoyl)-phenyl]-acrylamide $\delta_H$ (500 MHz, CDCl$_3$) 7.88 (1H, s), 7.82 (2H, d), 7.72 (2H, d), 6.51-6.26 (2H, m), 5.83 (1H, d), 5.42 (1H, br s), 3.76-3.69 (4H, m), 2.68-2.59 (4H, m), 2.39-2.32 (2H, m), 1.25 (6H, s). Tr=2.28 min, m/z (ES$^+$) (M+H)$^+$ 368.

Example J-3

N-[4-(1-Ethyl-piperidin-3-ylsulfamoyl)-phenyl]-acrylamide $\delta_H$ (500 MHz, MeOD) 7.82-7.65 (4H, m), 6.49-6.35 (2H, m), 5.82 (2H, dd), 3.23-3.21 (1H, m), 2.84-2.65 (2H, m), 2.34-2.25 (2H, m), 1.94-1.73 (2H, m), 1.69-1.58 (2H, m), 1.49-1.41 (1H, m), 1.40-1.08 (2H, m), 1.02 (3H, t). Tr=2.15 min, m/z (ES$^+$) (M+H)$^+$ 338.15.

Example J-4

N-[4-(3-Pyrrolidin-1-ylmethyl-benzylsulfamoyl)-phenyl]-acrylamide $\delta_H$ (500 MHz, MeOD) 7.81-7.74 (4H, m), 7.22-7.09 (4H, m), 6.48-6.37 (2H, m), 5.82 (2H, dd), 4.09 (2H, s), 3.54 (2H, s), 2.54-2.49 (4H, m), 1.85-1.74 (4H, m). Tr=2.63 min, m/z (ES$^+$) (M+H)$^+$ 400.

Example J-5

N-[4-(4-Pyrrolidin-1-ylmethyl-benzylsulfamoyl)-phenyl]-acrylamide $\delta_H$ (250 MHz, MeOD) 7.78-7.73 (4H, m), 7.46-7.30 (4H, m), 6.53-6.40 (2H, m), 5.82 (1H, dd), 4.33 (2H, s), 4.21 (2H, s), 3.36 (5H, obscured), 2.12-2.00 (4H, m). Tr=2.51 min, m/z (ES$^+$) (M+H)$^+$ 400.

Example J-6

N-{4-[3-(2-oxo-pyrrolidin-1-yl)-propylsulfamoyl]-phenyl}-acrylamide $\delta_H$ (500 MHz, MeOD) 7.87-7.78 (4H, m), 6.47-6.36 (2H, m), 5.81 (1H, dd), 3.41 (2H, t), 3.27 (2H, t), 2.84 (2H, t), 2.35 (2H, t), 2.02-1.96 (2H, m), 1.71-1.68 (2H, m). Tr=2.89 min, m/z (ES$^+$) (M+H)$^+$ 352.

Example J-7

N-{4-[(Tetrahydro-pyran-2-ylmethyl)-sulfamoyl]-phenyl}-acrylamide $\delta_H$ (500 MHz, d$_6$-acetone) 8.91 (1H, br s), 7.14 (2H, d), 7.05 (2H, d), 5.74-5.61 (2H, m), 5.46 (1H, t), 5.00 (1H, dd), 3.02 (1H, dd), 2.54-2.47 (2H, m), 2.21-2.15 (1H, m), 2.08-2.00 (4H, m), 1.02-0.98 (1H, m), 0.82-0.76 (1H, m), 0.67-0.61 (3H, m), 0.42-0.36 (1H, m). Tr=3.58 min, m/z (ES$^+$) (M+Na)$^+$ 347.

Example J-8

[4-(4-Acryloylamino-benzenesulfonylamino)-2-oxo-pyrrolidin-1-yl]-acetic acid ethyl ester $\delta_H$ (500 MHz, d$_6$-acetone) 9.75 (1H, br s), 7.94 (2H, d), 7.83 (2H, d), 6.95 (1H, d), 6.52-6.36 (2H, m), 5.78 (1H, dd), 4.13 (2H, q), 4.09-4.05 (1H, m), 3.97 (2H, s), 3.68-3.65 (1H, m), 3.38-3.36 (1H, m), 2.49-2.42 (1H, m), 2.20-2.15 (1H, m), 1.21 (3H, t). Tr=2.97 min, m/z (ES$^+$) (M+Na)$^+$ 418.

Example J-9

N-{4-[(6-Phenyl-pyridin-3-ylmethyl)-sulfamoyl]-phenyl}-acrylamide $\delta_H$ (500 MHz, d$_6$-acetone) 9.72 (1H, br s), 8.55 (1H, s), 8.06 (2H, d), 7.91 (2H, d), 7.82-7.78 (3H, m), 7.72 (1H, d), 7.47-7.38 (3H, m), 7.02 (1H, t), 6.49-6.32 (2H, m), 5.78 (1H, dd), 4.21 (2H, d). Tr=3.53 min, m/z (ES$^+$) (M+H)$^+$ 394.

Example J-10

N-[4-(1-Methyl-2-oxo-2-piperidin-1-yl-ethylsulfamoyl)-phenyl]-acrylamide $\delta_H$ (500 MHz, DMSO) 10.51 (1H, s), 7.78-7.64 (5H, m), 6.46-6.26 (2H, m), 5.82 (1H, d), 4.24-4.20 (1H, m), 3.26-3.21 (2H, m), 3.09-3.02 (1H, m), 1.54-1.18 (6H, m), 1.02 (3H, d). Tr=3.24 min, m/z (ES$^+$) (M+H)$^+$ 366.

Method K

Example K-1

1-(4-Acryloylamino-benzenesulfonyl)-piperidine-4-carboxylic acid dimethylamide 1-(4-Nitro-benzenesulfonyl)-piperidine-4-carboxylic acid methyl ester

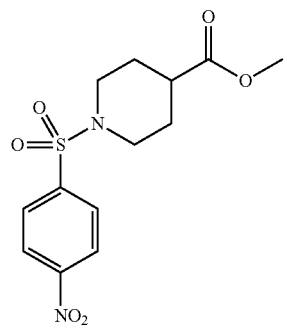 [SMILES: COC(=O)C1CCN(S(=O)(=O)c2ccc([N+](=O)[O-])cc2)CC1]

Diisopropylethylamine (9.4 ml, 54.1 mmol) was added in one portion to a stirred solution of methyl isonipecotate (6.78 g, 47.4 mmol) in THF (100 ml) at room temperature. To this mixture was added 4-nitrobenzenesulfonyl chloride (10.0 g, 45.1 mmol) in one portion and the mixture was stirred at room temperature under a nitrogen atmosphere for 18 hours. After this time, the resulting solid precipitate was collected by filtration and washed with cold THF (50 ml) before being dried under to give the title compound (14.8 g, 100% yield) as a white solid. $\delta_H$ (500 MHz, DMSO) 8.45 (2H, d), 8.02 (2H, d), 3.66-3.54 (5H, m), 2.52 (2H, obscured), 2.45-2.36 (1H, m), 1.96-1.88 (2H, m), 1.64-1.52 (2H, m). Tr=1.88 min m/z (ES$^+$) (M+H$^+$) 329.

1-(4-Nitro-benzenesulfonyl)-piperidine-4-carboxylic acid

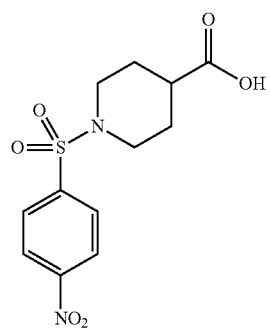 [SMILES: O=C(O)C1CCN(S(=O)(=O)c2ccc([N+](=O)[O-])cc2)CC1]

Lithium hydroxide (1.45 g, 60.9 mmol) was added in one portion to a stirred solution of 1-(4-nitro-benzenesulfonyl)-piperidine-4-carboxylic acid methyl ester (10.0 g, 30.4 mmol) in THF/H$_2$O (1:1,100 ml) and the reaction mixture was stirred at room temperature for 2 hours. After this time, the reaction mixture was partitioned between ethyl acetate (100 ml) and HCl (2M, 20 ml), the organic layer was separated, dried (MgSO$_4$), filtered and concentrated under vacuum to afford the title compound (5.1 g, 54% yield) as a colourless oil. $\delta_H$ (250 MHz, DMSO) 12.33 (1H, br s), 8.42 (2H, d), 7.99 (2H, d), 3.56-3.44 (2H, m), 2.51 (2H, obscured), 2.32-2.20 (1H, m), 1.90-1.81 (2H, m), 1.62-1.45 (2H, m). Tr=1.71 min m/z (ES$^+$) (M+H$^+$) 315.

1-(4-Nitro-benzenesulfonyl)-piperidine-4-carbonyl chloride

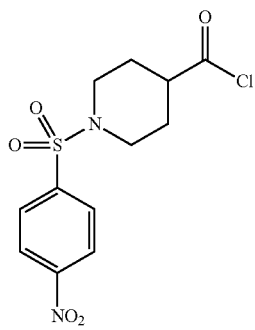 [SMILES: O=C(Cl)C1CCN(S(=O)(=O)c2ccc([N+](=O)[O-])cc2)CC1]

Thionyl chloride (4.0 ml, 55.0 mmol) was added dropwise to a stirred solution of 1-(4-nitro-benzenesulfonyl)-piperidine-4-carboxylic acid (1.25 g, 3.98 mmol) in toluene (12 ml) and the mixture was heated at 80° C. for 2 hours. After this time, the reaction mixture was concentrated under vacuum to afford the title compound as a white solid which was used without further purification.

1-(4-Nitro-benzenesulfonyl)-piperidine-4-carboxylic acid dimethylamide

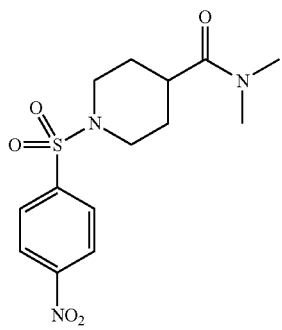 [SMILES: CN(C)C(=O)C1CCN(S(=O)(=O)c2ccc([N+](=O)[O-])cc2)CC1]

Diisopropylethylamine (0.35 ml, 2.0 mmol) was added in one portion to a stirred solution of dimethylamine (0.8 ml, 1.6 mmol) in DCM (2 ml) at room temperature. To this mixture was added 1-(4-nitro-benzenesulfonyl)-piperidine-4-carbonyl chloride (0.27, 0.8 mmol) in one portion and the mixture was stirred at room temperature under a nitrogen atmosphere for 18 hours. After this time, the mixture was diluted with DCM (20 ml) and washed sequentially by HCl (1M solution, 20 ml) and NaOH (1M solution, 20 ml) before being separated, dried (MgSO$_4$), filtered and concentrated under vacuum to afford the title compound (0.17 g, 33% yield) as an off white solid. Tr=1.65 min m/z (ES$^+$) (M+H$^+$) 342.

1-(4-Amino-benzenesulfonyl)-piperidine-4-carboxylic acid dimethylamide

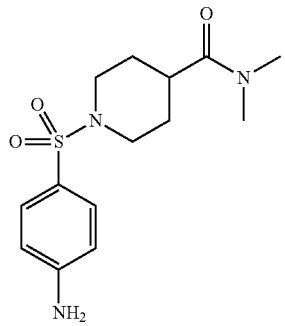 [SMILES: CN(C)C(=O)C1CCN(S(=O)(=O)c2ccc(N)cc2)CC1]

1-(4-Nitro-benzenesulfonyl)-piperidine-4-carboxylic acid dimethylamide (0.17 g, 0.49 mmol) was suspended in a 5:1 mixture of ethanol and water (3 ml). To this solution was added iron powder (0.08 g, 0.98 mmol) followed by saturated ammonium chloride solution (0.1 ml) and the mixture was stirred at room temperature for 18 hours. After this time, the reaction mixture was filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (0.15 g, 100% yield) as a yellow solid. Tr=1.71 min, m/z (ES$^+$) (M+H)$^+$ 312.

1-(4-Acryloylamino-benzenesulfonyl)-piperidine-4-carboxylic acid dimethylamide

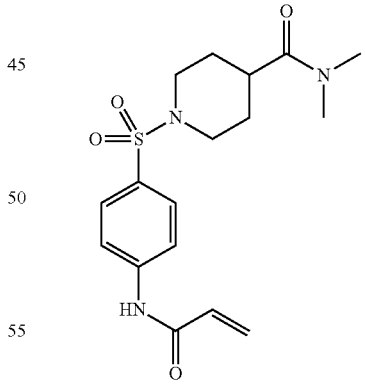

Diisopropylethylamine (0.1 ml, 0.7 mmol) was added in one portion to a stirred solution of 1-(4-amino-benzenesulfonyl)-piperidine-4-carboxylic acid dimethylamide (0.15 g, 0.49 mmol) in THF (3 ml) at room temperature. To this mixture was added acryloyl chloride (0.05 ml, 0.58 mmol) in one portion and the mixture was stirred at room temperature under a nitrogen atmosphere for 1 hour. After this time, the mixture was concentrated under vacuum and the resulting residue was purified by column chromatography (elution:

40% heptane, 60% ethyl acetate) to give the title compound (0.03 g, 15% yield) as a white solid.

Example K-1

1-(4-Acryloylamino-benzenesulfonyl)-piperidine-4-carboxylic acid dimethylamide $\delta_H$ (500 MHz, DMSO) 10.57 (1H, s), 7.91 (2H, d), 7.72 (2H, d), 6.49-6.29 (2H, m), 5.81 (1H, d), 3.57-3.53 (2H, d), 2.91 (3H, s), 2.74 (3H, s), 2.62-2.53 (1H, t), 2.33-2.26 (2H, m), 1.68-1.62 (2H, m), 1.53-1.48 (2H, m). Tr=3.32 min, m/z (ES$^+$) (M+H)$^+$ 366.

Example K-2

1-(4-Acryloylamino-benzenesulfonyl)-piperidine-4-carboxylic acid cyclopropylamide $\delta_H$ (250 MHz, DMSO) 10.53 (1H, s), 7.89 (2H, d), 7.77-7.63 (3H, m), 6.52-6.26 (2H, m), 5.81 (1H, dd), 3.59-3.50 (2H, m), 2.50 (1H, obscured), 2.28-2.16 (2H, m), 2.03-1.95 (1H, m), 1.72-1.40 (4H, m), 0.60-0.52 (2H, m), 0.36-0.28 (2H, m). Tr=3.25 min, m/z (ES$^+$) (M+H)$^+$ 378.

Example K-3

N-{4-[4-(3,3-Difluoro-azetidine-1-carbonyl)-piperidine-1-sulfonyl]-phenyl}-acrylamide $\delta_H$ (250 MHz, DMSO) 10.54 (1H, s), 7.88 (2H, d), 7.69 (2H, d), 6.52-6.24 (2H, m), 5.81 (1H, dd), 4.52 (2H, t), 4.20 (2H, t), 3.56 (2H, d), 2.31-2.20 (3H, m), 1.78-1.64 (2H, m), 1.58-1.40 (2H, m). Tr=3.52 min, m/z (ES$^+$) (M+H)$^+$ 414.

Example K-4

1-(4-Acryloylamino-benzenesulfonyl)-piperidine-4-carboxylic acid methyl-phenyl-amide $\delta_H$ (250 MHz, DMSO) 10.48 (1H, s), 7.82 (2H, d), 7.59 (2H, d), 7.39-7.20 (5H, m), 6.46-6.23 (2H, m), 5.80 (1H, dd), 3.56-3.48 (2H, m), 3.06 (3H, s), 2.08-1.82 (3H, m), 1.62-1.53 (4H, m). Tr=3.87 min, m/z (ES$^+$) (M+H)$^+$ 428.

Example K-5

1-(4-Acryloylamino-benzenesulfonyl)-piperidine-4-carboxylic acid methyl-phenyl-amide $\delta_H$ (250 MHz, DMSO) 10.52 (1H, s), 7.88 (2H, d), 7.68 (2H, d), 6.49-6.26 (2H, m), 5.82 (1H, dd), 3.58-3.50 (2H, m), 3.39-3.14 (5H, m), 2.36-2.18 (4H, m), 1.81-1.43 (8H, m,). Tr=3.27 min, m/z (ES$^+$) (M+H)$^+$ 392.

Example K-6

1-(4-Acryloylamino-benzenesulfonyl)-piperidine-4-carboxylic acid (2,2,2-trifluoro-ethyl)-amide $\delta_H$ (500 MHz, DMSO) 10.60 (1H, s), 8.42 (1H, t), 7.91 (2H, d), 7.72 (2H, d), 6.51-6.28 (2H, m), 5.83 (1H, dd), 3.90-3.83 (2H, m), 3.59-3.52 (2H, m), 2.33-2.18 (3H, m), 1.79-1.71 (2H, m), 1.59-1.50 (2H, m). Tr=3.38 min, m/z (ES$^+$) (M+H)$^+$ 420.

Example K-7

1-(4-Acryloylamino-benzenesulfonyl)-piperidine-4-carboxylic acid (2-methoxy-ethyl)-methyl-amide $\delta_H$ (250 MHz, DMSO) 10.65 (1H, s), 7.95 (2H, d), 7.74 (2H, d), 6.59-6.33 (2H, m), 5.91 (1H, dd), 3.71-3.63 (2H, m), 3.40 (2H, obscured), 3.27 (3H, s), 3.02 (2H, s), 2.82 (2H, s), 2.82 (2H, s), 2.72-2.68 (1H, m), 2.41-2.23 (2H, m), 1.81-1.53 (4H, m). Tr=3.37 min, m/z (ES$^+$) (M+H)$^+$ 410.

Example K-8

N-{4-[4-(Morpholine-4-carbonyl)-piperidine-1-sulfonyl]-phenyl}-acrylamide $\delta_H$ (500 MHz, DMSO) 10.59 (1H, br s), 7.89 (2H, d), 7.68 (2H, d), 6.48-6.30 (2H, m), 5.82 (1H, d), 4.16 (1H, br s), 3.62-3.34 (8H, m), 2.62-2.51 (2H, m), 2.31-2.28 (2H, m), 1.68-1.49 (4H, m). Tr=4.08 min, m/z (ES$^+$) (M+H)$^+$ 408.

Example K-9

1-(4-Acryloylamino-benzenesulfonyl)-piperidine-4-carboxylic acid cyclopropyl-methyl-amide $\delta_H$ (500 MHz, DMSO) 10.58 (1H, s), 7.92 (2H, d), 7.68 (2H, d), 6.49-6.30 (2H, m), 5.83 (1H, dd), 3.68-3.64 (2H, m), 2.99-2.96 (1H, m), 2.84-2.71 (4H, m), 2.29-2.22 (2H, m), 1.79-1.72 (2H, m), 1.56-1.43 (2H, m), 0.82-0.77 (2H, m), 0.68-0.62 (2H, m). Tr=3.41 min, m/z (ES$^+$) (M+H)$^+$ 392.

Example K-10

N-{4-[4-(Piperidine-1-carbonyl)-piperidine-1-sulfonyl]-phenyl}-acrylamide $\delta_H$ (500 MHz, DMSO) 10.59 (1H, s), 7.92 (2H, d), 7.69 (2H, d), 6.49-6.28 (2H, m), 5.82 (1H, d), 3.57 (2H, d), 3.36 (4H, obscured), 2.64-2.57 (1H, m), 2.36-2.27 (2H, m), 1.66-1.62 (2H, m), 1.59-1.48 (4H, m), 1.41-1.33 (4H, m). Tr=3.55 min, m/z (ES$^+$) (M+H)$^+$ 406.

Method L

Example L-1

4-(4-Acryloylamino-benzenesulfonyl)-piperidine-1-carboxylic acid tert-butyl ester 4-Methanesulfonyloxy-piperidine-1-carboxylic acid tert-butyl ester

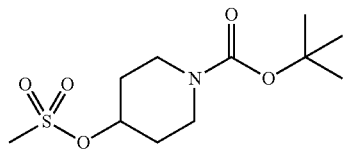 [SMILES: CC(C)(C)OC(=O)N1CCC(OS(C)(=O)=O)CC1]

Methane sulfonyl chloride (0.46 ml, 2.9 mmol) was added dropwise to a cool (0° C.) solution of tert-butyl 4-hydroxy-1-piperidinecarboxylate (1.0 g, 4.97 mmol) and triethylamine (0.83 ml, 10.9 mmol) in THF (10 ml) and the mixture was stirred at 0° C. under a nitrogen atmosphere for 3 hours. After this time, the mixture was diluted with ethyl acetate (50 ml) and washed sequentially with HCl (1M solution, 20 ml), NaHCO$_3$ (1M solution, 20 ml) and brine (20 ml). The organic layer was separated, dried (MgSO$_4$), filtered and concentrated under vacuum. The resulting residue was triturated with diethyl ether/hexane (1:1, 10 ml) and the resulting precipitate collected by filtration and dried under vacuum to afford the title compound (0.75 g, 55% yield) as a white solid.

4-(4-Nitro-phenylsulfanyl)-piperidine-1-carboxylic acid tert-butyl ester

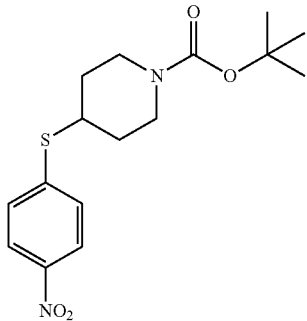 [SMILES: CC(C)(C)OC(=O)N1CCC(Sc2ccc([N+](=O)[O-])cc2)CC1]

Potassium carbonate (0.45 g, 3.5 mmol) was added in one portion to a stirred solution of 4-methanesulfonyloxy-piperidine-1-carboxylic acid tert-butyl ester (0.75 g, 2.5 mmol) and 4-nitrothiophenol (0.5 g, 3.2 mmol) in DMF (25 ml) and the mixture heated to 70° C. for 7 hours. After this time, the reaction mixture was concentrated under vacuum and re-dissolved in ethyl acetate (25 ml) and washed with NaOH (1M solution, 20 ml) and brine (20 ml). The organic layer was separated, dried (MgSO$_4$), filtered and concentrated under vacuum. The resulting residue was purified by column chromatography (elution: 60% heptane, 40% ethyl acetate) to afford the title compound (0.74 g, 68% yield) as an off-white solid. δ$_H$ (250 MHz, DMSO) 8.14 (2H, d), 7.55 (2H, d), 3.89-3.69 (3H, m), 3.07-2.90 (2H, m), 2.04-1.89 (2H, m), 1.51-1.33 (10H, m).

4-(4-Nitro-benzenesulfonyl)-piperidine-1-carboxylic acid tert-butyl ester

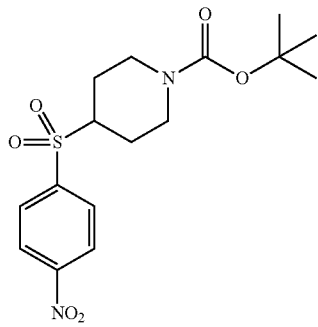 [SMILES: CC(C)(C)OC(=O)N1CCC(S(=O)(=O)c2ccc([N+](=O)[O-])cc2)CC1]

Meta-chloroperoxobenzoic acid (0.46 g, 1.9 mmol) was added in one portion to a cooled (0° C.) solution of 4-(4-nitrophenylsulfanyl)-piperidine-1-carboxylic acid tert-butyl ester (0.3 g, 0.88 mmol) and the reaction mixture was stirred at 0° C. under a nitrogen atmosphere for 1 hour before being warmed to room temperature and stirred for a further hour. The resulting mixture was filtered and the filtrate washed sequentially with sodium thiosulfate (20 ml) and saturated NaHCO$_3$ (20 ml). The organic layer was separated, dried (MgSO$_4$), filtered and concentrated under vacuum. The resulting residue was purified by column chromatography (elution: 70% heptane, 30% ethyl acetate) to afford the title compound (0.18 g, 55% yield) as an off-white solid. Tr=2.02 min, m/z (ES$^+$) (M+H)$^+$ 371.

4-(4-Amino-benzenesulfonyl)-piperidine-1-carboxylic acid tert-butyl ester

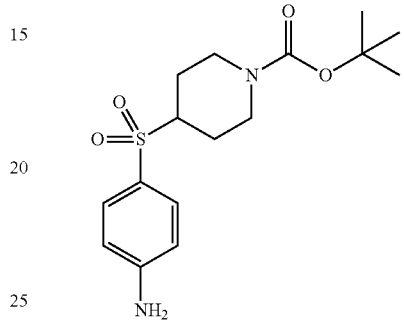

4-(4-Nitro-benzenesulfonyl)-piperidine-1-carboxylic acid tert-butyl ester (0.15 g, 0.4 mmol) was suspended in a 5:1 mixture of ethanol and water (3 ml). To this solution was added iron powder (0.4 g, 0.98 mmol) followed by saturated ammonium chloride solution (1 ml) and the mixture was stirred at room temperature for 18 hours. After this time, the reaction mixture was filtered through a pad of celite, the celite was washed with ethanol (10 ml) and ethyl acetate (50 ml) and the solution was concentrated under vacuum. The resulting residue was partitioned between DCM (50 ml) and water (20 ml), the organic layer was separated, dried with MgSO$_4$, filtered and concentrated to afford the title compound (0.114 g, 83% yield) as a yellow solid. Tr=1.37 min, m/z (ES$^+$) (M+Na)$^+$ 363.

4-(4-Acryloylamino-benzenesulfonyl)-piperidine-1-carboxylic acid tert-butyl ester

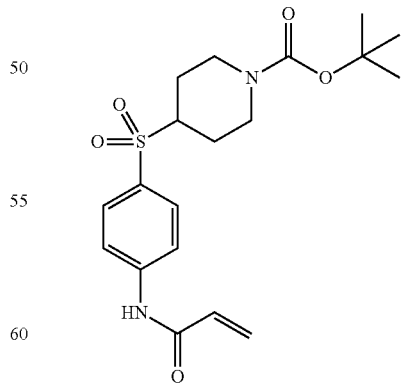

Diisopropylethylamine (0.09 ml, 0.5 mmol) was added in one portion to a stirred solution of 4-(4-Amino-benzenesulfonyl)-piperidine-1-carboxylic acid tert-butyl ester (0.11 g, 0.33 mmol) in THF (3 ml) at room temperature. To this mixture was added acryloyl chloride (0.03 ml, 0.5 mmol) in one portion and the mixture was stirred at room temperature under a nitrogen atmosphere for 1 hour. After this time, the mixture was concentrated under vacuum and the resulting residue was purified by column chromatography (elution: 40% heptane, 60% ethyl acetate) to give the title compound (0.02 g, 17% yield) as a white solid.

Example L-1

4-(4-Acryloylamino-benzenesulfonyl)-piperidine-1-carboxylic acid tert-butyl ester $\delta_H$ (250 MHz, DMSO) 10.62 (1H, s), 7.91 (2H, d), 7.76 (2H, d), 6.49-6.22 (2H, m), 5.82 (1H, dd), 4.03-3.91 (2H, m), 3.43-3.30 (1H, m), 2.78-2.56 (2H, m), 1.83-1.72 (2H, m), 1.38-1.21 (11H, m). Tr=3.81 min, m/z (ES$^+$) (M+Na)$^+$ 417.

Example L-2

4-(4-Acryloylamino-phenylsulfanyl)-piperidine-1-carboxylic acid tert-butyl ester $\delta_H$ (250 MHz, DMSO) 10.22 (1H, s), 7.62 (2H, d), 7.33 (2H, d), 6.47-6.17 (2H, m), 5.74 (1H, dd), 3.84-3.71 (2H, m), 3.28-3.21 (1H, m), 2.91-2.80 (2H, m), 1.81-1.73 (2H, m), 1.36-1.15 (11H, m). Tr=4.39 min, m/z (ES$^+$) (M+Na)$^+$ 385.

| Structure | IUPAC Name | MS |
| --- | --- | --- |
| 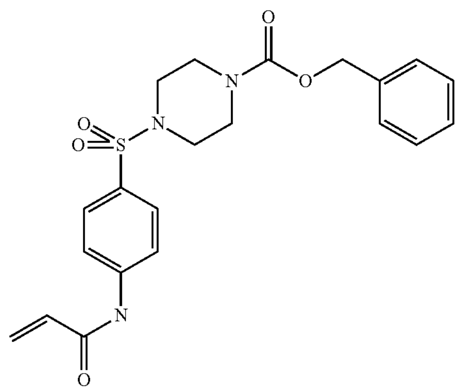 [SMILES: C=CC(=O)Nc1ccc(S(=O)(=O)N2CCN(C(=O)OCc3ccccc3)CC2)cc1] | 4-(4-Acryloylamino-benzenesulfonyl)-piperazine-1-carboxylic acid benzyl ester | Tr = 4.13 min, m/z (ES$^+$) (M + H)$^+$ 430 |
| 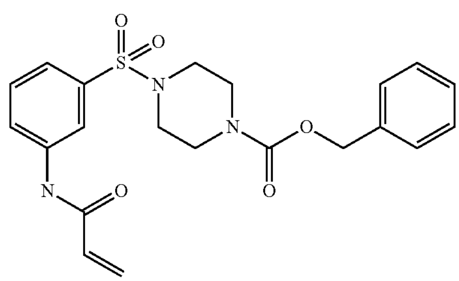 [SMILES: C=CC(=O)Nc1cccc(S(=O)(=O)N2CCN(C(=O)OCc3ccccc3)CC2)c1] | -(3-Acryloylamino-benzenesulfonyl)-piperazine-1-carboxylic acid benzyl ester | Tr = 4.11 min, m/z (ES$^+$) (M + H)$^+$ 430 |
| 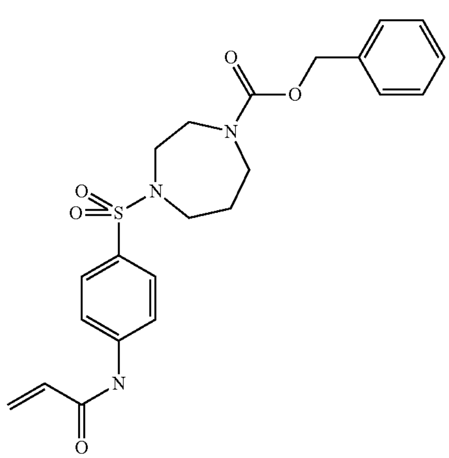 [SMILES: C=CC(=O)Nc1ccc(S(=O)(=O)N2CCCN(C(=O)OCc3ccccc3)CC2)cc1] | 4-(4-Acryloylamino-benzenesulfonyl)-[1,4]diazepane-1-carboxylic acid benzyl ester | Tr = 4.10 min, m/z (ES$^+$) (M + H)$^+$ 444 |

-continued

| Structure | IUPAC Name | MS |
|---|---|---|
| 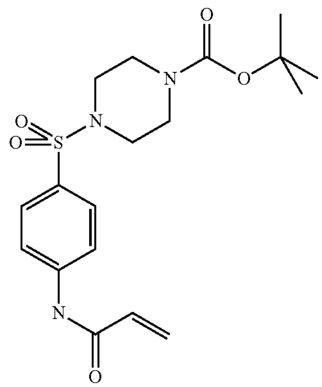 [SMILES: C=CC(=O)Nc1ccc(S(=O)(=O)N2CCN(C(=O)OC(C)(C)C)CC2)cc1] | 4-(4-Acryloylamino-benzenesulfonyl)-piperazine-1-carboxylic acid tert-butyl ester | Tr = 4.05 min, m/z (ES+) (M + Na)+ 418 |
| 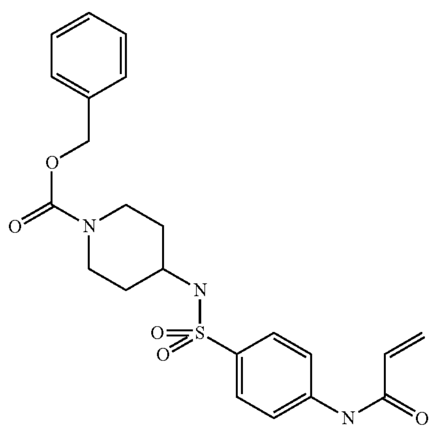 | 4-(4-Acryloylamino-benzenesulfonylamino)-piperazine-1-carboxylic acid benzyl ester | Tr = 2.00 min, m/z (ES+) (M + Na+) 408 |
| 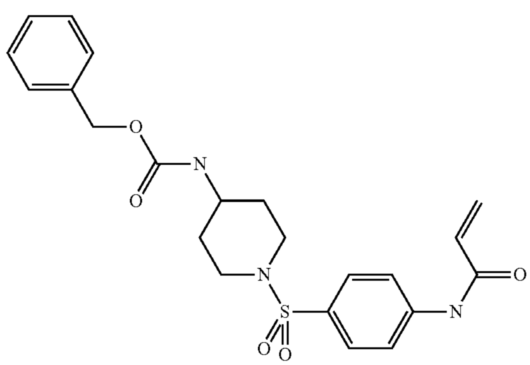 [SMILES: C=CC(=O)Nc1ccc(S(=O)(=O)N2CCC(NC(=O)OCc3ccccc3)CC2)cc1] | [1-(4-Acryloylamino-benzenesulfonyl)-piperidin-4-yl]-carbamic acid benzyl ester | Tr = 4.03 min, m/z (ES+) (M + H)+ 444 |
| 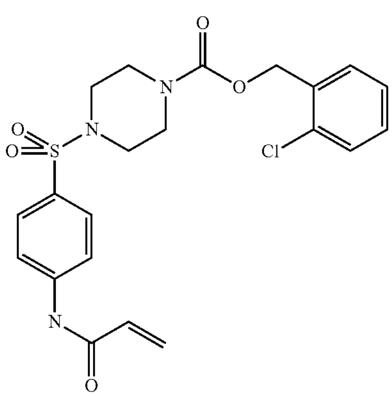 [SMILES: C=CC(=O)Nc1ccc(S(=O)(=O)N2CCN(C(=O)OCc3ccccc3Cl)CC2)cc1] | 4-(4-Acryloylamino-benzenesulfonyl)-piperazine-1-carboxylic acid 2-chloro-benzyl ester | Tr = 4.34 min, m/z (ES+) (M + H)+ 464 |

-continued

| Structure | IUPAC Name | MS |
|---|---|---|
| 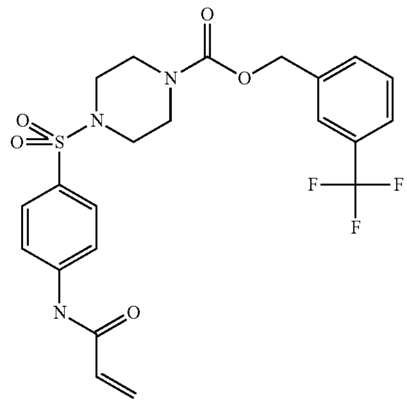 [SMILES: C=CC(=O)Nc1ccc(S(=O)(=O)N2CCN(C(=O)OCc3cccc(C(F)(F)F)c3)CC2)cc1] | 4-(4-Acryloylamino-benzenesulfonyl)-piperazine-1-carboxylic acid 3-trifluoromethyl-benzyl ester | Tr = 4.42 min, m/z (ES+) (M + H)+ 498 |
| 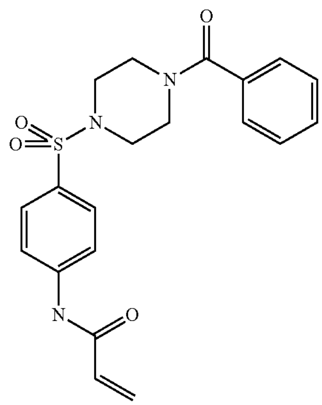 [SMILES: C=CC(=O)Nc1ccc(S(=O)(=O)N2CCN(C(=O)c3ccccc3)CC2)cc1] | 4-(4-Acryloylamino-benzenesulfonyl)-piperazine-1-carboxylic acid 2-chloro-benzyl ester | Tr = 3.63 min, m/z (ES+) (M + H)+ 400 |
| 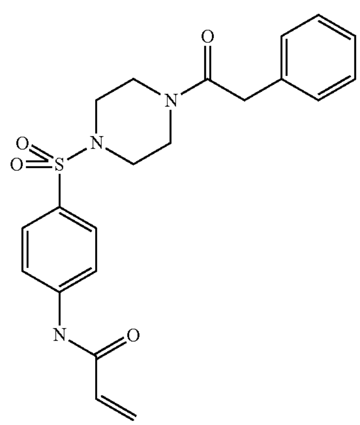 [SMILES: C=CC(=O)Nc1ccc(S(=O)(=O)N2CCN(C(=O)Cc3ccccc3)CC2)cc1] | N-[4-(4-Phenylacetyl-piperazine-1-sulfonyl)-phenyl]-acrylamide | Tr = 3.66 min, m/z (ES+) (M + H)+ 414 |
| 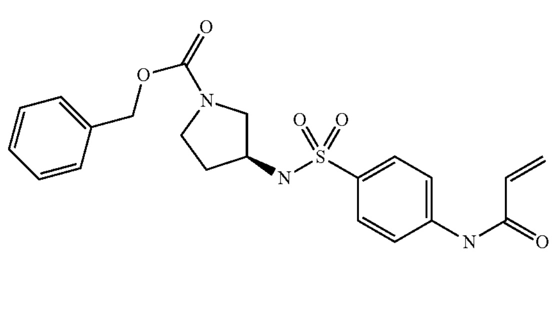 [SMILES: C=CC(=O)Nc1ccc(S(=O)(=O)N[C@H]2CCN(C(=O)OCc3ccccc3)C2)cc1] | 3-(4-Acryloylamino-benzenesulfonylamino)-(R)-pyrrolidine-1-carboxylic acid benzyl ester | Tr = 3.84 min, m/z (ES+) (M + H)+ 430 |

| Structure | IUPAC Name | MS |
|---|---|---|
| 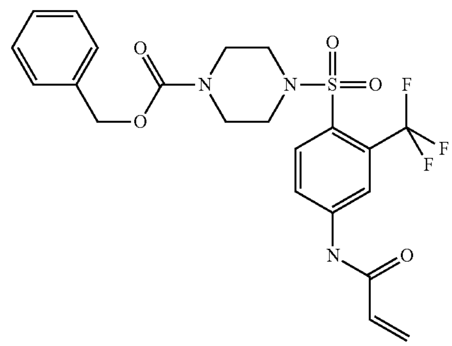 [SMILES: C=CC(=O)Nc1ccc(S(=O)(=O)N2CCN(C(=O)OCc3ccccc3)CC2)c(C(F)(F)F)c1] | 4-(4-Acryloylamino-2-trifluoromethyl-benzenesulfonyl)-piperazine-1-carboxylic acid benzyl ester | Tr = 4.57 min, m/z (ES⁺) (M + Na)⁺ 520 |
| 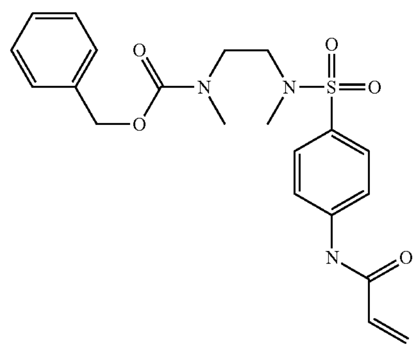 [SMILES: C=CC(=O)Nc1ccc(S(=O)(=O)N(C)CCN(C)C(=O)OCc2ccccc2)cc1] | {2-[(4-Acryloylamino-benzenesulfonyl)-methyl-amino]-ethyl}-methyk-carbamic acid benzyl ester | Tr = 4.17 min, m/z (ES⁺) (M + H)⁺ 432 |
| 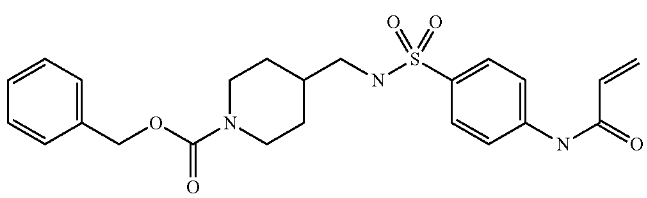 [SMILES: C=CC(=O)Nc1ccc(S(=O)(=O)NCC2CCN(C(=O)OCc3ccccc3)CC2)cc1] | 4-[(4-Acryloylamino-benzenesulfonylamino)-methyl]-piperidine-1-carboxylic acid benzyl ester | Tr = 4.09 min, m/z (ES⁺) (M + H)⁺ 458 |
| 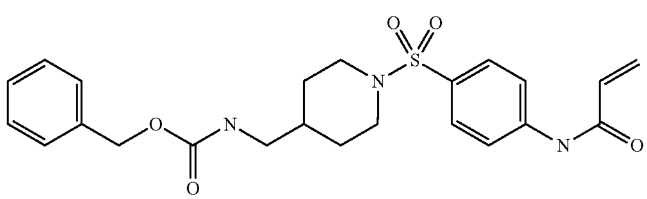 [SMILES: C=CC(=O)Nc1ccc(S(=O)(=O)N2CCC(CNC(=O)OCc3ccccc3)CC2)cc1] | [1-(4-Acryloylamino-benzenesulfonyl)-piperidin-4-ylmethyl]-carbamic acid benzyl ester | Tr = 4.10 min, m/z (ES⁺) (M + H)⁺ 458 |
| 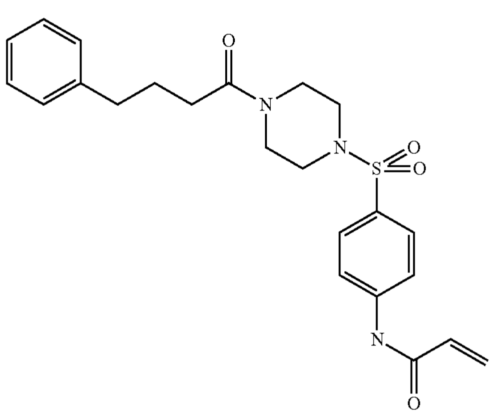 [SMILES: C=CC(=O)Nc1ccc(S(=O)(=O)N2CCN(C(=O)CCCc3ccccc3)CC2)cc1] | N-{4-[4-(4-Phenyl-butyryl)-piperazine-1-sulfonyl]-phenyl}-acrylamide | Tr = 4.13 min, m/z (ES⁺) (M + H)⁺ 442 |

-continued

| Structure | IUPAC Name | MS |
|---|---|---|
| 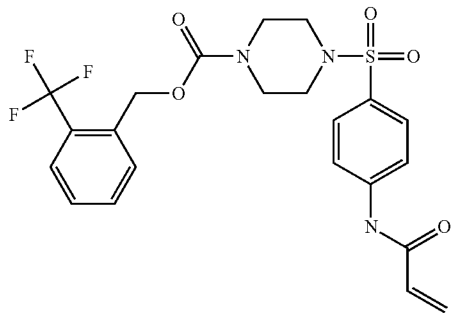 [SMILES: C=CC(=O)Nc1ccc(S(=O)(=O)N2CCN(C(=O)OCc3ccccc3C(F)(F)F)CC2)cc1] | 4-(4-Acryloylamino-benzenesulfonyl)-piperazine-1-carboxylic acid 2-trifluoromethyl-benzyl ester | Tr = 4.43 min, m/z (ES$^+$) (M + H)$^+$ 498 |
| 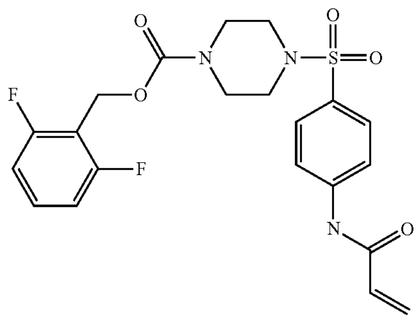 [SMILES: C=CC(=O)Nc1ccc(S(=O)(=O)N2CCN(C(=O)OCc3c(F)cccc3F)CC2)cc1] | 4-(4-Acryloylamino-benzenesulfonyl)-piperazine-1-carboxylic acid 2,6-difluoro-benzyl ester | Tr = 4.17 min, m/z (ES$^+$) (M + H)$^+$ 466 |
| 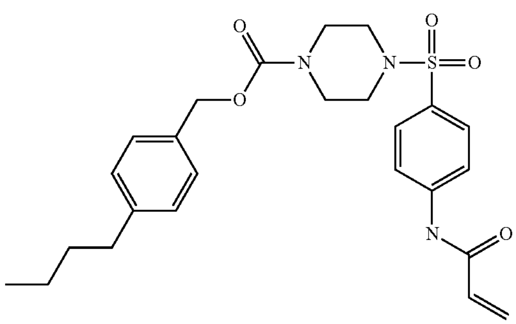 [SMILES: C=CC(=O)Nc1ccc(S(=O)(=O)N2CCN(C(=O)OCc3ccc(CCCC)cc3)CC2)cc1] | 4-(4-Acryloylamino-benzenesulfonyl)-piperazine-1-carboxylic acid 4-butyl-benzyl ester | Tr = 5.03 min, m/z (ES$^+$) (M + H)$^+$ 508 |
| 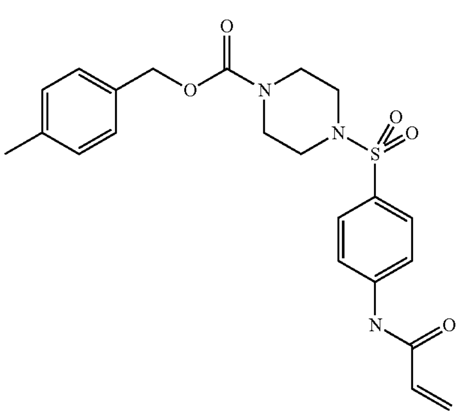 [SMILES: C=CC(=O)Nc1ccc(S(=O)(=O)N2CCN(C(=O)OCc3ccc(C)cc3)CC2)cc1] | 4-(4-Acryloylamino-benzenesulfonyl)-piperazine-1-carboxylic acid 4-methyl-benzyl ester | Tr = 4.42 min, m/z (ES$^+$) (M + H)$^+$ 466 |

| Structure | IUPAC Name | MS |
|---|---|---|
| 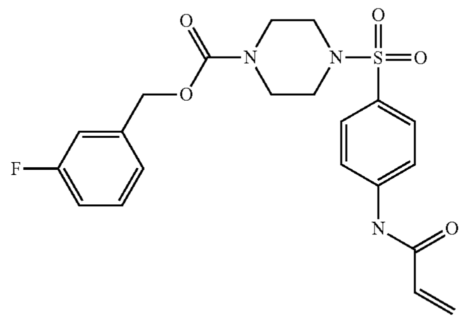 [SMILES: C=CC(=O)Nc1ccc(S(=O)(=O)N2CCN(C(=O)OCc3cccc(F)c3)CC2)cc1] | 4-(4-Acryloylamino-benzenesulfonyl)-piperazine-1-carboxylic acid 3-fluoro-benzyl ester | Tr = 4.27 min, m/z (ES$^+$) (M + H)$^+$ 448 |
| 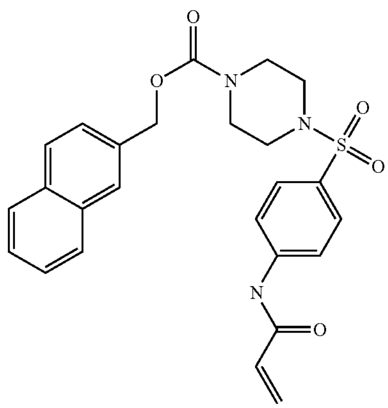 [SMILES: C=CC(=O)Nc1ccc(S(=O)(=O)N2CCN(C(=O)OCc3ccc4ccccc4c3)CC2)cc1] | 4-(4-Acryloylamino-benzenesulfonyl)-piperazine-1-carboxylic acid naphthalen-2-ylmethyl ester | Tr = 4.60 min, m/z (ES$^+$) (M + Na)$^+$ 502 |
| 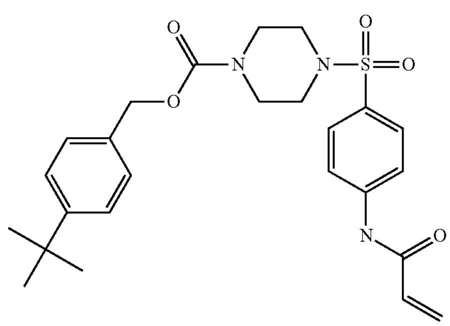 [SMILES: C=CC(=O)Nc1ccc(S(=O)(=O)N2CCN(C(=O)OCc3ccc(C(C)(C)C)cc3)CC2)cc1] | 4-(4-Acryloylamino-benzenesulfonyl)-piperazine-1-carboxylic acid 4-tert-butyl-benzyl ester | Tr = 4.89 min, m/z (ES$^+$) (M + H)$^+$ 508 |
| 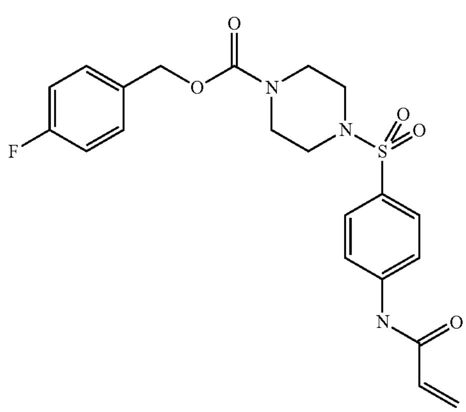 [SMILES: C=CC(=O)Nc1ccc(S(=O)(=O)N2CCN(C(=O)OCc3ccc(F)cc3)CC2)cc1] | 4-(4-Acryloylamino-benzenesulfonyl)-piperazine-1-carboxylic acid 4-fluoro-benzyl ester | Tr = 4.26 min, m/z (ES$^+$) (M + H)$^+$ 448 |

-continued

| Structure | IUPAC Name | MS |
|---|---|---|
| 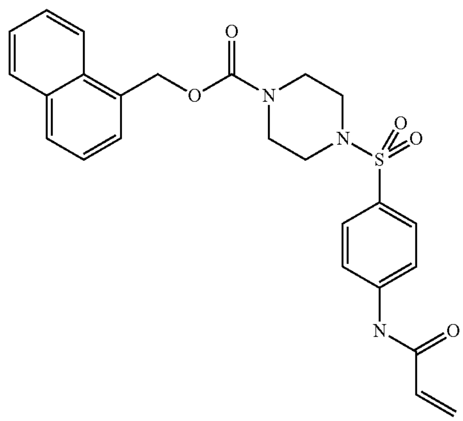 [SMILES: C=CC(=O)Nc1ccc(S(=O)(=O)N2CCN(C(=O)OCc3cccc4ccccc34)CC2)cc1] | 4-(4-Acryloylamino-benzenesulfonyl)-piperazine-1-carboxylic acid naphthalen-1-ylmethyl ester | Tr = 4.53 min, m/z (ES⁺) (M + Na)⁺ 502 |
| 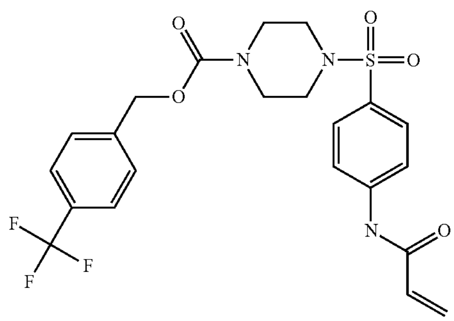 [SMILES: C=CC(=O)Nc1ccc(S(=O)(=O)N2CCN(C(=O)OCc3ccc(C(F)(F)F)cc3)CC2)cc1] | 4-(4-Acryloylamino-benzenesulfonyl)-piperazine-1-carboxylic acid 4-trifluoromethyl-benzyl ester | Tr = 4.59 min, m/z (ES⁺) (M + H)⁺ 498 |
| 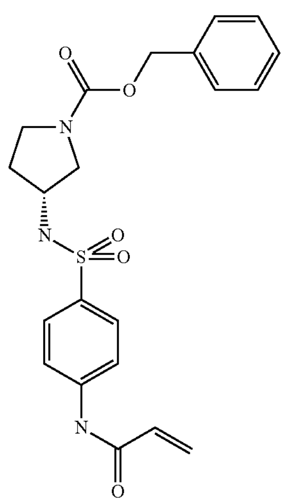 [SMILES: C=CC(=O)Nc1ccc(S(=O)(=O)N[C@@H]2CCN(C(=O)OCc3ccccc3)C2)cc1] | 3-(4-Acryloylamino-benzenesulfonylamino)-(S)-pyrrolidine-1-carboxylic acid benzyl ester | Tr = 3.85 min, m/z (ES⁺) (M + H)⁺ 430 |
| 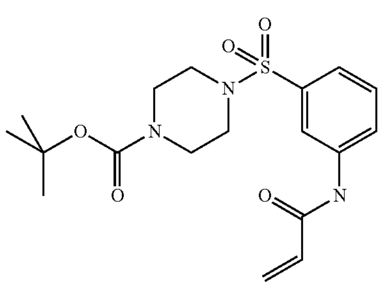 [SMILES: C=CC(=O)Nc1cccc(S(=O)(=O)N2CCN(C(=O)OC(C)(C)C)CC2)c1] | 4-(3-Acryloylamino-benzenesulfonyl)-piperazine-1-carboxylic acid tert-butyl ester | Tr = 3.77 min, m/z (ES⁺) (M + H)⁺ 418 |

-continued

| Structure | IUPAC Name | MS |
|---|---|---|
| 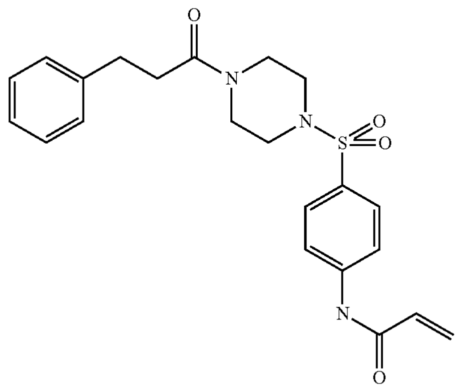 [SMILES: C=CC(=O)Nc1ccc(S(=O)(=O)N2CCN(C(=O)CCc3ccccc3)CC2)cc1] | N-{4-[4-(3-Phenyl-propionyl)-piperazine-1-sulfonyl]-phenyl}-acrylamide | Tr = 3.91 min, m/z (ES+) (M + H)+ 428.00 |
| 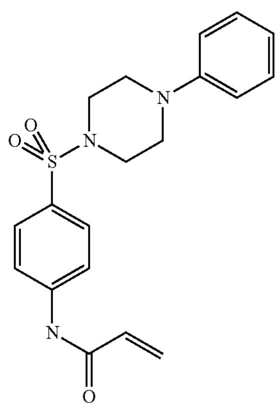 [SMILES: C=CC(=O)Nc1ccc(S(=O)(=O)N2CCN(c3ccccc3)CC2)cc1] | N-[4-(4-Phenyl-piperazine-1-sulfonyl)-phenyl]-acrylamide | Tr = 4.25 min, m/z (ES+) (M + H)+ 372 |
| 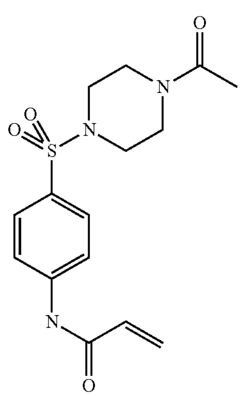 [SMILES: C=CC(=O)Nc1ccc(S(=O)(=O)N2CCN(C(C)=O)CC2)cc1] | N-[4-(4-Acetyl-piperazine-1-sulfonyl)-phenyl]-acrylamide | Tr = 3.08 min, m/z (ES+) (M + H)+ 338.40 |

-continued

| Structure | IUPAC Name | MS |
|---|---|---|
| 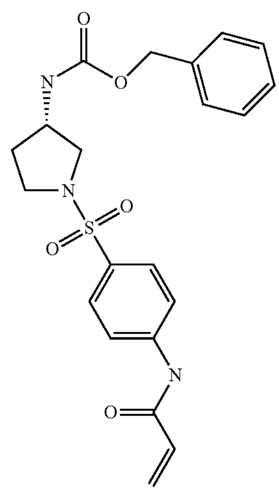 [SMILES: C=CC(=O)Nc1ccc(S(=O)(=O)N2CC[C@H](NC(=O)OCc3ccccc3)C2)cc1] | 1-(4-Acryloylamino-benzenesulfonyl)-(S)-pyrrolidin-3-yl]-carbamic acid benzyl ester | Tr = 3.93 min, m/z (ES+) (M + H)+ 430 |
| 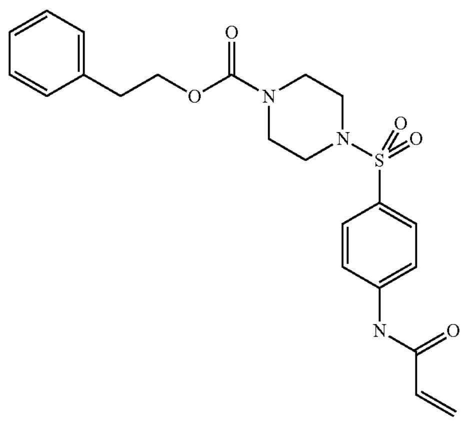 [SMILES: C=CC(=O)Nc1ccc(S(=O)(=O)N2CCN(C(=O)OCCc3ccccc3)CC2)cc1] | 4-(4-Acryloylamino-benzenesulfonyl)-piperazine-1-carboxylic acid phenethyl ester | Tr = 4.23 min, m/z (ES+) (M + H)+ 444 |
| 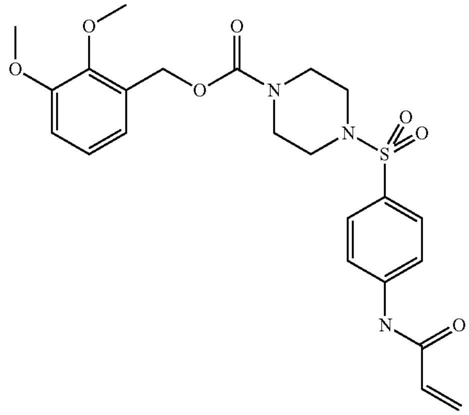 [SMILES: C=CC(=O)Nc1ccc(S(=O)(=O)N2CCN(C(=O)OCc3cccc(OC)c3OC)CC2)cc1] | 4-(4-Acryloylamino-benzenesulfonyl)-piperazine-1-carboxylic acid 2,3-dimethoxy-benzyl ester | Tr = 4.13 min, m/z (ES+) (M + H)+ 490 |

-continued

| Structure | IUPAC Name | MS |
|---|---|---|
| 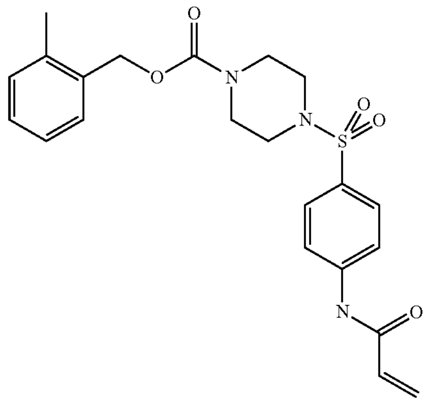 [SMILES: C=CC(=O)Nc1ccc(S(=O)(=O)N2CCN(C(=O)OCc3ccccc3C)CC2)cc1] | 4-(4-Acryloylamino-benzenesulfonyl)-piperazine-1-carboxylic acid 2-methyl-benzyl ester | Tr = 4.30 min, m/z (ES+) (M + H)+ 444 |
| 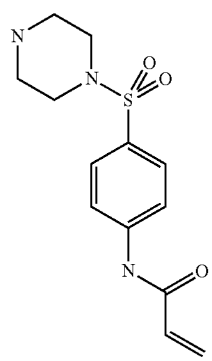 [SMILES: C=CC(=O)Nc1ccc(S(=O)(=O)N2CCNCC2)cc1] | N-[4-(Piperazine-1-sulfonyl)-phenyl]-acrylamide | Tr = 2.35 min, m/z (ES+) (M + H)+ 296 |
| 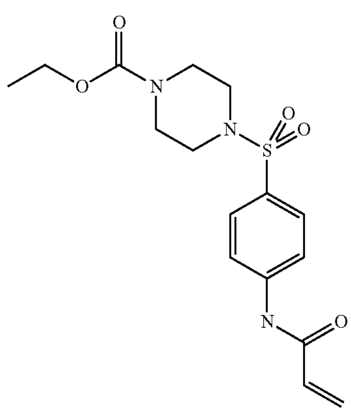 [SMILES: C=CC(=O)Nc1ccc(S(=O)(=O)N2CCN(C(=O)OCC)CC2)cc1] | 4-(4-Acryloylamino-benzenesulfonyl)-piperazine-1-carboxylic acid ethyl ester | Tr = 3.66 min, m/z (ES+) (M + H)+ 368 |
| 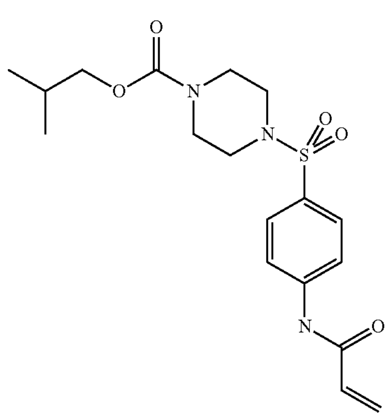 [SMILES: C=CC(=O)Nc1ccc(S(=O)(=O)N2CCN(C(=O)OCC(C)C)CC2)cc1] | 4-(4-Acryloylamino-benzenesulfonyl)-piperazine-1-carboxylic acid isobutyl ester | Tr = 4.11 min, m/z (ES+) (M + H)+ 396 |

-continued

| Structure | IUPAC Name | MS |
|---|---|---|
| 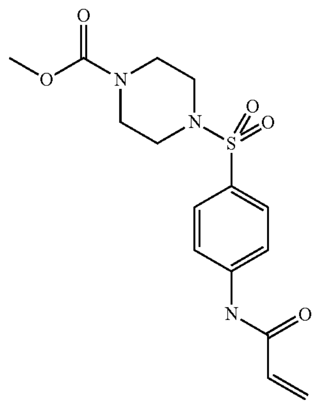 [SMILES: C=CC(=O)Nc1ccc(S(=O)(=O)N2CCN(C(=O)OC)CC2)cc1] | 4-(4-Acryloylamino-benzenesulfonyl)-piperazine-1-carboxylic acid methyl ester | Tr = 3.44 min, m/z (ES+) (M + H)+ 354 |
| 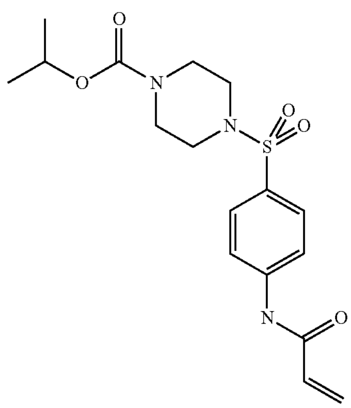 [SMILES: C=CC(=O)Nc1ccc(S(=O)(=O)N2CCN(C(=O)OC(C)C)CC2)cc1] | 4-(4-Acryloylamino-benzenesulfonyl)-piperazine-1-carboxylic acid isopropyl ester | Tr = 3.87 min, m/z (ES+) (M + H)+ 382 |
| 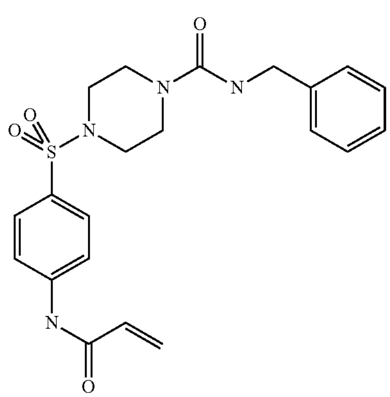 [SMILES: C=CC(=O)Nc1ccc(S(=O)(=O)N2CCN(C(=O)NCc3ccccc3)CC2)cc1] | 4-(4-Acryloylamino-benzenesulfonyl)-piperazine-1-carboxylic acid benzylamide | Tr = 3.68 min, m/z (ES+) (M + H)+ 428 |

| Structure | IUPAC Name | MS |
|---|---|---|
| 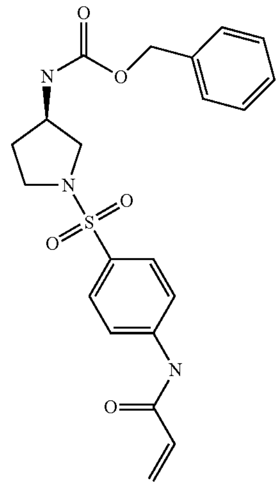 [SMILES: C=CC(=O)Nc1ccc(S(=O)(=O)N2CC[C@@H](NC(=O)OCc3ccccc3)C2)cc1] | [1-(4-Acryloylamino-benzenesulfonyl)-(R)-pyrrolidin-3-yl]-carbamic acid benzyl ester | Tr = 3.94 min, m/z (ES⁺) (M + H)⁺ 430 |
| 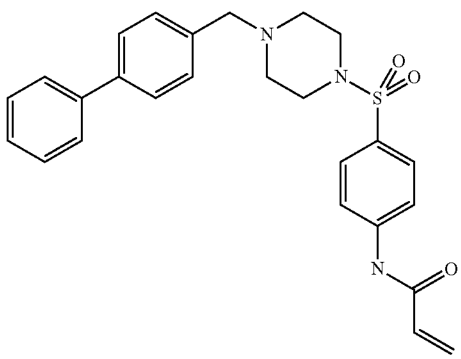 [SMILES: C=CC(=O)Nc1ccc(S(=O)(=O)N2CCN(Cc3ccc(-c4ccccc4)cc3)CC2)cc1] | N-[4-(4-Biphenyl-4-ylmethyl-piperazine-1-sulfonyl)-phenyl]-acrylamide | Tr = 3.40 min, m/z (ES⁺) (M + H)⁺ 462 |
| 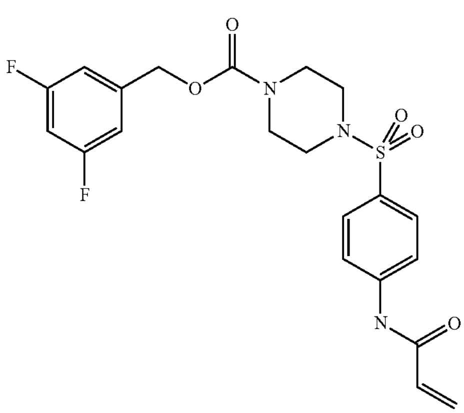 [SMILES: C=CC(=O)Nc1ccc(S(=O)(=O)N2CCN(C(=O)OCc3cc(F)cc(F)c3)CC2)cc1] | 4-(4-Acryloylamino-benzenesulfonyl)-piperazine-1-carboxylic acid 3,5-difluoro-benzyl ester | Tr = 4.26 min, m/z (ES⁺) (M + H)⁺ 466 |

| Structure | IUPAC Name | MS |
|---|---|---|
| 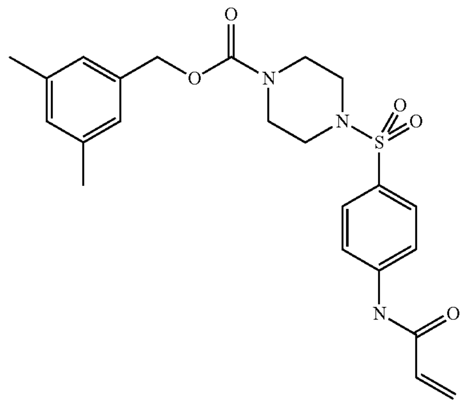 [SMILES: C=CC(=O)Nc1ccc(S(=O)(=O)N2CCN(C(=O)OCc3cc(C)cc(C)c3)CC2)cc1] | 4-(4-Acryloylamino-benzenesulfonyl)-piperazine-1-carboxylic acid 3,5-dimethyl-benzyl ester | Tr = 4.52 min, m/z (ES⁺) (M + H)⁺ 458 |
| 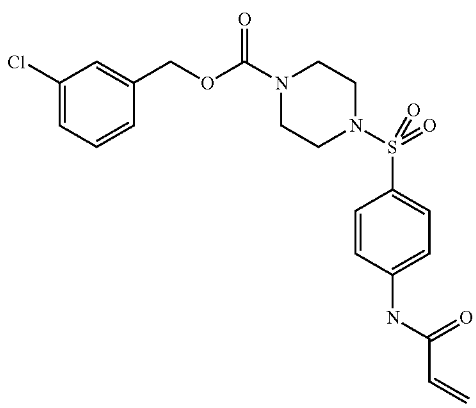 [SMILES: C=CC(=O)Nc1ccc(S(=O)(=O)N2CCN(C(=O)OCc3cccc(Cl)c3)CC2)cc1] | 4-(4-Acryloylamino-benzenesulfonyl)-piperazine-1-carboxylic acid 3-chloro-benzyl ester | Tr = 4.37 min, m/z (ES⁺) (M + H)⁺ 464 |
| 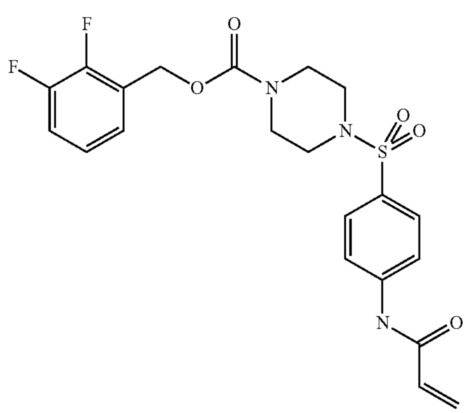 [SMILES: C=CC(=O)Nc1ccc(S(=O)(=O)N2CCN(C(=O)OCc3cccc(F)c3F)CC2)cc1] | 4-(4-Acryloylamino-benzenesulfonyl)-piperazine-1-carboxylic acid 2,3-difluoro-benzyl ester | Tr = 4.23 min, m/z (ES⁺) (M + H)⁺ 466 |

| Structure | IUPAC Name | MS |
|---|---|---|
| 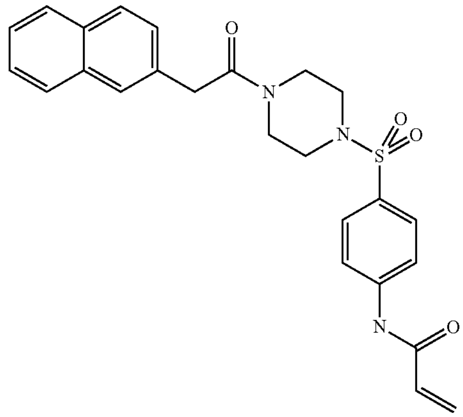 [SMILES: C=CC(=O)Nc1ccc(S(=O)(=O)N2CCN(C(=O)Cc3ccc4ccccc4c3)CC2)cc1] | N-{4-[4-(2-Naphthalen-2-yl-acetyl)-piperazine-1-sulfonyl]-phenyl}-acrylamide | Tr = 4.08 min, m/z (ES+) (M + H)+ 464.05 |
| 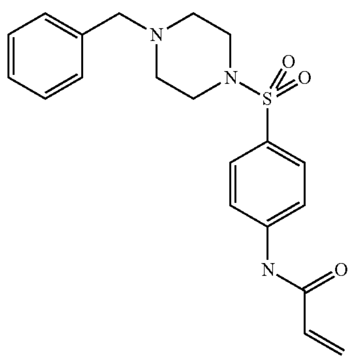 [SMILES: C=CC(=O)Nc1ccc(S(=O)(=O)N2CCN(Cc3ccccc3)CC2)cc1] | N-[4-(4-Benzyl-piperazine-1-sulfonyl)-phenyl]-acrylamide | Tr = 2.91 min, m/z (ES+) (M + H)+ 386 |
| 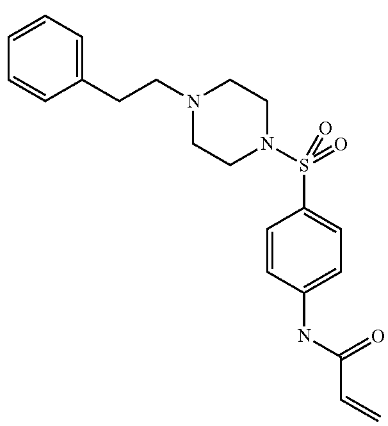 [SMILES: C=CC(=O)Nc1ccc(S(=O)(=O)N2CCN(CCc3ccccc3)CC2)cc1] | N-[4-(4-Phenethyl-piperazine-1-sulfonyl)-phenyl]-acrylamide | Tr = 3.01 min, m/z (ES+) (M + H)+ 400 |
| 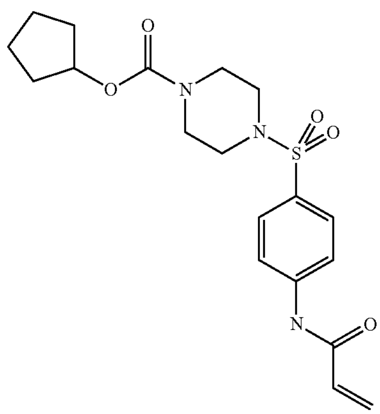 [SMILES: C=CC(=O)Nc1ccc(S(=O)(=O)N2CCN(C(=O)OC3CCCC3)CC2)cc1] | 4-(4-Acryloylamino-benzenesulfonyl)-piperazine-1-carboxylic acid cyclopentyl ester | Tr = 4.25 min, m/z (ES+) (M + H)+ 408 |

-continued

| Structure | IUPAC Name | MS |
|---|---|---|
| 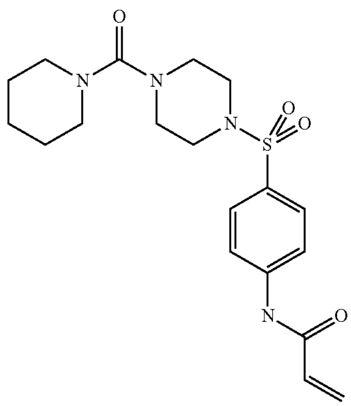 [SMILES: C=CC(=O)Nc1ccc(S(=O)(=O)N2CCN(C(=O)N3CCCCC3)CC2)cc1] | N-{4-[4-(Piperidine-1-carbonyl)-piperazine-1-sulfonyl]-phenyl}-acrylamide | Tr = 3.89 min, m/z (ES⁺) (M + H)⁺ 407 |
| 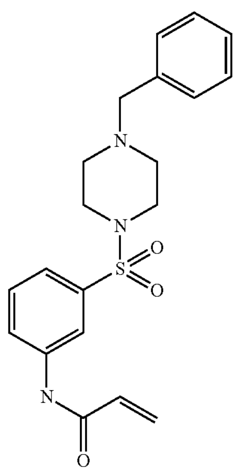 [SMILES: C=CC(=O)Nc1cccc(S(=O)(=O)N2CCN(Cc3ccccc3)CC2)c1] | N-[3-(4-Benzyl-piperazine-1-sulfonyl)-phenyl]-acrylamide | Tr = 2.88 min, m/z (ES⁺) (M + H)⁺ 386 |
| 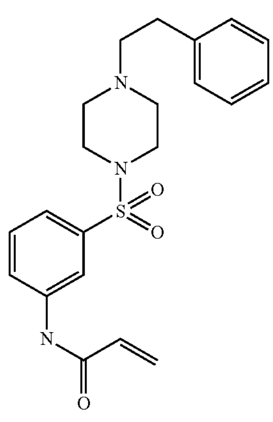 [SMILES: C=CC(=O)Nc1cccc(S(=O)(=O)N2CCN(CCc3ccccc3)CC2)c1] | N-[3-(4-Phenethyl-piperazine-1-sulfonyl)-phenyl]-acrylamide | Tr = 3.03 min, m/z (ES⁺) (M + H)⁺ 400 |

-continued

| Structure | IUPAC Name | MS |
|---|---|---|
| 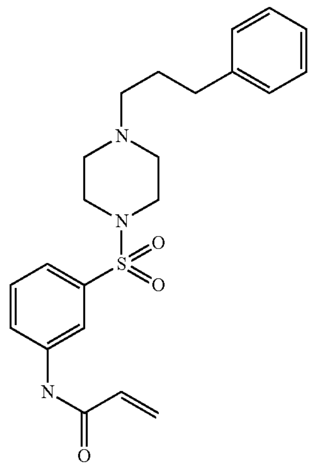 [SMILES: C=CC(=O)Nc1cccc(S(=O)(=O)N2CCN(CCCc3ccccc3)CC2)c1] | N-{3-[4-(3-Phenyl-propyl)-piperazine-1-sulfonyl]-phenyl}-acrylamide | Tr = 3.14 min, m/z (ES$^+$) (M + H)$^+$ 414 |
| 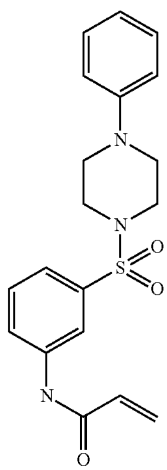 [SMILES: C=CC(=O)Nc1cccc(S(=O)(=O)N2CCN(c3ccccc3)CC2)c1] | N-[3-(4-Phenyl-piperazine-1-sulfonyl)-phenyl]-acrylamide | Tr = 4.30 min, m/z (ES$^+$) (M + H)$^+$ 372 |
| 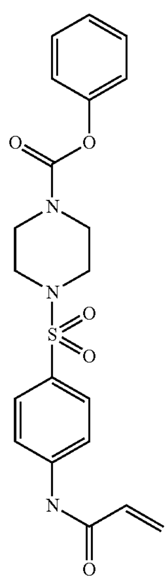 [SMILES: C=CC(=O)Nc1ccc(S(=O)(=O)N2CCN(C(=O)Oc3ccccc3)CC2)cc1] | 4-(4-Acryloylamino-benzenesulfonyl)-piperazine-1-carboxylic acid phenyl ester | Tr = 4.08 min, m/z (ES$^+$) (M + H)$^+$ 416 |

-continued

| Structure | IUPAC Name | MS |
|---|---|---|
| 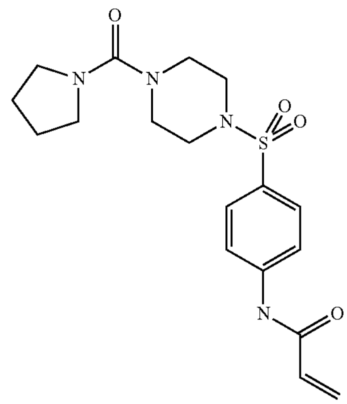 [SMILES: C=CC(=O)Nc1ccc(S(=O)(=O)N2CCN(C(=O)N3CCCC3)CC2)cc1] | N-{4-[4-(Pyrrolidine-1-carbonyl)-piperazine-1-sulfonyl]-phenyl}-acrylamide | Tr = 3.82 min, m/z (ES+) (M + H)+ 393 |
| 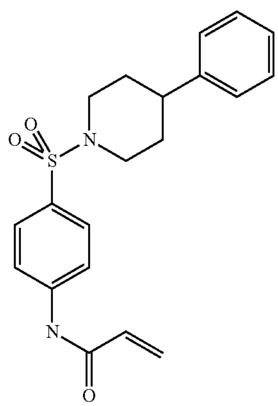 | N-[4-(4-Phenyl-piperidine-1-sulfonyl)-phenyl]-acrylamide | Tr = 4.51 min, m/z (ES+) (M + H)+ 371 |
| 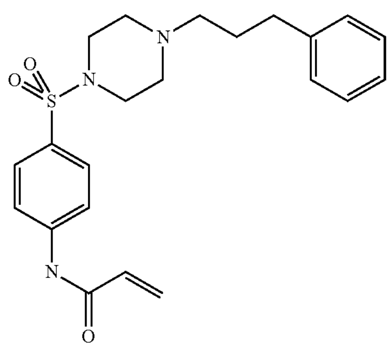 [SMILES: C=CC(=O)Nc1ccc(S(=O)(=O)N2CCN(CCCc3ccccc3)CC2)cc1] | N-{4-[4-(3-Phenyl-propyl)-piperazine-1-sulfonyl]-phenyl}-acrylamide | Tr = 2.94 min, m/z (ES+) (M + H)+ 414 |
| 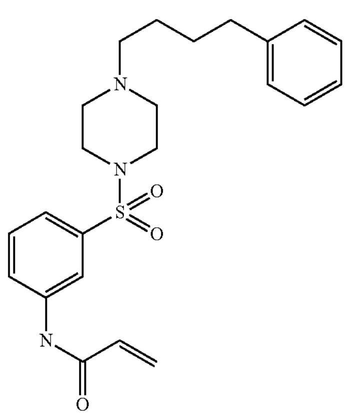 [SMILES: C=CC(=O)Nc1cccc(S(=O)(=O)N2CCN(CCCCc3ccccc3)CC2)c1] | N-{3-[4-(4-Phenyl-butyl)-piperazine-1-sulfonyl]-phenyl}-acrylamide | Tr = 3.22 min, m/z (ES+) (M + H)+ 428 |

-continued

| Structure | IUPAC Name | MS |
|---|---|---|
| 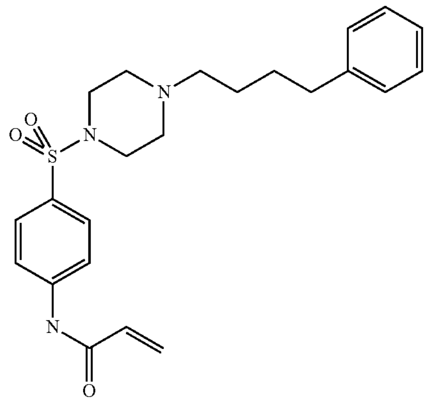 [SMILES: C=CC(=O)Nc1ccc(S(=O)(=O)N2CCN(CCCCc3ccccc3)CC2)cc1] | N-{4-[4-(4-Phenyl-butyl)-piperazine-1-sulfonyl]-phenyl}-acrylamide | Tr = 3.07 min, m/z (ES+) (M + H)+ 428 |
| 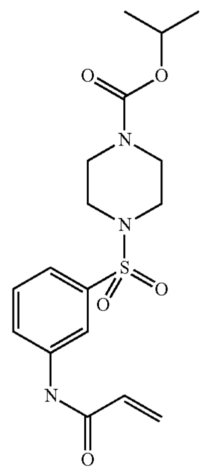 [SMILES: C=CC(=O)Nc1cccc(S(=O)(=O)N2CCN(C(=O)OC(C)C)CC2)c1] | 4-(3-Acryloylamino-benzenesulfonyl)-piperazine-1-carboxylic acid isopropyl ester | Tr = 4.09 min, m/z (ES+) (M + H)+ 382 |
| 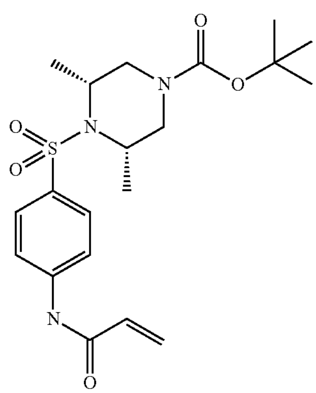 [SMILES: C=CC(=O)Nc1ccc(S(=O)(=O)N2[C@H](C)CN(C(=O)OC(C)(C)C)C[C@@H]2C)cc1] | 4-(4-Acryloylamino-benzenesulfonyl)-3,5-dimethyl-piperazine-1-carboxylic acid tert-butyl ester | Tr = 4.34 min, m/z (ES+) (M + Na)+ 446 |
| 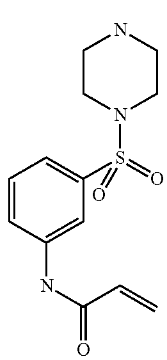 [SMILES: C=CC(=O)Nc1cccc(S(=O)(=O)N2CCNCC2)c1] | N-[3-(Piperazine-1-sulfonyl)-phenyl]-acrylamide | Tr = 2.29 min, m/z (ES+) (M + H)+ 296 |

-continued

| Structure | IUPAC Name | MS |
|---|---|---|
| 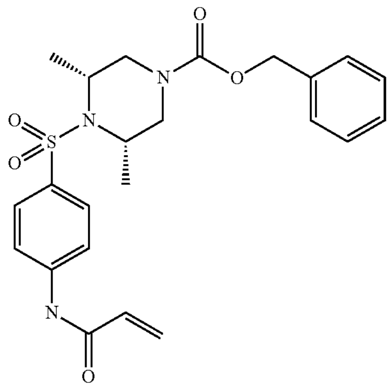 [SMILES: C=CC(=O)Nc1ccc(S(=O)(=O)N2[C@H](C)CN(C(=O)OCc3ccccc3)C[C@@H]2C)cc1] | 4-(4-Acryloylamino-benzenesulfonyl)-3,5-dimethyl-piperazine-1-carboxylic acid benzyl ester | Tr = 4.15 min, m/z (ES⁺) (M + H)⁺ 458 |
| 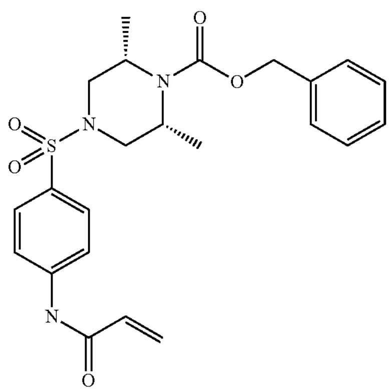 [SMILES: C=CC(=O)Nc1ccc(S(=O)(=O)N2C[C@@H](C)N(C(=O)OCc3ccccc3)[C@@H](C)C2)cc1] | 4-(4-Acryloylamino-benzenesulfonyl)-2,6-dimethyl-piperazine-1-carboxylic acid benzyl ester | Tr = 4.20 min, m/z (ES⁺) (M + H)⁺ 458 |
| 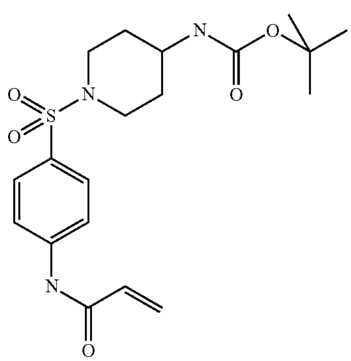 [SMILES: C=CC(=O)Nc1ccc(S(=O)(=O)N2CCC(NC(=O)OC(C)(C)C)CC2)cc1] | [1-(4-Acryloylamino-benzenesulfonyl)-piperidin-4-yl]-carbamic acid tert-butyl ester | Tr = 4.26 min, m/z (ES⁺) (M + Na)⁺ 432 |
| 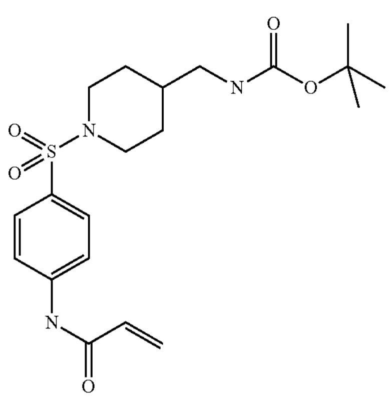 [SMILES: C=CC(=O)Nc1ccc(S(=O)(=O)N2CCC(CNC(=O)OC(C)(C)C)CC2)cc1] | [1-(4-Acryloylamino-benzenesulfonyl)-piperidin-4-ylmethyl]-carbamic acid tert-butyl ester | Tr = 4.09 min, m/z (ES⁺) (M + Na)⁺ 446 |

-continued

| Structure | IUPAC Name | MS |
|---|---|---|
| 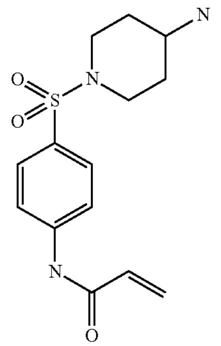 [SMILES: C=CC(=O)Nc1ccc(S(=O)(=O)N2CCC(N)CC2)cc1] | N-[4-(4-Amino-piperidine-1-sulfonyl)-phenyl]-acrylamide | Tr = 2.13 min, m/z (ES⁺) (M + H)⁺ 310 |
| 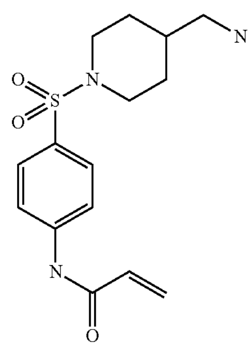 [SMILES: C=CC(=O)Nc1ccc(S(=O)(=O)N2CCC(CN)CC2)cc1] | N-[4-(4-Aminomethyl-piperidine-1-sulfonyl)-phenyl]-acrylamide | Tr = 2.24 min, m/z (ES⁺) (M + H)⁺ 324 |
| | 4-(3-Acryloylamino-benzenesulfonyl)-piperazine-1-carboxylic acid benzyl ester | Tr = 3.92 min, m/z (ES⁺) (M + H)⁺ 368 |
| | 4-(3-Acryloylamino-benzenesulfonyl)-piperazine-1-carboxylic acid benzyl ester | Tr = 3.47 min, m/z (ES⁺) (M + H)⁺ 354 |

-continued

| Structure | IUPAC Name | MS |
|---|---|---|
| 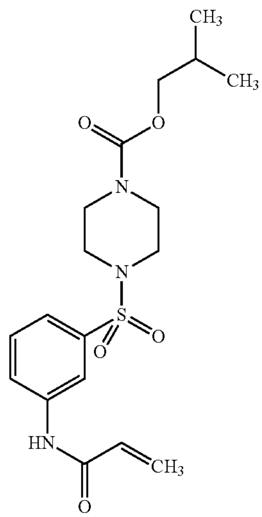 [SMILES: C=CC(=O)Nc1cccc(S(=O)(=O)N2CCN(C(=O)OCC(C)C)CC2)c1] | 4-(3-Acryloylamino-benzenesulfonyl)-piperazine-1-carboxylic acid isobutyl ester | Tr = 4.46 min, m/z (ES$^+$) (M + H)$^+$ 396 |
| 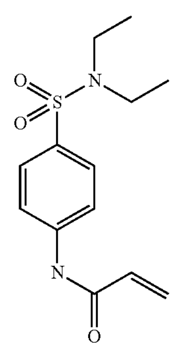 [SMILES: C=CC(=O)Nc1ccc(S(=O)(=O)N(CC)CC)cc1] | N-(4-Diethylsulfamoyl-phenyl)-acrylamide | Tr = 3.64 min, m/z (ES$^+$) (M + H)$^+$ 283 |
| 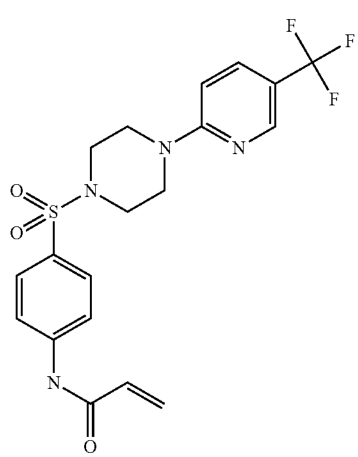 [SMILES: C=CC(=O)Nc1ccc(S(=O)(=O)N2CCN(c3ccc(C(F)(F)F)cn3)CC2)cc1] | N-{4-[4-(6-Trifluoromethyl-pyridin-3-yl)-piperazine-1-sulfonyl]-phenyl}-acrylamide | Tr = 4.24 min, m/z (ES$^+$) (M + H)$^+$ 441 |

| Structure | IUPAC Name | MS |
|---|---|---|
| 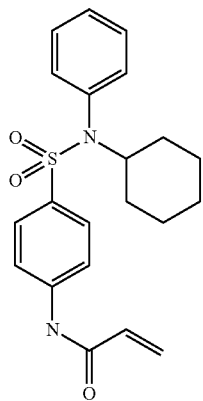 [SMILES: C=CC(=O)Nc1ccc(S(=O)(=O)N(c2ccccc2)C2CCCCC2)cc1] | N-[4-(Cyclohexyl-phenyl-sulfamoyl)-phenyl]-acrylamide | Tr = 4.54 min, m/z (ES+) (M + H)+ 385 |
| 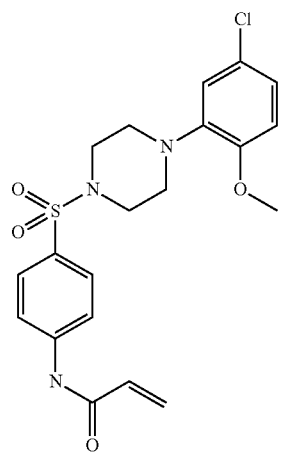 [SMILES: C=CC(=O)Nc1ccc(S(=O)(=O)N2CCN(c3cc(Cl)ccc3OC)CC2)cc1] | N-{4-[4-(5-Chloro-2-methoxy-phenyl)-piperazine-1-sulfonyl]-phenyl}-acrylamide | Tr = 4.33 min, m/z (ES+) (M + H)+ 436 |
| 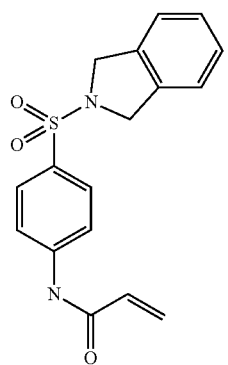 [SMILES: C=CC(=O)Nc1ccc(S(=O)(=O)N2Cc3ccccc3C2)cc1] | N-[4-(1,3-Dihydro-isoindole-2-sulfonyl)-phenyl]-acrylamide | Tr = 3.82 min, m/z (ES+) (M + H)+ 329 |

-continued

| Structure | IUPAC Name | MS |
|---|---|---|
| 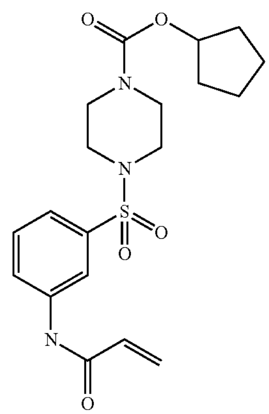 | 4-(3-Acryloylamino-benzenesulfonyl)-piperazine-1-carboxylic acid cyclopentyl ester | Tr = 4.21 min, m/z (ES$^+$) (M + Na)$^+$ 429 |
| 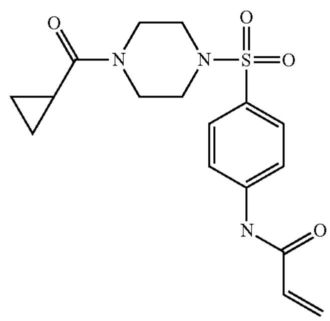 [SMILES: C=CC(=O)Nc1ccc(S(=O)(=O)N2CCN(C(=O)C3CC3)CC2)cc1] | N-[4-(4-Cyclopropanecarbonyl-piperazine-1-sulfonyl)-phenyl]-acrylamide | Tr = 3.25 min, m/z (ES$^+$) (M + H)$^+$ 364 |
| 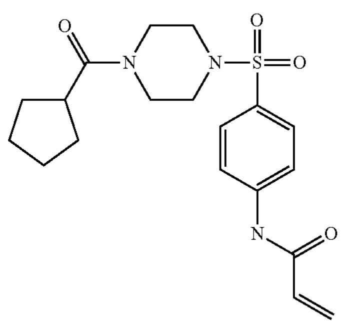 [SMILES: C=CC(=O)Nc1ccc(S(=O)(=O)N2CCN(C(=O)C3CCCC3)CC2)cc1] | N-[4-(4-Cyclopentanecarbonyl-piperazine-1-sulfonyl)-phenyl]-acrylamide | Tr = 3.67 min, m/z (ES$^+$) (M + H)$^+$ 392 |
| 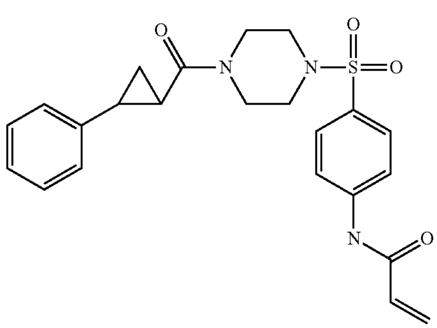 [SMILES: C=CC(=O)Nc1ccc(S(=O)(=O)N2CCN(C(=O)C3CC3c3ccccc3)CC2)cc1] | N-{4-[4-(2-Phenyl-cyclopropanecarbonyl)-piperazine-1-sulfonyl]-phenyl}-acrylamide | Tr = 3.90 min, m/z (ES$^+$) (M + H)$^+$ 440 |

-continued
| Structure | IUPAC Name | MS |
|---|---|---|
| 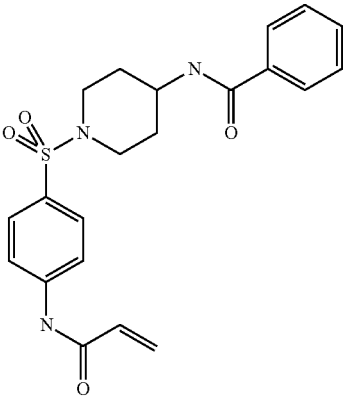 [SMILES: C=CC(=O)Nc1ccc(S(=O)(=O)N2CCC(NC(=O)c3ccccc3)CC2)cc1] | N-[1-(4-Acryloylamino-benzenesulfonyl)-piperidin-4-yl]-benzamide | Tr = 3.72 min, m/z (ES$^+$) (M + H)$^+$ 414 |
| 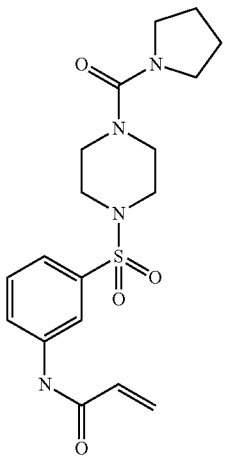 [SMILES: C=CC(=O)Nc1cccc(S(=O)(=O)N2CCN(C(=O)N3CCCC3)CC2)c1] | N-{3-[4-(Pyrrolidine-1-carbonyl)-piperazine-1-sulfonyl]-phenyl}-acrylamide | Tr = 3.56 min, m/z (ES$^+$) (M + H)$^+$ 393 |
| 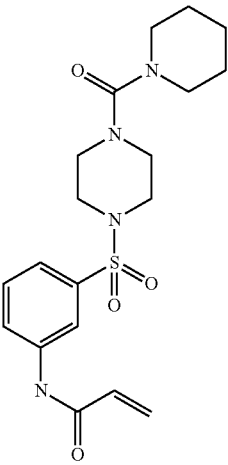 [SMILES: C=CC(=O)Nc1cccc(S(=O)(=O)N2CCN(C(=O)N3CCCCC3)CC2)c1] | N-{3-[4-(Piperidine-1-carbonyl)-piperazine-1-sulfonyl]-phenyl}-acrylamide | Tr = 3.71 min, m/z (ES$^+$) (M + H)$^+$ 407 |

-continued

| Structure | IUPAC Name | MS |
|---|---|---|
| 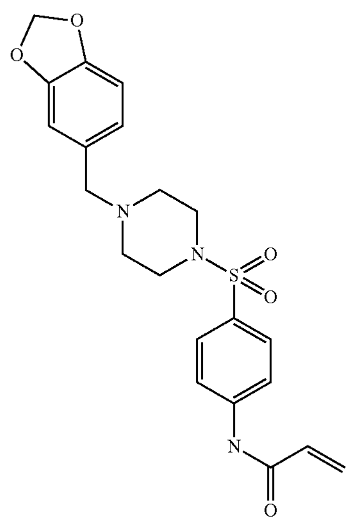 [SMILES: C=CC(=O)Nc1ccc(S(=O)(=O)N2CCN(Cc3ccc4c(c3)OCO4)CC2)cc1] | N-[4-(4-Benzo[1,3]dioxol-5-ylmethyl-piperazine-1-sulfonyl)-phenyl]-acrylamide | Tr = 2.73 min, m/z (ES⁺) (M + H)⁺ 430 |
| 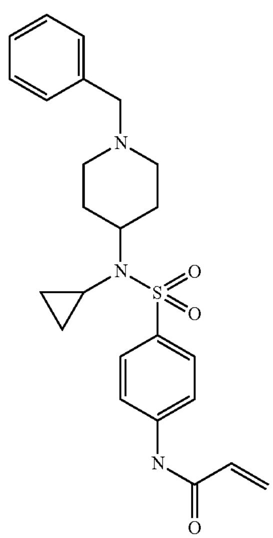 [SMILES: C=CC(=O)Nc1ccc(S(=O)(=O)N(C2CC2)C2CCN(Cc3ccccc3)CC2)cc1] | N-{4-[(1-Benzyl-piperidin-4-yl)-cyclopropyl-sulfamoyl]-phenyl}-acrylamide | Tr = 2.90 min, m/z (ES⁺) (M + H)⁺ 440 |
| 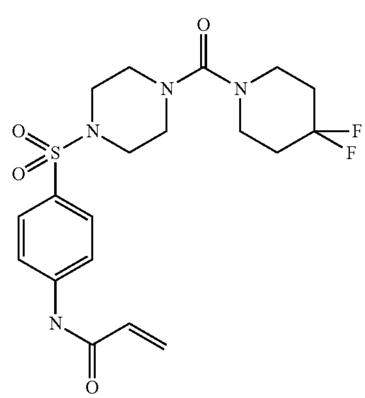 [SMILES: C=CC(=O)Nc1ccc(S(=O)(=O)N2CCN(C(=O)N3CCC(F)(F)CC3)CC2)cc1] | N-{4-[4-(4,4-Difluoro-piperidine-1-carbonyl)-piperazine-1-sulfonyl]-phenyl}-acrylamide | Tr = 3.64 min, m/z (ES⁺) (M + H)⁺ 443 |

-continued

| Structure | IUPAC Name | MS |
|---|---|---|
| 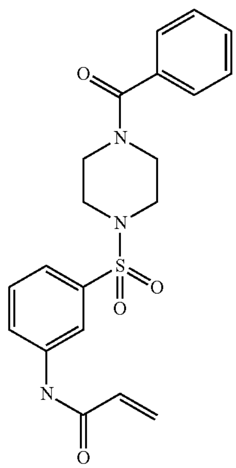 [SMILES: C=CC(=O)Nc1cccc(S(=O)(=O)N2CCN(C(=O)c3ccccc3)CC2)c1] | N-[3-(4-Benzoyl-piperazine-1-sulfonyl)-phenyl]-acrylamide | Tr = 3.69 min, m/z (ES+) (M + H)+ 400 |
| 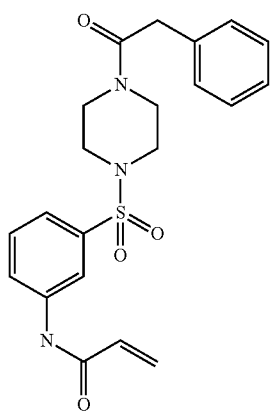 [SMILES: C=CC(=O)Nc1cccc(S(=O)(=O)N2CCN(C(=O)Cc3ccccc3)CC2)c1] | N-[3-(4-Phenylacetyl-piperazine-1-sulfonyl)-phenyl]-acrylamide | Tr = 3.78 min, m/z (ES+) (M + H)+ 414 |
| 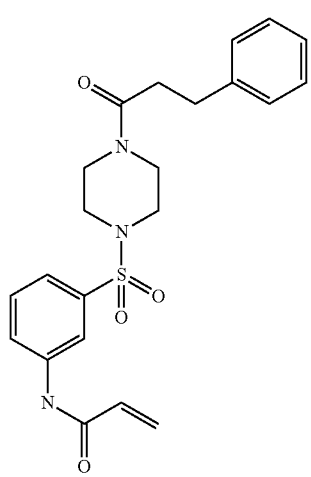 [SMILES: C=CC(=O)Nc1cccc(S(=O)(=O)N2CCN(C(=O)CCc3ccccc3)CC2)c1] | N-{3-[4-(3-Phenyl-propionyl)-piperazine-1-sulfonyl]-phenyl}-acrylamide | Tr = 3.87 min, m/z (ES+) (M + H)+ 428 |

-continued

| Structure | IUPAC Name | MS |
|---|---|---|
| 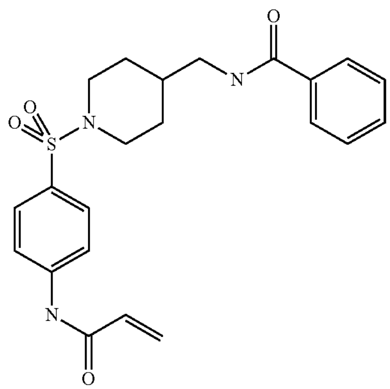 [SMILES: C=CC(=O)Nc1ccc(S(=O)(=O)N2CCC(CNC(=O)c3ccccc3)CC2)cc1] | N-[1-(4-Acryloylamino-benzenesulfonyl)-piperidin-4-ylmethyl]-benzamide | Tr = 3.62 min, m/z (ES⁺) (M + H)⁺ 428 |
| 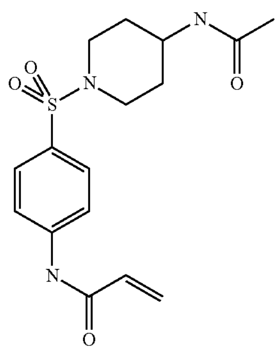 [SMILES: C=CC(=O)Nc1ccc(S(=O)(=O)N2CCC(NC(C)=O)CC2)cc1] | N-[4-(4-Acetylamino-piperidine-1-sulfonyl)-phenyl]-acrylamide | Tr = 2.92 min, m/z (ES⁺) (M + H)⁺ 352 |
| 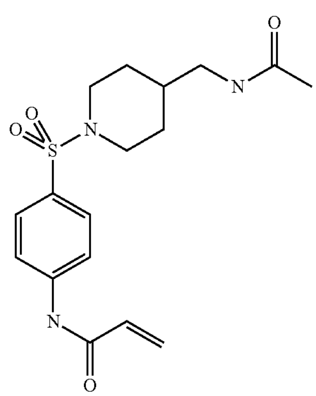 [SMILES: C=CC(=O)Nc1ccc(S(=O)(=O)N2CCC(CNC(C)=O)CC2)cc1] | N-{4-[4-(Acetylamino-methyl)-piperidine-1-sulfonyl]-phenyl}-acrylamide | Tr = 2.97 min, m/z (ES⁺) (M + H)⁺ 366 |
| 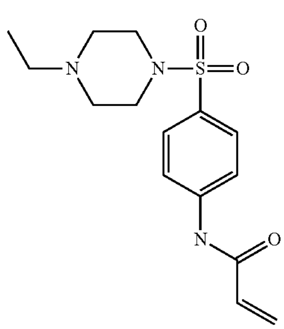 [SMILES: C=CC(=O)Nc1ccc(S(=O)(=O)N2CCN(CC)CC2)cc1] | N-[4-(4-Ethyl-piperazine 1-sulfonyl)-phenyl]-acrylamide | Tr = 2.33 min, m/z (ES⁺) (M + H)⁺ 324 |

-continued

| Structure | IUPAC Name | MS |
|---|---|---|
| 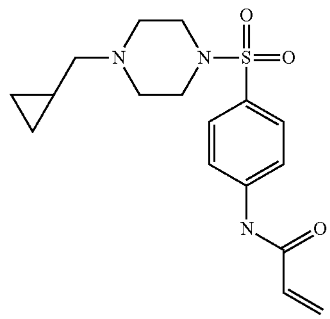 [SMILES: C=CC(=O)Nc1ccc(S(=O)(=O)N2CCN(CC3CC3)CC2)cc1] | N-[4-(4-Cyclopropylmethyl-piperazine-1-sulfonyl)-phenyl]-acrylamide | Tr = 2.39 min, m/z (ES+) (M + H)+ 350 |
| 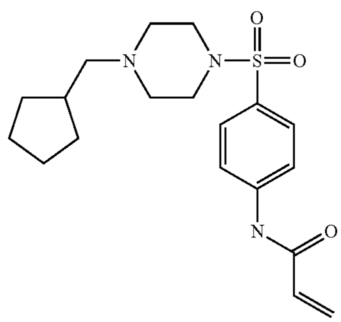 [SMILES: C=CC(=O)Nc1ccc(S(=O)(=O)N2CCN(CC3CCCC3)CC2)cc1] | N-[4-(4-Cyclopentylmethyl-piperazine-1-sulfonyl)-phenyl]-acrylamide | Tr = 2.64 min, m/z (ES+) (M + H)+ 378 |
| 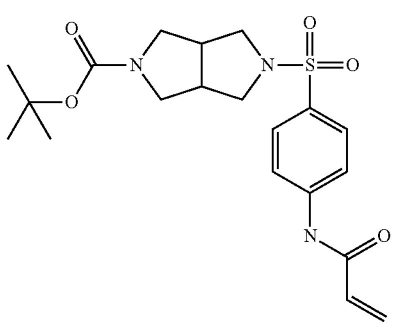 [SMILES: C=CC(=O)Nc1ccc(S(=O)(=O)N2CC3CN(C(=O)OC(C)(C)C)CC3C2)cc1] | 5-(4-Acryloylamino-benzenesulfonyl)-hexahydro-pyrrolo[3,4-c]pyrrole-2-carboxylic acid tert-butyl ester | Tr = 3.83 min, m/z (ES+) (M + H)+ 422 |
| 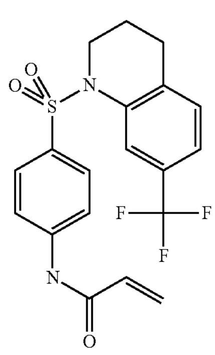 [SMILES: C=CC(=O)Nc1ccc(S(=O)(=O)N2CCCc3ccc(C(F)(F)F)cc32)cc1] | N-[4-(7-Trifluoromethyl-3,4-dihydro-2H-quinoline-1-sulfonyl)-phenyl]-acrylamide | Tr = 4.65 min, m/z (ES+) (M + H)+ 411 |

-continued

| Structure | IUPAC Name | MS |
|---|---|---|
| 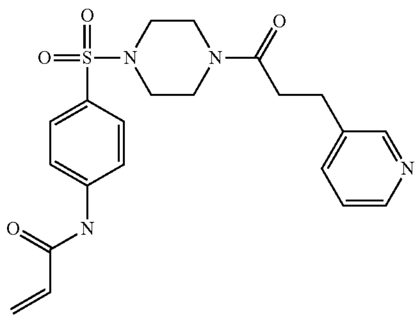 [SMILES: C=CC(=O)Nc1ccc(S(=O)(=O)N2CCN(C(=O)CCc3cccnc3)CC2)cc1] | N-{4-[4-(3-Pyridin-3-yl-propionyl)-piperazine-1-sulfonyl]-phenyl}-acrylamide | Tr = 2.40 min, m/z (ES+) (M + H)+ 430 |
| 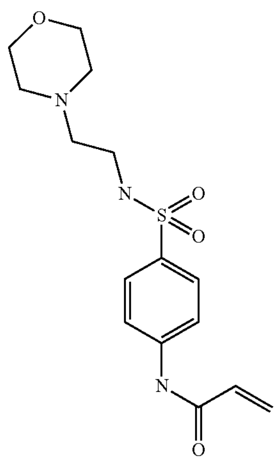 [SMILES: C=CC(=O)Nc1ccc(S(=O)(=O)NCCN2CCOCC2)cc1] | N-[1-(4-Acryloylamino-benzenesulfonyl)-piperidin-4-yl]-benzamide | Tr = 2.04 min, m/z (ES+) (M + H)+ 340 |
| 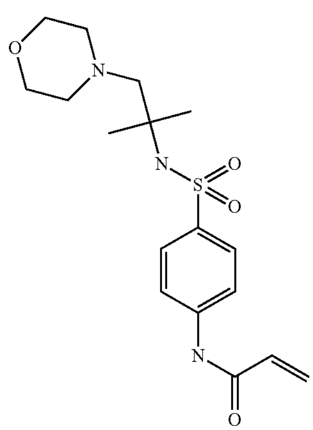 [SMILES: C=CC(=O)Nc1ccc(S(=O)(=O)NC(C)(C)CN2CCOCC2)cc1] | N-[4-(1,1-Dimethyl-2-morpholin-4-yl-ethylsulfamoyl)-phenyl]-acrylamide | Tr = 2.28 min, m/z (ES+) (M + H)+ 368 |
| 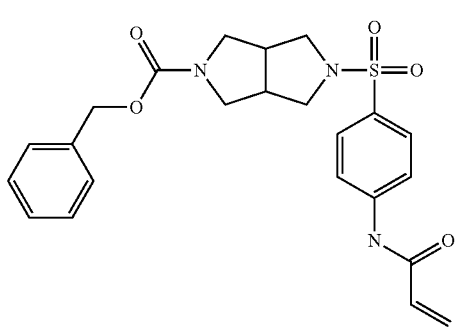 [SMILES: C=CC(=O)Nc1ccc(S(=O)(=O)N2CC3CN(C(=O)OCc4ccccc4)CC3C2)cc1] | 5-(4-Acryloylamino-benzenesulfonyl)-hexahydro-pyrrolo[3,4-c]pyrrole-2-carboxylic acid benzyl ester | Tr = 3.91 min, m/z (ES+) (M + H)+ 456 |

-continued

| Structure | IUPAC Name | MS |
|---|---|---|
| 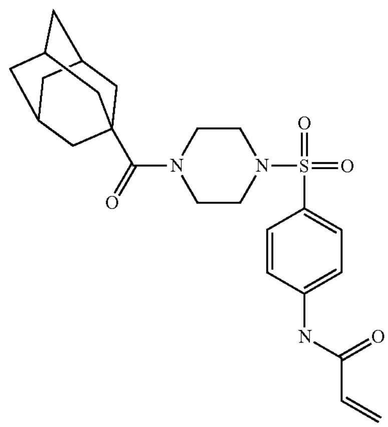 [SMILES: C=CC(=O)Nc1ccc(S(=O)(=O)N2CCN(C(=O)C34CC5CC(CC(C5)C3)C4)CC2)cc1] | N-{4-[4-(Adamantane-1-carbonyl)-piperazine-1-sulfonyl]-phenyl}-acrylamide | Tr = 4.46 min, m/z (ES+) (M + H)+ 458 |
| 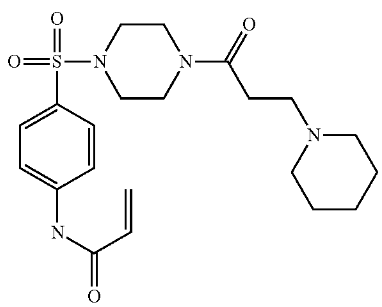 [SMILES: C=CC(=O)Nc1ccc(S(=O)(=O)N2CCN(C(=O)CCN3CCCCC3)CC2)cc1] | N-{4-[4-(3-Piperidin-1-yl-propionyl)-piperazine-1-sulfonyl]-phenyl}-acrylamide | Tr = 2.53 min, m/z (ES+) (M + H)+ 435 |
| 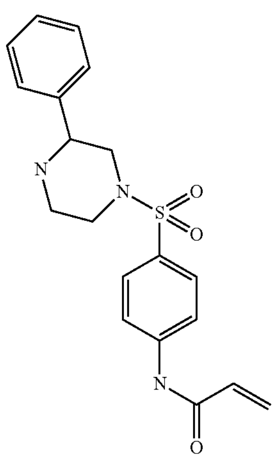 | 4-(4-Acryloylamino-benzenesulfonyl)-2-phenyl-piperazine-1-carboxylic acid tert-butyl ester | Tr = 4.65 min, m/z (ES+) (M + H)+ 494 |
| 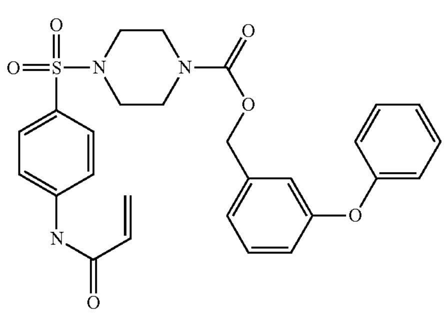 [SMILES: C=CC(=O)Nc1ccc(S(=O)(=O)N2CCN(C(=O)OCc3cccc(Oc4ccccc4)c3)CC2)cc1] | 4-(4-Acryloylamino-benzenesulfonyl)-piperazine-1-carboxylic acid 3-phenoxy-benzyl ester | Tr = 4.72 min, m/z (ES+) (M + H)+ 522 |

-continued

| Structure | IUPAC Name | MS |
|---|---|---|
| 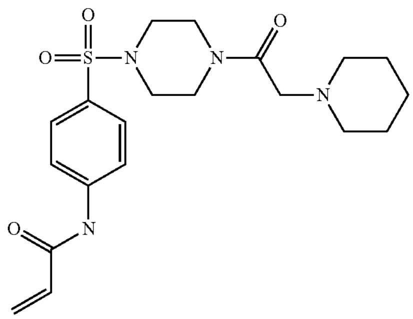 [SMILES: C=CC(=O)Nc1ccc(S(=O)(=O)N2CCN(C(=O)CN3CCCCC3)CC2)cc1] | N-{4-[4-(2-Piperidin-1-yl-acetyl)-piperazine-1-sulfonyl]-phenyl}-acrylamide | Tr = 2.52 min, m/z (ES$^+$) (M + H)$^+$ 421 |
| 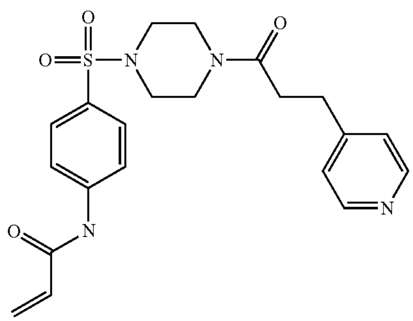 [SMILES: C=CC(=O)Nc1ccc(S(=O)(=O)N2CCN(C(=O)CCc3ccncc3)CC2)cc1] | N-{4-[4-(3-Pyridin-4-yl-propionyl)-piperazine-1-sulfonyl]-phenyl}-acrylamide | Tr = 2.53 min, m/z (ES$^+$) (M + H)$^+$ 429 |
| 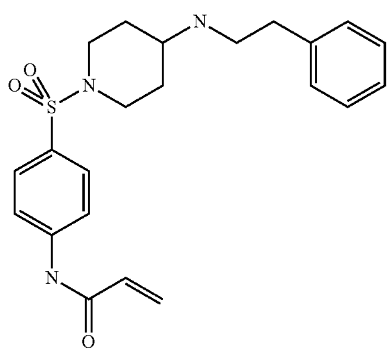 [SMILES: C=CC(=O)Nc1ccc(S(=O)(=O)N2CCC(NCCc3ccccc3)CC2)cc1] | N-[4-(4-Phenethylamino-piperidine-1-sulfonyl)-phenyl]-acrylamide | Tr = 2.86 min, m/z (ES$^+$) (M + H)$^+$ 414 |
| 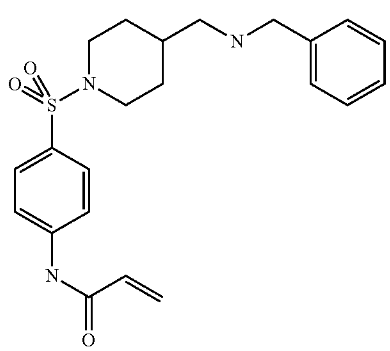 [SMILES: C=CC(=O)Nc1ccc(S(=O)(=O)N2CCC(CNCc3ccccc3)CC2)cc1] | N-{4-[4-(Benzylamino-methyl)-piperidine-1-sulfonyl]-phenyl}-acrylamide | Tr = 2.86 min, m/z (ES$^+$) (M + H)$^+$ 414 |

| Structure | IUPAC Name | MS |
| --- | --- | --- |
| 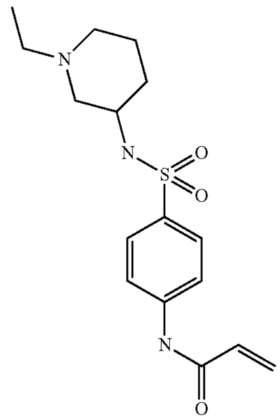 [SMILES: C=CC(=O)Nc1ccc(S(=O)(=O)NC2CCCN(CC)C2)cc1] | N-[4-(1-Ethyl-piperidin-3-ylsulfamoyl)-phenyl]-acrylamide | Tr = 2.15 min, m/z (ES$^+$) (M + H)$^+$ 338 |
| 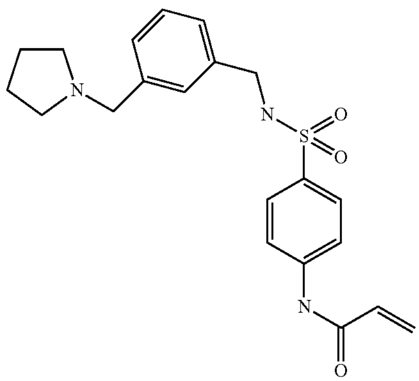 [SMILES: C=CC(=O)Nc1ccc(S(=O)(=O)NCc2cccc(CN3CCCC3)c2)cc1] | N-[4-(3-Pyrrolidin-1-ylmethyl-benzylsulfamoyl)-phenyl]-acrylamide | Tr = 2.63 min, m/z (ES$^+$) (M + H)$^+$ 400 |
| 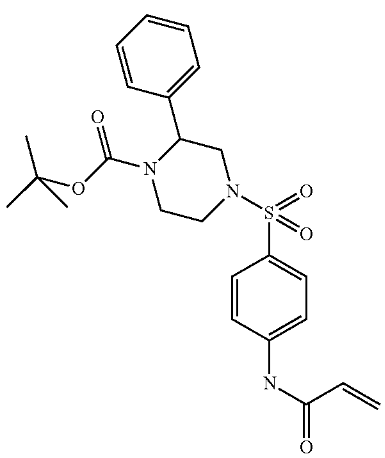 [SMILES: C=CC(=O)Nc1ccc(S(=O)(=O)N2CCN(C(=O)OC(C)(C)C)C(c3ccccc3)C2)cc1] | 4-(4-Acryloylamino-benzenesulfonyl)-2-phenyl-piperazine-1-carboxylic acid tert-butyl ester | Tr = 4.65 min, m/z (ES$^+$) (M + Na)$^+$ 494 |
| 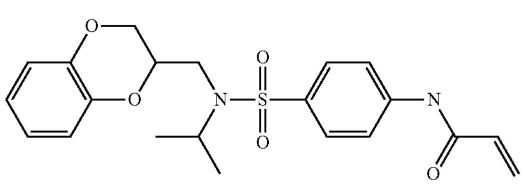 [SMILES: C=CC(=O)Nc1ccc(S(=O)(=O)N(CC2COc3ccccc3O2)C(C)C)cc1] | N-{4-[(2,3-Dihydro-benzo[1,4]dioxin-2-ylmethyl)-isopropyl-sulfamoyl]-phenyl}-acrylamide | Tr = 4.32 min, m/z (ES$^+$) (M + H)$^+$ 417 |
| 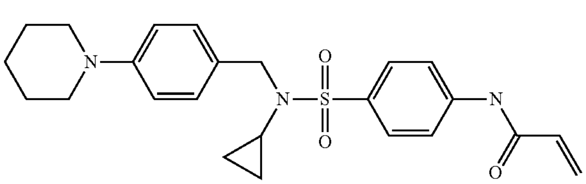 [SMILES: C=CC(=O)Nc1ccc(S(=O)(=O)N(Cc2ccc(N3CCCCC3)cc2)C2CC2)cc1] | N-{4-[Cyclopropyl-(4-piperidin-1-yl-benzyl)-sulfamoyl]-phenyl}-acrylamide | Tr = 3.11 min, m/z (ES$^+$) (M + H)$^+$ 440 |

| Structure | IUPAC Name | MS |
|---|---|---|
| 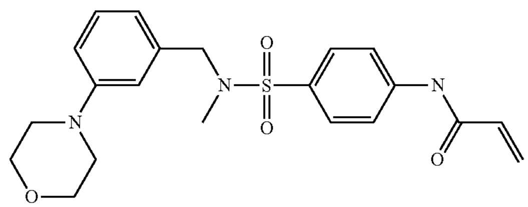 [SMILES: C=CC(=O)Nc1ccc(S(=O)(=O)N(C)Cc2cccc(N3CCOCC3)c2)cc1] | N-{4-[Methyl-(3-morpholin-4-yl-benzyl)-sulfamoyl]-phenyl}-acrylamide | Tr = 4.03 min, m/z (ES+) (M + H)+ 416 |
| 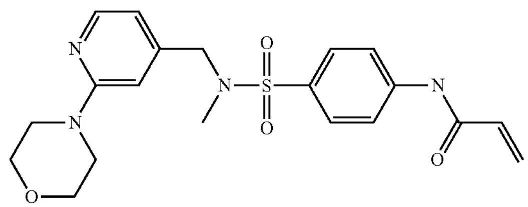 [SMILES: C=CC(=O)Nc1ccc(S(=O)(=O)N(C)Cc2ccnc(N3CCOCC3)c2)cc1] | N-{4-[Methyl-(2-morpholin-4-yl-pyridin-4-ylmethyl)-sulfamoyl]-phenyl}-acrylamide | Tr = 2.73 min, m/z (ES+) (M + H)+ 417 |
| 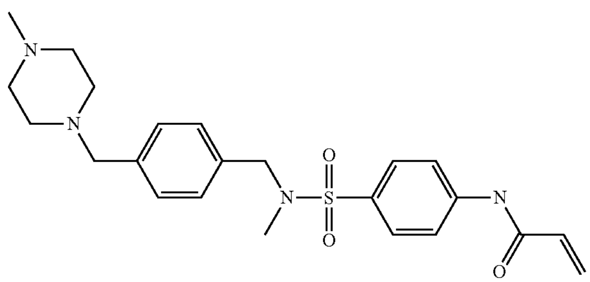 [SMILES: C=CC(=O)Nc1ccc(S(=O)(=O)N(C)Cc2ccc(CN3CCN(C)CC3)cc2)cc1] | N-(4-{Methyl-[4-(4-methyl-piperazin-1-ylmethyl)-benzyl]-sulfamoyl}-phenyl)-acrylamide | Tr = 2.65 min, m/z (ES+) (M + H)+ 443 |
| 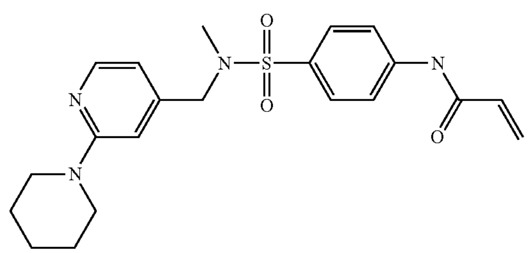 [SMILES: C=CC(=O)Nc1ccc(S(=O)(=O)N(C)Cc2ccnc(N3CCCCC3)c2)cc1] | N-{4-[Methyl-(3,4,5,6-tetrahydro-2H-[1,2']bipyridinyl-4'-ylmethyl)-sulfamoyl]-phenyl}-acrylamide | Tr = 2.89 min, m/z (ES+) (M + H)+ 415 |
| 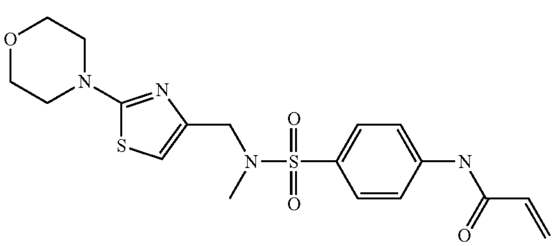 [SMILES: C=CC(=O)Nc1ccc(S(=O)(=O)N(C)Cc2csc(N3CCOCC3)n2)cc1] | N-{4-[Methyl-(2-morpholin-4-yl-thiazol-4-ylmethyl)-sulfamoyl]-phenyl}-acrylamide | Tr = 3.73 min, m/z (ES+) (M + H)+ 423 |
| 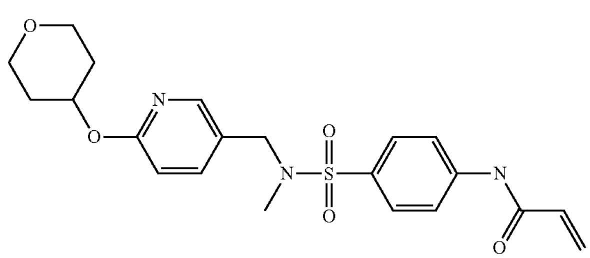 [SMILES: C=CC(=O)Nc1ccc(S(=O)(=O)N(C)Cc2ccc(OC3CCOCC3)nc2)cc1] | N-(4-{Methyl-[6-(tetrahydro-pyran-4-yloxy)-pyridin-3-ylmethyl]-sulfamoyl}-phenyl)-acrylamide | Tr = 3.97 min, m/z (ES+) (M + H)+ 432 |

-continued

| Structure | IUPAC Name | MS |
|---|---|---|
| 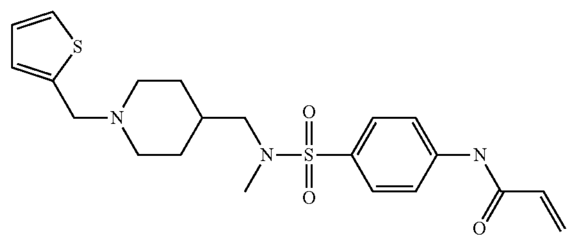 [SMILES: C=CC(=O)Nc1ccc(S(=O)(=O)N(C)CC2CCN(Cc3cccs3)CC2)cc1] | N-{4-[Methyl-(1-thiophen-2-ylmethyl-piperidin-4-ylmethyl)-sulfamoyl]-phenyl}-acrylamide | Tr = 2.90 min, m/z (ES$^+$) (M + H)$^+$ 434 |
| 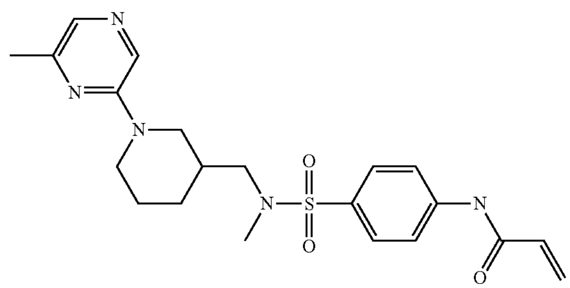 [SMILES: C=CC(=O)Nc1ccc(S(=O)(=O)N(C)CC2CCCN(c3cncc(C)n3)C2)cc1] | N-(4-{Methyl-[1-(6-methyl-pyrazin-2-yl)-piperidin-3-ylmethyl]-sulfamoyl}-phenyl)-acrylamide | Tr = 4.04 min, m/z (ES$^+$) (M + H)$^+$ 430 |
| 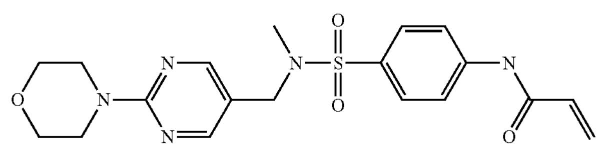 [SMILES: C=CC(=O)Nc1ccc(S(=O)(=O)N(C)Cc2cnc(N3CCOCC3)nc2)cc1] | N-{4-[Methyl-(2-morpholin-4-yl-pyrimidin-5-ylmethyl)-sulfamoyl]-phenyl}-acrylamide | Tr = 3.66 min, m/z (ES$^+$) (M + H)$^+$ 418 |
| 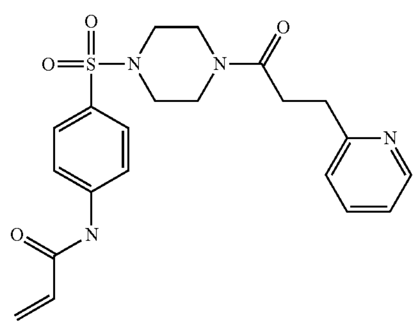 [SMILES: C=CC(=O)Nc1ccc(S(=O)(=O)N2CCN(C(=O)CCc3ccccn3)CC2)cc1] | N-{4-[4-(3-Pyridin-2-yl-propionyl)-piperazine-1-sulfonyl]-phenyl}-acrylamide | Tr = 2.57 min, m/z (ES$^+$) (M + H)$^+$ 429 |
| 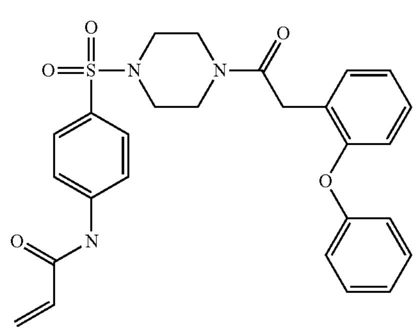 [SMILES: C=CC(=O)Nc1ccc(S(=O)(=O)N2CCN(C(=O)Cc3ccccc3Oc3ccccc3)CC2)cc1] | N-(4-{4-[2-(2-Phenoxy-phenyl)-acetyl]-piperazine-1-sulfonyl}-phenyl)-acrylamide | Tr = 4.28 min, m/z (ES$^+$) (M + H)$^+$ 506 |

-continued

| Structure | IUPAC Name | MS |
|---|---|---|
| 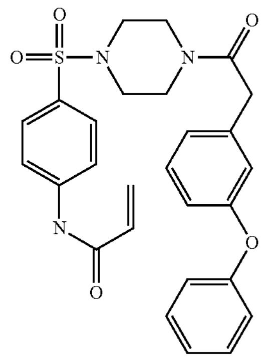 [SMILES: C=CC(=O)Nc1ccc(S(=O)(=O)N2CCN(C(=O)Cc3cccc(Oc4ccccc4)c3)CC2)cc1] | N-(4-{4-[2-(3-Phenoxy-phenyl)-acetyl]-piperazine-1-sulfonyl}-phenyl)-acrylamide | Tr = 4.30 min, m/z (ES+) (M + H)+ 506 |
| 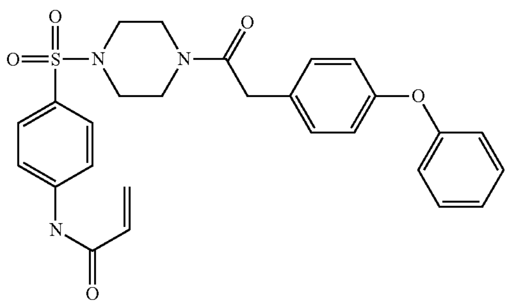 [SMILES: C=CC(=O)Nc1ccc(S(=O)(=O)N2CCN(C(=O)Cc3ccc(Oc4ccccc4)cc3)CC2)cc1] | N-(4-{4-[2-(4-Phenoxy-phenyl)-acetyl]-piperazine-1-sulfonyl}-phenyl)-acrylamide | Tr = 4.32 min, m/z (ES+) (M + H)+ 506 |
| 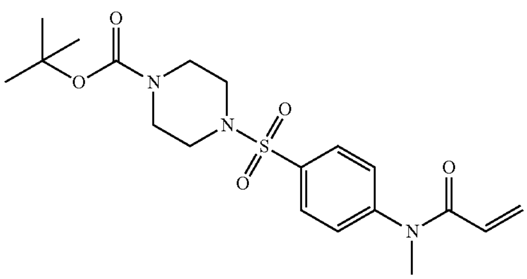 [SMILES: C=CC(=O)N(C)c1ccc(S(=O)(=O)N2CCN(C(=O)OC(C)(C)C)CC2)cc1] | 4-[4-(Acryloyl-methyl-amino)-benzenesulfonyl]-piperazine-1-carboxylic acid tert-butyl ester | Tr = 3.95 min, m/z (ES+) (M + Na)+ 432 |
| 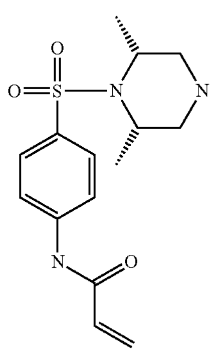 | N-[4-(4-Amino-piperidine-1-sulfonyl)-phenyl]-acrylamide | Tr = 1.14 min, m/z (ES+) (M + H)+ 324 |
| 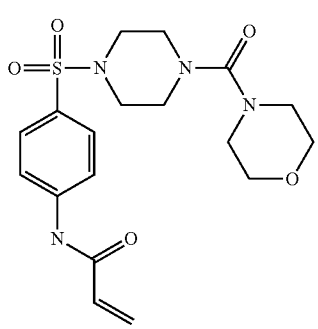 [SMILES: C=CC(=O)Nc1ccc(S(=O)(=O)N2CCN(C(=O)N3CCOCC3)CC2)cc1] | N-{4-[4-(Morpholine-4-carbonyl)-piperazine-1-sulfonyl]-phenyl}-acrylamide | Tr = 3.22 min, m/z (ES+) (M + H)+ 409 |

-continued

| Structure | IUPAC Name | MS |
|---|---|---|
| | N-{4-[4-(Adamantane-1-carbonyl)-2,6-dimethyl-piperazine-1-sulfonyl]-phenyl}-acrylamide | Tr = 4.70 min, m/z (ES+) (M + H)+ 486 |
| 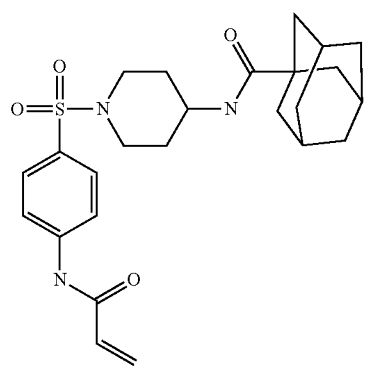 [SMILES: C=CC(=O)Nc1ccc(S(=O)(=O)N2CCC(NC(=O)C34CC5CC(CC(C5)C3)C4)CC2)cc1] | Adamantane-1-carboxylic acid [1-(4-acryloylamino-benzenesulfonyl)-piperidin-4-yl]-amide | |
| 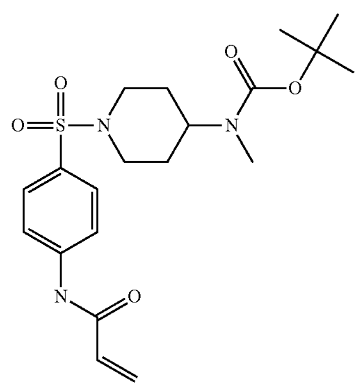 [SMILES: C=CC(=O)Nc1ccc(S(=O)(=O)N2CCC(N(C)C(=O)OC(C)(C)C)CC2)cc1] | [1-(4-Acryloylamino-benzenesulfonyl)-piperidin-4-yl]-methyl-carbamic acid tert-butyl ester | Tr = 4.25 min, m/z (ES+) (M + Na)+ 446 |
| 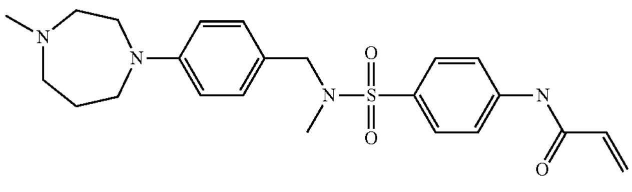 [SMILES: C=CC(=O)Nc1ccc(S(=O)(=O)N(C)Cc2ccc(N3CCCN(C)CC3)cc2)cc1] | N-(4-{Methyl-[4-(4-methyl-[1,4]diazepan-1-yl)-benzyl]-sulfamoyl}-phenyl)-acrylamide | Tr = 2.99 min, m/z (ES+) (M + H)+ 443 |
| 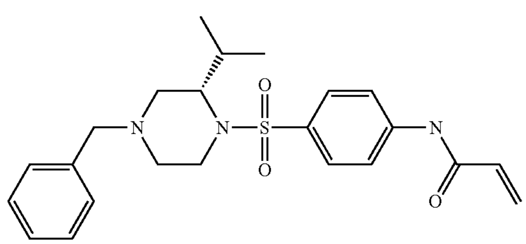 [SMILES: C=CC(=O)Nc1ccc(S(=O)(=O)N2CCN(Cc3ccccc3)C[C@@H]2C(C)C)cc1] | N-[4-(4-Benzyl-2-isopropyl-piperazine-1-sulfonyl)-phenyl]-acrylamide | Tr = 3.10 min, m/z (ES+) (M + H)+ 428 |

| Structure | IUPAC Name | MS |
|---|---|---|
| 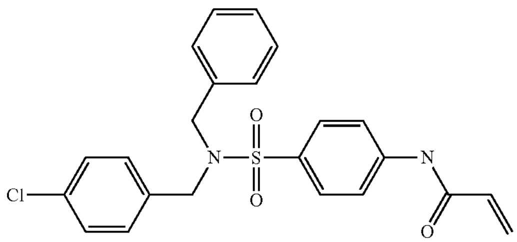 [SMILES: C=CC(=O)Nc1ccc(S(=O)(=O)N(Cc2ccccc2)Cc2ccc(Cl)cc2)cc1] | N-{4-[Benzyl-(4-chloro-benzyl)-sulfamoyl]-phenyl}-acrylamide | Tr = 4.94 min, m/z (ES⁺) (M + H)⁺ 463 |
| 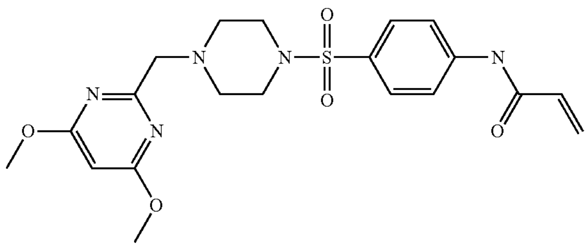 [SMILES: C=CC(=O)Nc1ccc(S(=O)(=O)N2CCN(Cc3nc(OC)cc(OC)n3)CC2)cc1] | N-{4-[4-(4,6-Dimethoxy-pyrimidin-2-ylmethyl)-piperazine-1-sulfonyl]-phenyl}-acrylamide | Tr = 2.72 min, m/z (ES⁺) (M + H)⁺ 448 |
| 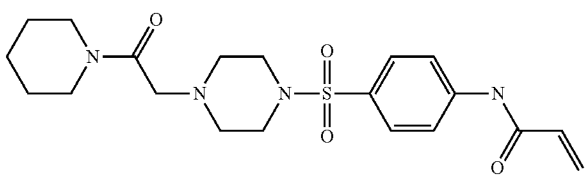 [SMILES: C=CC(=O)Nc1ccc(S(=O)(=O)N2CCN(CC(=O)N3CCCCC3)CC2)cc1] | N-{4-[4-(2-Oxo-2-piperidin-1-yl-ethyl)-piperazine-1-sulfonyl]-phenyl}-acrylamide | Tr = 2.58 min, m/z (ES⁺) (M + H)⁺ 421 |
| 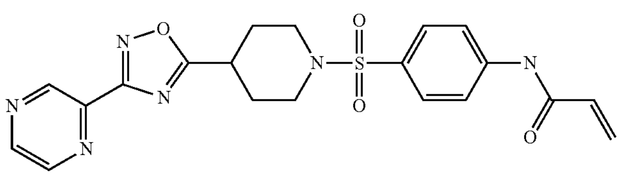 [SMILES: C=CC(=O)Nc1ccc(S(=O)(=O)N2CCC(c3nc(-c4cnccn4)no3)CC2)cc1] | N-{4-[4-(3-Pyrazin-2-yl-[1,2,4]oxadiazol-5-yl)-piperidine-1-sulfonyl]-phenyl}-acrylamide | Tr = 3.64 min, m/z (ES⁺) (M + Na)⁺ 463 |
| 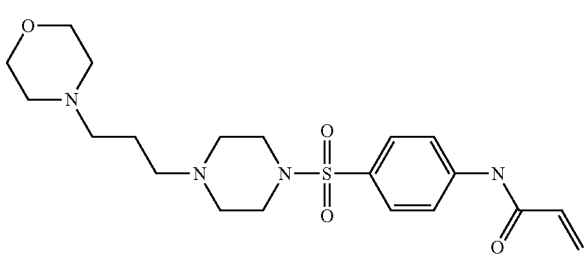 [SMILES: C=CC(=O)Nc1ccc(S(=O)(=O)N2CCN(CCCN3CCOCC3)CC2)cc1] | N-{4-[4-(3-Morpholin-4-yl-propyl)-piperazine-1-sulfonyl]-phenyl}-acrylamide | Tr = 1.90 min, m/z (ES⁺) (M + H)⁺ 423 |
| 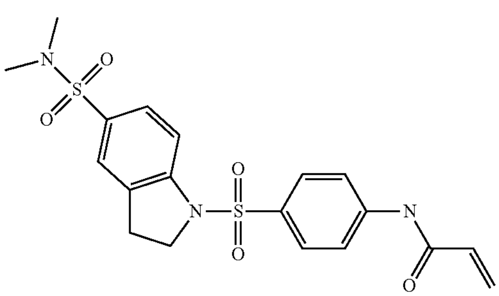 | N-[4-(5-Dimethylsulfamoyl-2,3-dihydro-indole-1-sulfonyl)-phenyl]-acrylamide | Tr = 3.98 min, m/z (ES⁺) (M + Na)⁺ 457 |

| Structure | IUPAC Name | MS |
|---|---|---|
| 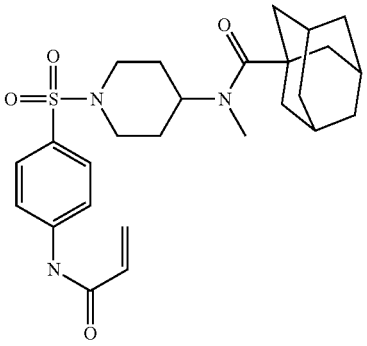 [SMILES: C=CC(=O)Nc1ccc(S(=O)(=O)N2CCC(N(C)C(=O)C34CC5CC(CC(C5)C3)C4)CC2)cc1] | Adamantane-1-carboxylic acid [1-(4-acryloylamino-benzenesulfonyl)-piperidin-4-yl]-methyl-amide | Tr = 4.61 min, m/z (ES+) (M + H)+ 486 |
| 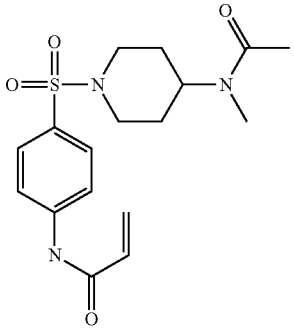 [SMILES: C=CC(=O)Nc1ccc(S(=O)(=O)N2CCC(N(C)C(C)=O)CC2)cc1] | N-{4-[4-(Acetyl-methyl-amino)-piperidine-1-sulfonyl]-phenyl}-acrylamide | Tr = 3.08 min, m/z (ES+) (M + H)+ 366 |
| 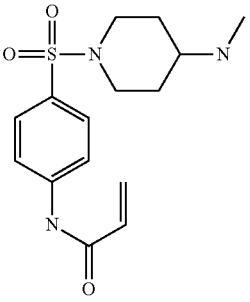 [SMILES: C=CC(=O)Nc1ccc(S(=O)(=O)N2CCC(NC)CC2)cc1] | N-[4-(4-Methylamino-piperidine-1-sulfonyl)-phenyl]-acrylamide | Tr = 2.20 min, m/z (ES+) (M + H)+ 324 |
| 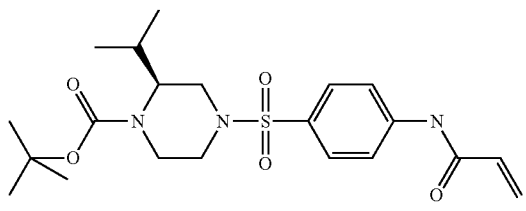 [SMILES: C=CC(=O)Nc1ccc(S(=O)(=O)N2CCN(C(=O)OC(C)(C)C)[C@@H](C(C)C)C2)cc1] | 4-(4-Acryloylamino-benzenesulfonyl)-2-isopropyl-piperazine-1-carboxylic acid tert-butyl ester | Tr = 4.40 min, m/z (ES+) (M + Na)+ 460 |
| 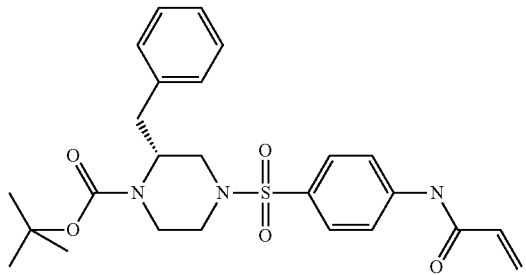 [SMILES: C=CC(=O)Nc1ccc(S(=O)(=O)N2CCN(C(=O)OC(C)(C)C)[C@H](Cc3ccccc3)C2)cc1] | 4-(4-Acryloylamino-benzenesulfonyl)-2-benzyl-piperazine-1-carboxylic acid tert-butyl ester | Tr = 4.81 min, m/z (ES+) (M + Na)+ 508 |

| Structure | IUPAC Name | MS |
|---|---|---|
| 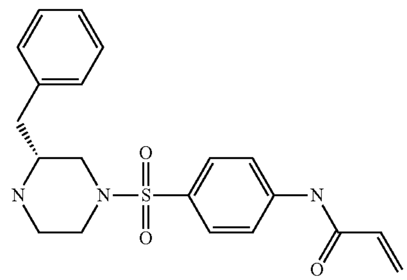 [SMILES: C=CC(=O)Nc1ccc(S(=O)(=O)N2CCN[C@H](Cc3ccccc3)C2)cc1] | N-[4-(3-Benzyl-piperazine-1-sulfonyl)-phenyl]-acrylamide | Tr = 2.80 min, m/z (ES⁺) (M + H)⁺ 386 |
| 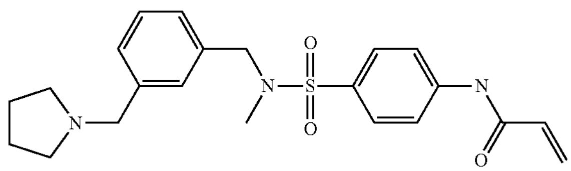 [SMILES: C=CC(=O)Nc1ccc(S(=O)(=O)N(C)Cc2cccc(CN3CCCC3)c2)cc1] | N-{4-[Methyl-(3-pyrrolidin-1-ylmethyl-benzyl)-sulfamoyl]-phenyl}-acrylamide | Tr = 2.83 min, m/z (ES⁺) (M + H)⁺ 414 |
| 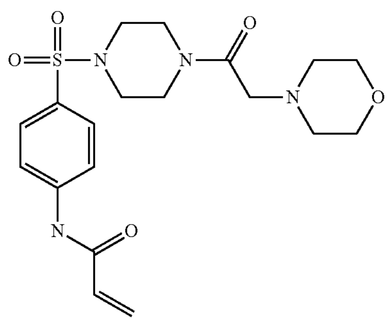 [SMILES: C=CC(=O)Nc1ccc(S(=O)(=O)N2CCN(C(=O)CN3CCOCC3)CC2)cc1] | N-{4-[4-(2-Morpholin-4-yl-acetyl)-piperazine-1-sulfonyl]-phenyl}-acrylamide | Tr = 2.39 min, m/z (ES⁺) (M + H)⁺ 423 |
| 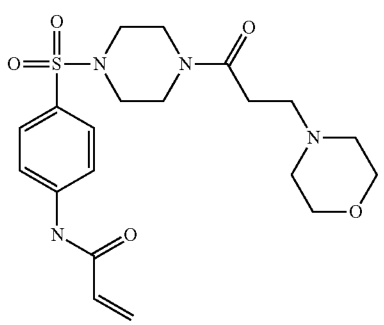 [SMILES: C=CC(=O)Nc1ccc(S(=O)(=O)N2CCN(C(=O)CCN3CCOCC3)CC2)cc1] | N-{4-[4-(3-Morpholin-4-yl-propionyl)-piperazine-1-sulfonyl]-phenyl}-acrylamide | Tr = 2.42 min, m/z (ES⁺) (M + H)⁺ 437 |
| 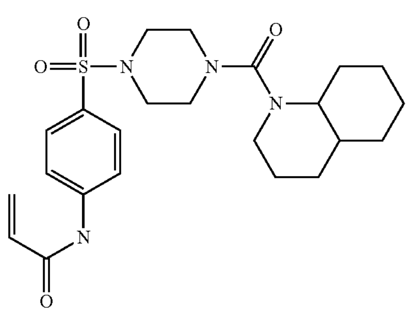 [SMILES: C=CC(=O)Nc1ccc(S(=O)(=O)N2CCN(C(=O)N3CCCC4CCCCC43)CC2)cc1] | N-{4-[4-(Octahydro-quinoline-1-carbonyl)-piperazine-1-sulfonyl]-phenyl}-acrylamide | Tr = 4.40 min, m/z (ES⁺) (M + H)⁺ 461 |

| Structure | IUPAC Name | MS |
|---|---|---|
| 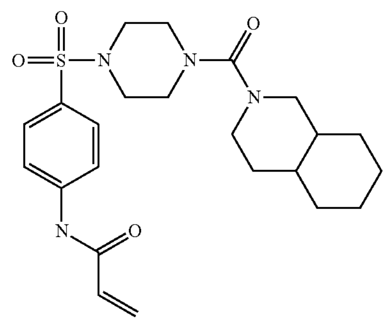 [SMILES: C=CC(=O)Nc1ccc(S(=O)(=O)N2CCN(C(=O)N3CCC4CCCCC4C3)CC2)cc1] | N-{4-[4-(Octahydro-isoquinoline-2-carbonyl)-piperazine-1-sulfonyl]-phenyl}-acrylamide | Tr = 4.42 min, m/z (ES⁺) (M + H)⁺ 461 |
| 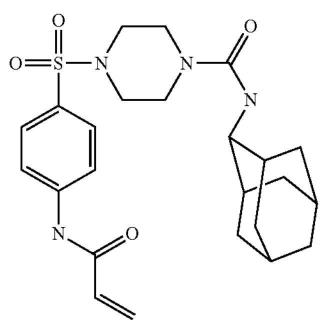 [SMILES: C=CC(=O)Nc1ccc(S(=O)(=O)N2CCN(C(=O)NC3C4CC5CC(C4)CC3C5)CC2)cc1] | 4-(4-Acryloylamino-benzenesulfonyl)-piperazine-1-carboxylic acid adamantan-2-ylamide | Tr = 4.31 min, m/z (ES⁺) (M + H)⁺ 473 |
| 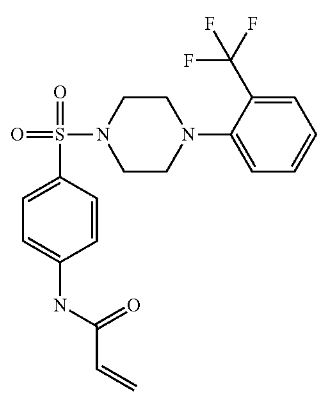 [SMILES: C=CC(=O)Nc1ccc(S(=O)(=O)N2CCN(c3ccccc3C(F)(F)F)CC2)cc1] | N-{4-[4-(2-Trifluoromethyl-phenyl)-piperazine-1-sulfonyl]-phenyl}-acrylamide | Tr = 4.36 min, m/z (ES⁺) (M + H)⁺ 440 |
| 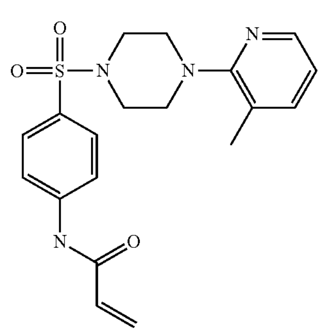 [SMILES: C=CC(=O)Nc1ccc(S(=O)(=O)N2CCN(c3ncccc3C)CC2)cc1] | N-{4-[4-(3-Methyl-pyridin-2-yl)-piperazine-1-sulfonyl]-phenyl}-acrylamide | Tr = 3.02 min, m/z (ES⁺) (M + H)⁺ 387 |

| Structure | IUPAC Name | MS |
|---|---|---|
| 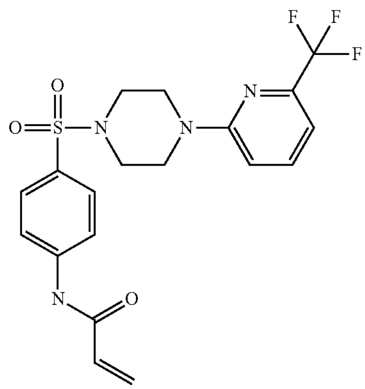 [SMILES: C=CC(=O)Nc1ccc(S(=O)(=O)N2CCN(c3cccc(C(F)(F)F)n3)CC2)cc1] | N-{4-[4-(6-Trifluoromethyl-pyridin-2-yl)-piperazine-1-sulfonyl]-phenyl}-acrylamide | Tr = 4.32 min, m/z (ES+) (M + H)+ 441 |
| 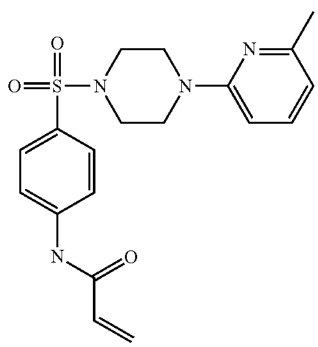 [SMILES: C=CC(=O)Nc1ccc(S(=O)(=O)N2CCN(c3cccc(C)n3)CC2)cc1] | N-{4-[4-(6-Methyl-pyridin-2-yl)-piperazine-1-sulfonyl]-phenyl}-acrylamide | Tr = 2.64 min, m/z (ES+) (M + H)+ 387 |
| 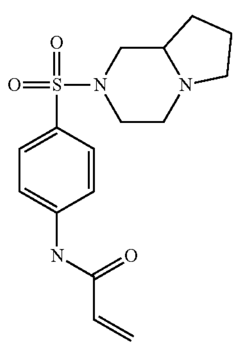 [SMILES: C=CC(=O)Nc1ccc(S(=O)(=O)N2CCN3CCCC3C2)cc1] | N-[4-(Hexahydro-pyrrolo[1,2-a]pyrazine-2-sulfonyl)-phenyl]-acrylamide | Tr = 2.38 min, m/z (ES+) (M + H)+ 336 |
| 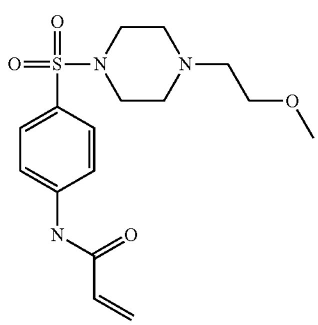 [SMILES: C=CC(=O)Nc1ccc(S(=O)(=O)N2CCN(CCOC)CC2)cc1] | N-{4-[4-(2-Methoxy-ethyl)-piperazine-1-sulfonyl]-phenyl}-acrylamide | Tr = 2.32 min, m/z (ES+) (M + H)+ 354 |

-continued

| Structure | IUPAC Name | MS |
|---|---|---|
| 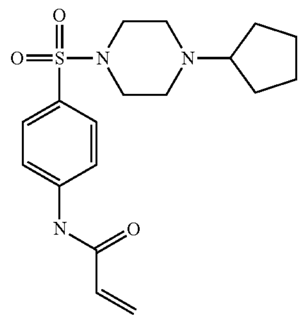 [SMILES: C=CC(=O)Nc1ccc(S(=O)(=O)N2CCN(C3CCCC3)CC2)cc1] | N-[4-(4-Cyclopentyl-piperazine-1-sulfonyl)-phenyl]-acrylamide | Tr = 2.58 min, m/z (ES+) (M + H)+ 364 |
| 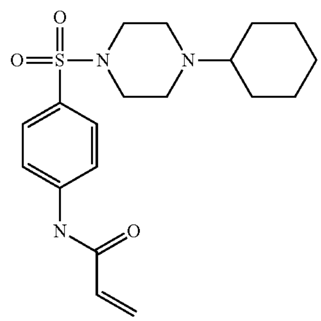 [SMILES: C=CC(=O)Nc1ccc(S(=O)(=O)N2CCN(C3CCCCC3)CC2)cc1] | N-[4-(4-Cyclohexyl-piperazine-1-sulfonyl)-phenyl]-acrylamide | Tr = 2.74 min, m/z (ES+) (M + H)+ 378 |
| 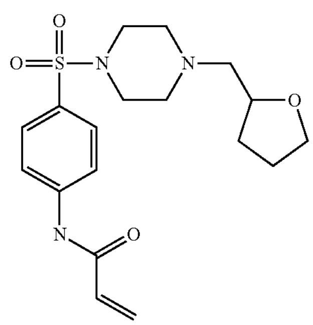 [SMILES: C=CC(=O)Nc1ccc(S(=O)(=O)N2CCN(CC3CCCO3)CC2)cc1] | N-{4-[4-(Tetrahydro-furan-2-ylmethyl)-piperazine-1-sulfonyl]-phenyl}-acrylamide | Tr = 2.51 min, m/z (ES+) (M + H)+ 380 |
| 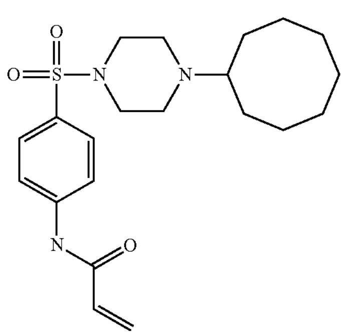 [SMILES: C=CC(=O)Nc1ccc(S(=O)(=O)N2CCN(C3CCCCCCC3)CC2)cc1] | N-[4-(4-Cyclooctyl-piperazine-1-sulfonyl)-phenyl]-acrylamide | Tr = 2.99 min, m/z (ES+) (M + H)+ 406 |
| 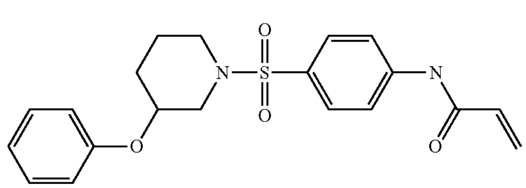 [SMILES: C=CC(=O)Nc1ccc(S(=O)(=O)N2CCCC(Oc3ccccc3)C2)cc1] | N-[4-(3-Phenoxy-piperidine-1-sulfonyl)-phenyl]-acrylamide | Tr = 4.22 min, m/z (ES+) (M + H)+ 387 |

-continued

| Structure | IUPAC Name | MS |
|---|---|---|
| 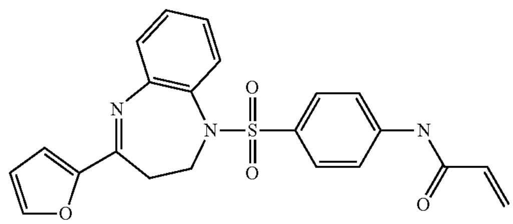 [SMILES: C=CC(=O)Nc1ccc(S(=O)(=O)N2CCC(c3ccco3)=Nc3ccccc32)cc1] | N-[4-(4-Furan-2-yl-2,3-dihydro-benzo[β][1,4]diazepine-1-sulfonyl)-phenyl]-acrylamide | Tr = 3.64 min, m/z (ES$^+$) (M + H)$^+$ 422 |
| 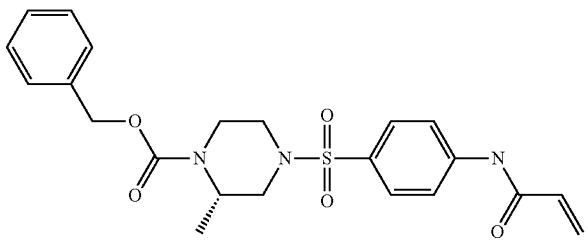 [SMILES: C=CC(=O)Nc1ccc(S(=O)(=O)N2CCN(C(=O)OCc3ccccc3)[C@@H](C)C2)cc1] | 4-(4-Acryloylamino-benzenesulfonyl)-2-methyl-piperazine-1-carboxylic acid benzyl ester | Tr = 4.28 min, m/z (ES$^+$) (M + Na)$^+$ 466 |
| 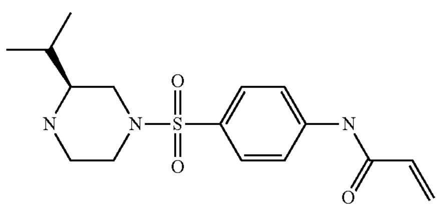 [SMILES: C=CC(=O)Nc1ccc(S(=O)(=O)N2CCN[C@@H](C(C)C)C2)cc1] | N-[4-(3-Isopropyl-piperazine-1-sulfonyl)-phenyl]-acrylamide | Tr = 2.65 min, m/z (ES$^+$) (M + H)$^+$ 338 |
| 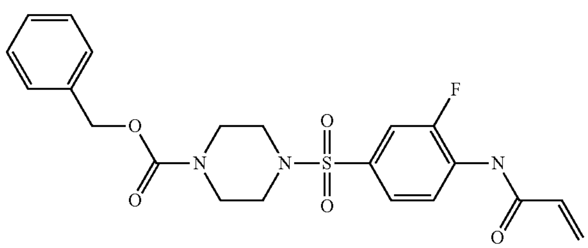 [SMILES: C=CC(=O)Nc1ccc(S(=O)(=O)N2CCN(C(=O)OCc3ccccc3)CC2)cc1F] | 4-(4-Acryloylamino-3-fluoro-benzenesulfonyl)-piperazine-1-carboxylic acid benzyl ester | Tr = 4.35 min, m/z (ES$^+$) (M + H)$^+$ 448 |
| 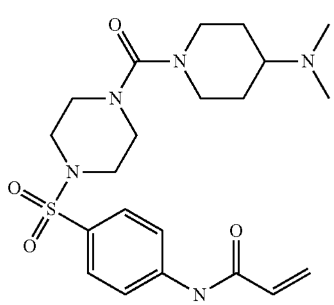 [SMILES: C=CC(=O)Nc1ccc(S(=O)(=O)N2CCN(C(=O)N3CCC(N(C)C)CC3)CC2)cc1] | N-{4-[4-(4-Dimethylamino-piperidine-1-carbonyl)-piperazine-1-sulfonyl]-phenyl}-acrylamide | Tr = 2.43 min, m/z (ES$^+$) (M + H)$^+$ 450 |
| 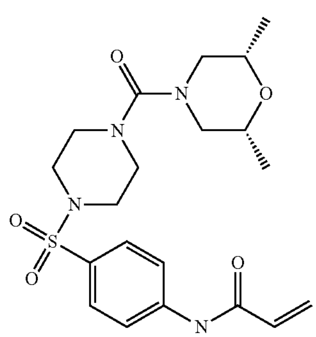 [SMILES: C=CC(=O)Nc1ccc(S(=O)(=O)N2CCN(C(=O)N3C[C@@H](C)O[C@@H](C)C3)CC2)cc1] | N-{4-[4-(2,6-Dimethyl-morpholine-4-carbonyl)-piperazine-1-sulfonyl]-phenyl}-acrylamide | Tr = 3.41 min, m/z (ES$^+$) (M + H)$^+$ 437 |

-continued

| Structure | IUPAC Name | MS |
|---|---|---|
| 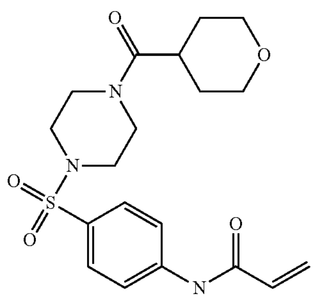 [SMILES: C=CC(=O)Nc1ccc(S(=O)(=O)N2CCN(C(=O)C3CCOCC3)CC2)cc1] | N-{4-[4-(Tetrahydro-pyran-4-carbonyl)-piperazine-1-sulfonyl]-phenyl}-acrylamide | Tr = 3.07 min, m/z (ES$^+$) (M + H)$^+$ 408 |
| 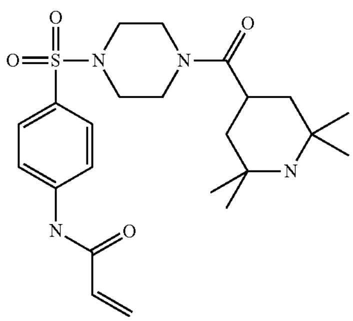 [SMILES: C=CC(=O)Nc1ccc(S(=O)(=O)N2CCN(C(=O)C3CC(C)(C)NC(C)(C)C3)CC2)cc1] | N-{4-[4-(2,2,6,6-Tetramethyl-piperidine-4-carbonyl)-piperazine-1-sulfonyl]-phenyl}-acrylamide | Tr = 2.59 min, m/z (ES$^+$) (M + H)$^+$ 463 |
| 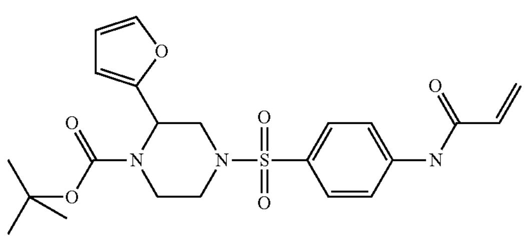 [SMILES: C=CC(=O)Nc1ccc(S(=O)(=O)N2CCN(C(=O)OC(C)(C)C)C(c3ccco3)C2)cc1] | 4-(4-Acryloylamino-benzenesulfonyl)-2-furan-2-yl-piperazine-1-carboxylic acid tert-butyl ester | Tr = 4.26 min, m/z (ES$^+$) (M + Na)$^+$ 484 |
| 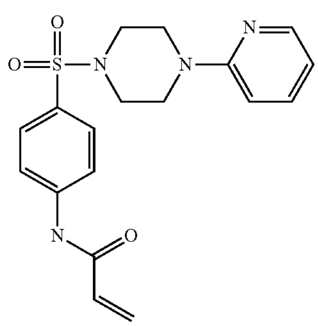 [SMILES: C=CC(=O)Nc1ccc(S(=O)(=O)N2CCN(c3ccccn3)CC2)cc1] | N-[4-(4-Pyridin-2-yl-piperazine-1-sulfonyl)-phenyl]-acrylamide | Tr = 2.55 min, m/z (ES$^+$) (M + H)$^+$ 373 |
| 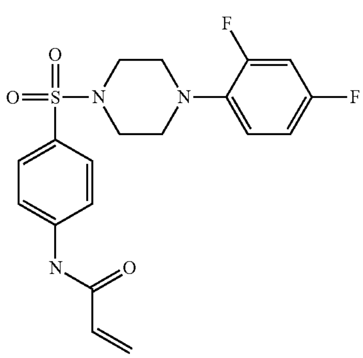 [SMILES: C=CC(=O)Nc1ccc(S(=O)(=O)N2CCN(c3ccc(F)cc3F)CC2)cc1] | N-{4-[4-(2,4-Difluoro-phenyl)-piperazine-1-sulfonyl]-phenyl}-acrylamide | Tr = 4.24 min, m/z (ES$^+$) (M + H)$^+$ 408 |

| Structure | IUPAC Name | MS |
|---|---|---|
| 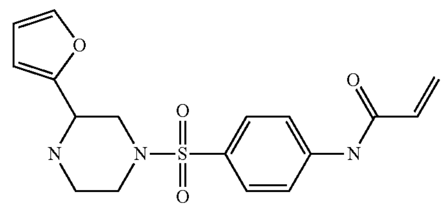 [SMILES: C=CC(=O)Nc1ccc(S(=O)(=O)N2CCNC(c3ccco3)C2)cc1] | N-[4-(3-Furan-2-yl-piperazine-1-sulfonyl)-phenyl]-acrylamide | Tr = 2.47 min, m/z (ES⁺) (M + H)⁺ 362 |
| 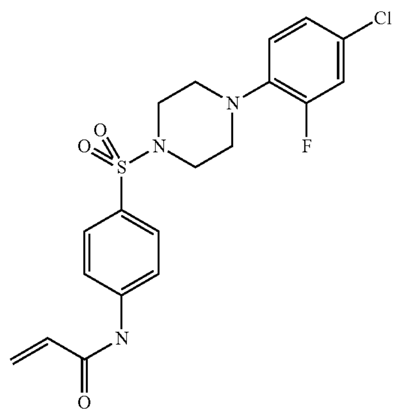 [SMILES: C=CC(=O)Nc1ccc(S(=O)(=O)N2CCN(c3ccc(Cl)cc3F)CC2)cc1] | N-{4-[4-(4-Chloro-2-fluoro-phenyl)-piperazine-1-sulfonyl]-phenyl}-acrylamide | Tr = 4.47 min, m/z (ES⁺) (M + H)⁺ 424 |
| 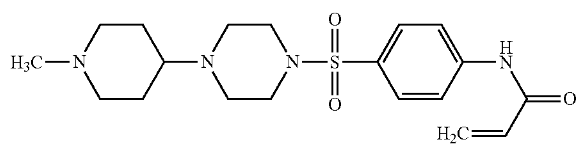 [SMILES: C=CC(=O)Nc1ccc(S(=O)(=O)N2CCN(C3CCN(C)CC3)CC2)cc1] | N-{4-[4-(1-Methyl-piperidin-4-yl)-piperazine-1-sulfonyl]-phenyl}-acrylamide | Tr = 1.88 min, m/z (ES⁺) (M + H)⁺ 393 |
| 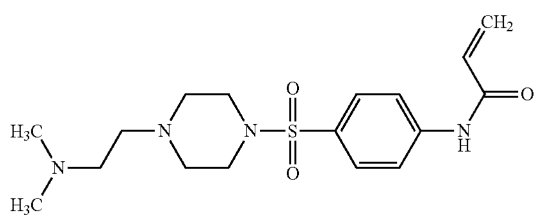 [SMILES: C=CC(=O)Nc1ccc(S(=O)(=O)N2CCN(CCN(C)C)CC2)cc1] | N-{4-[4-(2-Dimethylamino-ethyl)-piperazine-1-sulfonyl]-phenyl}-acrylamide | Tr = 2.28 min, m/z (ES⁺) (M + H)⁺ 367 |
| 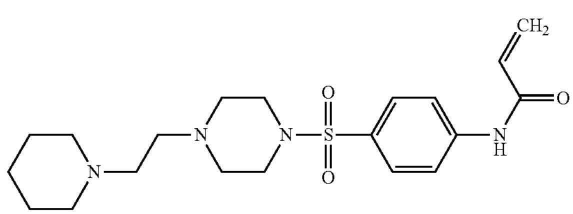 [SMILES: C=CC(=O)Nc1ccc(S(=O)(=O)N2CCN(CCN3CCCCC3)CC2)cc1] | N-{4-[4-(2-Piperidin-1-yl-ethyl)-piperazine-1-sulfonyl]-phenyl}-acrylamide | Tr = 2.41 min, m/z (ES⁺) (M + H)⁺ 407 |
| 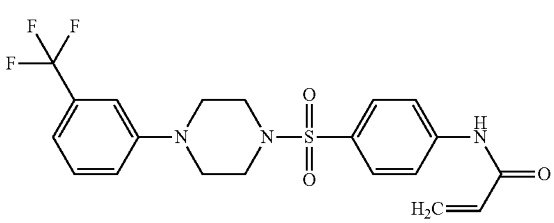 [SMILES: C=CC(=O)Nc1ccc(S(=O)(=O)N2CCN(c3cccc(C(F)(F)F)c3)CC2)cc1] | N-{4-[4-(3-Trifluoromethyl-phenyl)-piperazine-1-sulfonyl]-phenyl}-acrylamide | Tr = 4.43 min, m/z (ES⁺) (M + H)⁺ 440 |
| 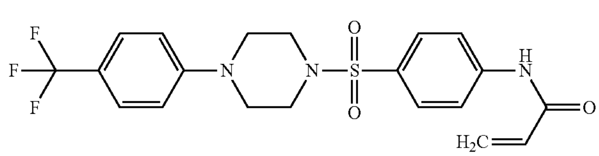 | N-{4-[4-(4-Trifluoromethyl-phenyl)-piperazine-1-sulfonyl]-phenyl}-acrylamide | Tr = 4.51 min, m/z (ES⁺) (M + H)⁺ 440 |

-continued

| Structure | IUPAC Name | MS |
|---|---|---|
| 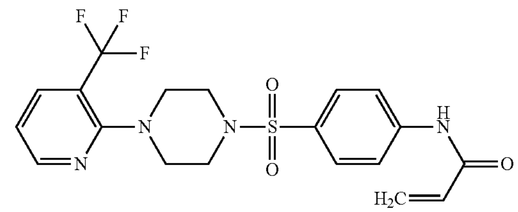 [SMILES: C=CC(=O)Nc1ccc(S(=O)(=O)N2CCN(c3ncccc3C(F)(F)F)CC2)cc1] | N-{4-[4-(3-Trifluoromethyl-pyridin-2-yl)-piperazine-1-sulfonyl]-phenyl}-acrylamide | Tr = 4.19 min, m/z (ES⁺) (M + H)⁺ 441 |
| 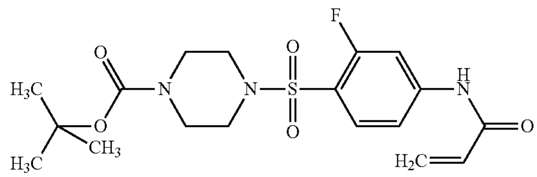 [SMILES: C=CC(=O)Nc1ccc(S(=O)(=O)N2CCN(C(=O)OC(C)(C)C)CC2)c(F)c1] | 4-(4-Acryloylamino-2-fluoro-benzenesulfonyl)-piperazine-1-carboxylic acid tert-butyl ester | Tr = 4.10 min, m/z (ES⁺) (M + Na)⁺ 436 |
| 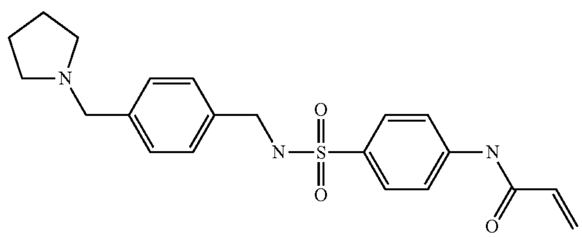 [SMILES: C=CC(=O)Nc1ccc(S(=O)(=O)NCc2ccc(CN3CCCC3)cc2)cc1] | N-[4-(4-Pyrrolidin-1-ylmethyl-benzylsulfamoyl)-phenyl]-acrylamide | Tr = 2.51 min, m/z (ES⁺) (M + H)⁺ 400 |
| 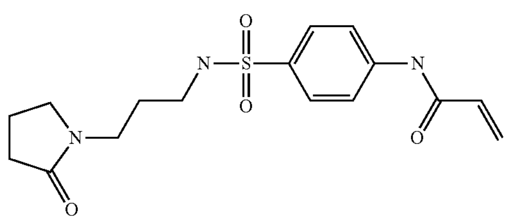 [SMILES: C=CC(=O)Nc1ccc(S(=O)(=O)NCCCN2CCCC2=O)cc1] | N-{4-[3-(2-Oxo-pyrrolidin-1-yl)-propylsulfamoyl]-phenyl}-acrylamide | Tr = 2.89 min, m/z (ES⁺) (M + H)⁺ 352 |
| 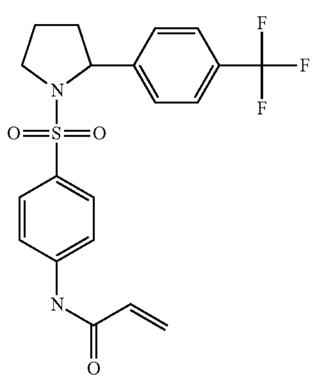 [SMILES: C=CC(=O)Nc1ccc(S(=O)(=O)N2CCCC2c2ccc(C(F)(F)F)cc2)cc1] | N-{4-[2-(4-Trifluoromethyl-phenyl)-pyrrolidine-1-sulfonyl]-phenyl}-acrylamide | Tr = 4.41 min, m/z (ES⁺) (M + H)⁺ 425 |

-continued

| Structure | IUPAC Name | MS |
|---|---|---|
| 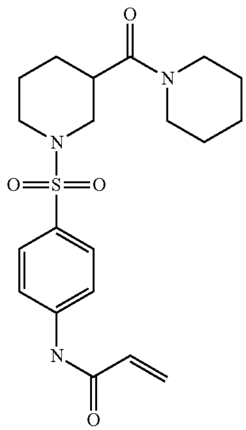 [SMILES: C=CC(=O)Nc1ccc(S(=O)(=O)N2CCCC(C(=O)N3CCCCC3)C2)cc1] | N-{4-[3-(Piperidine-1-carbonyl)-piperidine-1-sulfonyl]-phenyl}-acrylamide | Tr = 3.70 min, m/z (ES+) (M + H)+ 406 |
| 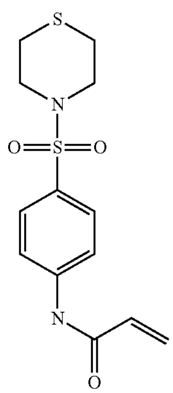 [SMILES: C=CC(=O)Nc1ccc(S(=O)(=O)N2CCSCC2)cc1] | N-[4-(Thiomorpholine-4-sulfonyl)-phenyl]-acrylamide | Tr = 3.54 min, m/z (ES+) (M + H)+ 313 |
| 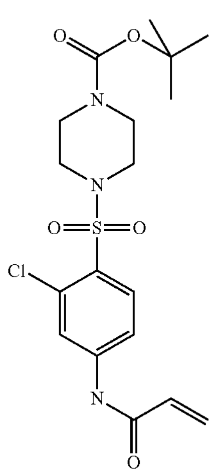 [SMILES: C=CC(=O)Nc1ccc(S(=O)(=O)N2CCN(C(=O)OC(C)(C)C)CC2)c(Cl)c1] | 4-(4-Acryloylamino-2-chloro-benzenesulfonyl)-piperazine-1-carboxylic acid tert-butyl ester | Tr = 4.38 min, m/z (ES+) (M + Na)+ 452/454 |

-continued

| Structure | IUPAC Name | MS |
|---|---|---|
| 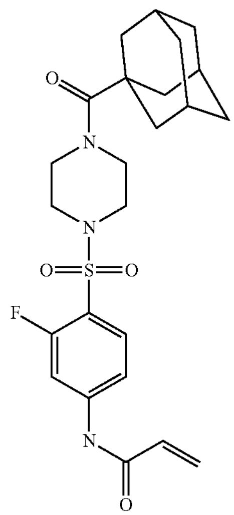 [SMILES: C=CC(=O)Nc1ccc(S(=O)(=O)N2CCN(C(=O)C34CC5CC(CC(C5)C3)C4)CC2)c(F)c1] | N-{4-[4-(Adamantane-1-carbonyl)-piperazine-1-sulfonyl]-3-fluoro-phenyl}-acrylamide | Tr = 4.76 min, m/z (ES⁺) (M + Na)⁺ 476 |
| 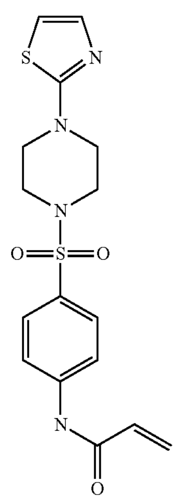 [SMILES: C=CC(=O)Nc1ccc(S(=O)(=O)N2CCN(c3nccs3)CC2)cc1] | N-[4-(4-Thiazol-2-yl-piperazine-1-sulfonyl)-phenyl]-acrylamide | Tr = 3.27 min, m/z (ES⁺) (M + H)⁺ 379 |
| 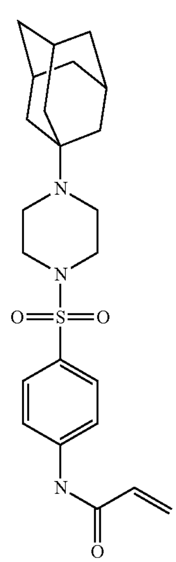 [SMILES: C=CC(=O)Nc1ccc(S(=O)(=O)N2CCN(C34CC5CC(CC(C5)C3)C4)CC2)cc1] | N-[4-(4-Adamantan-1-yl-piperazine-1-sulfonyl)-phenyl]-acrylamide | Tr = 2.80 min, m/z (ES⁺) (M + H)⁺ 430 |

-continued

| Structure | IUPAC Name | MS |
|---|---|---|
| 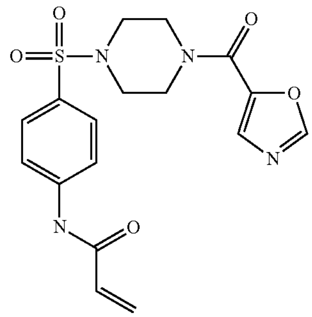 [SMILES: C=CC(=O)Nc1ccc(S(=O)(=O)N2CCN(C(=O)c3cnco3)CC2)cc1] | N-{4-[4-(Oxazole-5-carbonyl)-piperazine-1-sulfonyl]-phenyl}-acrylamide | Tr = 3.45 min, m/z (ES$^+$) (M + H)$^+$ 391 |
| 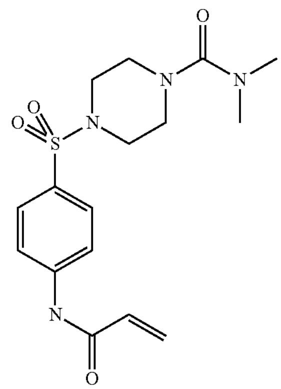 [SMILES: C=CC(=O)Nc1ccc(S(=O)(=O)N2CCN(C(=O)N(C)C)CC2)cc1] | 4-(4-Acryloylamino-benzenesulfonyl)-piperazine-1-carboxylic acid dimethylamide | Tr = 3.15 min, m/z (ES$^+$) (M + H)$^+$ 367 |
| 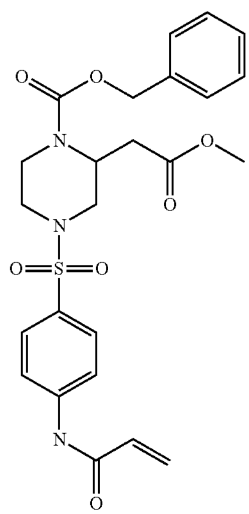 [SMILES: C=CC(=O)Nc1ccc(S(=O)(=O)N2CCN(C(=O)OCc3ccccc3)C(CC(=O)OC)C2)cc1] | 4-(4-Acryloylamino-benzenesulfonyl)-2-methoxycarbonylmethyl-piperazine-1-carboxylic acid benzyl ester | Tr = 4.07 min, m/z (ES$^+$) (M + H)$^+$ 524 |
| 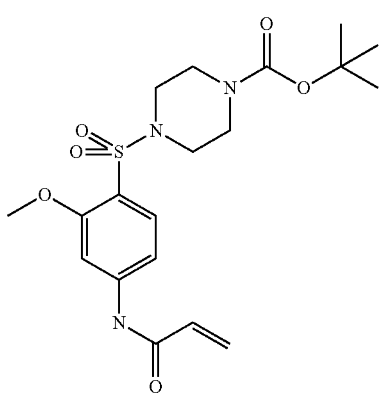 [SMILES: C=CC(=O)Nc1ccc(S(=O)(=O)N2CCN(C(=O)OC(C)(C)C)CC2)c(OC)c1] | 4-(4-Acryloylamino-2-methoxy-benzenesulfonyl)-piperazine-1-carboxylic acid tert-butyl ester | Tr = 3.93 min, m/z (ES$^+$) (M + Na)$^+$ 448 |

| Structure | IUPAC Name | MS |
| --- | --- | --- |
| 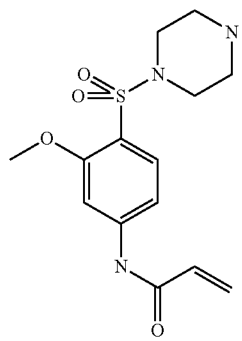 [SMILES: C=CC(=O)Nc1ccc(S(=O)(=O)N2CCNCC2)c(OC)c1] | N-[3-Methoxy-4-(piperazine-1-sulfonyl)-phenyl]-acrylamide | Tr = 2.14 min, m/z (ES+) (M + H)+ 326 |
| 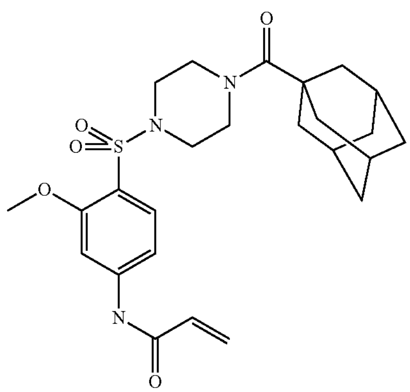 [SMILES: C=CC(=O)Nc1ccc(S(=O)(=O)N2CCN(C(=O)C34CC5CC(CC(C5)C3)C4)CC2)c(OC)c1] | N-{4-[4-(Adamantane-1-carbonyl)-piperazine-1-sulfonyl]-3-methoxy-phenyl}-acrylamide | Tr = 4.24 min, m/z (ES+) (M + H)+ 488 |
| 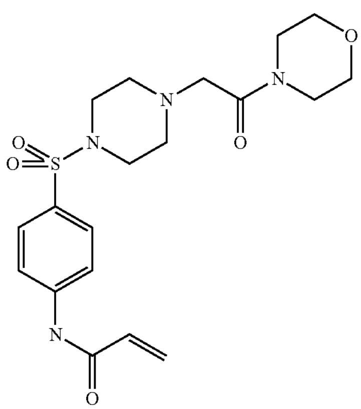 [SMILES: C=CC(=O)Nc1ccc(S(=O)(=O)N2CCN(CC(=O)N3CCOCC3)CC2)cc1] | N-{4-[4-(2-Morpholin-4-yl-2-oxo-ethyl)-piperazine-1-sulfonyl]-phenyl}-acrylamide | Tr = 2.36 min, m/z (ES+) (M + H)+ 423 |
| 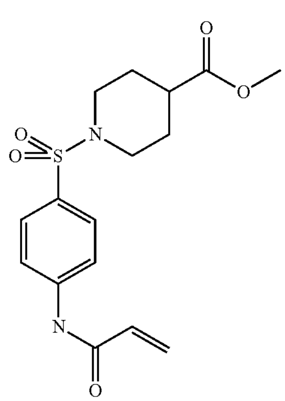 [SMILES: C=CC(=O)Nc1ccc(S(=O)(=O)N2CCC(C(=O)OC)CC2)cc1] | 1-(4-Acryloylamino-bonzenesulfonyl)-piperidine-4-carboxylic acid methyl ester | Tr = 3.50 min, m/z (ES+) (M + H)+ 353 |

| Structure | IUPAC Name | MS |
|---|---|---|
| 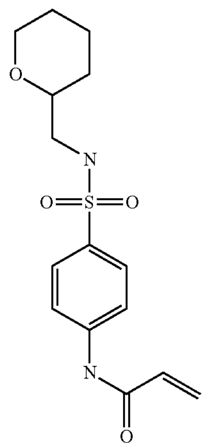 [SMILES: C=CC(=O)Nc1ccc(S(=O)(=O)NCC2CCCCO2)cc1] | N-{4-[(Tetrahydro-pyran-2-ylmethyl)-sulfamoyl]-phenyl}-acrylamide | Tr = 3.58 min, m/z (ES⁺) (M + Na)⁺ 347 |
| 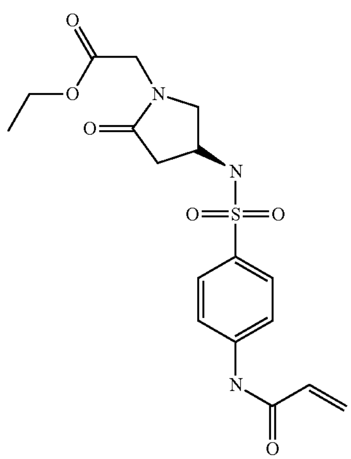 | [4-(4-Acryloylamino-benzenesulfonylamino)-2-oxo-pyrrolidin-1-yl]-acetic acid ethyl ester | Tr = 2.97 min, m/z (ES⁺) (M + Na)⁺ 418 |
| 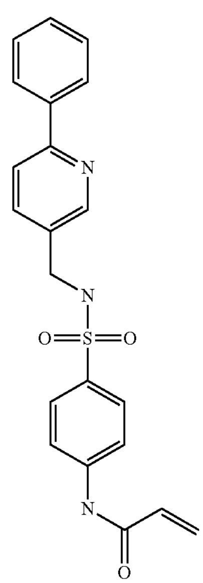 [SMILES: C=CC(=O)Nc1ccc(S(=O)(=O)NCc2ccc(-c3ccccc3)nc2)cc1] | N-{4-[(6-Phenyl-pyridin-3-ylmethyl)-sulfamoyl]-phenyl}-acrylamide | Tr = 3.53 min, m/z (ES⁺) (M + H)⁺ 394 |

| Structure | IUPAC Name | MS |
|---|---|---|
| 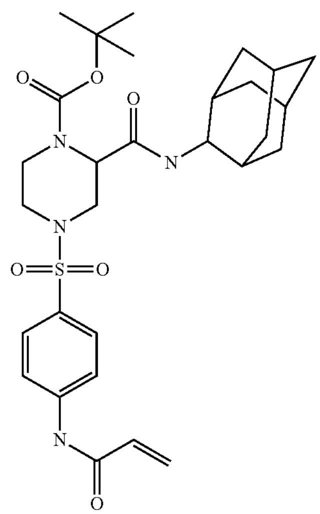 [SMILES: C=CC(=O)Nc1ccc(S(=O)(=O)N2CCN(C(=O)OC(C)(C)C)C(C(=O)NC3C4CC5CC(C4)CC3C5)C2)cc1] | 4-(4-Acryloylamino-benzenesulfonyl)-2-(adamantan-2-ylcarbamoyl)-piperazine-1-carboxylic acid tert-butyl ester | Tr = 4.88 min, m/z (ES$^+$) (M + H)$^+$ 573 |
| 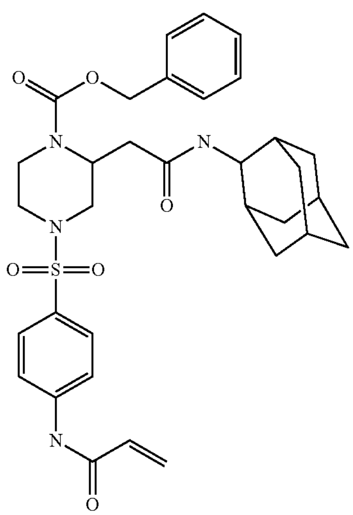 [SMILES: C=CC(=O)Nc1ccc(S(=O)(=O)N2CCN(C(=O)OCc3ccccc3)C(CC(=O)NC3C4CC5CC(C4)CC3C5)C2)cc1] | 4-(4-Acryloylamino-benzenesulfonyl)-2-(adamantan-2-ylcarbamoylmethyl)-piperazine-1-carboxylic acid benzyl ester | Tr = 4.59 min, m/z (ES$^+$) (M + H)$^+$ 621 |
| 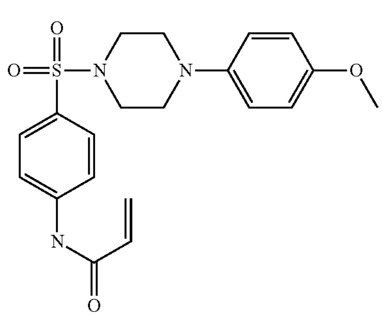 [SMILES: C=CC(=O)Nc1ccc(S(=O)(=O)N2CCN(c3ccc(OC)cc3)CC2)cc1] | N-{4-[4-(4-Methoxy-phenyl)-piperazine-1-sulfonyl]-phenyl}-acrylamide | Tr = 4.25 min, m/z (ES$^+$) (M + H)$^+$ 402 |

| Structure | IUPAC Name | MS |
|---|---|---|
| 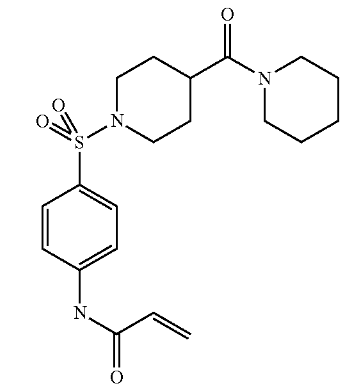 [SMILES: C=CC(=O)Nc1ccc(S(=O)(=O)N2CCC(C(=O)N3CCCCC3)CC2)cc1] | N-{4-[4-(Piperidine-1-carbonyl)-piperidine-1-sulfonyl]-phenyl}-acrylamide | Tr = 3.55 min, m/z (ES$^+$) (M + H)$^+$ 406 |
| 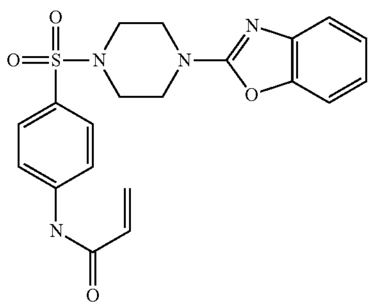 [SMILES: C=CC(=O)Nc1ccc(S(=O)(=O)N2CCN(c3nc4ccccc4o3)CC2)cc1] | N-[4-(4-Benzooxazol-2-yl-piperazine-1-sulfonyl)-phenyl]-acrylamide | Tr = 3.83 min, m/z (ES$^+$) (M + H)$^+$ 413 |
| 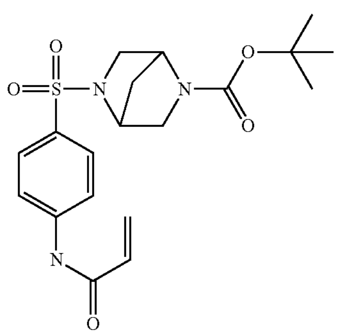 [SMILES: C=CC(=O)Nc1ccc(S(=O)(=O)N2CC3CC2CN3C(=O)OC(C)(C)C)cc1] | 5-(4-Acryloylamino-benzenesulfonyl)-2,5-diaza-bicyclo[2.2.1]heptane-2-carboxylic acid tert-butyl ester | Tr = 3.81 min, m/z (ES$^+$) (M + Na)$^+$ 430 |
| 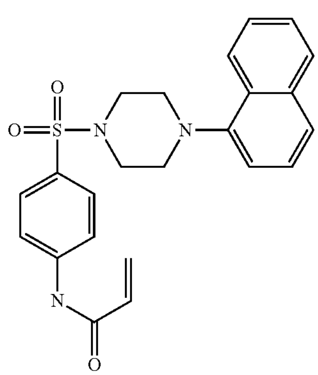 [SMILES: C=CC(=O)Nc1ccc(S(=O)(=O)N2CCN(c3cccc4ccccc34)CC2)cc1] | N-[4-(4-Naphthalen-1-yl-piperazine-1-sulfonyl)-phenyl]-acrylamide | Tr = 4.56 min, m/z (ES$^+$) (M + H)$^+$ 422 |

-continued

| Structure | IUPAC Name | MS |
|---|---|---|
| 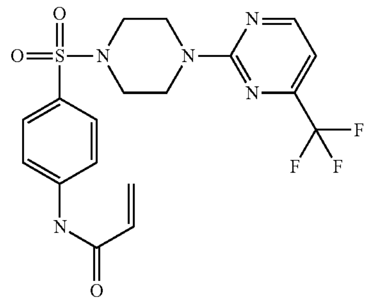 [SMILES: C=CC(=O)Nc1ccc(S(=O)(=O)N2CCN(c3nccc(C(F)(F)F)n3)CC2)cc1] | N-{4-[4-(4-Trifluoromethyl-pyrimidin-2-yl)-piperazine-1-sulfonyl]-phenyl}-acrylamide | Tr = 4.26 min, m/z (ES⁺) (M + H)⁺ 442 |
| 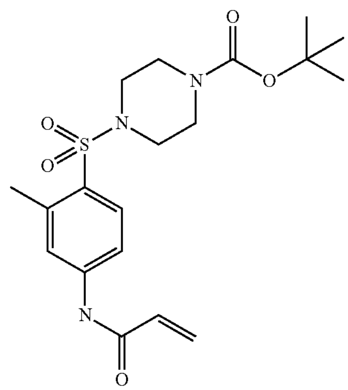 [SMILES: C=CC(=O)Nc1ccc(S(=O)(=O)N2CCN(C(=O)OC(C)(C)C)CC2)c(C)c1] | 4-(4-Acryloylamino-2-methyl-benzenesulfonyl)-piperazine-1-carboxylic acid tert-butyl ester | Tr = 4.04 min, m/z (ES⁺) (M + Na)⁺ 432 |
| 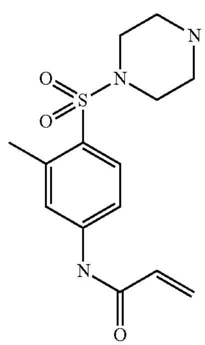 [SMILES: C=CC(=O)Nc1ccc(S(=O)(=O)N2CCNCC2)c(C)c1] | N-[3-Methyl-4-(piperazine-1-sulfonyl)-phenyl]-acrylamide | Tr = 2.5 min, m/z (ES⁺) (M + H)⁺ 310 |
| 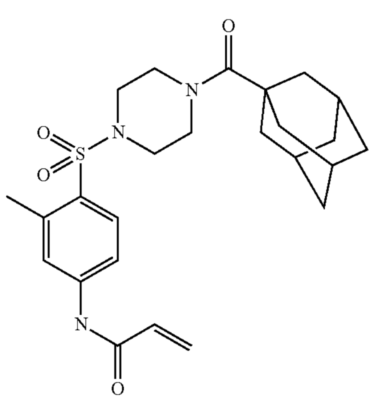 [SMILES: C=CC(=O)Nc1ccc(S(=O)(=O)N2CCN(C(=O)C34CC5CC(CC(C5)C3)C4)CC2)c(C)c1] | N-{4-[4-(Adamantane-1-carbonyl)-piperazine-1-sulfonyl]-3-methyl-phenyl}-acrylamide | Tr = 4.41 min, m/z (ES⁺) (M + H)⁺ 472 |

-continued

| Structure | IUPAC Name | MS |
|---|---|---|
| 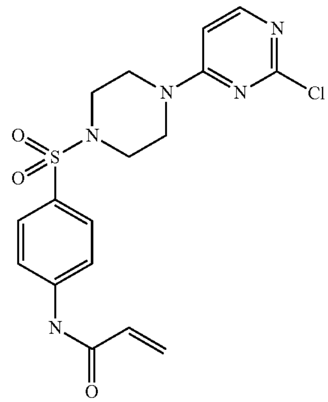 [SMILES: C=CC(=O)Nc1ccc(S(=O)(=O)N2CCN(c3ccnc(Cl)n3)CC2)cc1] | N-{4-[4-(2-Chloro-pyrimidin-4-yl)-piperazine-1-sulfonyl]-phenyl}-acrylamide | Tr = 4.14 min, m/z (ES+) (M + H)+ 408 |
| 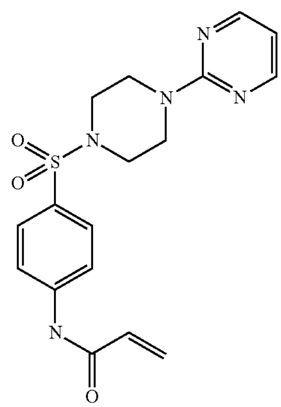 [SMILES: C=CC(=O)Nc1ccc(S(=O)(=O)N2CCN(c3ncccn3)CC2)cc1] | N-[4-(4-Pyrimidin-2-yl-piperazine-1-sulfonyl)-phenyl]-acrylamide | Tr = 3.60 min, m/z (ES+) (M + H)+ 374 |
| 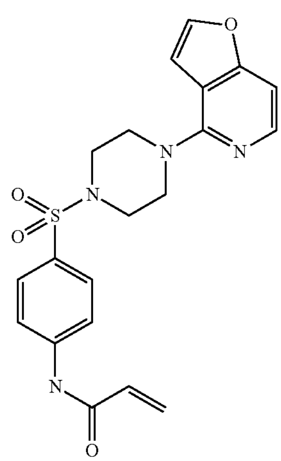 [SMILES: C=CC(=O)Nc1ccc(S(=O)(=O)N2CCN(c3nccc4occc34)CC2)cc1] | N-[4-(4-Furo[3,2-c]pyridin-4-yl-piperazine-1-sulfonyl)-phenyl]-acrylamide | Tr = 1.26 min, m/z (ES+) (M + H)+ 413 |

-continued

| Structure | IUPAC Name | MS |
|---|---|---|
| 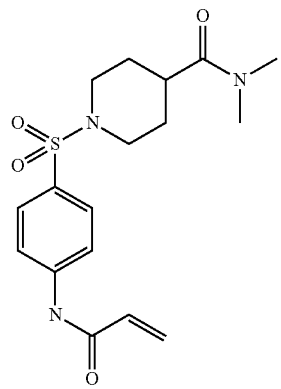 [SMILES: C=CC(=O)Nc1ccc(S(=O)(=O)N2CCC(C(=O)N(C)C)CC2)cc1] | 1-(4-Acryloylamino-benzenesulfonyl)-piperidine-4-carboxylic acid dimethylamide | Tr = 3.32 min, m/z (ES+) (M + H)+ 366 |
| 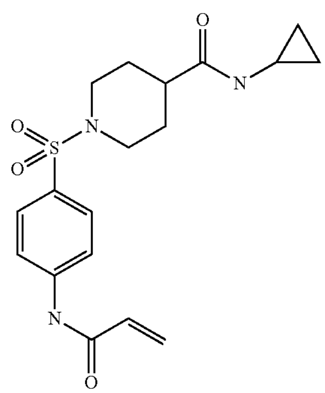 [SMILES: C=CC(=O)Nc1ccc(S(=O)(=O)N2CCC(C(=O)NC3CC3)CC2)cc1] | 1-(4-Acryloylamino-benzenesulfonyl)-piperidine-4-carboxylic acid cyclopropylamide | Tr = 3.25 min, m/z (ES+) (M + H)+ 378 |
| 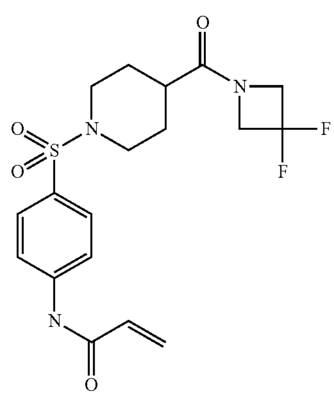 [SMILES: C=CC(=O)Nc1ccc(S(=O)(=O)N2CCC(C(=O)N3CC(F)(F)C3)CC2)cc1] | N-{4-[4-(3,3-Difluoro-azetidine-1-carbonyl)-piperidine-1-sulfonyl]-phenyl}-acrylamide | Tr = 3.52 min, m/z (ES+) (M + H)+ 414 |
| 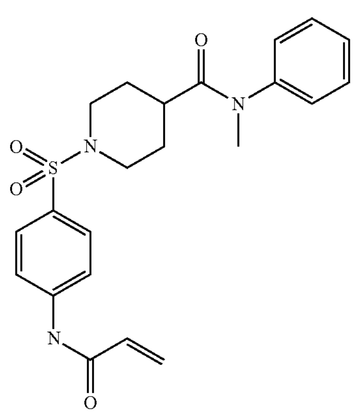 [SMILES: C=CC(=O)Nc1ccc(S(=O)(=O)N2CCC(C(=O)N(C)c3ccccc3)CC2)cc1] | 1-(4-Acryloylamino-benzenesulfonyl)-piperidine-4-carboxylic acid methyl-phenyl-amide | Tr = 3.87 min, m/z (ES+) (M + H)+ 428 |

-continued

| Structure | IUPAC Name | MS |
|---|---|---|
| 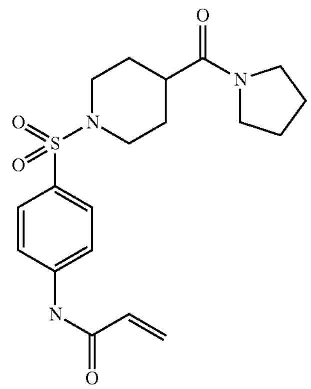 [SMILES: C=CC(=O)Nc1ccc(S(=O)(=O)N2CCC(C(=O)N3CCCC3)CC2)cc1] | N-{4-[4-(Pyrrolidine-1-carbonyl)-piperidine-1-sulfonyl]-phenyl}-acrylamide | Tr = 3.27 min, m/z (ES⁺) (M + H)⁺ 392 |
| 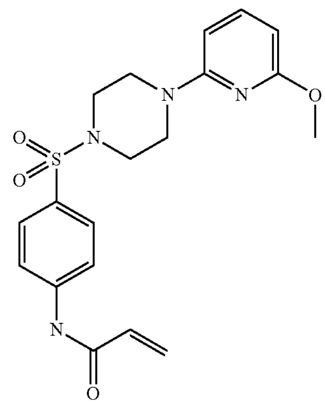 [SMILES: C=CC(=O)Nc1ccc(S(=O)(=O)N2CCN(c3cccc(OC)n3)CC2)cc1] | N-{4-[4-(6-Methoxy-pyridin-2-yl)-piperazine-1-sulfonyl]-phenyl}-acrylamide | Tr = 4.09 min, m/z (ES⁺) (M + H)⁺ 403 |
| 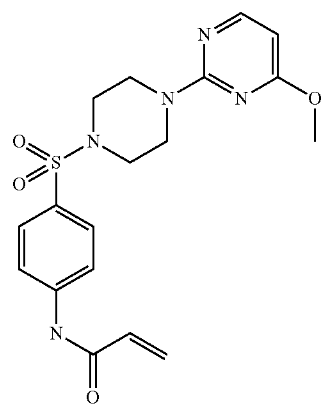 [SMILES: C=CC(=O)Nc1ccc(S(=O)(=O)N2CCN(c3nccc(OC)n3)CC2)cc1] | N-{4-[4-(4-Methoxy-pyrimidin-2-yl)-piperazine-1-sulfonyl]-phenyl}-acrylamide | Tr = 3.28 min, m/z (ES⁺) (M + H)⁺ 404 |
| 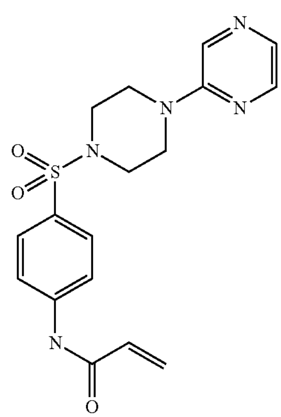 [SMILES: C=CC(=O)Nc1ccc(S(=O)(=O)N2CCN(c3cnccn3)CC2)cc1] | N-[4-(2,3,5,6-Tetrahydro-[1,2']bipyrazinyl-4-sulfonyl)-phenyl]-acrylamide | Tr = 3.40 min, m/z (ES⁺) (M + H)⁺ 374 |

-continued

| Structure | IUPAC Name | MS |
|---|---|---|
| 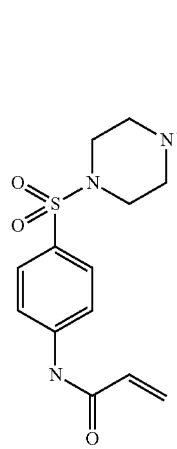 | N-{4-[4-(4-Methyl-pyridin-2-yl)-piperazine-1-sulfonyl]-phenyl}-acrylamide | Tr = 2.71 min, m/z (ES+) (M + H)+ 387 |
| 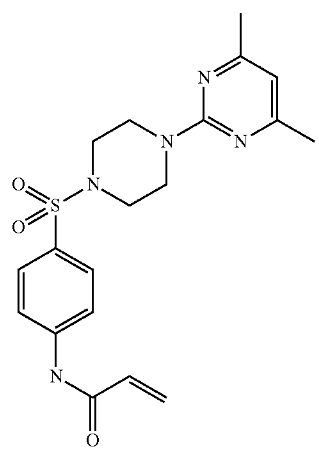 [SMILES: C=CC(=O)Nc1ccc(S(=O)(=O)N2CCN(c3nc(C)cc(C)n3)CC2)cc1] | N-{4-[4-(4,6-Dimethyl-pyrimidin-2-yl)-piperazine-1-sulfonyl]-phenyl}-acrylamide | Tr = 3.78 min, m/z (ES+) (M + H)+ 402 |
| 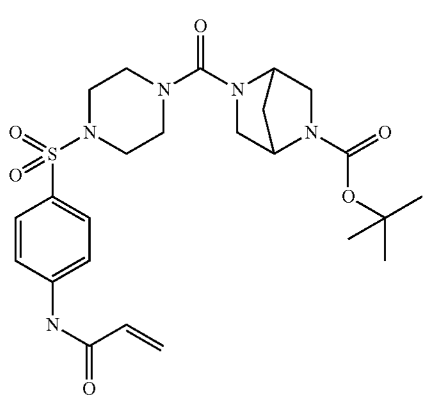 [SMILES: C=CC(=O)Nc1ccc(S(=O)(=O)N2CCN(C(=O)N3CC4CC3CN4C(=O)OC(C)(C)C)CC2)cc1] | 5-[4-(4-Acryloylamino-benzenesulfonyl)-piperazine-1-carbonyl]-2,5-diaza-bicyclo[2.2.1]heptane-2-carboxylic acid tert-butyl ester | Tr = 3.70 min, m/z (ES+) (M + H)+ 520 |

-continued

| Structure | IUPAC Name | MS |
|---|---|---|
| 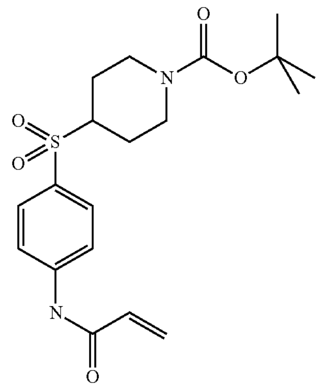 [SMILES: C=CC(=O)Nc1ccc(S(=O)(=O)C2CCN(C(=O)OC(C)(C)C)CC2)cc1] | 4-(4-Acryloylamino-benzenesulfonyl)-piperidine-1-carboxylic acid tert-butyl ester | Tr = 3.81 min, m/z (ES⁺) (M + Na)⁺ 417 |
| 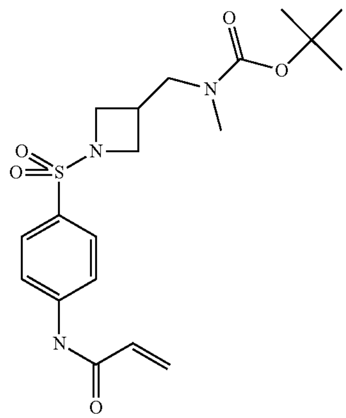 [SMILES: C=CC(=O)Nc1ccc(S(=O)(=O)N2CC(CN(C)C(=O)OC(C)(C)C)C2)cc1] | [1-(4-Acryloylamino-benzenesulfonyl)-azetidin-3-ylmethyl]-methyl-carbamic acid tert-butyl ester | Tr = 4.70 min, m/z (ES⁺) (M + Na)⁺ 432 |
| 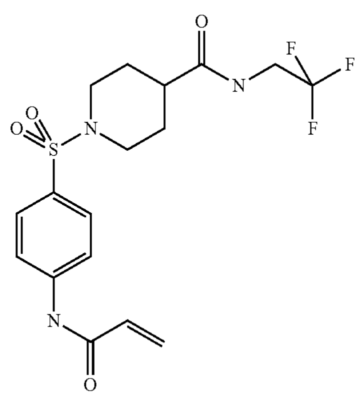 [SMILES: C=CC(=O)Nc1ccc(S(=O)(=O)N2CCC(C(=O)NCC(F)(F)F)CC2)cc1] | 1-(4-Acryloylamino-benzenesulfonyl)-piperidine-4-carboxylic acid (2,2,2-trifluoro-ethyl)-amide | Tr = 3.38 min, m/z (ES⁺) (M + H)⁺ 420 |
| 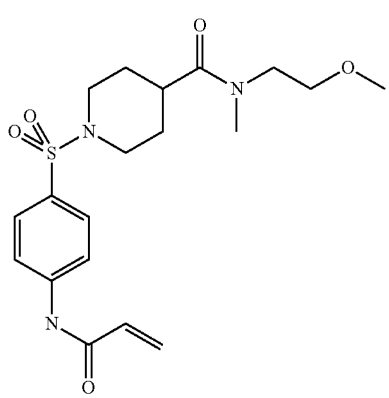 [SMILES: C=CC(=O)Nc1ccc(S(=O)(=O)N2CCC(C(=O)N(C)CCOC)CC2)cc1] | 1-(4-Acryloylamino-benzenesulfonyl)-piperidine-4-carboxylic acid (2-methoxy-ethyl)-methyl-amide | Tr = 3.37 min, m/z (ES⁺) (M + H)⁺ 410 |

| Structure | IUPAC Name | MS |
|---|---|---|
| 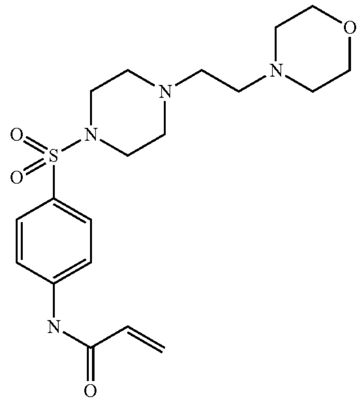 [SMILES: C=CC(=O)Nc1ccc(S(=O)(=O)N2CCN(CCN3CCOCC3)CC2)cc1] | N-{4-[4-(2-Morpholin-4-yl-ethyl)-piperazine-1-sulfonyl]-phenyl}-acrylamide | Tr = 2.33 min, m/z (ES+) (M + H)+ 409 |
| 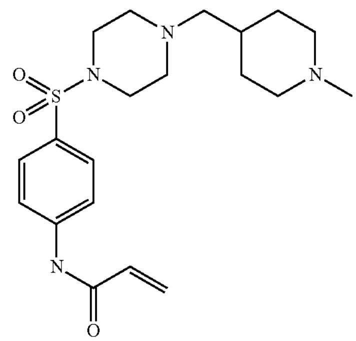 [SMILES: C=CC(=O)Nc1ccc(S(=O)(=O)N2CCN(CC3CCN(C)CC3)CC2)cc1] | N-{4-[4-(1-Methyl-piperidin-4-ylmethyl)-piperazine-1-sulfonyl]-phenyl}-acrylamide | Tr = 1.84 min, m/z (ES+) (M + H)+ 407 |
| 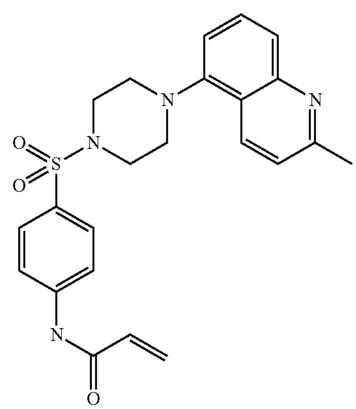 [SMILES: C=CC(=O)Nc1ccc(S(=O)(=O)N2CCN(c3cccc4nc(C)ccc34)CC2)cc1] | N-{4-[4-(2-Methyl-quinolin-5-yl)-piperazine-1-sulfonyl]-phenyl}-acrylamide | Tr = 2.86 min, m/z (ES+) (M + H)+ 437 |
| 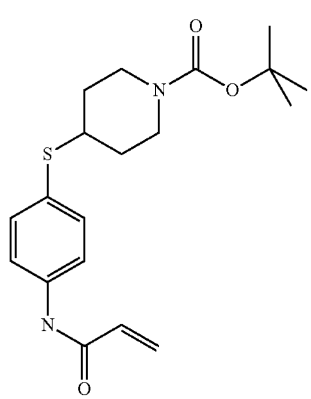 [SMILES: C=CC(=O)Nc1ccc(SC2CCN(C(=O)OC(C)(C)C)CC2)cc1] | 4-(4-Acryloylamino-phenylsulfanyl)-piperidine-1-carboxylic acid tert-butyl ester | Tr = 4.39 min, m/z (ES+) (M + Na)+ 385 |

| Structure | IUPAC Name | MS |
|---|---|---|
| 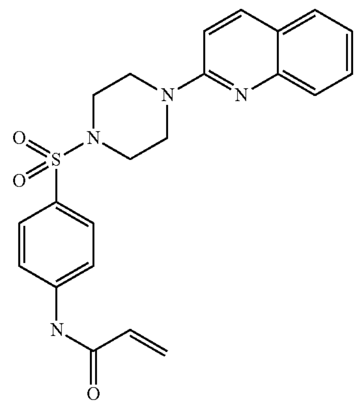 [SMILES: C=CC(=O)Nc1ccc(S(=O)(=O)N2CCN(c3ccc4ccccc4n3)CC2)cc1] | N-[4-(4-Quinolin-2-yl-piperazine-1-sulfonyl)-phenyl]-acrylamide | Tr = 2.83 min, m/z (ES+) (M + H)+ 423 |
| 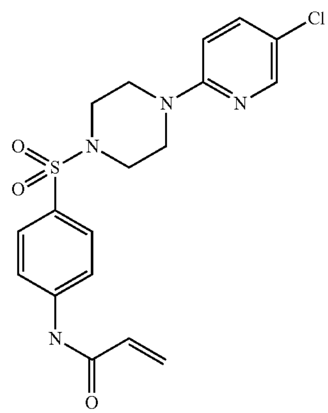 [SMILES: C=CC(=O)Nc1ccc(S(=O)(=O)N2CCN(c3ccc(Cl)cn3)CC2)cc1] | N-{4-[4-(5-Chloro-pyridin-2-yl)-piperazine-1-sulfonyl]-phenyl}-acrylamide | Tr = 4.08 min, m/z (ES+) (M + H)+ 407 |
| 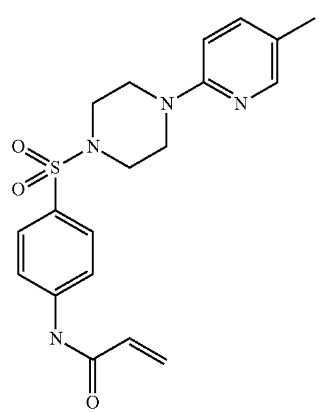 [SMILES: C=CC(=O)Nc1ccc(S(=O)(=O)N2CCN(c3ccc(C)cn3)CC2)cc1] | N-{4-[4-(5-Methyl-pyridin-2-yl)-piperazine-1-sulfonyl]-phenyl}-acrylamide | Tr = 2.65 min, m/z (ES+) (M + H)+ 387 |

-continued

| Structure | IUPAC Name | MS |
|---|---|---|
| 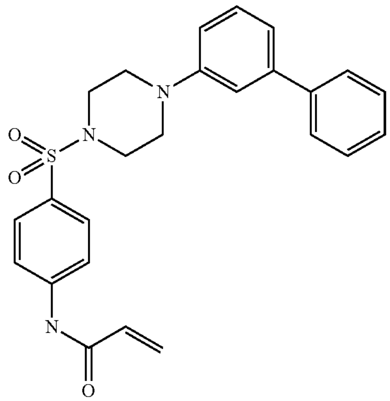 [SMILES: C=CC(=O)Nc1ccc(S(=O)(=O)N2CCN(c3cccc(-c4ccccc4)c3)CC2)cc1] | N-[4-(4-Biphenyl-3-yl-piperazine-1-sulfonyl)-phenyl]-acrylamide | Tr = 4.64 min, m/z (ES$^+$) (M + H)$^+$ 448 |
| 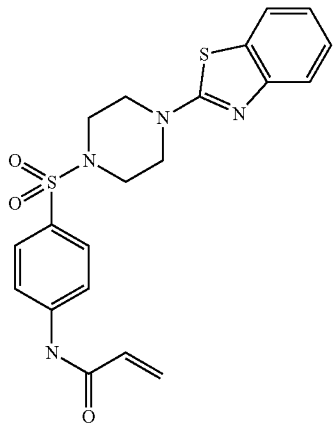 [SMILES: C=CC(=O)Nc1ccc(S(=O)(=O)N2CCN(c3nc4ccccc4s3)CC2)cc1] | N-[4-(4-Benzothiazol-2-yl-piperazine-1-sulfonyl)-phenyl]-acrylamide | Tr = 4.03 min, m/z (ES$^+$) (M + H)$^+$ 429 |
| 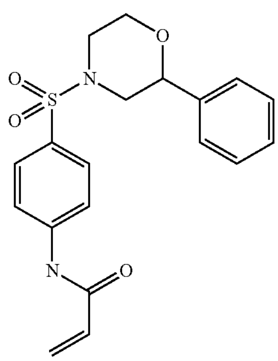 [SMILES: C=CC(=O)Nc1ccc(S(=O)(=O)N2CCOC(c3ccccc3)C2)cc1] | N-[4-(2-Phenyl-morpholine-4-sulfonyl)-phenyl]-acrylamide | Tr = 3.99 min, m/z (ES$^+$) (M + Na)$^+$ 395 |
| 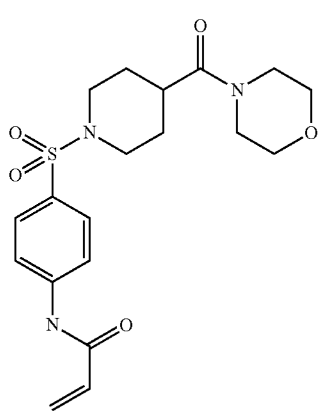 [SMILES: C=CC(=O)Nc1ccc(S(=O)(=O)N2CCC(C(=O)N3CCOCC3)CC2)cc1] | N-{4-[4-(Morpholine-4-carbonyl)-piperidine-1-sulfonyl]-phenyl}-acrylamide | Tr = 4.08 min, m/z (ES$^+$) (M + H)$^+$ 408 |

| Structure | IUPAC Name | MS |
| --- | --- | --- |
| 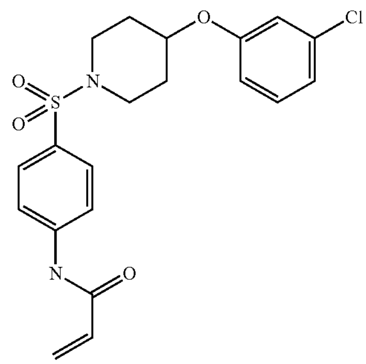 [SMILES: C=CC(=O)Nc1ccc(S(=O)(=O)N2CCC(Oc3cccc(Cl)c3)CC2)cc1] | N-{4-[4-(3-Chloro-phenoxy)-piperidine-1-sulfonyl]-phenyl}-acrylamide | Tr = 4.44 min, m/z (ES$^+$) (M + Na)$^+$ 443 |
| 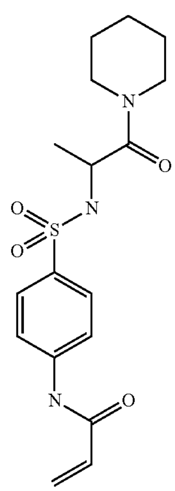 [SMILES: C=CC(=O)Nc1ccc(S(=O)(=O)NC(C)C(=O)N2CCCCC2)cc1] | N-[4-(1-Methyl-2-oxo-2-piperidin-1-yl-ethylsulfamoyl)-phenyl]-acrylamide | Tr = 3.24 min, m/z (ES$^+$) (M + H)$^+$ 366 |
| 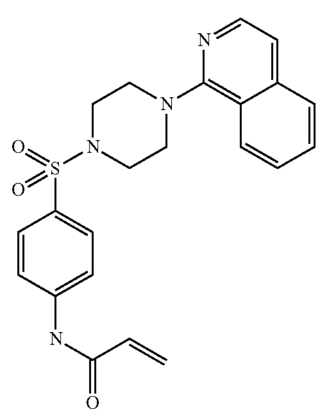 [SMILES: C=CC(=O)Nc1ccc(S(=O)(=O)N2CCN(c3nccc4ccccc34)CC2)cc1] | N-[4-(4-Isoquinolin-1-yl-piperazine-1-sulfonyl)-phenyl]-acrylamide | Tr = 1.65 min, m/z (ES$^+$) (M + H)$^+$ 423 |

-continued

| Structure | IUPAC Name | MS |
|---|---|---|
| 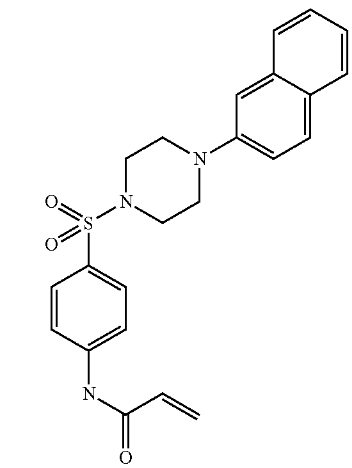 [SMILES: C=CC(=O)Nc1ccc(S(=O)(=O)N2CCN(c3ccc4ccccc4c3)CC2)cc1] | N-[4-(4-Naphthalen-2-yl-piperazine-1-sulfonyl)-phenyl]-acrylamide | Tr = 4.48 min, m/z (ES$^+$) (M + H)$^+$ 422 |
| 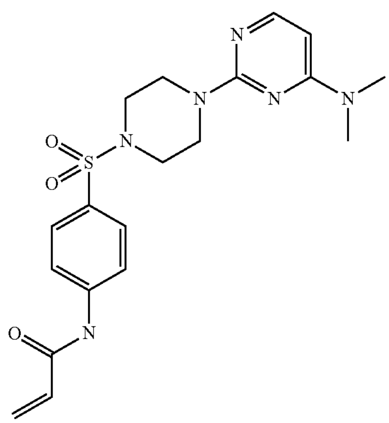 [SMILES: C=CC(=O)Nc1ccc(S(=O)(=O)N2CCN(c3nccc(N(C)C)n3)CC2)cc1] | N-{4-[4-(4-Dimethylamino-pyrimidin-2-yl)-piperazine-1-sulfonyl]-phenyl}-acrylamide | Tr = 2.95 min, m/z (ES$^+$) (M + H)$^+$ 417 |
| 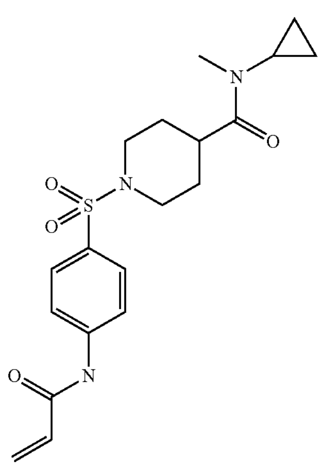 [SMILES: C=CC(=O)Nc1ccc(S(=O)(=O)N2CCC(C(=O)N(C)C3CC3)CC2)cc1] | 1-(4-Acryloylamino-benzenesulfonyl)-piperidine-4-carboxylic acid cyclopropyl-methyl-amide | Tr = 3.41 min, m/z (ES$^+$) (M + H)$^+$ 392 |

| Structure | IUPAC Name | MS |
|---|---|---|
| 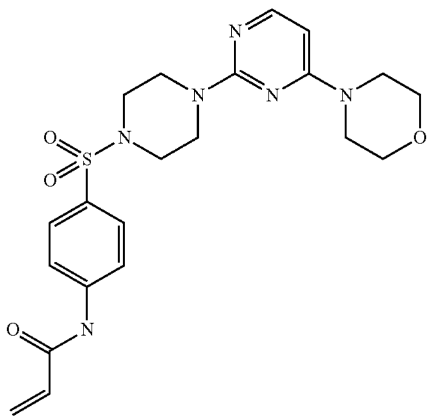 [SMILES: C=CC(=O)Nc1ccc(S(=O)(=O)N2CCN(c3nccc(N4CCOCC4)n3)CC2)cc1] | N-{4-[4-(4-Morpholin-4-yl-pyrimidin-2-yl)-piperazine-1-sulfonyl]-phenyl}-acrylamide | Tr = 3.17 min, m/z (ES+) (M + H)+ 459 |
| 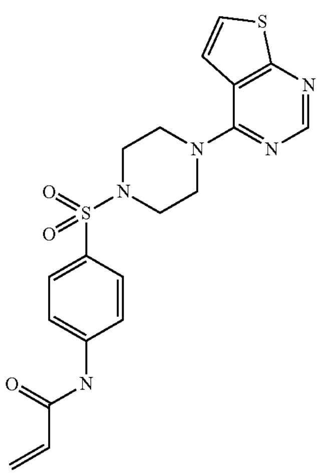 [SMILES: C=CC(=O)Nc1ccc(S(=O)(=O)N2CCN(c3ncnc4sccc34)CC2)cc1] | N-[4-(4-Thieno[2,3-d]pyrimidin-4-yl-piperazine-1-sulfonyl)-phenyl]-acrylamide | Tr = 3.64 min, m/z (ES+) (M + H)+ 430 |
| 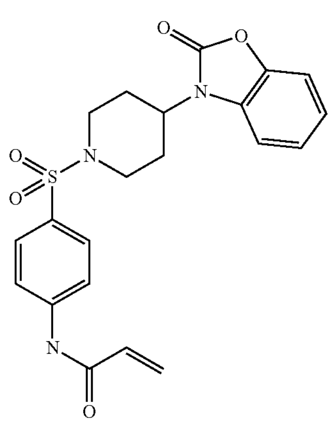 [SMILES: C=CC(=O)Nc1ccc(S(=O)(=O)N2CCC(n3c(=O)oc4ccccc43)CC2)cc1] | N-{4-[4-(2-Oxo-benzooxazol-3-yl)-piperidine-1-sulfonyl]-phenyl}-acrylamide | Tr = 3.95 min, m/z (ES+) (M + H)+ 428 |

-continued
| Structure | IUPAC Name | MS |
|---|---|---|
| 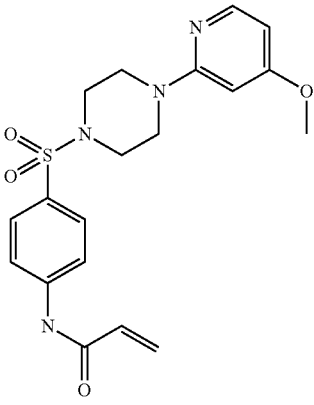 | N-{4-[4-(4-Methoxy-pyridin-2-yl)-piperazine-1-sulfonyl]-phenyl}-acrylamide | Tr = 2.82 min, m/z (ES$^+$) (M + H)$^+$ 403 |
| 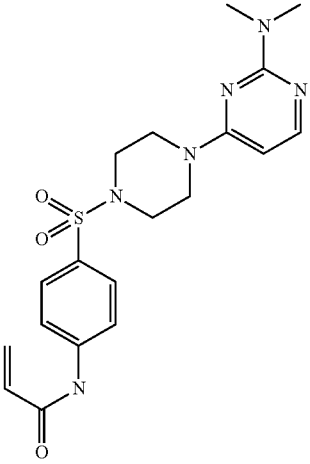 [SMILES: C=CC(=O)Nc1ccc(S(=O)(=O)N2CCN(c3ccnc(N(C)C)n3)CC2)cc1] | N-{4-[4-(2-Dimethylamino-pyrimidin-4-yl)-piperazine-1-sulfonyl]-phenyl}-acrylamide | Tr = 3.72 min, m/z (ES$^+$) (M + H)$^+$ 417 |
| 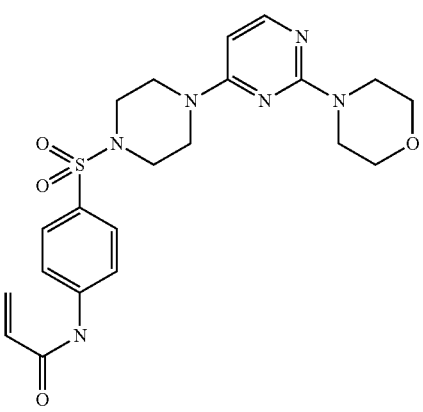 [SMILES: C=CC(=O)Nc1ccc(S(=O)(=O)N2CCN(c3ccnc(N4CCOCC4)n3)CC2)cc1] | N-{4-[4-(2-Morpholin-4-yl-pyrimidin-4-yl)-piperazine-1-sulfonyl]-phenyl}-acrylamide | Tr = 3.12 min, m/z (ES$^+$) (M + H)$^+$ 459 |

| Structure | IUPAC Name | MS |
|---|---|---|
| 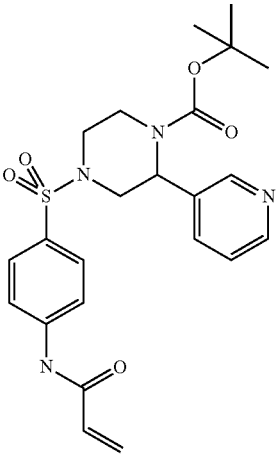 [SMILES: C=CC(=O)Nc1ccc(S(=O)(=O)N2CCN(C(=O)OC(C)(C)C)C(c3cccnc3)C2)cc1] | 4-(4-Acryloylamino-benzenesulfonyl)-2-pyridin-3-yl-piperazine-1-carboxylic acid tert-butyl ester | Tr = 3.30 min, m/z (ES+) (M + H)+ 473 |
| 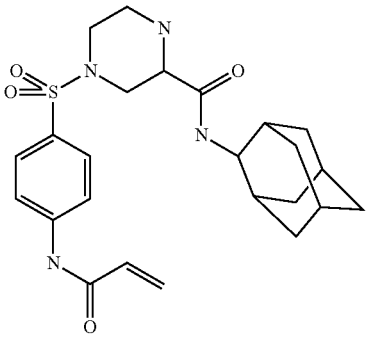 [SMILES: C=CC(=O)Nc1ccc(S(=O)(=O)N2CCNC(C(=O)NC3C4CC5CC(C4)CC3C5)C2)cc1] | 4-(4-Acryloylamino-benzenesulfonyl)-piperazine-2-carboxylic acid adamantan-2-ylamide | Tr = 3.21 min, m/z (ES+) (M + H)+ 473 |
| 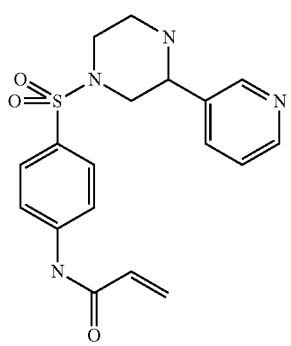 [SMILES: C=CC(=O)Nc1ccc(S(=O)(=O)N2CCNC(c3cccnc3)C2)cc1] | N-[4-(3-Pyridin-3-yl-piperazine-1-sulfonyl)phenyl]-acrylamide | Tr = 2.34 min, m/z (ES+) (M + H)+ 373 |
| 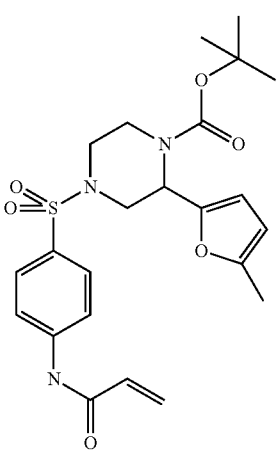 [SMILES: C=CC(=O)Nc1ccc(S(=O)(=O)N2CCN(C(=O)OC(C)(C)C)C(c3ccc(C)o3)C2)cc1] | 4-(4-Acryloylamino-benzenesulfonyl)-2-(5-methyl-furan-2-yl)-piperazine-1-carboxylic acid tert-butyl ester | Tr = 4.40 min, m/z (ES+) (M + Na)+ 498 |

| Structure | IUPAC Name | MS |
|---|---|---|
| 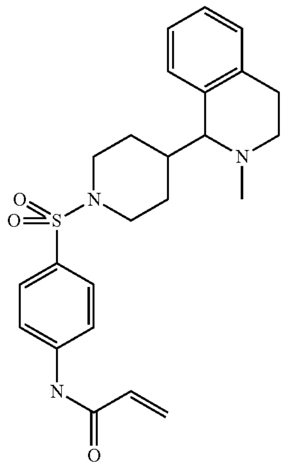 [SMILES: C=CC(=O)Nc1ccc(S(=O)(=O)N2CCC(C3c4ccccc4CCN3C)CC2)cc1] | N-{4-[4-(2-Methyl-1,2,3,4-tetrahydro-isoquinolin-1-yl)-piperidine-1-sulfonyl]-phenyl}-acrylamide | Tr = 4.11 min, m/z (ES$^+$) (M + H)$^+$ 440 |
| 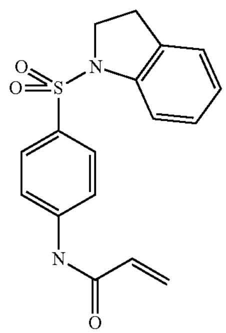 [SMILES: C=CC(=O)Nc1ccc(S(=O)(=O)N2CCc3ccccc32)cc1] | N-[4-(2,3-Dihydro-indole-1-sulfonyl)-phenyl]-acrylamide | Tr = 4.50 min, m/z (ES$^+$) (M + Na)$^+$ 351 |
| 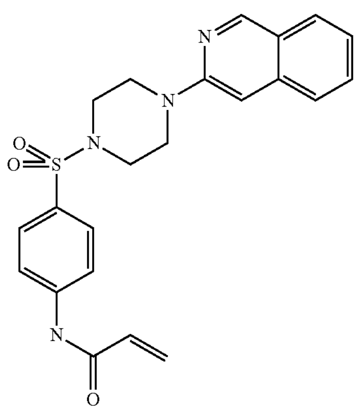 [SMILES: C=CC(=O)Nc1ccc(S(=O)(=O)N2CCN(c3cc4ccccc4cn3)CC2)cc1] | N-[4-(4-Isoquinolin-3-yl-piperazine-1-sulfonyl)-phenyl]-acrylamide | Tr = 4.92 min, m/z (ES$^+$) (M + H)$^+$ 423 |
| 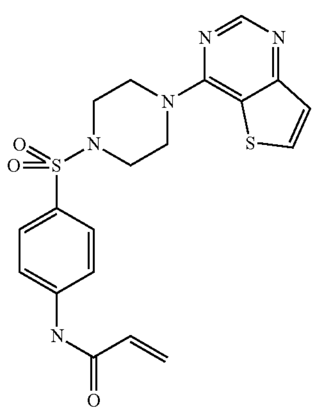 [SMILES: C=CC(=O)Nc1ccc(S(=O)(=O)N2CCN(c3ncnc4ccsc34)CC2)cc1] | N-[4-(4-Thieno[3,2-d]pyrimidin-4-yl-piperazine-1-sulfonyl)-phenyl]-acrylamide | Tr = 2.57 min, m/z (ES$^+$) (M + H)$^+$ 430 |

-continued

| Structure | IUPAC Name | MS |
|---|---|---|
| 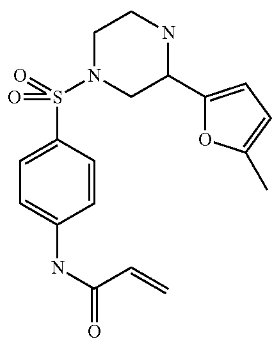 [SMILES: C=CC(=O)Nc1ccc(S(=O)(=O)N2CCNC(c3ccc(C)o3)C2)cc1] | N-{4-[3-(5-Methyl-furan-2-yl)-piperazine-1-sulfonyl]-phenyl}-acrylamide | Tr = 2.63 min, m/z (ES$^+$) (M + H)$^+$ 376 |
| 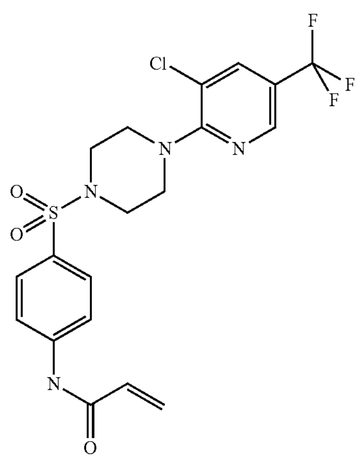 [SMILES: C=CC(=O)Nc1ccc(S(=O)(=O)N2CCN(c3ncc(C(F)(F)F)cc3Cl)CC2)cc1] | N-{4-[4-(3-Chloro-5-trifluoromethyl-pyridin 2-yl)-piperazine-1-sulfonyl]-phenyl}-acrylamide | Tr = 4.67 min, m/z (ES$^+$) (M + H)$^+$ 475 |
| 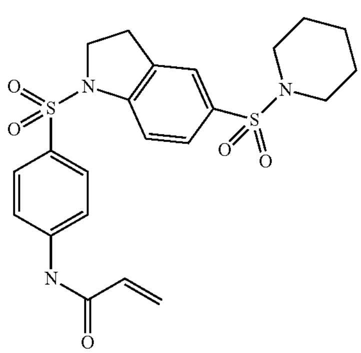 [SMILES: C=CC(=O)Nc1ccc(S(=O)(=O)N2CCc3cc(S(=O)(=O)N4CCCCC4)ccc32)cc1] | N-{4-[5-(Piperidine-1-sulfonyl)-2,3-dihydro-indole-1-sulfonyl]-phenyl}-acrylamide | Tr = 4.32 min, m/z (ES$^+$) (M + H)$^+$ 476 |
| 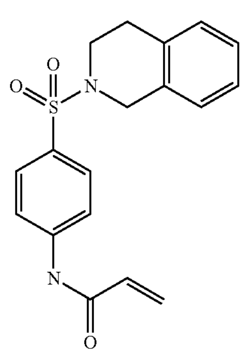 [SMILES: C=CC(=O)Nc1ccc(S(=O)(=O)N2CCc3ccccc3C2)cc1] | N-[4-(3,4-Dihydro-1H-isoquinoline-2-sulfonyl)-phenyl]-acrylamide | Tr = 4.15 min, m/z (ES$^+$) (M + Na)$^+$ 365 |

-continued

| Structure | IUPAC Name | MS |
|---|---|---|
| 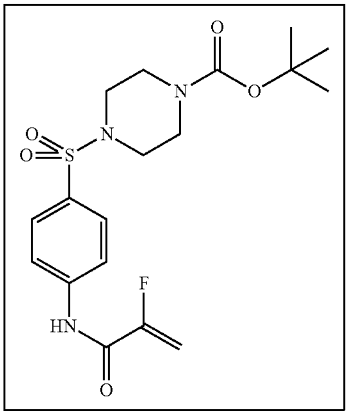 [SMILES: C=C(F)C(=O)Nc1ccc(S(=O)(=O)N2CCN(C(=O)OC(C)(C)C)CC2)cc1] | 4-[4-(2-Fluoro-acryloylamino)-benzenesulfonyl]-piperazine-1-carboxylic acid tert-butyl ester | Tr = 4.19 min, m/z (ES$^+$) (M + Na)$^+$ 436 |
| 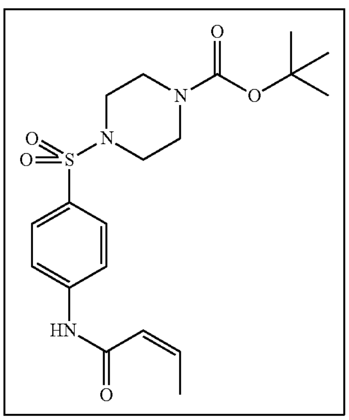 [SMILES: C/C=C\C(=O)Nc1ccc(S(=O)(=O)N2CCN(C(=O)OC(C)(C)C)CC2)cc1] | 4-((Z)-4-But-2-enoylamino-benzenesulfonyl)-piperazine-1-carboxylic acid tert-butyl ester | Tr = 4.26 min, m/z (ES$^+$) (M + Na)$^+$ 432 |
| 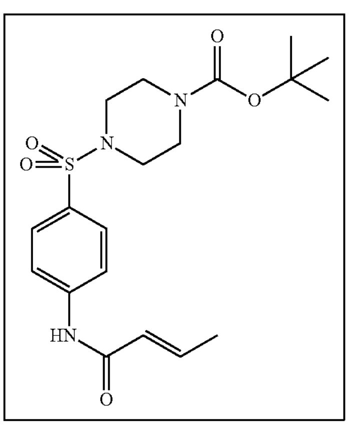 [SMILES: C/C=C/C(=O)Nc1ccc(S(=O)(=O)N2CCN(C(=O)OC(C)(C)C)CC2)cc1] | 4-((E)-4-But-2-enoylamino-benzenesulfonyl)-piperazine-1-carboxylic acid tert-butyl ester | Tr = 4.26 min, m/z (ES$^+$) (M + Na)$^+$ 432 |

| Structure | IUPAC Name | MS |
|---|---|---|
| 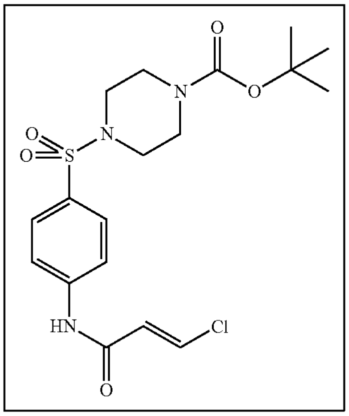 [SMILES: CC(C)(C)OC(=O)N1CCN(S(=O)(=O)c2ccc(NC(=O)/C=C/Cl)cc2)CC1] | 4-[4-((E)-3-Chloro-acryloylamino)-benzenesulfonyl]-piperazine-1-carboxylic acid tert-butyl ester | Tr = 4.36 min, m/z (ES$^+$) (M + Na)$^+$ 452/453 |
| 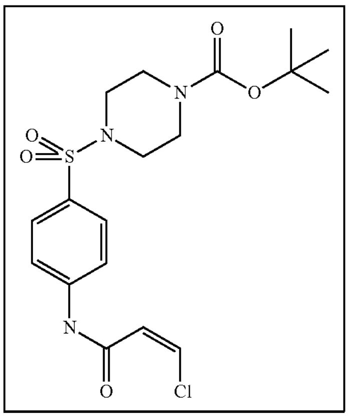 [SMILES: CC(C)(C)OC(=O)N1CCN(S(=O)(=O)c2ccc(NC(=O)/C=C\Cl)cc2)CC1] | 4-[4-((Z)-3-Chloro-acryloylamino)-benzenesulfonyl]-piperazine-1-carboxylic acid tert-butyl ester | Tr = 4.36 min, m/z (ES$^+$) (M + Na)$^+$ 452/453 |

Biology Example 1

A fluorescent screening assay for human TG2 was performed as described herein: Assay conditions were 20 nM TG2, 8 µM N,N-dimethylated Casein (NMC) and 16 µM K×D (used for all transglutaminase assays) in 25 mM Hepes, pH 7.4, 250 mM NaCl, 2 mM MgCl$_2$, 0.5 mM CaCl$_2$, 0.2 mM DTT, 0.05% Pluronic F-127 at 37° C. A time point was taken with a microplate reader (Safire or Ultra, Tecan; ex: 350 nm, em: 535 nm) every 3 minutes for up to 2 hours and the initial linear reaction progress was used to determine the reaction velocity as a measure for enzyme activity. Assay conditions were identical for human TG6 and similar for human TG1 and mouse TG2 apart from enzyme concentration (mTG2 at 5 nM; TG1 at 10 nM) and CaCl$_2$ concentration (0.2 mM for mTG2; 0.05 mM for TG1). Factor XIIIa was activated using 0.1 µg/µl thrombin (Sigma) in 35 mM Tris pH 8.0 for 20 min at 30° C. and the transamidation reaction was performed with 20 nM Factor XIIIa in 50 mM Tris pH 8.0, 1.25 mM CaCl2, 0.05% Pluronic, 0.2 mM DTT. TG3 was activated with 0.02 µg/µl thrombin under the same conditions as Factor XIIIa and assay conditions were 10 nM TG3 in 50 mM Hepes, pH 8, 20 mM CaCl$_2$, 0.2 mM DTT, 0.05% Pluronic F-127.

Certain compounds described herein were tested and found to have IC$_{50}$ value less than 100 nanomolar (denoted as "+++" in the table below). Certain compounds described herein were tested and found to have an IC$_{50}$ value from 100 nanomolar to 1 micromolar (denoted as "++" in the table below). Certain compounds described herein were tested and found to have an IC$_{50}$ value from 1 to 25 micromolar (denoted as "+" in the table below).

| IUPAC Name | IC$_{50}$ |
|---|---|
| 4-(4-Acryloylamino-benzenesulfonyl)-piperazine-1-carboxylic acid 2-chloro-benzyl ester | +++ |
| 4-(4-Acryloylamino-benzenesulfonyl)-piperazine-1-carboxylic acid 2,6-difluoro-benzyl ester | +++ |
| 4-(4-Acryloylamino-benzenesulfonyl)-piperazine-1-carboxylic acid 4-methyl-benzyl ester | +++ |
| 4-(4-Acryloylamino-benzenesulfonyl)-piperazine-1-carboxylic acid 3-fluoro-benzyl ester | +++ |
| 4-(4-Acryloylamino-benzenesulfonyl)-piperazine-1-carboxylic acid 4-fluoro-benzyl ester | +++ |

| IUPAC Name | IC$_{50}$ |
|---|---|
| 4-(4-Acryloylamino-benzenesulfonyl)-piperazine-1-carboxylic acid phenethyl ester | +++ |
| 4-(4-Acryloylamino-benzenesulfonyl)-piperazine-1-carboxylic acid 2,3-dimethoxy-benzyl ester | +++ |
| 4-(4-Acryloylamino-benzenesulfonyl)-piperazine-1-carboxylic acid 2-methyl-benzyl ester | +++ |
| 4-(4-Acryloylamino-benzenesulfonyl)-piperazine-1-carboxylic acid ethyl ester | +++ |
| 4-(4-Acryloylamino-benzenesulfonyl)-piperazine-1-carboxylic acid isobutyl ester | +++ |
| 4-(4-Acryloylamino-benzenesulfonyl)-piperazine-1-carboxylic acid isopropyl ester | +++ |
| 4-(4-Acryloylamino-benzenesulfonyl)-piperazine-1-carboxylic acid benzylamide | +++ |
| 4-(4-Acryloylamino-benzenesulfonyl)-piperazine-1-carboxylic acid 3,5-difluoro-benzyl ester | +++ |
| 4-(4-Acryloylamino-benzenesulfonyl)-piperazine-1-carboxylic acid 3-chloro-benzyl ester | +++ |
| 4-(4-Acryloylamino-benzenesulfonyl)-piperazine-1-carboxylic acid 2,3-difluoro-benzyl ester | +++ |
| N-{4-[4-(2-Naphthalen-2-yl-acetyl)-piperazine-1-sulfonyl]-phenyl}-acrylamide | +++ |
| 4-(4-Acryloylamino-benzenesulfonyl)-piperazine-1-carboxylic acid cyclopentyl ester | +++ |
| N-{4-[4-(Piperidine-1-carbonyl)-piperazine-1-sulfonyl]-phenyl}-acrylamide | +++ |
| 4-(4-Acryloylamino-benzenesulfonyl)-piperazine-1-carboxylic acid phenyl ester | +++ |
| N-{4-[4-(Pyrrolidine-1-carbonyl)-piperazine-1-sulfonyl]-phenyl}-acrylamide | +++ |
| N-{4-[4-(6-Trifluoromethyl-pyridin-3-yl)-piperazine-1-sulfonyl]-phenyl}-acrylamide | +++ |
| N-[4-(4-Cyclopropanecarbonyl-piperazine-1-sulfonyl)-phenyl]-acrylamide | +++ |
| N-[4-(4-Cyclopentanecarbonyl-piperazine-1-sulfonyl)-phenyl]-acrylamide | +++ |
| N-{4-[4-(2-Phenyl-cyclopropanecarbonyl)-piperazine-1-sulfonyl]-phenyl}-acrylamide | +++ |
| N-{4-[4-(4,4-Difluoro-piperidine-1-carbonyl)-piperazine-1-sulfonyl]-phenyl}-acrylamide | +++ |
| N-{4-[4-(Adamantane-1-carbonyl)-piperazine-1-sulfonyl]-phenyl}-acrylamide | +++ |
| N-{4-[4-(3-Pyridin-2-yl-propionyl)-piperazine-1-sulfonyl]-phenyl}-acrylamide | +++ |
| N-(4-{4-[2-(3-Phenoxy-phenyl)-acetyl]-piperazine-1-sulfonyl}-phenyl)-acrylamide | +++ |
| N-(4-{4-[2-(4-Phenoxy-phenyl)-acetyl]-piperazine-1-sulfonyl}-phenyl)-acrylamide | +++ |
| N-{4-[4-(Morpholine-4-carbonyl)-piperazine-1-sulfonyl]-phenyl}-acrylamide | +++ |
| [1-(4-Acryloylamino-benzenesulfonyl)-piperidin-4-yl]-methyl-carbamic acid tert-butyl ester | +++ |
| N-[4-(5-Dimethylsulfamoyl-2,3-dihydro-indole-1-sulfonyl)-phenyl]-acrylamide | +++ |
| Adamantane-1-carboxylic acid [1-(4-acryloylamino-benzenesulfonyl)-piperidin-4-yl]-methyl-amide | +++ |
| 4-(4-Acryloylamino-benzenesulfonyl)-2-isopropyl-piperazine-1-carboxylic acid tert-butyl ester | +++ |
| N-{4-[4-(Octahydro-quinoline-1-carbonyl)-piperazine-1-sulfonyl]-phenyl}-acrylamide | +++ |
| N-{4-[4-(Octahydro-isoquinoline-2-carbonyl)-piperazine-1-sulfonyl]-phenyl}-acrylamide | +++ |
| 4-(4-Acryloylamino-benzenesulfonyl)-piperazine-1-carboxylic acid adamantan-2-ylamide | +++ |
| N-{4-[4-(3-Methyl-pyridin-2-yl)-piperazine-1-sulfonyl]-phenyl}-acrylamide | +++ |
| N-{4-[4-(6-Methyl-pyridin-2-yl)-piperazine-1-sulfonyl]-phenyl}-acrylamide | +++ |
| 4-(4-Acryloylamino-benzenesulfonyl)-2-methyl-piperazine-1-carboxylic acid benzyl ester | +++ |
| N-{4-[4-(2,6-Dimethyl-morpholine-4-carbonyl)-piperazine-1-sulfonyl]-phenyl}-acrylamide | +++ |
| N-{4-[4-(Tetrahydro-pyran-4-carbonyl)-piperazine-1-sulfonyl]-phenyl}-acrylamide | +++ |
| 4-(4-Acryloylamino-benzenesulfonyl)-2-furan-2-yl-piperazine-1-carboxylic acid tert-butyl ester | +++ |
| N-[4-(4-Pyridin-2-yl-piperazine-1-sulfonyl)-phenyl]-acrylamide | +++ |
| N-{4-[4-(3-Trifluoromethyl-pyridin-2-yl)-piperazine-1-sulfonyl]-phenyl}-acrylamide | +++ |

| IUPAC Name | IC$_{50}$ |
|---|---|
| 4-(4-Acryloylamino-2-chloro-benzenesulfonyl)-piperazine-1-carboxylic acid tert-butyl ester | +++ |
| N-{4-[4-(Adamantane-1-carbonyl)-piperazine-1-sulfonyl]-3-fluoro-phenyl}-acrylamide | +++ |
| N-[4-(4-Thiazol-2-yl-piperazine-1-sulfonyl)-phenyl]-acrylamide | +++ |
| 4-(4-Acryloylamino-benzenesulfonyl)-piperazine-1-carboxylic acid dimethylamide | +++ |
| 4-(4-Acryloylamino-benzenesulfonyl)-2-methoxycarbonylmethyl-piperazine-1-carboxylic acid benzyl ester | +++ |
| 4-(4-Acryloylamino-benzenesulfonyl)-2-(adamantan-2-ylcarbamoylmethyl)-piperazine-1-carboxylic acid benzyl ester | +++ |
| N-{4-[4-(Piperidine-1-carbonyl)-piperidine-1-sulfonyl]-phenyl}-acrylamide | +++ |
| N-[4-(4-Benzooxazol-2-yl-piperazine-1-sulfonyl)-phenyl]-acrylamide | +++ |
| N-{4-[4-(4-Trifluoromethyl-pyrimidin-2-yl)-piperazine-1-sulfonyl]-phenyl}-acrylamide | +++ |
| N-{4-[4-(2-Chloro-pyrimidin-4-yl)-piperazine-1-sulfonyl]-phenyl}-acrylamide | +++ |
| N-[4-(4-Pyrimidin-2-yl-piperazine-1-sulfonyl)-phenyl]-acrylamide | +++ |
| N-[4-(4-Furo[3,2-c]pyridin-4-yl-piperazine-1-sulfonyl)-phenyl]-acrylamide | +++ |
| 1-(4-Acryloylamino-benzenesulfonyl)-piperidine-4-carboxylic acid methyl-phenyl-amide | +++ |
| N-{4-[4-(4-Methoxy-pyrimidin-2-yl)-piperazine-1-sulfonyl]-phenyl}-acrylamide | +++ |
| N-[4-(2,3,5,6-Tetrahydro-[1,2']bipyrazinyl-4-sulfonyl)-phenyl]-acrylamide | +++ |
| N-{4-[4-(4-Methyl-pyridin-2-yl)-piperazine-1-sulfonyl]-phenyl}-acrylamide | +++ |
| N-{4-[4-(4,6-Dimethyl-pyrimidin-2-yl)-piperazine-1-sulfonyl]-phenyl}-acrylamide | +++ |
| N-{4-[4-(2-Methyl-quinolin-5-yl)-piperazine-1-sulfonyl]-phenyl}-acrylamide | +++ |
| N-[4-(4-Quinolin-2-yl-piperazine-1-sulfonyl)-phenyl]-acrylamide | +++ |
| N-{4-[4-(5-Chloro-pyridin-2-yl)-piperazine-1-sulfonyl]-phenyl}-acrylamide | +++ |
| N-{4-[4-(5-Methyl-pyridin-2-yl)-piperazine-1-sulfonyl]-phenyl}-acrylamide | +++ |
| N-[4-(4-Benzothiazol-2-yl-piperazine-1-sulfonyl)-phenyl]-acrylamide | +++ |
| N-[4-(4-Isoquinolin-1-yl-piperazine-1-sulfonyl)-phenyl]-acrylamide | +++ |
| N-[4-(4-Thieno[3,2-d]pyrimidin-4-yl-piperazine-1-sulfonyl)-phenyl]-acrylamide | +++ |
| 4-(4-Acryloylamino-benzenesulfonyl)-piperazine-1-carboxylic acid 2-chloro-benzyl ester | ++ |
| 4-(4-Acryloylamino-benzenesulfonyl)-piperazine-1-carboxylic acid 2,6-difluoro-benzyl ester | ++ |
| 4-(4-Acryloylamino-benzenesulfonyl)-piperazine-1-carboxylic acid 4-methyl-benzyl ester | ++ |
| 4-(4-Acryloylamino-benzenesulfonyl)-piperazine-1-carboxylic acid 3-fluoro-benzyl ester | ++ |
| 4-(4-Acryloylamino-benzenesulfonyl)-piperazine-1-carboxylic acid 4-fluoro-benzyl ester | ++ |
| 4-(4-Acryloylamino-benzenesulfonyl)-piperazine-1-carboxylic acid phenethyl ester | ++ |
| 4-(4-Acryloylamino-benzenesulfonyl)-piperazine-1-carboxylic acid 2,3-dimethoxy-benzyl ester | ++ |
| 4-(4-Acryloylamino-benzenesulfonyl)-piperazine-1-carboxylic acid 2-methyl-benzyl ester | ++ |
| 4-(4-Acryloylamino-benzenesulfonyl)-piperazine-1-carboxylic acid ethyl ester | ++ |
| 4-(4-Acryloylamino-benzenesulfonyl)-piperazine-1-carboxylic acid isobutyl ester | ++ |
| 4-(4-Acryloylamino-benzenesulfonyl)-piperazine-1-carboxylic acid isopropyl ester | ++ |
| 4-(4-Acryloylamino-benzenesulfonyl)-piperazine-1-carboxylic acid benzylamide | ++ |
| 4-(4-Acryloylamino-benzenesulfonyl)-piperazine-1-carboxylic acid 3,5-difluoro-benzyl ester | ++ |
| 4-(4-Acryloylamino-benzenesulfonyl)-piperazine-1-carboxylic acid 3-chloro-benzyl ester | ++ |
| 4-(4-Acryloylamino-benzenesulfonyl)-piperazine-1-carboxylic acid 2,3-difluoro-benzyl ester | ++ |
| N-{4-[4-(2-Naphthalen-2-yl-acetyl)-piperazine-1-sulfonyl]-phenyl}-acrylamide | ++ |
| 4-(4-Acryloylamino-benzenesulfonyl)-piperazine-1-carboxylic acid cyclopentyl ester | ++ |
| N-{4-[4-(Piperidine-1-carbonyl)-piperazine-1-sulfonyl]-phenyl}-acrylamide | ++ |
| 4-(4-Acryloylamino-benzenesulfonyl)-piperazine-1-carboxylic acid phenyl ester | ++ |
| N-{4-[4-(Pyrrolidine-1-carbonyl)-piperazine-1-sulfonyl]-phenyl}-acrylamide | ++ |

| IUPAC Name | IC$_{50}$ |
|---|---|
| N-{4-[4-(6-Trifluoromethyl-pyridin-3-yl)-piperazine-1-sulfonyl]-phenyl}-acrylamide | ++ |
| N-[4-(4-Cyclopropanecarbonyl-piperazine-1-sulfonyl)-phenyl]-acrylamide | ++ |
| N-[4-(4-Cyclopentanecarbonyl-piperazine-1-sulfonyl)-phenyl]-acrylamide | ++ |
| N-{4-[4-(2-Phenyl-cyclopropanecarbonyl)-piperazine-1-sulfonyl]-phenyl}-acrylamide | ++ |
| N-{4-[4-(4,4-Difluoro-piperidine-1-carbonyl)-piperazine-1-sulfonyl]-phenyl}-acrylamide | ++ |
| N-{4-[4-(Adamantane-1-carbonyl)-piperazine-1-sulfonyl]-phenyl}-acrylamide | ++ |
| N-{4-[4-(3-Pyridin-2-yl-propionyl)-piperazine-1-sulfonyl]-phenyl}-acrylamide | ++ |
| N-(4-{4-[2-(3-Phenoxy-phenyl)-acetyl]-piperazine-1-sulfonyl}-phenyl)-acrylamide | ++ |
| N-(4-{4-[2-(4-Phenoxy-phenyl)-acetyl]-piperazine-1-sulfonyl}-phenyl)-acrylamide | ++ |
| N-{4-[4-(Morpholine-4-carbonyl)-piperazine-1-sulfonyl]-phenyl}-acrylamide | ++ |
| [1-(4-Acryloylamino-benzenesulfonyl)-piperidin-4-yl]-methyl-carbamic acid tert-butyl ester | ++ |
| N-[4-(5-Dimethylsulfamoyl-2,3-dihydro-indole-1-sulfonyl)-phenyl]-acrylamide | ++ |
| Adamantane-1-carboxylic acid [1-(4-acryloylamino-benzenesulfonyl)-piperidin-4-yl]-methyl-amide | ++ |
| 4-(4-Acryloylamino-benzenesulfonyl)-2-isopropyl-piperazine-1-carboxylic acid tert-butyl ester | ++ |
| N-{4-[4-(Octahydro-quinoline-1-carbonyl)-piperazine-1-sulfonyl]-phenyl}-acrylamide | ++ |
| N-{4-[4-(Octahydro-isoquinoline-2-carbonyl)-piperazine-1-sulfonyl]-phenyl}-acrylamide | ++ |
| 4-(4-Acryloylamino-benzenesulfonyl)-piperazine-1-carboxylic acid adamantan-2-ylamide | ++ |
| N-{4-[4-(3-Methyl-pyridin-2-yl)-piperazine-1-sulfonyl]-phenyl}-acrylamide | ++ |
| N-{4-[4-(6-Methyl-pyridin-2-yl)-piperazine-1-sulfonyl]-phenyl}-acrylamide | ++ |
| 4-(4-Acryloylamino-benzenesulfonyl)-2-methyl-piperazine-1-carboxylic acid benzyl ester | ++ |
| N-{4-[4-(2,6-Dimethyl-morpholine-4-carbonyl)-piperazine-1-sulfonyl]-phenyl}-acrylamide | ++ |
| N-{4-[4-(Tetrahydro-pyran-4-carbonyl)-piperazine-1-sulfonyl]-phenyl}-acrylamide | ++ |
| 4-(4-Acryloylamino-benzenesulfonyl)-2-furan-2-yl-piperazine-1-carboxylic acid tert-butyl ester | ++ |
| N-[4-(4-Pyridin-2-yl-piperazine-1-sulfonyl)-phenyl]-acrylamide | ++ |
| N-{4-[4-(3-Trifluoromethyl-pyridin-2-yl)-piperazine-1-sulfonyl]-phenyl}-acrylamide | ++ |
| 4-(4-Acryloylamino-2-chloro-benzenesulfonyl)-piperazine-1-carboxylic acid tert-butyl ester | ++ |
| N-{4-[4-(Adamantane-1-carbonyl)-piperazine-1-sulfonyl]-3-fluoro-phenyl}-acrylamide | ++ |
| N-[4-(4-Thiazol-2-yl-piperazine-1-sulfonyl)-phenyl]-acrylamide | ++ |
| 4-(4-Acryloylamino-benzenesulfonyl)-piperazine-1-carboxylic acid dimethylamide | ++ |
| 4-(4-Acryloylamino-benzenesulfonyl)-2-methoxycarbonylmethyl-piperazine-1-carboxylic acid benzyl ester | ++ |
| 4-(4-Acryloylamino-benzenesulfonyl)-2-(adamantan-2-ylcarbamoylmethyl)-piperazine-1-carboxylic acid benzyl ester | ++ |
| N-{4-[4-(Piperidine-1-carbonyl)-piperidine-1-sulfonyl]-phenyl}-acrylamide | ++ |
| N-[4-(4-Benzooxazol-2-yl-piperazine-1-sulfonyl)-phenyl]-acrylamide | ++ |
| N-{4-[4-(4-Trifluoromethyl-pyrimidin-2-yl)-piperazine-1-sulfonyl]-phenyl}-acrylamide | ++ |
| N-{4-[4-(2-Chloro-pyrimidin-4-yl)-piperazine-1-sulfonyl]-phenyl}-acrylamide | ++ |
| N-[4-(4-Pyrimidin-2-yl-piperazine-1-sulfonyl)-phenyl]-acrylamide | ++ |
| N-[4-(4-Furo[3,2-c]pyridin-4-yl-piperazine-1-sulfonyl)-phenyl]-acrylamide | ++ |
| 1-(4-Acryloylamino-benzenesulfonyl)-piperidine-4-carboxylic acid methyl-phenyl-amide | ++ |
| N-{4-[4-(4-Methoxy-pyrimidin-2-yl)-piperazine-1-sulfonyl]-phenyl}-acrylamide | ++ |

| IUPAC Name | IC$_{50}$ |
|---|---|
| N-[4-(2,3,5,6-Tetrahydro-[1,2']bipyrazinyl-4-sulfonyl)-phenyl]-acrylamide | ++ |
| N-{4-[4-(4-Methyl-pyridin-2-yl)-piperazine-1-sulfonyl]-phenyl}-acrylamide | ++ |
| N-{4-[4-(4,6-Dimethyl-pyrimidin-2-yl)-piperazine-1-sulfonyl]-phenyl}-acrylamide | ++ |
| N-{4-[4-(2-Methyl-quinolin-5-yl)-piperazine-1-sulfonyl]-phenyl}-acrylamide | ++ |
| N-{4-(4-Quinolin-2-yl-piperazine-1-sulfonyl)-phenyl]-acrylamide | ++ |
| N-{4-[4-(5-Chloro-pyridin-2-yl)-piperazine-1-sulfonyl]-phenyl}-acrylamide | ++ |
| N-{4-[4-(5-Methyl-pyridin-2-yl)-piperazine-1-sulfonyl]-phenyl}-acrylamide | ++ |
| N-[4-(4-Benzothiazol-2-yl-piperazine-1-sulfonyl)-phenyl]-acrylamide | ++ |
| N-[4-(4-Isoquinolin-1-yl-piperazine-1-sulfonyl)-phenyl]-acrylamide | ++ |
| N-[4-(4-Thieno[3,2-d]pyrimidin-4-yl-piperazine-1-sulfonyl)-phenyl]-acrylamide | ++ |
| {2-[(4-Acryloylamino-benzenesulfonyl)-methyl-amino]-ethyl}-methyl-carbamic acid benzyl ester | + |
| 4-(4-Acryloylamino-benzenesulfonyl)-piperazine-1-carboxylic acid 4-butyl-benzyl ester | + |
| 4-(4-Acryloylamino-benzenesulfonyl)-piperazine-1-carboxylic acid 4-tert-butyl-benzyl ester | + |
| N-[4-(Piperazine-1-sulfonyl)-phenyl]-acrylamide | + |
| N-[4-(4-Biphenyl-4-ylmethyl-piperazine-1-sulfonyl)-phenyl]-acrylamide | + |
| N-[3-(4-Benzyl-piperazine-1-sulfonyl)-phenyl]-acrylamide | + |
| N-[3-(4-Phenethyl-piperazine-1-sulfonyl)-phenyl]-acrylamide | + |
| N-{3-[4-(3-Phenyl-propyl)-piperazine-1-sulfonyl]-phenyl}-acrylamide | + |
| N-[3-(4-Phenyl-piperazine-1-sulfonyl)-phenyl]-acrylamide | + |
| N-{3-[4-(4-Phenyl-butyl)-piperazine-1-sulfonyl]-phenyl}-acrylamide | + |
| N-[3-(Piperazine-1-sulfonyl)-phenyl]-acrylamide | + |
| N-(4-(1-Ethyl-piperidin-3-ylsulfamoyl)-phenyl]-acrylamide | + |
| N-(4-{Methyl-[4-(4-methyl-piperazin-1-ylmethyl)-benzyl]-sulfamoyl}-phenyl)-acrylamide | + |
| N-{4-[Methyl-(2-morpholin-4-yl-thiazol-4-ylmethyl)-sulfamoyl]-phenyl}-acrylamide | + |
| 4-[4-(Acryloyl-methyl-amino)-benzenesulfonyl]-piperazine-1-carboxylic acid tert-butyl ester | + |
| N-[4-(4-Amino-piperidine-1-sulfonyl)-phenyl]-acrylamide | + |
| N-{4-[Benzyl-(4-chloro-benzyl)-sulfamoyl]-phenyl}-acrylamide | + |
| N-{4-[Methyl-(3-pyrrolidin-1-ylmethyl-benzyl)-sulfamoyl]-phenyl}-acrylamide | + |
| N-[4-(4-Furan-2-yl-2,3-dihydro-benzo[b][1,4]diazepine-1-sulfonyl)-phenyl]-acrylamide | + |
| 4-(4-Acryloylamino-3-fluoro-benzenesulfonyl)-piperazine-1-carboxylic acid benzyl ester | + |
| N-{4-[2-(4-Trifluoromethyl-phenyl)-pyrrolidine-1-sulfonyl]-phenyl}-acrylamide | + |
| N-[4-(4-Adamantan-1-yl-piperazine-1-sulfonyl)-phenyl]-acrylamide | + |
| 4-(4-Acryloylamino-2-methoxy-benzenesulfonyl)-piperazine-1-carboxylic acid tert-butyl ester | + |
| N-[3-Methoxy-4-(piperazine-1-sulfonyl)-phenyl]-acrylamide | + |
| N-{4-[(6-Phenyl-pyridin-3-ylmethyl)-sulfamoyl]-phenyl}-acrylamide | + |
| 4-(4-Acryloylamino-2-methyl-benzenesulfonyl)-piperazine-1-carboxylic acid tert-butyl ester | + |
| N-[3-Methyl-4-(piperazine-1-sulfonyl)-phenyl]-acrylamide | + |
| N-[4-(4-Biphenyl-3-yl-piperazine-1-sulfonyl)-phenyl]-acrylamide | + |
| N-[4-(1-Methyl-2-oxo-2-piperidin-1-yl-ethylsulfamoyl)-phenyl]-acrylamide | + |
| N-[4-(4-Naphthalen-2-yl-piperazine-1-sulfonyl)-phenyl]-acrylamide | + |
| N-{4-[3-(5-Methyl-furan-2-yl)-piperazine-1-sulfonyl]-phenyl}-acrylamide | + |
| 4-[4-(2-Fluoro-acryloylamino)-benzenesulfonyl]-piperazine-1-carboxylic acid tert-butyl ester | + |
| (Z)-tert-butyl 4-(4-but-2-enamidophenylsulfonyl)piperazine-1-carboxylate | + |
| (E)-tert-butyl 4-(4-but-2-enamidophenylsulfonyl)piperazine-1-carboxylate | + |
| (Z)-tert-butyl 4-(4-(3-chloroacrylamido)phenylsulfonyl)piperazine-1-carboxylate | ++ |
| (E)-tert-butyl 4-(4-(3-chloroacrylamido)phenylsulfonyl)piperazine-1-carboxylate | + |
| 4-[4-(1-Oxo-but-2-ynylamino)-benzenesulfonyl]-piperazine-1-carboxylic acid tert-butyl ester | + |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound of Formula II

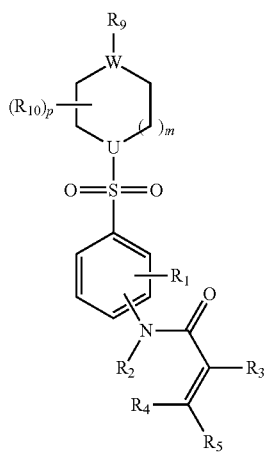

Formula II or a pharmaceutically acceptable salt thereof, wherein
U is N or CH;
$R_1$ is chosen from hydrogen, —$R^a$, —$OR^b$, —$SR^b$, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$ —$SO_2NR^bR^c$, and —$NR^cSO_2R^a$,
where $R^a$ is chosen from optionally substituted $C_1$-$C_6$ alkyl, optionally substituted aryl, and optionally substituted heteroaryl;
$R^b$ is chosen from H, optionally substituted $C_1$-$C_6$ alkyl, optionally substituted aryl, and optionally substituted heteroaryl; and
$R^c$ is chosen from hydrogen and optionally substituted $C_1$-$C_4$ alkyl; or
$R^b$ and $R^c$, and the nitrogen to which they are attached, form an optionally substituted heterocycloalkyl group; and
where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl);
$R_2$ is chosen from hydrogen and optional substituted alkyl;
$R_3$, $R_4$, and $R_5$ are independently chosen from hydrogen, halo, and optional substituted alkyl or $R_3$ taken together with $R_4$ forms a bond and $R_5$ is chosen from hydrogen and optionally substituted alkyl;
m is 0, 1, or 2;
p is 0, 1, or 2;
W is —CH or N;
$R_9$ is chosen from
hydrogen,
lower alkyl optionally substituted with optionally substituted amino, cycloalkyl, heterocycloalkyl, heteroaryl, or alkoxy, each of which, excluding optionally substituted amino, is optionally substituted with one or more groups chosen from lower alkoxy and halo,
cycloalkyl optionally substituted with optionally substituted amino, heterocycloalkyl, heteroaryl, or alkoxy, each of which, excluding optionally substituted amino, is optionally substituted with one or more groups chosen from lower alkoxy and halo,
—$NR_{12}R_{13}$ wherein $R_{12}$ and $R_{13}$ are independently chosen from hydrogen, lower alkyl, aralkyl, heteroaralkyl, —C(O)$R_{14}$, —C(O)O$R_{14}$, and —C(O)N$R_{14}R_{14}$ wherein for each occurrence $R_{14}$ is chosen from hydrogen, lower alkyl, cycloalkyl, aralkyl, aryl, heterocycloalkyl, heteroaralkyl, and heteroaryl,
phenyl optionally substituted with one or more groups chosen from halo, lower alkyl, $CF_3$, lower alkoxy, and phenyl,
aralkyl optionally substituted with one or more groups chosen from lower alkyl, lower alkoxy, alkylenedioxy, and phenyl,
heteroaryl optionally substituted with one or more groups chosen from halo, heteroaryl, lower alkyl, $CF_3$, and lower alkoxy, and
—X—Y—C(O)—Z—(CH$_2$)$_r$—$R_{11}$ wherein
X is absent or is —CH$_2$—;
Y is absent or Y is chosen from —CH$_2$—or —$NR_{12}$—;
Z is absent or Z is chosen from —O— and —$NR_{12}$—;
r is 0, 1, 2, or 3; and
$R_{11}$ is chosen from optionally substituted amino, lower alkyl, lower alkenyl, cycloalkyl, heterocycloalkyl, aryl, and heteroaryl, each of which, excluding optionally substituted amino, is optionally substituted with one or more groups chosen from halo, lower alkyl, lower alkoxy, $CF_3$, and phenoxy; and
for each occurrence, $R_{10}$ is chosen from optionally substituted lower alkyl, optionally substituted alkoxy, optionally substituted aryloxy, optionally substituted heteroaryl, and optionally substituted aryl.

2. The compound of claim 1, or a pharmaceutically acceptable salt thereof, wherein W is N.

3. The compound of claim 1, or a pharmaceutically acceptable salt thereof, wherein W is CH.

4. The compound of claim 1, or a pharmaceutically acceptable salt thereof, wherein m is 0.

5. The compound of claim 1, or a pharmaceutically acceptable salt thereof, wherein m is 1.

6. The compound of claim 1, or a pharmaceutically acceptable salt thereof, wherein m is 2.

7. The compound of claim 1, or a pharmaceutically acceptable salt thereof, wherein $R_9$ is —X—Y—C(O)—Z—$(CH_2)_r$—$R_{11}$ wherein X is absent.

8. The compound of claim 1, or a pharmaceutically acceptable salt thereof, wherein $R_9$ is —X—Y—C(O)—Z—$(CH_2)_r$—$R_{11}$ wherein X is —$CH_2$—.

9. The compound of claim 1, or a pharmaceutically acceptable salt thereof, wherein $R_9$ is —X—Y—C(O)—Z—$(CH_2)_r$—$R_{11}$ wherein Y is absent.

10. The compound of claim 1, or a pharmaceutically acceptable salt thereof, wherein $R_9$ is —X—Y—C(O)—Z—$(CH_2)_r$—$R_{11}$ wherein Y is —$CH_2$—.

11. The compound of claim 1, or a pharmaceutically acceptable salt thereof, wherein $R_9$ is —X—Y—C(O)—Z—$(CH_2)_r$—$R_{11}$ wherein Y is —$NR_{12}$—.

12. The compound of claim 1, or a pharmaceutically acceptable salt thereof, wherein $R_9$ is —X—Y—C(O)—Z—$(CH_2)_r$—$R_{11}$ wherein Z is absent.

13. The compound of claim 1, or a pharmaceutically acceptable salt thereof, wherein $R_9$ is —X—Y—C(O)—Z—$(CH_2)_r$—$R_{11}$ wherein Z is —O—.

14. The compound of claim 1, or a pharmaceutically acceptable salt thereof, wherein $R_9$ is —X—Y—C(O)—Z—$(CH_2)_r$—$R_{11}$ wherein Z is —$NR_{12}$—.

15. The compound of claim 1, or a pharmaceutically acceptable salt thereof, wherein $R_9$ is —X—Y—C(O)—Z—$(CH_2)_r$—$R_{11}$ wherein r is 0.

16. The compound of claim 1, or a pharmaceutically acceptable salt thereof, wherein $R_9$ is —X—Y—C(O)—Z—$(CH_2)_r$—$R_{11}$ wherein r is 1.

17. The compound of claim 1, or a pharmaceutically acceptable salt thereof, wherein $R_9$ is —X—Y—C(O)—Z—$(CH_2)_r$—$R_{11}$ wherein r is 2.

18. The compound of claim 1, or a pharmaceutically acceptable salt thereof, wherein $R_9$ is —X—Y—C(O)—Z—$(CH_2)_r$—$R_{11}$ wherein r is 3.

19. The compound of claim 1, or a pharmaceutically acceptable salt thereof, wherein $R_9$ is hydrogen.

20. The compound of claim 1, or a pharmaceutically acceptable salt thereof, wherein $R_9$ is lower alkyl optionally substituted with cycloalkyl, morpholino, piperidinyl, —$NR_{15}R_{16}$ wherein $R_{15}$ and $R_{16}$ are independently chosen from hydrogen, lower alkyl, aralkyl, heteroaralkyl, —C(O)$R_{17}$, —C(O)O$R_{17}$, and —C(O)$NR_{17}R_{17}$ wherein for each occurrence $R_{17}$ is chosen from hydrogen, lower alkyl, cycloalkyl, aralkyl, aryl, heterocycloalkyl, heteroaralkyl, and heteroaryl.

21. The compound of claim 1, or a pharmaceutically acceptable salt thereof, wherein $R_9$ is phenyl optionally substituted with one or more groups chosen from halo, lower alkyl, $CF_3$, lower alkoxy, and phenyl.

22. The compound of claim 1, or a pharmaceutically acceptable salt thereof, wherein $R_9$ is cycloalkyl.

23. The compound of claim 1, or a pharmaceutically acceptable salt thereof, wherein $R_9$ is —$NR_{12}R_{13}$ wherein $R_{12}$ and $R_{13}$ are independently chosen from hydrogen, lower alkyl, aralkyl, heteroaralkyl, —C(O)$R_{14}$, —C(O)O$R_{14}$, and —C(O)$NR_{14}R_{14}$ wherein for each occurrence $R_{14}$ is chosen from hydrogen, lower alkyl, cycloalkyl, aralkyl, aryl, heterocycloalkyl, heteroaralkyl, and heteroaryl.

24. The compound of claim 1, or a pharmaceutically acceptable salt thereof, wherein $R_9$ is aralkyl optionally substituted with one or more groups chosen from lower alkyl and lower alkoxy.

25. The compound of claim 1, or a pharmaceutically acceptable salt thereof, wherein $R_9$ is 1,2,4-oxadiazolyl or pyridinyl, each of which is optionally substituted with one or more groups chosen from halo, heteroaryl, lower alkyl, $CF_3$, and lower alkoxy.

26. The compound of claim 1, or a pharmaceutically acceptable salt thereof, wherein p is 1.

27. The compound of claim 1, or a pharmaceutically acceptable salt thereof, wherein p is 2.

28. The compound of claim 1, or a pharmaceutically acceptable salt thereof, wherein for each occurrence, $R_{10}$ is chosen from lower alkyl, benzyl, and phenyl.

29. The compound of claim 28, or a pharmaceutically acceptable salt thereof, wherein for each occurrence, $R_{10}$ is lower alkyl.

30. The compound of claim 1, or a pharmaceutically acceptable salt thereof, wherein p is 0.

31. The compound of claim 1, or a pharmaceutically acceptable salt thereof, wherein $R_2$ is chosen from hydrogen and optionally substituted lower alkyl.

32. The compound of claim 31, or a pharmaceutically acceptable salt thereof, wherein $R_2$ is chosen from hydrogen and lower alkyl.

33. The compound of claim 32 or a pharmaceutically acceptable salt thereof, wherein $R_2$ is hydrogen.

34. The compound of claim 1, or a pharmaceutically acceptable salt thereof, wherein $R_3$ is chosen from hydrogen, halo, and optionally substituted lower alkyl.

35. The compound of claim 34, or a pharmaceutically acceptable salt thereof, wherein $R_3$ is chosen from hydrogen, fluoro, chloro, and lower alkyl.

36. The compound of claim 35, or a pharmaceutically acceptable salt thereof, wherein $R_3$ is hydrogen.

37. The compound of claim 1, or a pharmaceutically acceptable salt thereof, wherein $R_4$ is chosen from hydrogen, halo, and optionally substituted lower alkyl.

38. The compound of claim 37, or a pharmaceutically acceptable salt thereof, wherein $R_4$ is chosen from hydrogen, halo, and lower alkyl.

39. The compound of claim 38, or a pharmaceutically acceptable salt thereof, wherein $R_4$ is hydrogen, methyl, fluoro, or chloro.

40. The compound of claim 1, or a pharmaceutically acceptable salt thereof, wherein $R_5$ is chosen from hydrogen, halo, and optionally substituted lower alkyl.

41. The compound of claim 40, or a pharmaceutically acceptable salt thereof, wherein $R_5$ is chosen from hydrogen, halo, and lower alkyl.

42. The compound of claim 41, or a pharmaceutically acceptable salt thereof, wherein $R_5$ is hydrogen, methyl, fluoro, or chloro.

43. The compound of claim 1, or a pharmaceutically acceptable salt thereof, wherein $R_1$ is chosen from hydrogen, lower alkyl, —$CF_3$, amino, alkylamino, dialkylamino, lower alkoxy, lower haloalkoxy, and halo.

44. The compound of claim 43, or a pharmaceutically acceptable salt thereof, wherein $R_1$ is hydrogen.

45. The compound of claim 1, or a pharmaceutically acceptable salt thereof, wherein the amide residue —N($R_2$)C(O)C($R_3$)=C($R_4$)($R_5$) is attached to the 3-position of the phenyl ring.

46. The compound of claim 1, or a pharmaceutically acceptable salt thereof, wherein the amide residue —N(R$_2$)C(O)C(R$_3$)═C(R$_4$)(R$_5$) is attached to the 4-position of the phenyl ring.

47. The compound of claim 1, or a pharmaceutically acceptable salt thereof, wherein U is N.

48. The compound of claim 1, or a pharmaceutically acceptable salt thereof, wherein U is CH.

49. A pharmaceutical composition comprising a compound of claim 1, or a pharmaceutically acceptable salt thereof, and a pharmaceutically acceptable excipient.

50. A compound chosen from
- 4-(4-Acryloylamino-benzenesulfonyl)-piperazine-1-carboxylic acid benzyl ester;
- 4-(3-Acryloylamino-benzenesulfonyl)-piperazine-1-carboxylic acid benzyl ester;
- 4-(4-Acryloylamino-benzenesulfonyl)-[1,4]diazepane-1-carboxylic acid benzyl ester;
- 4-(4-Acryloylamino-benzenesulfonyl)-piperazine-1-carboxylic acid tert-butyl ester;
- [1-(4-Acryloylamino-benzenesulfonyl)-piperidin-4-yl]-carbamic acid benzyl ester;
- 4-(4-Acryloylamino-benzenesulfonyl)-piperazine-1-carboxylic acid 2-chloro-benzyl ester;
- 4-(4-Acryloylamino-benzenesulfonyl)-piperazine-1-carboxylic acid 3-trifluoromethyl-benzyl ester;
- 4-(4-Acryloylamino-benzenesulfonyl)-piperazine-1-carboxylic acid 2-chloro-benzyl ester;
- N-[4-(4-Phenylacetyl-piperazine-1-sulfonyl)-phenyl]-acrylamide;
- 4-(4-Acryloylamino-2-trifluoromethyl-benzenesulfonyl)-piperazine-1-carboxylic acid benzyl ester;
- [1-(4-Acryloylamino-benzenesulfonyl)-piperidin-4-ylmethyl]-carbamic acid benzyl ester;
- N-{4-[4-(4-Phenyl-butyryl)-piperazine-1-sulfonyl]-phenyl}-acrylamide;
- 4-(4-Acryloylamino-benzenesulfonyl)-piperazine-1-carboxylic acid 2-trifluoromethyl-benzyl ester;
- 4-(4-Acryloylamino-benzenesulfonyl)-piperazine-1-carboxylic acid 2,6-difluoro-benzyl ester;
- 4-(4-Acryloylamino-benzenesulfonyl)-piperazine-1-carboxylic acid 4-butyl-benzyl ester;
- 4-(4-Acryloylamino-benzenesulfonyl)-piperazine-1-carboxylic acid 4-methyl-benzyl ester;
- 4-(4-Acryloylamino-benzenesulfonyl)-piperazine-1-carboxylic acid 3-fluoro-benzyl ester;
- 4-(4-Acryloylamino-benzenesulfonyl)-piperazine-1-carboxylic acid naphthalen-2-ylmethyl ester;
- 4-(4-Acryloylamino-benzenesulfonyl)-piperazine-1-carboxylic acid 4-tert-butyl-benzyl ester;
- 4-(4-Acryloylamino-benzenesulfonyl)-piperazine-1-carboxylic acid 4-fluoro-benzyl ester;
- 4-(4-Acryloylamino-benzenesulfonyl)-piperazine-1-carboxylic acid naphthalen-1-ylmethyl ester;
- 4-(4-Acryloylamino-benzenesulfonyl)-piperazine-1-carboxylic acid 4-trifluoromethyl-benzyl ester;
- 4-(3-Acryloylamino-benzenesulfonyl)-piperazine-1-carboxylic acid tert-butyl ester;
- N-{4-[4-(3-Phenyl-propionyl)-piperazine-1-sulfonyl]-phenyl}-acrylamide;
- N-[4-(4-Phenyl-piperazine-1-sulfonyl)-phenyl]-acrylamide;
- N-[4-(4-Acetyl-piperazine-1-sulfonyl)-phenyl]-acrylamide;
- 1-(4-Acryloylamino-benzenesulfonyl)-(S)-pyrrolidin-3-yl]-carbamic acid benzyl ester;
- 4-(4-Acryloylamino-benzenesulfonyl)-piperazine-1-carboxylic acid phenethyl ester;
- 4-(4-Acryloylamino-benzenesulfonyl)-piperazine-1-carboxylic acid 2,3-dimethoxy-benzyl ester;
- 4-(4-Acryloylamino-benzenesulfonyl)-piperazine-1-carboxylic acid 2-methyl-benzyl ester;
- N-[4-(Piperazine-1-sulfonyl)-phenyl]-acrylamide;
- 4-(4-Acryloylamino-benzenesulfonyl)-piperazine-1-carboxylic acid ethyl ester;
- 4-(4-Acryloylamino-benzenesulfonyl)-piperazine-1-carboxylic acid isobutyl ester;
- 4-(4-Acryloylamino-benzenesulfonyl)-piperazine-1-carboxylic acid methyl ester;
- 4-(4-Acryloylamino-benzenesulfonyl)-piperazine-1-carboxylic acid isopropyl ester;
- 4-(4-Acryloylamino-benzenesulfonyl)-piperazine-1-carboxylic acid benzylamide;
- [1-(4-Acryloylamino-benzenesulfonyl)-(R)-pyrrolidin-3-yl]-carbamic acid benzyl ester;
- 4-(4-Acryloylamino-benzenesulfonyl)-piperazine-1-carboxylic acid 3,5-difluoro-benzyl ester;
- 4-(4-Acryloylamino-benzenesulfonyl)-piperazine-1-carboxylic acid 3,5-dimethyl-benzyl ester;
- 4-(4-Acryloylamino-benzenesulfonyl)-piperazine-1-carboxylic acid 3-chloro-benzyl ester;
- 4-(4-Acryloylamino-benzenesulfonyl)-piperazine-1-carboxylic acid 2,3-difluoro-benzyl ester;
- N-{4-[4-(2-Naphthalen-2-yl-acetyl)-piperazine-1-sulfonyl]-phenyl}-acrylamide;
- N[4-(4-Benzyl-piperazine-1-sulfonyl)-phenyl]-acrylamide;
- N-[4-(4-Phenethyl-piperazine-1-sulfonyl)-phenyl]-acrylamide;
- 4-(4-Acryloylamino-benzenesulfonyl)-piperazine-1-carboxylic acid cyclopentyl ester;
- N-{4-[4-(Piperidine-1-carbonyl)-piperazine-1-sulfonyl]-phenyl}-acrylamide;
- N-[3-(4-Benzyl-piperazine-1-sulfonyl)-phenyl]-acrylamide;
- N-[3-(4-Phenethyl-piperazine-1-sulfonyl)-phenyl]-acrylamide;
- N-{3-[4-(3-Phenyl-propyl)-piperazine-1-sulfonyl]-phenyl}-acrylamide;
- N-[3-(4-Phenyl-piperazine-1-sulfonyl)-phenyl]-acrylamide;
- 4-(4-Acryloylamino-benzenesulfonyl)-piperazine-1-carboxylic acid phenyl ester;
- N-{4-[4-(Pyrrolidine-1-carbonyl)-piperazine-1-sulfonyl]-phenyl}-acrylamide;
- N-[4-(4-Phenyl-piperidine-1-sulfonyl)-phenyl]-acrylamide;
- N-{4-[4-(3-Phenyl-propyl)-piperazine-1-sulfonyl]-phenyl}-acrylamide;
- N-{3-[4-(4-Phenyl-butyl)-piperazine-1-sulfonyl]-phenyl}-acrylamide;
- N-{4-[4-(4-Phenyl-butyl)-piperazine-1-sulfonyl]-phenyl}-acrylamide;
- 4-(3-Acryloylamino-benzenesulfonyl)-piperazine-1-carboxylic acid isopropyl ester;
- 4-(4-Acryloylamino-benzenesulfonyl)-3,5-dimethyl-piperazine-1-carboxylic acid tert-butyl ester;
- N-[3-(Piperazine-1-sulfonyl)-phenyl]-acrylamide;
- 4-(4-Acryloylamino-benzenesulfonyl)-3,5-dimethyl-piperazine-1-carboxylic acid benzyl ester;
- 4-(4-Acryloylamino-benzenesulfonyl)-2,6-dimethyl-piperazine-1-carboxylic acid benzyl ester;

[1-(4-Acryloylamino-benzenesulfonyl)-piperidin-4-yl]-carbamic acid tert-butyl ester;
[1-(4-Acryloylamino-benzenesulfonyl)-piperidin-4-ylmethyl]-carbamic acid tert-butyl ester;
N-[4-(4-Amino-piperidine-1-sulfonyl)-phenyl]-acrylamide;
N-[4-(4-Aminomethyl-piperidine-1-sulfonyl)-phenyl]-acrylamide;
4-(3-Acryloylamino-benzenesulfonyl)-piperazine-1-carboxylic acid ethyl ester;
4-(3-Acryloylamino-benzenesulfonyl)-piperazine-1-carboxylic acid methyl ester;
4-(3-Acryloylamino-benzenesulfonyl)-piperazine-1-carboxylic acid isobutyl ester;
N-{4-[4-(6-Trifluoromethyl-pyridin-3-yl)-piperazine-1-sulfonyl]-phenyl}-acrylamide;
N-{4-[4-(5-Chloro-2-methoxy-phenyl)-piperazine-1-sulfonyl]-phenyl}-acrylamide;
4-(3-Acryloylamino-benzenesulfonyl)-piperazine-1-carboxylic acid cyclopentyl ester;
N-[4-(4-Cyclopropanecarbonyl-piperazine-1-sulfonyl)-phenyl]-acrylamide;
N-[4-(4-Cyclopentanecarbonyl-piperazine-1-sulfonyl)-phenyl]-acrylamide;
N-{4-[4-(2-Phenyl-cyclopropanecarbonyl)-piperazine-1-sulfonyl]-phenyl}-acrylamide;
N-[1-(4-Acryloylamino-benzenesulfonyl)-piperidin-4-yl]-benzamide;
N-{3-[4-(Pyrrolidine-1-carbonyl)-piperazine-1-sulfonyl]-phenyl}-acrylamide;
N-{3-[4-(Piperidine-1-carbonyl)-piperazine-1-sulfonyl]-phenyl}-acrylamide;
N-[4-(4-Benzo[1,3]dioxol-5-ylmethyl-piperazine-1-sulfonyl)-phenyl]-acrylamide;
N-{4-[4-(4,4-Difluoro-piperidine-1-carbonyl)-piperazine-1-sulfonyl]-phenyl}-acrylamide;
N-[3-(4-Benzoyl-piperazine-1-sulfonyl)-phenyl]-acrylamide;
N-[3-(4-Phenylacetyl-piperazine-1-sulfonyl)-phenyl]-acrylamide;
N-{3-[4-(3-Phenyl-propionyl)-piperazine-1-sulfonyl]-phenyl}-acrylamide;
N-[1-(4-Acryloylamino-benzenesulfonyl)-piperidin-4-ylmethyl]-benzamide;
N-[4-(4-Acetylamino-piperidine-1-sulfonyl)-phenyl]-acrylamide;
N-{4-[(Acetylamino-methyl)-piperidine-1-sulfonyl]-phenyl}-acrylamide;
N-[4-(4-Ethyl-piperazine-1-sulfonyl)-phenyl]-acrylamide;
N-[4-(4-Cyclopropylmethyl-piperazine-1-sulfonyl)-phenyl]-acrylamide;
N-[4-(4-Cyclopentylmethyl-piperazine-1-sulfonyl)-phenyl]-acrylamide;
N-{4-[4-(3-Pyridin-3-yl-propionyl)-piperazine-1-sulfonyl]-phenyl}-acrylamide;
N-{4-[4-(Adamantane-1-carbonyl)-piperazine-1-sulfonyl]-phenyl}-acrylamide;
N-{4-[4-(3-Piperidin-1-yl-propionyl)-piperazine-1-sulfonyl]-phenyl}-acrylamide;
4-(4-Acryloylamino-benzenesulfonyl)-2-phenyl-piperazine-1-carboxylic acid tert-butyl ester;
4-(4-Acryloylamino-benzenesulfonyl)-piperazine-1-carboxylic acid 3-phenoxy-benzyl ester;
N-{4-[4-(2-Piperidin-1-yl-acetyl)-piperazine-1-sulfonyl]-phenyl}-acrylamide;
N-{4-[4-(3-Pyridin-4-yl-propionyl)-piperazine-1-sulfonyl]-phenyl}-acrylamide;
N-[4-(4-Phenethylamino-piperidine-1-sulfonyl)-phenyl]-acrylamide;
N-{4-[4-(Benzylamino-methyl)-piperidine-1-sulfonyl]-phenyl}-acrylamide;
4-(4-Acryloylamino-benzenesulfonyl)-2-phenyl-piperazine-1-carboxylic acid tert-butyl ester;
N-{4-[4-(3-Pyridin-2-yl-propionyl)-piperazine-1-sulfonyl]-phenyl}-acrylamide;
N-(4-{4-[2-(2-Phenoxy-phenyl)-acetyl]-piperazine-1-sulfonyl}-phenyl)-acrylamide;
N-(4-{4-[2-(3-Phenoxy-phenyl)-acetyl]-piperazine-1-sulfonyl}-phenyl)-acrylamide;
N-(4-{4-[2-(4-Phenoxy-phenyl)-acetyl]-piperazine-1-sulfonyl}-phenyl)-acrylamide;
4-[4-(Acryloyl-methyl-amino)-benzenesulfonyl]-piperazine-1-carboxylic acid tert-butyl ester;
N-[4-(4-Amino-piperidine-1-sulfonyl)-phenyl]-acrylamide;
N-{4-[4-(Morpholine-4-carbonyl)-piperazine-1-sulfonyl]-phenyl}-acrylamide;
N-{4-[4-(Adamantane-1-carbonyl)-2,6-dimethyl-piperazine-1-sulfonyl]-phenyl}-acrylamide;
Adamantane-1-carboxylic acid [1-(4-acryloylamino-benzenesulfonyl)-piperidin-4-yl]-amide;
[1-(4-Acryloylamino-benzenesulfonyl)-piperidin-4-yl]-methyl-carbamic acid tert-butyl ester;
N-[4-(4-Benzyl-2-isopropyl-piperazine-1-sulfonyl)-phenyl]-acrylamide;
N-{4-[4-(4,6-Dimethoxy-pyrimidin-2-ylmethyl)-piperazine-1-sulfonyl]-phenyl}-acrylamide;
N-{4-[4-(2-Oxo-2-piperidin-1-yl-ethyl)-piperazine-1-sulfonyl]-phenyl}-acrylamide;
N-{4-[4-(3-Pyrazin-2-yl-[1,2,4]oxadiazol-5-yl)-piperidine-1-sulfonyl]-phenyl}-acrylamide;
N-{4-[4-(3-Morpholin-4-yl-propyl)-piperazine-1-sulfonyl]-phenyl}-acrylamide;
Adamantane-1-carboxylic acid [1-(4-acryloylamino-benzenesulfonyl)-piperidin-4-yl]-methyl-amide;
N-{4-[4-(Acetyl-methyl-amino)-piperidine-1-sulfonyl]-phenyl}-acrylamide;
N-[4-(4-Methylamino-piperidine-1-sulfonyl)-phenyl]-acrylamide;
4-(4-Acryloylamino-benzenesulfonyl)-2-isopropyl-piperazine-1-carboxylic acid tert-butyl ester;
4-(4-Acryloylamino-benzenesulfonyl)-2-benzyl-piperazine-1-carboxylic acid tert-butyl ester;
N-[4-(3-Benzyl-piperazine-1-sulfonyl)-phenyl]-acrylamide;
N-{4-[4-(2-Morpholin-4-yl-acetyl)-piperazine-1-sulfonyl]-phenyl}-acrylamide;
N-{4-[4-(3-Morpholin-4-yl-propionyl)-piperazine-1-sulfonyl]-phenyl}-acrylamide;
N-{4-[4-(Octahydro-quinoline-1-carbonyl)-piperazine-1-sulfonyl]-phenyl}-acrylamide;
N-{4-[4-(Octahydro-isoquinoline-2-carbonyl)-piperazine-1-sulfonyl]-phenyl}-acrylamide;
4-(4-Acryloylamino-benzenesulfonyl)-piperazine-1-carboxylic acid adamantan-2-ylamide;
N-{4-[4-(2-Trifluoromethyl-phenyl)-piperazine-1-sulfonyl]-phenyl}-acrylamide;
N-{4-[4-(3-Methyl-pyridin-2-yl)-piperazine-1-sulfonyl]-phenyl}-acrylamide;
N-{4-[4-(6-Trifluoromethyl-pyridin-2-yl)-piperazine-1-sulfonyl]-phenyl}-acrylamide;

N-{4-[4-(6-Methyl-pyridin-2-yl)-piperazine-1-sulfonyl]-phenyl}-acrylamide;
N-{4-[4-(2-Methoxy-ethyl)-piperazine-1-sulfonyl]-phenyl}-acrylamide;
N-[4-(4-Cyclopentyl-piperazine-1-sulfonyl)-phenyl]-acrylamide;
N-[4-(4-Cyclohexyl-piperazine-1-sulfonyl)-phenyl]-acrylamide;
N-{4-[4-(Tetrahydro-furan-2-ylmethyl)-piperazine-1-sulfonyl]-phenyl}-acrylamide;
N-[4-(4-Cyclooctyl-piperazine-1-sulfonyl)-phenyl]-acrylamide;
N-[4-(3-Phenoxy-piperidine-1-sulfonyl)-phenyl]-acrylamide;
4-(4-Acryloylamino-benzenesulfonyl)-2-methyl-piperazine-1-carboxylic acid benzyl ester;
N-[4-(3-Isopropyl-piperazine-1-sulfonyl)-phenyl]-acrylamide;
4-(4-Acryloylamino-3-fluoro-benzenesulfonyl)-piperazine-1-carboxylic acid benzyl ester;
N-{4-[4-(4-Dimethylamino-piperidine-1-carbonyl)-piperazine-1-sulfonyl]-phenyl}-acrylamide;
N-{4-[4-(2,6-Dimethyl-morpholine-4-carbonyl)-piperazine-1-sulfonyl]-phenyl}-acrylamide;
N-{4-[4-(Tetrahydro-pyran-4-carbonyl)-piperazine-1-sulfonyl]-phenyl}-acrylamide;
N-{4-[4-(2,2,6,6-Tetramethyl-piperidine-4-carbonyl)-piperazine-1-sulfonyl]-phenyl}-acrylamide;
4-(4-Acryloylamino-benzenesulfonyl)-2-furan-2-yl-piperazine-1-carboxylic acid tert-butyl ester;
N-[4-(4-Pyridin-2-yl-piperazine-1-sulfonyl)-phenyl]-acrylamide;
N-{4-[4-(2,4-Difluoro-phenyl)-piperazine-1-sulfonyl]-phenyl}-acrylamide;
N-[4-(3-Furan-2-yl-piperazine-1-sulfonyl)-phenyl]-acrylamide;
N-{4-[4-(4-Chloro-2-fluoro-phenyl)-piperazine-1-sulfonyl]-phenyl}-acrylamide;
N-{4-[4-(1-Methyl-piperidin-4-yl)-piperazine-1-sulfonyl]-phenyl}-acrylamide;
N-{4-[4-(2-Dimethylamino-ethyl)-piperazine-1-sulfonyl]-phenyl}-acrylamide;
N-{4-[4-(2-Piperidin-1-yl-ethyl)-piperazine-1-sulfonyl]-phenyl}-acrylamide;
N-{4-[4-(3-Trifluoromethyl-phenyl)-piperazine-1-sulfonyl]-phenyl}-acrylamide;
N-{4-[4-(4-Trifluoromethyl-phenyl)-piperazine-1-sulfonyl]-phenyl}-acrylamide;
N-{4-[4-(3-Trifluoromethyl-pyridin-2-yl)-piperazine-1-sulfonyl]-phenyl}-acrylamide;
4-(4-Acryloylamino-2-fluoro-benzenesulfonyl)-piperazine-1-carboxylic acid tert-butyl ester;
N-{4-[2-(4-Trifluoromethyl-phenyl)-pyrrolidine-1-sulfonyl]-phenyl}-acrylamide;
4-(4-Acryloylamino-2-chloro-benzenesulfonyl)-piperazine-1-carboxylic acid tert-butyl ester;
N-{4-[4-(Adamantane-1-carbonyl)-piperazine-1-sulfonyl]-3-fluoro-phenyl}-acrylamide;
N-[4-(4-Thiazol-2-yl-piperazine-1-sulfonyl)-phenyl]-acrylamide;
N-[4-(4-Adamantan-1-yl-piperazine-1-sulfonyl)-phenyl]-acrylamide;
N-{4-[4-(Oxazole-5-carbonyl)-piperazine-1-sulfonyl]-phenyl}-acrylamide;
4-(4-Acryloylamino-benzenesulfonyl)-piperazine-1-carboxylic acid dimethylamide;
4-(4-Acryloylamino-benzenesulfonyl)-2-methoxycarbonylmethyl-piperazine-1-carboxylic acid benzyl ester;
4-(4-Acryloylamino-2-methoxy-benzenesulfonyl)-piperazine-1-carboxylic acid tert-butyl ester;
N-[3-Methoxy-4-(piperazine-1-sulfonyl)-phenyl]-acrylamide;
N-{4-[4-(Adamantane-1-carbonyl)-piperazine-1-sulfonyl]-3-methoxy-phenyl}-acrylamide;
N-{4-[4-(2-Morpholin-4-yl-2-oxo-ethyl)-piperazine-1-sulfonyl]-phenyl}-acrylamide;
1-(4-Acryloylamino-benzenesulfonyl)-piperidine-4-carboxylic acid methyl ester;
4-(4-Acryloylamino-benzenesulfonyl)-2-(adamantan-2-ylcarbamoylmethyl)-piperazine-1-carboxylic acid benzyl ester;
N-{4-[4-(4-Methoxy-phenyl)-piperazine-1-sulfonyl]-phenyl}-acrylamide;
N-{4-[4-(Piperidine-1-carbonyl)-piperidine-1-sulfonyl]-phenyl}-acrylamide;
N-[4-(4-Benzooxazol-2-yl-piperazine-1-sulfonyl)-phenyl]-acrylamide;
N-[4-(4-Naphthalen-1-yl-piperazine-1-sulfonyl)-phenyl]-acrylamide;
N-{4-[4-(4-Trifluoromethyl-pyrimidin-2-yl)-piperazine-1-sulfonyl]-phenyl}-acrylamide;
4-(4-Acryloylamino-2-methyl-benzenesulfonyl)-piperazine-1-carboxylic acid tert-butyl ester;
N-[3-Methyl-4-(piperazine-1-sulfonyl)-phenyl]-acrylamide;
N-{4-[4-(Adamantane-1-carbonyl)-piperazine-1-sulfonyl]-3-methyl-phenyl}-acrylamide;
N-{4-[4-(2-Chloro-pyrimidin-4-yl)-piperazine-1-sulfonyl]-phenyl}-acrylamide;
N-[4-(4-Pyrimidin-2-yl-piperazine-1-sulfonyl)-phenyl]-acrylamide;
N-[4-(4-Furo[3,2-c]pyridin-4-yl-piperazine-1-sulfonyl)-phenyl]-acrylamide;
1-(4-Acryloylamino-benzenesulfonyl)-piperidine-4-carboxylic acid dimethylamide;
1-(4-Acryloylamino-benzenesulfonyl)-piperidine-4-carboxylic acid cyclopropylamide;
N-{4-[4-(3,3-Difluoro-azetidine-1-carbonyl)-piperidine-1-sulfonyl]-phenyl}-acrylamide;
1-(4-Acryloylamino-benzenesulfonyl)-piperidine-4-carboxylic acid methyl-phenyl-amide;
N-{4-[4-(Pyrrolidine-1-carbonyl)-piperidine-1-sulfonyl]-phenyl}-acrylamide;
N-{4-[4-(6-Methoxy-pyridin-2-yl)-piperazine-1-sulfonyl]-phenyl}-acrylamide;
N-{4-[4-(4-Methoxy-pyrimidin-2-yl)-piperazine-1-sulfonyl]-phenyl}-acrylamide;
N-[4-(2,3,5,6-Tetrahydro-[1,2']bipyrazinyl-4-sulfonyl)-phenyl]-acrylamide;
N-{4-[4-(4-Methyl-pyridin-2-yl)-piperazine-1-sulfonyl]-phenyl}-acrylamide;
N-{4-[4-(4,6-Dimethyl-pyrimidin-2-yl)-piperazine-1-sulfonyl]-phenyl}-acrylamide;
5-[4-(4-Acryloylamino-benzenesulfonyl)-piperazine-1-carbonyl]-2,5-diaza-bicyclo[2.2.1]heptane-2-carboxylic acid tert-butyl ester;
4-(4-Acryloylamino-benzenesulfonyl)-piperidine-1-carboxylic acid tert-butyl ester;
1-(4-Acryloylamino-benzenesulfonyl)-piperidine-4-carboxylic acid (2,2,2-trifluoro-ethyl)-amide;
1-(4-Acryloylamino-benzenesulfonyl)-piperidine-4-carboxylic acid (2-methoxy-ethyl)-methyl-amide;

N-{4-[4-(2-Morpholin-4-yl-ethyl)-piperazine-1-sulfonyl]-phenyl}-acrylamide;
N-{4-[4-(1-Methyl-piperidin-4-ylmethyl)-piperazine-1-sulfonyl]-phenyl}-acrylamide;
N-{4-[4-(2-Methyl-quinolin-5-yl)-piperazine-1-sulfonyl]-phenyl}-acrylamide;
N-[4-(4-Quinolin-2-yl-piperazine-1-sulfonyl)-phenyl]-acrylamide;
N-{4-[4-(5-Chloro-pyridin-2-yl)-piperazine-1-sulfonyl]-phenyl}-acrylamide;
N-{4-[4-(5-Methyl-pyridin-2-yl)-piperazine-1-sulfonyl]-phenyl}-acrylamide;
N-[4-(4-Biphenyl-3-yl-piperazine-1-sulfonyl)-phenyl]-acrylamide;
N-[4-(4-Benzothiazol-2-yl-piperazine-1-sulfonyl)-phenyl]-acrylamide;
N-{4-[4-(Morpholine-4-carbonyl)-piperidine-1-sulfonyl]-phenyl}-acrylamide;
N-[4-(4-Isoquinolin-1-yl-piperazine-1-sulfonyl)-phenyl]-acrylamide;
N-[4-(4-Naphthalen-2-yl-piperazine-1-sulfonyl)-phenyl]-acrylamide;
N-{4-[4-(4-Dimethylamino-pyrimidin-2-yl)-piperazine-1-sulfonyl]-phenyl}-acrylamide;
1-(4-Acryloylamino-benzenesulfonyl)-piperidine-4-carboxylic acid cyclopropyl-methyl-amide;
N-{4-[4-(4-Morpholin-4-yl-pyrimidin-2-yl)-piperazine-1-sulfonyl]-phenyl}-acrylamide;
N-[4-(4-Thieno[2,3-d]pyrimidin-4-yl-piperazine-1-sulfonyl)-phenyl]-acrylamide;
N-{4-[4-(2-Oxo-benzooxazol-3-yl)-piperidine-1-sulfonyl]-phenyl}-acrylamide;
N-{4-[4-(4-Methoxy-pyridin-2-yl)-piperazine-1-sulfonyl]-phenyl}-acrylamide;
N-{4-[4-(2-Dimethylamino-pyrimidin-4-yl)-piperazine-1-sulfonyl]-phenyl}-acrylamide;
N-{4-[4-(2-Morpholin-4-yl-pyrimidin-4-yl)-piperazine-1-sulfonyl]-phenyl}-acrylamide;
4-(4-Acryloylamino-benzenesulfonyl)-2-pyridin-3-yl-piperazine-1-carboxylic acid tert-butyl ester;
N-[4-(3-Pyridin-3-yl-piperazine-1-sulfonyl)-phenyl]-acrylamide;
4-(4-Acryloylamino-benzenesulfonyl)-2-(5-methyl-furan-2-yl)-piperazine-1-carboxylic acid tert-butyl ester;
N-{4-[4-(2-Methyl-1,2,3,4-tetrahydro-isoquinolin-1-yl)-piperidine-1-sulfonyl]-phenyl}-acrylamide;
N-[4-(4-Isoquinolin-3-yl-piperazine-1-sulfonyl)-phenyl]-acrylamide;
N-[4-(4-Thieno[3,2-d]pyrimidin-4-yl-piperazine-1-sulfonyl)-phenyl]-acrylamide;
N-{4-[3-(5-Methyl-furan-2-yl)-piperazine-1-sulfonyl]-phenyl}-acrylamide; and
N-{4-[4-(3-Chloro-5-trifluoromethyl-pyridin-2-yl)-piperazine-1-sulfonyl]-phenyl}-acrylamide,
or a pharmaceutically acceptable salt thereof.

\* \* \* \* \*